(12) United States Patent
Molteni et al.

(10) Patent No.: US 8,293,757 B2
(45) Date of Patent: Oct. 23, 2012

(54) 5-(4-(HALOALKOXY)PHENYL) PYRIMIDINE-2-AMINE COMPOUNDS AND COMPOSITIONS AS KINASE INHIBITORS

(75) Inventors: Valentina Molteni, San Diego, CA (US); Xiaolin Li, San Diego, CA (US); Xiaodong Liu, San Diego, CA (US); Donatella Chianelli, San Diego, CA (US); Juliet Nabakka, San Diego, CA (US); Jon Loren, San Diego, CA (US); Shuli You, Shanghai (CN)

(73) Assignee: IRM LLC, Hamilton (BM)

( * ) Notice: Subject to any disclaimer, the term of this patent is extended or adjusted under 35 U.S.C. 154(b) by 0 days.

(21) Appl. No.: 12/674,416

(22) PCT Filed: Aug. 19, 2008

(86) PCT No.: PCT/US2008/073573
§ 371 (c)(1),
(2), (4) Date: Jun. 14, 2011

(87) PCT Pub. No.: WO2009/026276
PCT Pub. Date: Feb. 26, 2009

(65) Prior Publication Data
US 2011/0301175 A1    Dec. 8, 2011

Related U.S. Application Data

(60) Provisional application No. 60/957,260, filed on Aug. 22, 2007.

(51) Int. Cl.
*A61K 31/506* (2006.01)
*C07D 403/10* (2006.01)
*C07D 239/42* (2006.01)

(52) U.S. Cl. .......... 514/275; 544/295; 544/332
(58) Field of Classification Search .......... 514/275; 544/338
See application file for complete search history.

(56) References Cited

U.S. PATENT DOCUMENTS

| | | | |
|---|---|---|---|
| 5,516,775 A | 5/1996 | Zimmermann et al. | |
| 6,562,817 B1 | 5/2003 | Tanimoto et al. | |
| 7,034,019 B2 | 4/2006 | Kukla et al. | |
| 7,514,447 B2 * | 4/2009 | Molteni et al. | 514/275 |
| 7,563,894 B2 * | 7/2009 | Molteni et al. | 544/330 |
| 7,589,197 B2 | 9/2009 | Yen et al. | |
| 7,592,349 B2 * | 9/2009 | Molteni et al. | 514/275 |
| 2003/0176443 A1 | 9/2003 | Stein-Gerlach et al. | |
| 2003/0186990 A1 | 10/2003 | Kukla et al. | |
| 2004/0106634 A1 | 6/2004 | Satoh et al. | |
| 2006/0079543 A1 | 4/2006 | Sum et al. | |
| 2006/0281712 A1 | 12/2006 | Yen et al. | |
| 2007/0099938 A1 | 5/2007 | Ohmoto et al. | |
| 2008/0096892 A1 | 4/2008 | Cheng et al. | |

FOREIGN PATENT DOCUMENTS

| | | |
|---|---|---|
| EP | 0164204 * | 12/1985 |
| EP | 1052238 | 11/2000 |
| EP | 1679309 | 7/2006 |
| WO | WO9509847 | 4/1995 |
| WO | WO0222597 | 3/2002 |
| WO | WO0246170 | 6/2002 |
| WO | WO0246171 | 6/2002 |
| WO | WO2004005281 | 1/2004 |
| WO | WO2004029038 | 4/2004 |
| WO | WO2004089286 | 10/2004 |
| WO | WO2004110350 | 12/2004 |
| WO | WO2005020921 | 3/2005 |
| WO | WO2005040155 | 5/2005 |
| WO | WO2006027795 | 3/2006 |
| WO | WO2006051311 | 5/2006 |
| WO | WO2006081034 | 8/2006 |
| WO | WO2007038669 * | 4/2007 |
| WO | WO2007056151 | 5/2007 |
| WO | WO2008058037 | 5/2008 |
| WO | WO2008137605 | 11/2008 |
| WO | WO2008137794 | 11/2008 |
| WO | WO2009026204 | 2/2009 |

OTHER PUBLICATIONS

Patani, Bioisosterism: A Rational Approach in Drug Design, 1996, Chem Rev, vol. 96, p. 3147-3176.*

* cited by examiner

*Primary Examiner* — Golam M M Shameem
*Assistant Examiner* — Karen Cheng
(74) *Attorney, Agent, or Firm* — Daniel E. Raymond; Genomics Institute of the Novartis Research Foundation

(57) ABSTRACT

The invention provides compounds of formula (1) and pharmaceutical compositions thereof, which are useful as protein kinase inhibitors, as well as methods for using such compounds to treat, ameliorate or prevent a condition associated with abnormal or deregulated kinase activity. In some embodiments, the invention provides methods for using such compounds to treat, ameliorate or prevent diseases or disorders that involve abnormal activation of c-kit, PDGFRα, PDGFRβ, CSF1R, Abl, BCR-Abl, CSK, JNK1, JNK2, p38, p70S6K, TGFβ, SRC, EGFR, trkB, FGFR3. Fes, Lck, Syk, RAF, MKK4, MKK6, SAPK2β, BRK, Fms, KDR, c-rapor b-raf kinases.

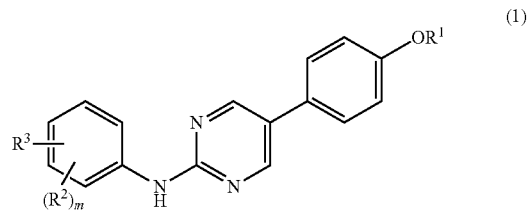

(1)

7 Claims, No Drawings

5-(4-(HALOALKOXY)PHENYL)PYRIMIDINE-2-AMINE COMPOUNDS AND COMPOSITIONS AS KINASE INHIBITORS

CROSS-REFERENCE TO RELATED APPLICATIONS

This application is a 371 U.S. national phase application of international application number PCT/US2008/073573 filed 19 Aug. 2008, which claims the benefit of U.S. provisional patent application Ser. No. 60/957,260, filed 22 Aug. 2007. The full disclosure of these applications is incorporated herein by reference in their entirety and for all purposes.

TECHNICAL FIELD

The invention relates to protein kinase inhibitors, and methods of using such compounds. More particularly, the invention relates to c-kit and PDGFR inhibitors, and uses thereof for the treatment and prevention of c-kit and PDGFR mediated disorders.

BACKGROUND ART

The protein kinases represent a large family of proteins, which play a central role in the regulation of a wide variety of cellular processes and maintaining control over cellular function. A partial, non-limiting, list of these kinases include: receptor tyrosine kinases such as platelet-derived growth factor receptor kinase (PDGFR), the receptor kinase for stem cell factor, c-kit, the nerve growth factor receptor, trkB, and the fibroblast growth factor receptor, FGFR3; non-receptor tyrosine kinases such Abl and the fusion kinase BCR-Abl, Fes, Lck and Syk; and serine/threonine kinases such as b-RAF, MAP kinases (e.g., MKK6) and SAPK2β. Aberrant kinase activity has been observed in many disease states including benign and malignant proliferative disorders as well as diseases resulting from inappropriate activation of the immune and nervous systems.

DISCLOSURE OF THE INVENTION

The invention provides compounds and pharmaceutical compositions thereof, which may be useful as protein kinase inhibitors.

In one aspect, the present invention provides compounds of Formula (1):

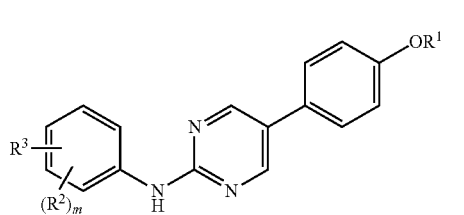

or a pharmaceutically acceptable salt thereof;
$R^1$ is a haloalkyl having 1-6 fluorine atoms;
$R^2$ is $C_{1-6}$ alkyl, $C_{2-6}$ alkenyl or $C_{2-6}$ alkynyl, each of which may be optionally substituted with halo, amino or hydroxyl groups; halo, cyano, nitro, $(CR_2)_kOR^7$, $(CR_2)_kO(CR_2)_{1-4}R^7$, $(CR_2)_kSR^7$, $(CR_2)_kNR^9R^{10}$, $(CR_2)_kC(O)O_{0-1}R^7$, $OC(O)R^7$, $(CR_2)_kC(S)R^7$, $(CR_2)_kC(O)NR^9R^{10}$, $(CR_2)_kC(O)NR(CR_2)_{0-6}C(O)O_{0-1}R^7$, $(CR_2)_kNRC(O)O_{0-1}R^7$, $(CR_2)_kS(O)_{1-2}NR^9R^{10}$, $(CR_2)_kS(O)_{1-2}R^8$, $(CR_2)_kNRS(O)_{1-2}R^8$ or $(CR_2)_kR^6$; or any two adjacent $R^2$ groups together may form an optionally substituted 5-8 membered carbocyclic, heterocyclic, aryl or heteroaryl ring;

$R^3$ is -L-$NR^4R^5$, —X—NR—C(O)$R^8$ or —X—NR—C(O)NR$^4R^5$ wherein L is —X—C(O), —X—OC(O), —(CR$_2$)$_j$, —SO$_{0-2}$(CR$_2$)$_j$, —O(CR$_2$)$_{1-4}$, or

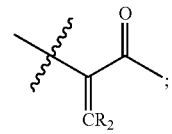

and X is $(CR_2)_j$ or $[C(R)(CR_2OR)]$;
$R^4$, $R^5$, $R^9$ and $R^{10}$ are independently H; $C_{1-6}$ alkyl, $C_{2-6}$ alkenyl or $C_{2-6}$ alkynyl, each of which may be optionally substituted with halo, amino, hydroxyl, alkoxy, cyano, carboxyl or $R^6$; $(CR_2)_kCN$, $(CR_2)_{1-6}NR^7R^7$, $(CR_2)_{1-6}OR^7$, $(CR_2)_kC(O)O_{0-1}R^7$, $(CR_2)_kC(O)NR^7R^7$ or $(CR_2)_k$—$R^6$;
$R^6$ is an optionally substituted $C_{3-7}$ cycloalkyl, $C_6$ aryl, or a 5-6 membered heteroaryl or 5-7 membered heterocyclic ring;
$R^7$ and $R^8$ are independently $(CR_2)_k$—$R^6$ or $C_{1-6}$ alkyl, $C_{2-6}$ alkenyl or $C_{2-6}$ alkynyl, each of which may be optionally substituted with halo, amino, amido, hydroxyl, alkoxy, cyano, carboxyl or $R^6$; or $R^7$ is H;
alternatively, $R^4$ and $R^5$ together with N in each $NR^4R^5$, $R^7$ and $R^7$ together with N in $NR^7R^7$ or $R^9$ and $R^{10}$ together with N in $NR^9R^{10}$ may form a 4-7 membered heterocyclic ring optionally substituted with 1-3 $R^{11}$ groups;
$R^{11}$ is $R^8$, $(CR_2)_k$—$OR^7$, $CO_2R^7$, $(CR_2)_k$—$C(O)$—$(CR_2)_k$—$R^8$, $(CR_2)_kC(O)NR^7R^7$, $(CR_2)_kC(O)NR(CR_2)_{0-6}C(O)O_{0-1}R^7$, $(CR_2)_kNRC(O)O_{0-1}R^7$, $(CR_2)_kS(O)_{1-2}NR^7R^7$, $(CR_2)_kS(O)_{1-2}R^8$ or $(CR_2)_kNRS(O)_{1-2}R^8$;
each R is H or $C_{1-6}$ alkyl;
each k is 0-6; and
j and m are independently 0-4;
provided $R^1$ is not trifluoromethoxy when $R^3$ is $C(O)NH_2$, $C(O)NR^{12}R^{13}$ or $SO_2NH(CH_2)_{2-3}NR^{14}R^{15}$; wherein $R^{12}$ and $R^{13}$ together form piperazinyl and $R^{14}$ and $R^{15}$ together form morpholinyl.

In the above Formula (1), $R^1$ may be $OCHF_2$, $OCF_3$, $OCH_2CF_3$, $OCF_2CH_2$ or $OCH_2CF_3$. In particular examples, $R^1$ is $OCHF_2$.

In some examples, $R^3$ in the above Formula (1) is selected from the group consisting of

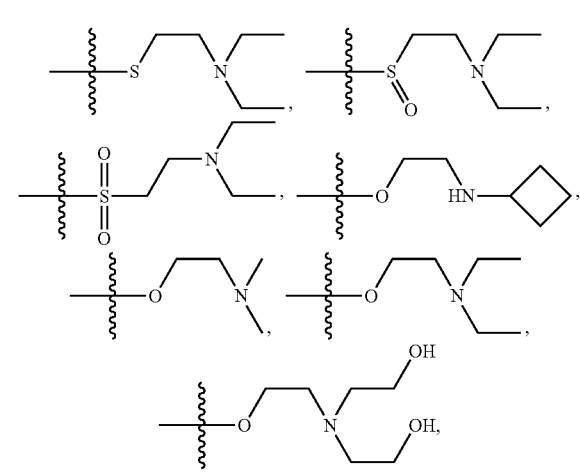

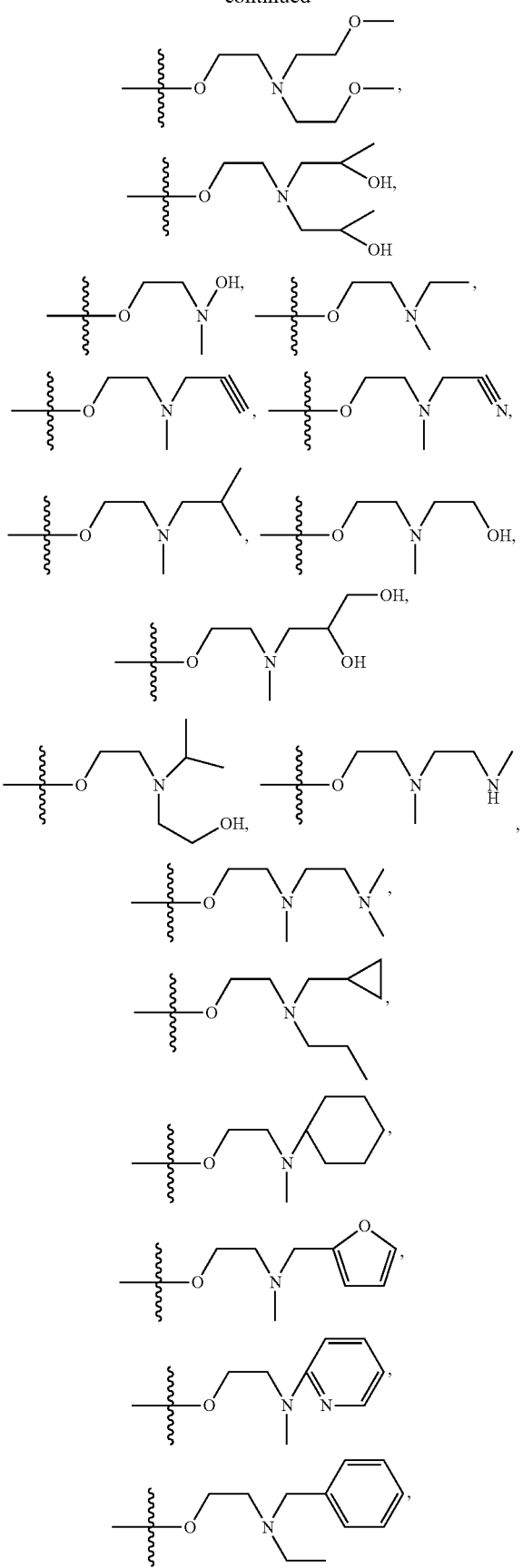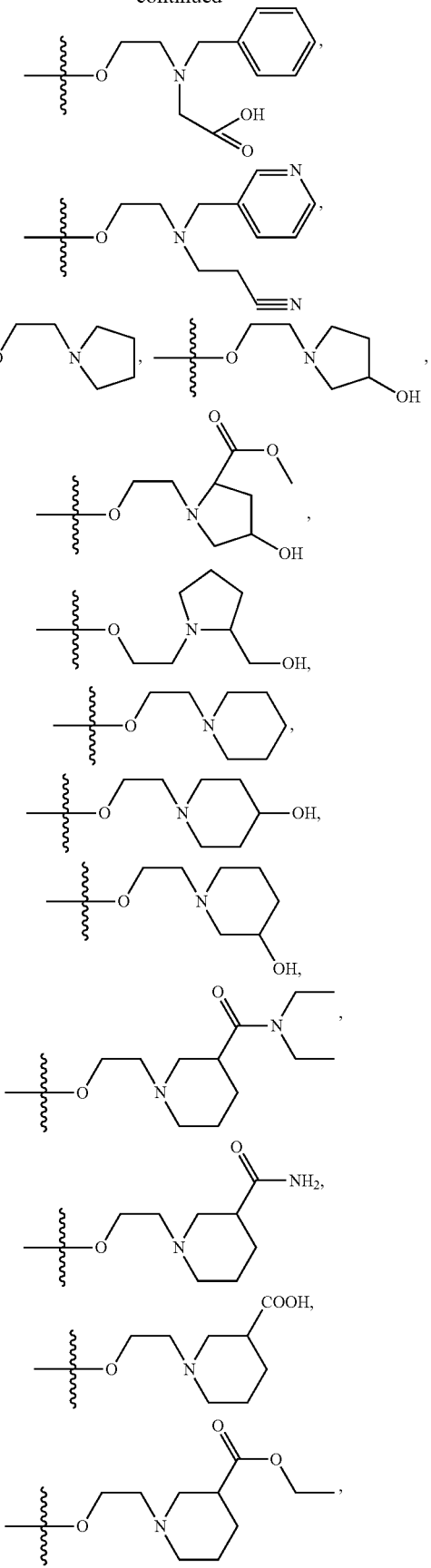

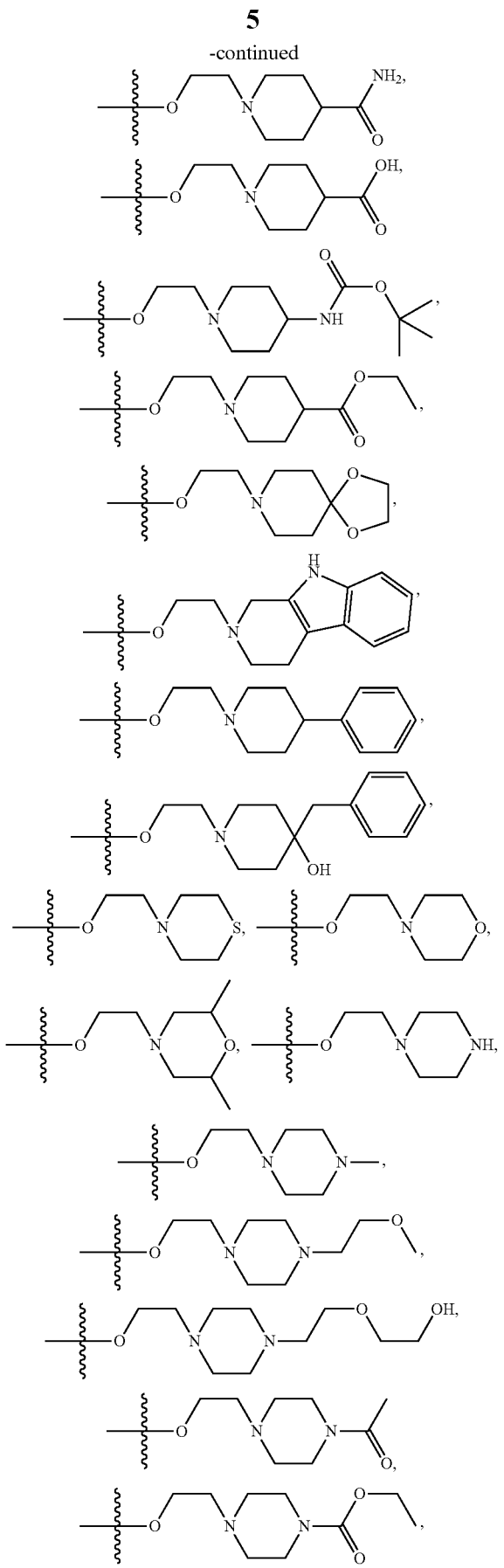
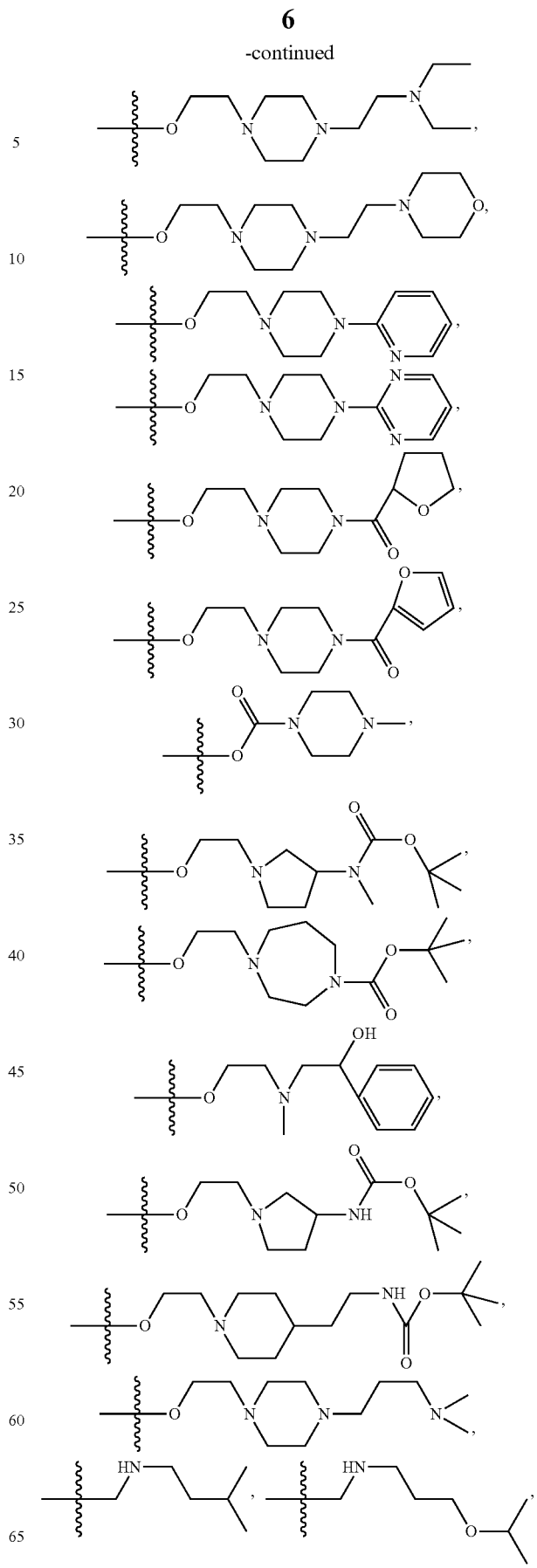

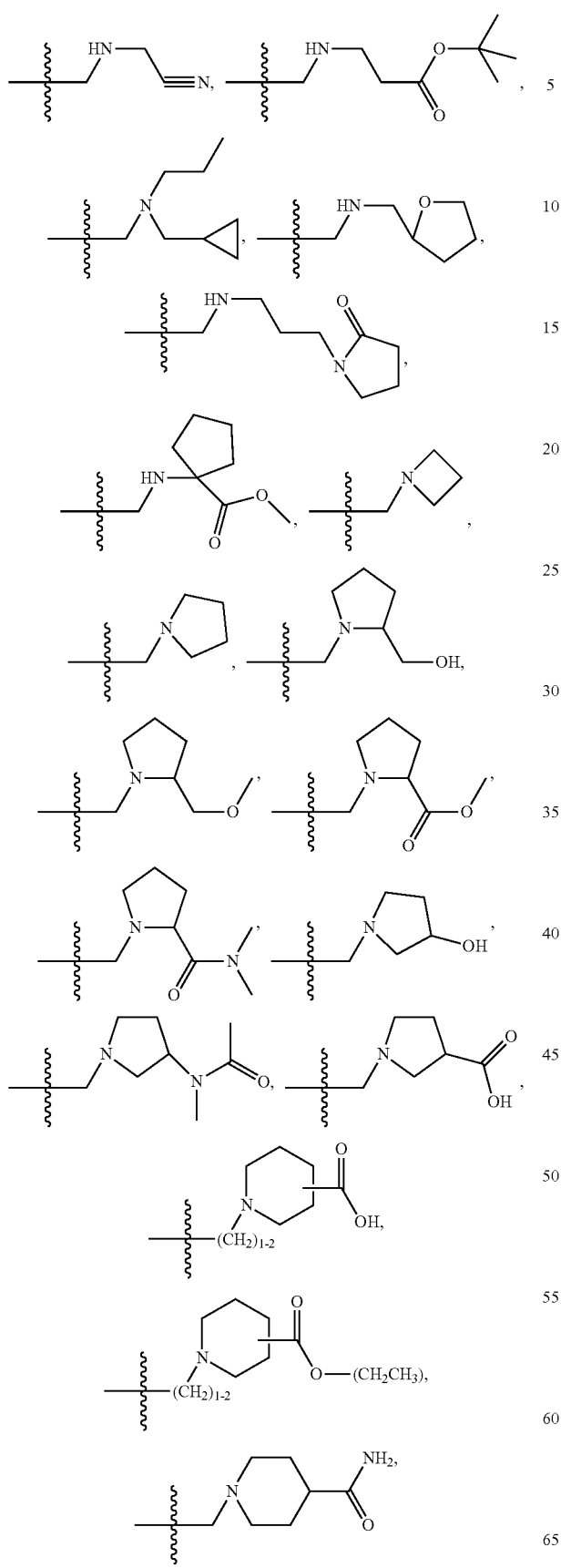
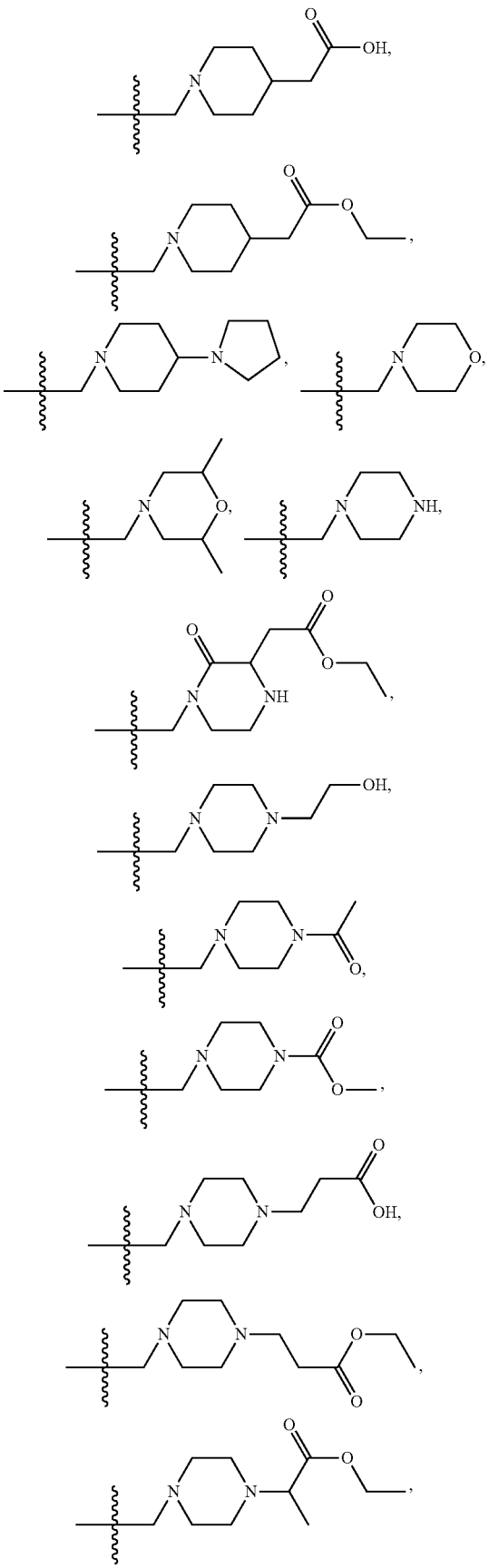

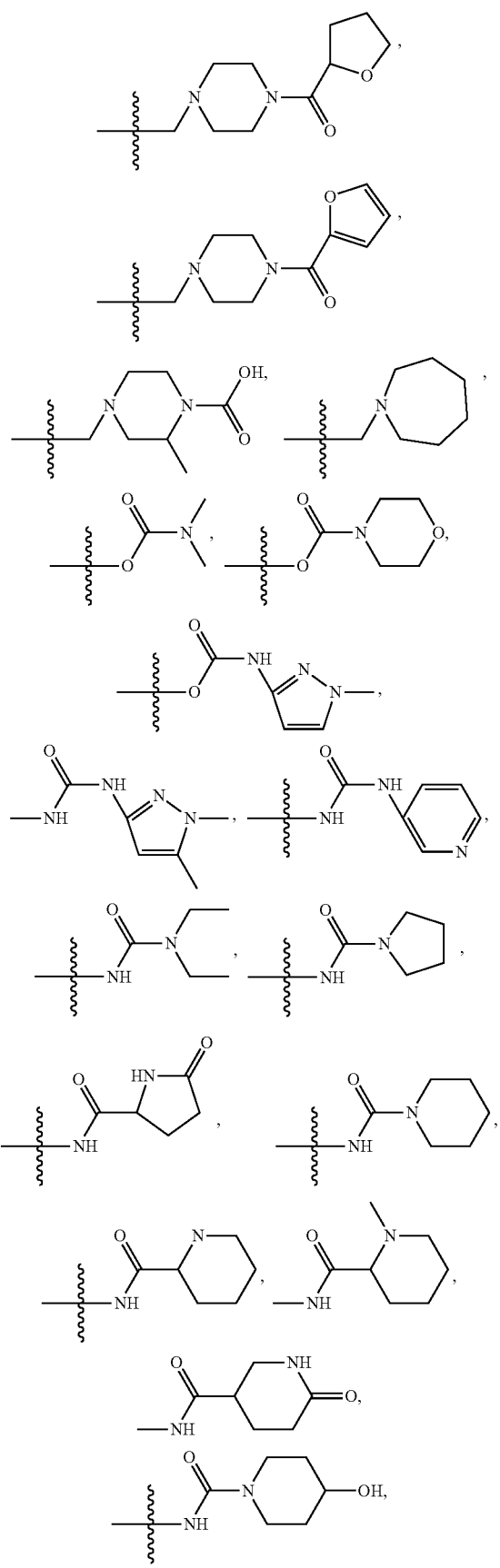
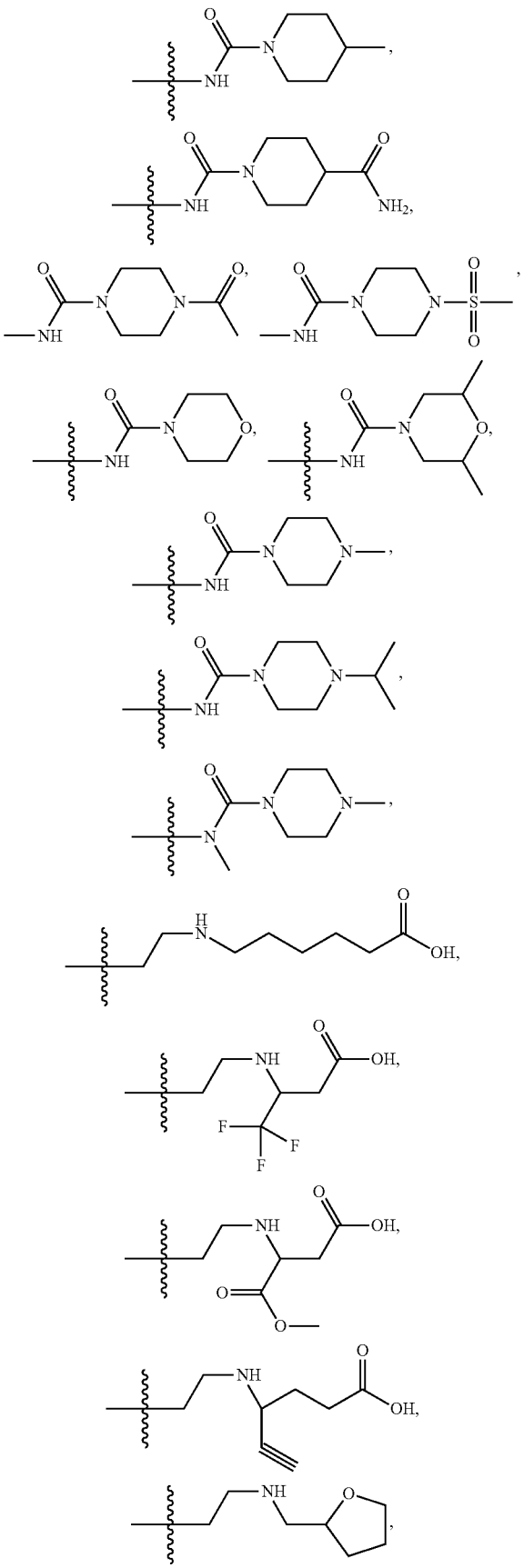

11
-continued
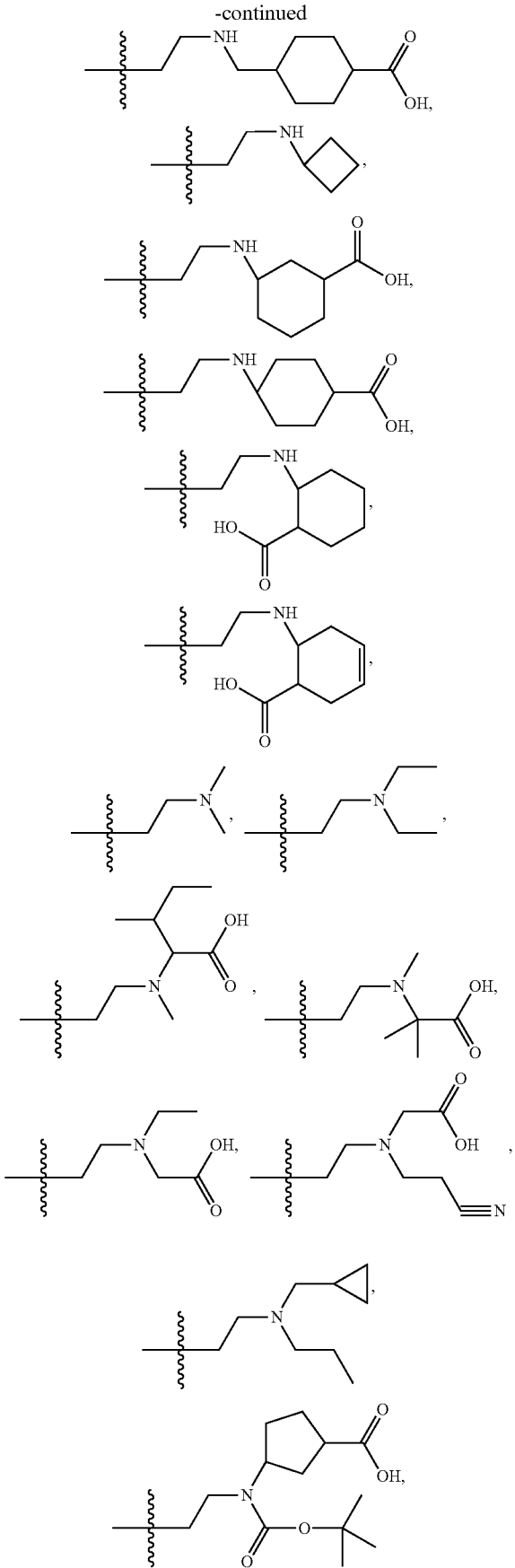
12
-continued
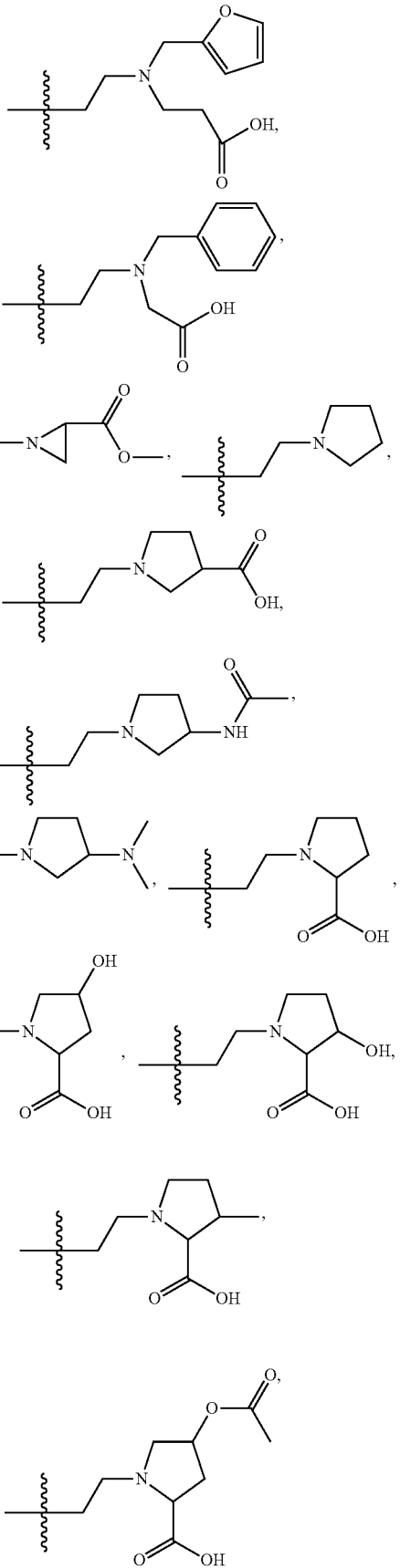

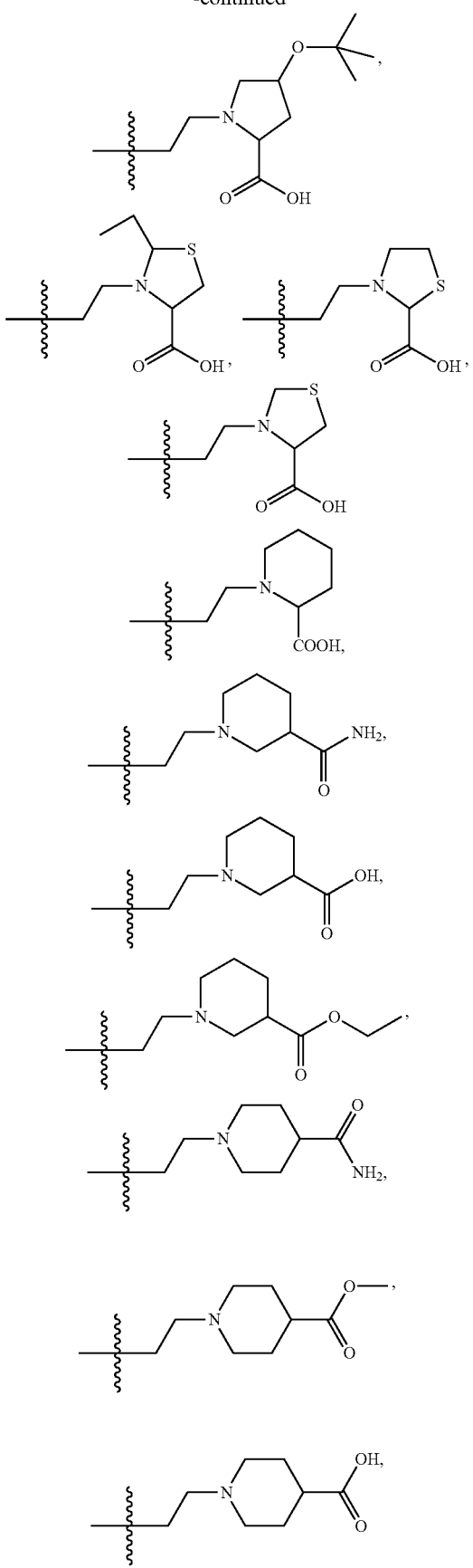
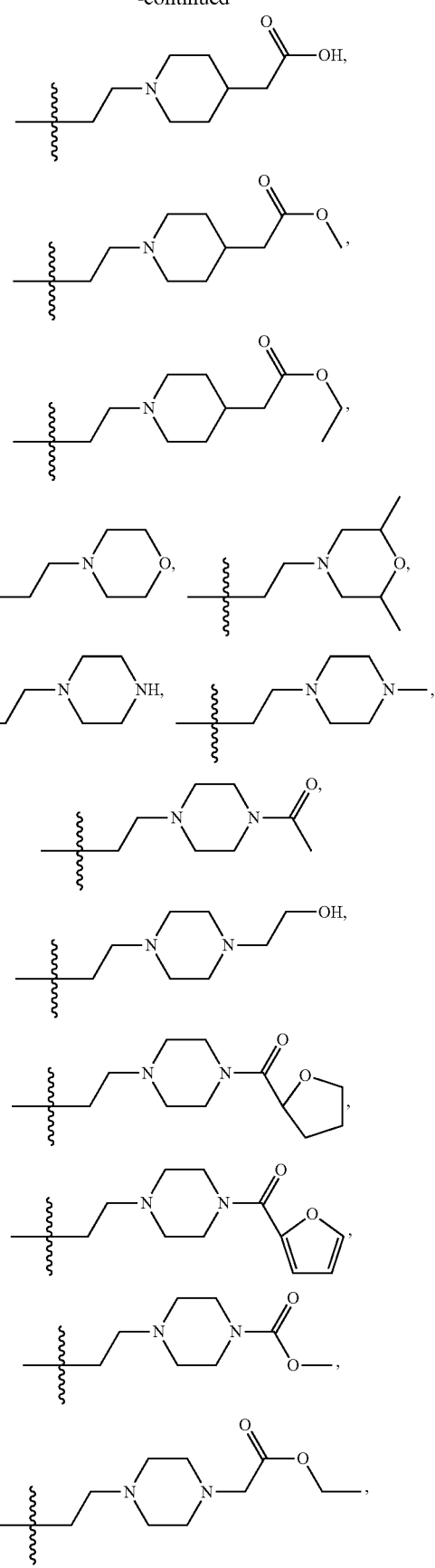

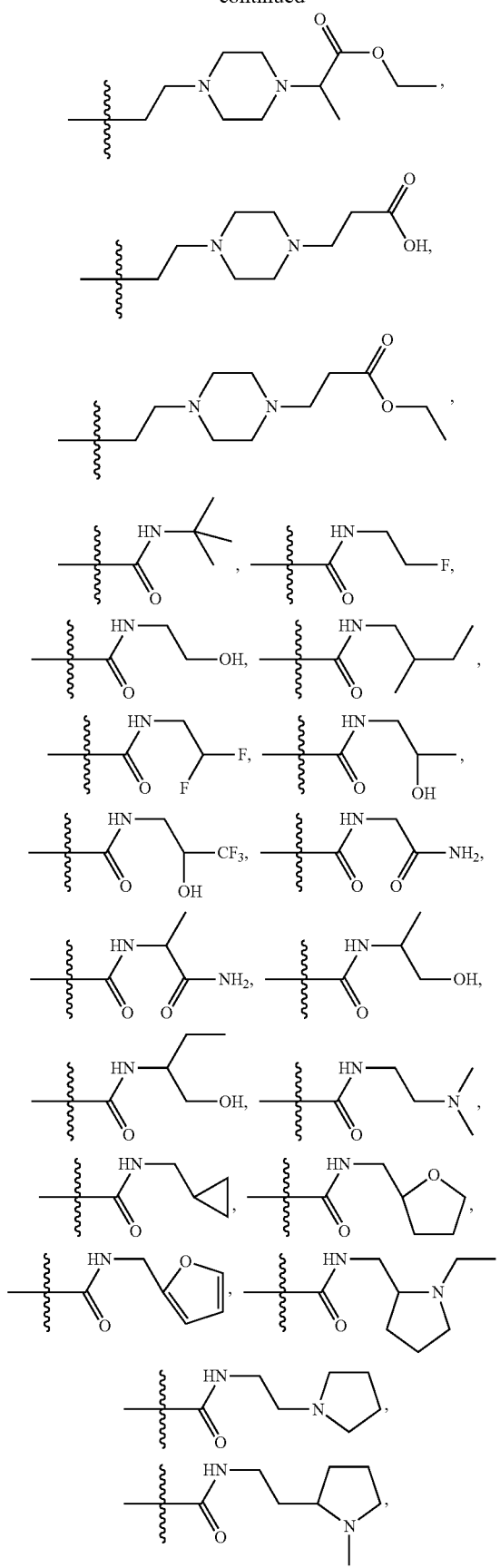
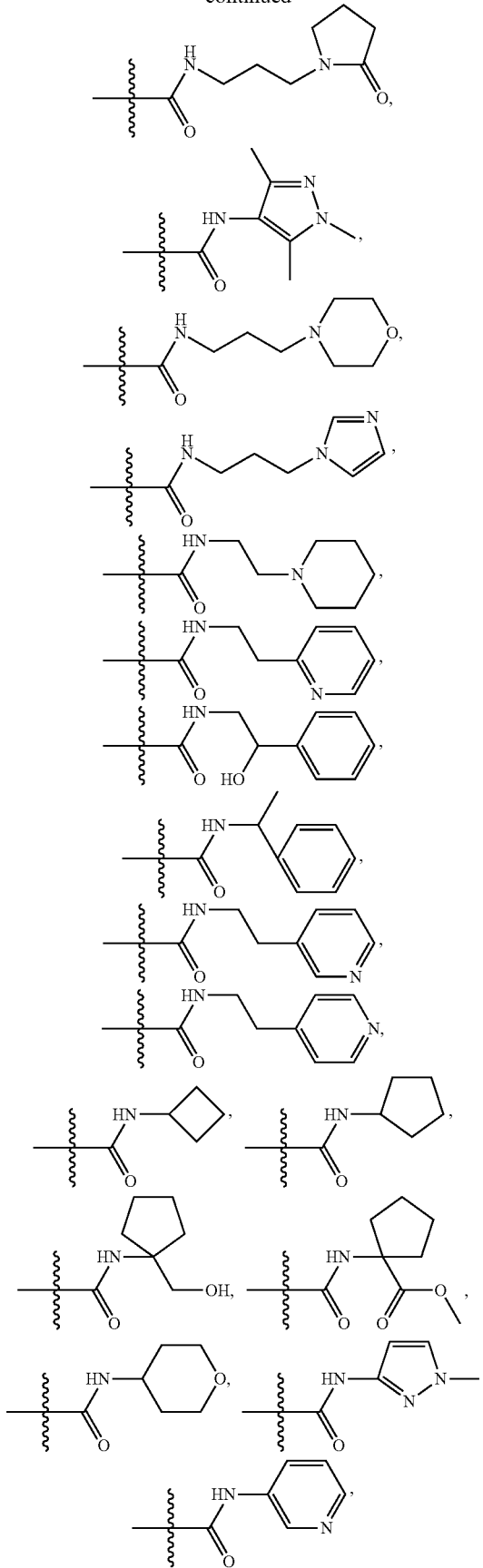

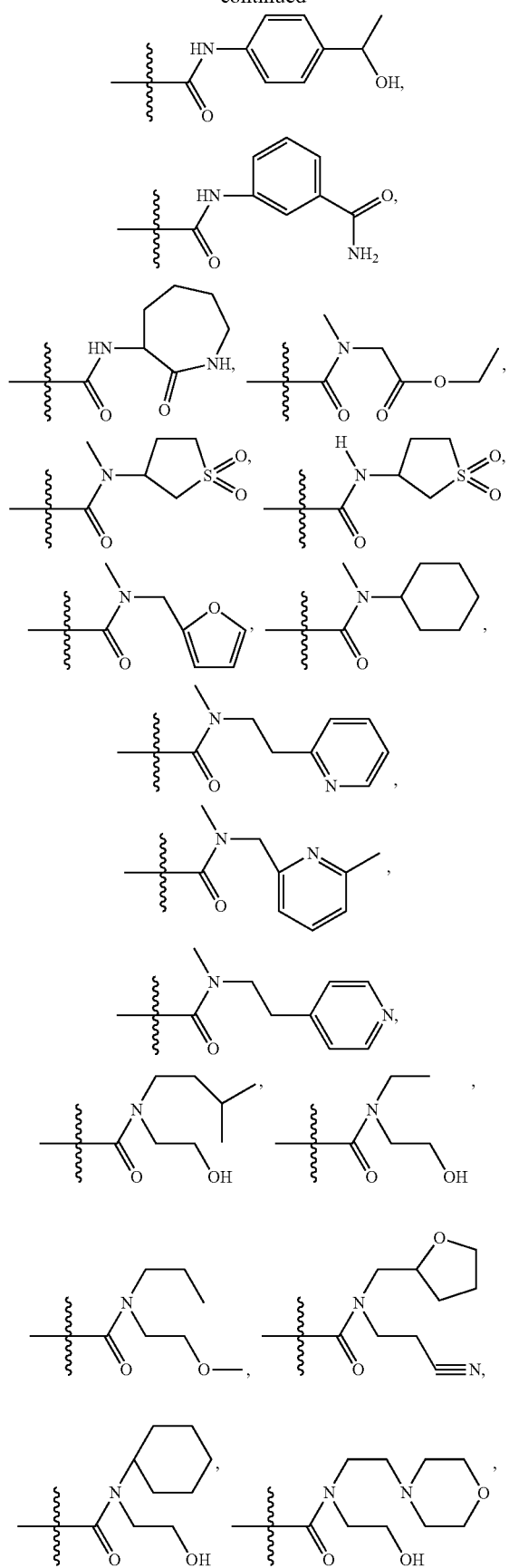
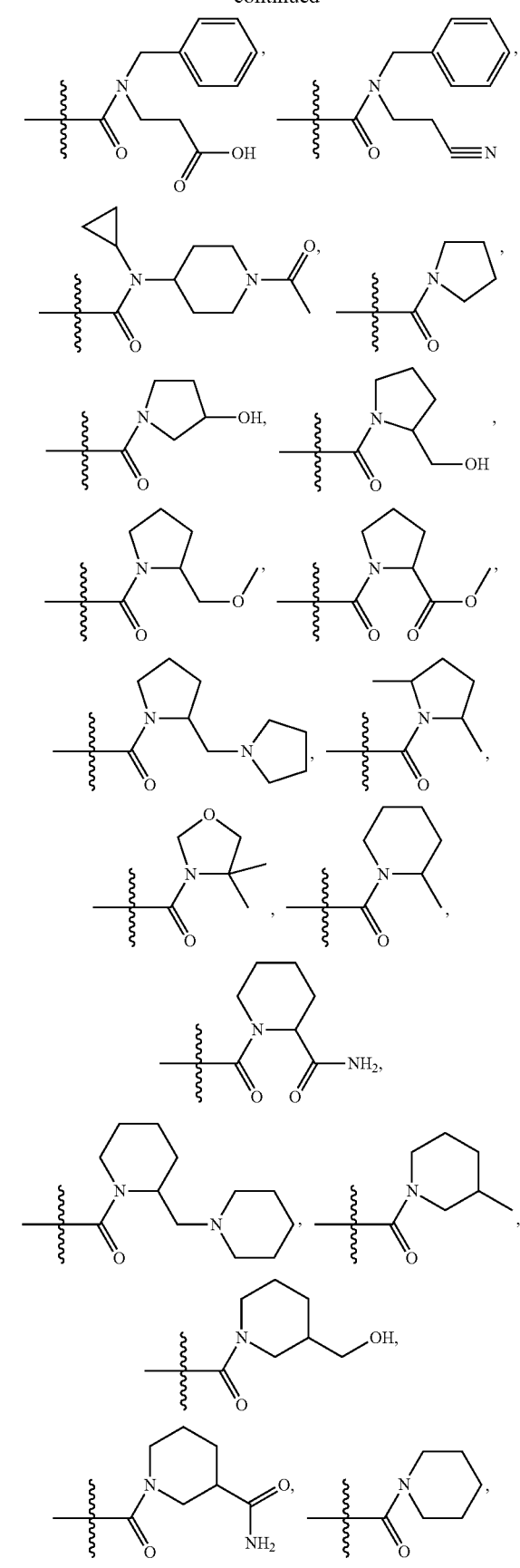

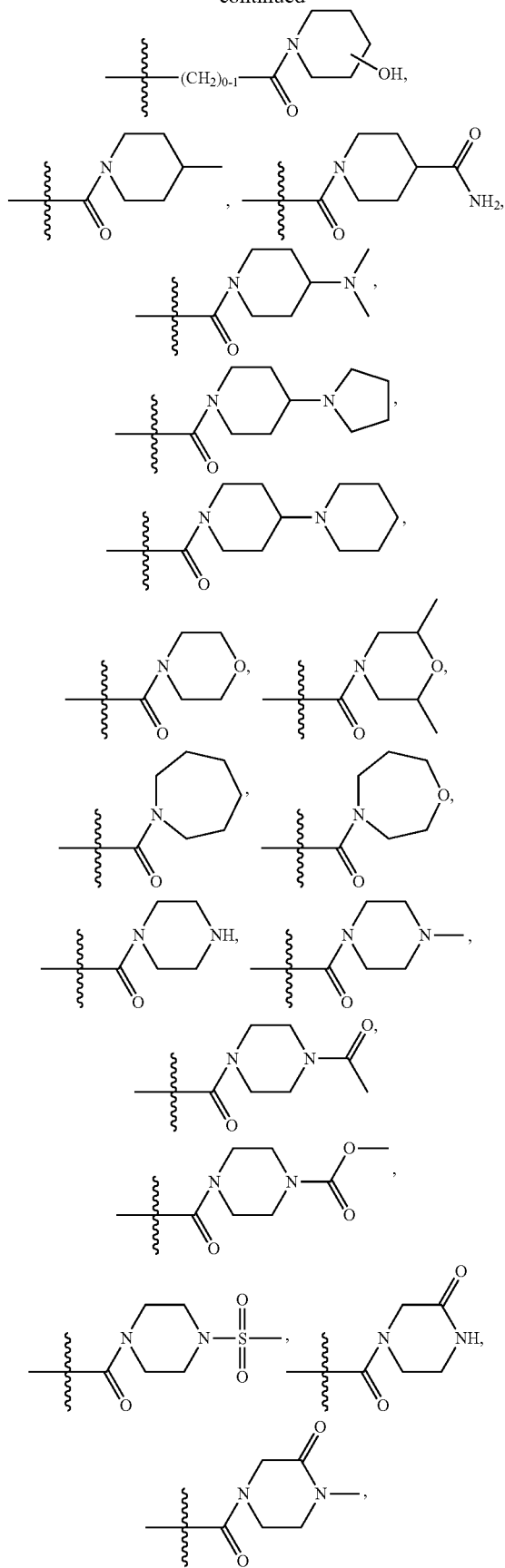
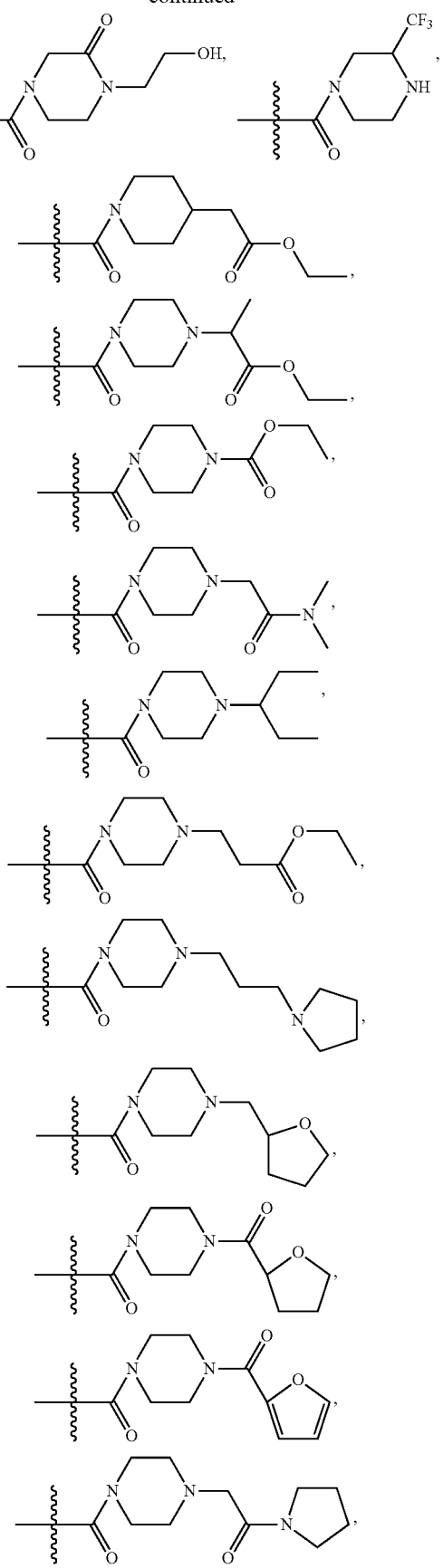

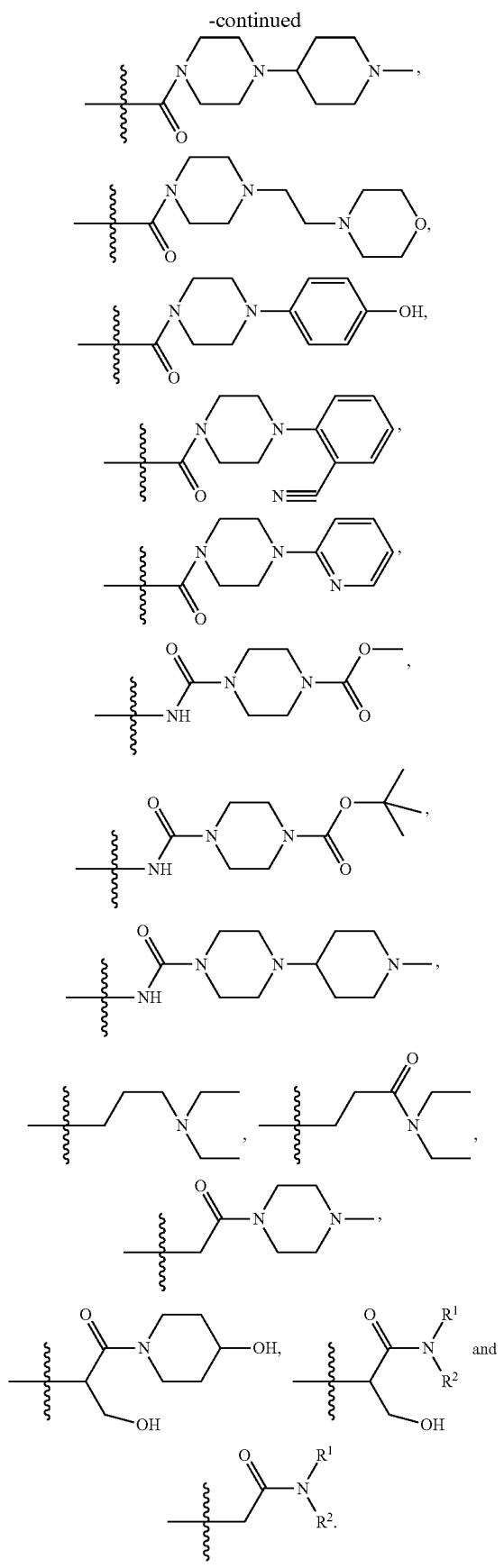
In other examples, $R^3$ in the above Formula (1) is selected from the group consisting of
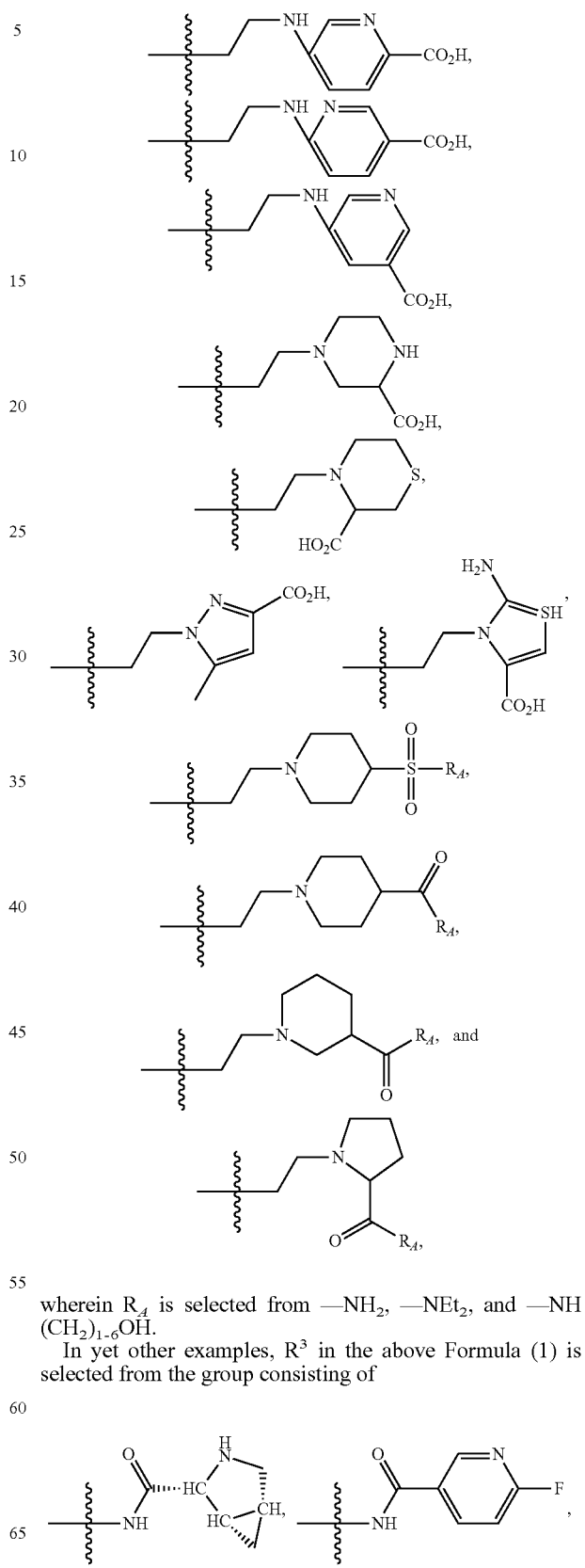
wherein $R_A$ is selected from $-NH_2$, $-NEt_2$, and $-NH(CH_2)_{1-6}OH$.
In yet other examples, $R^3$ in the above Formula (1) is selected from the group consisting of -continued
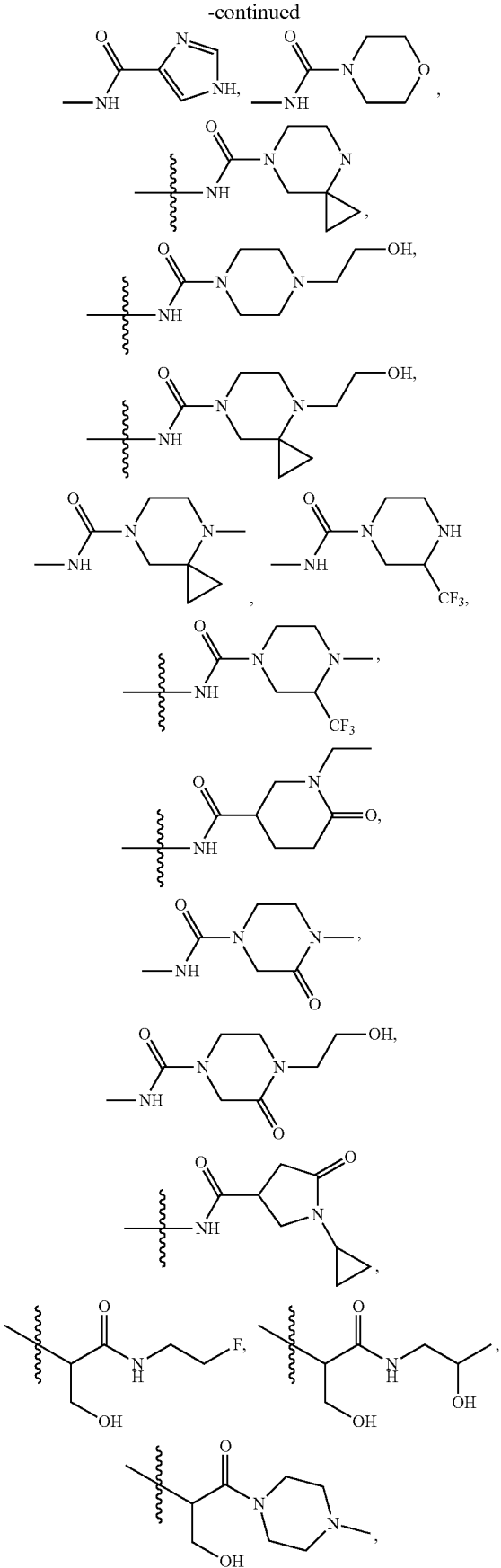
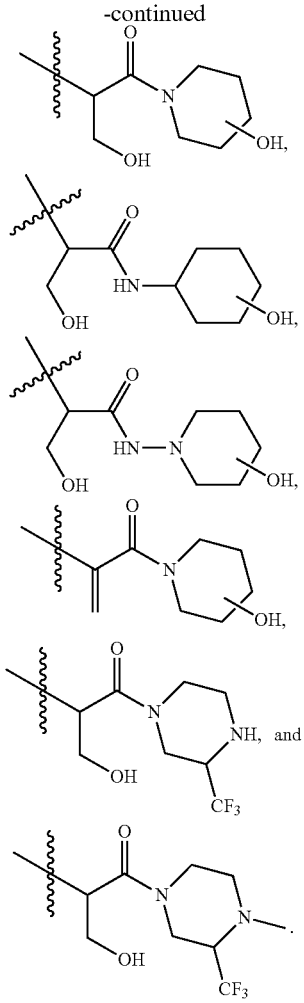
In one embodiment, the compounds have Formula (2A) or (2B):
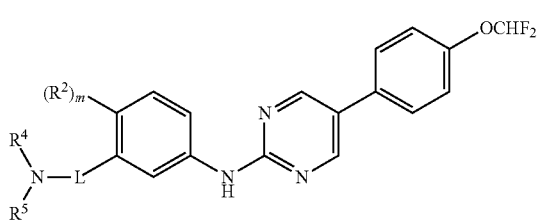
(2A)
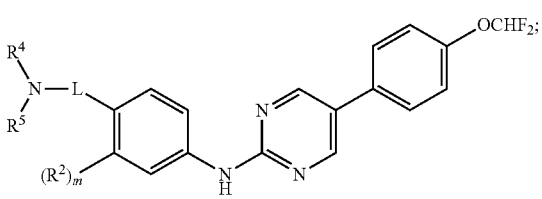
(2B)
wherein $R^4$ and $R^5$ together with N form a 5-6 membered heterocyclic ring optionally containing $NR^{16}$, O, S, =O or a double bond; wherein said heterocyclic ring is optionally substituted with 1-2 $R^{11}$ groups;

R$^{16}$ is H, R$^8$, —(CR$_2$)$_{1-4}$CO$_2$R$^7$, (CR$_2$)$_k$—C(O)—(CR$_2$)$_k$—R$^8$, (CR$_2$)$_k$C(O)NR$^7$R$^7$, (CR$_2$)$_k$C(O)NR(CR$_2$)$_{0-6}$C(O)O$_{0-1}$R$^7$, (CR$_2$)$_{1-4}$NRC(O)O$_{0-1}$R$^7$, (CR$_2$)$_k$S(O)$_{1-2}$NR$^7$R$^7$, (CR$_2$)$_k$S(O)$_{1-2}$R$^8$ or (CR$_2$)$_k$NRS(O)$_{1-2}$R$^8$; and R$^4$, R$^5$, R$^7$, R$^8$, R$^{11}$, R and k are as defined in Formula (1).

In the above Formula (2A) or (2B), R$^4$ and R$^5$ together with N in NR$^4$R$^5$ may form an optionally substituted piperidinyl, piperazinyl or morpholinyl. In some examples, L is —X—C(O), —(CR$_2$)$_{1-4}$ or —O(CR$_2$)$_{1-4}$; wherein X is (CR$_2$)$_{0-1}$ or [C(R)(CR$_2$OR)]. In other examples, L is (CR$_2$)$_{1-2}$.

In the above Formula (1), (2A) or (2B), R$^2$ if present, is halo, C$_{1-6}$ alkyl, C$_{1-6}$ alkoxy, hydroxy or CO$_2$R$^7$ and R$^7$ is H or C$_{1-6}$ alkyl.

In one embodiment, the present invention provides a compound selected from the group consisting of:

N-(4-(2-(diethylamino)ethoxy)phenyl)-5-(4-(trifluoromethoxy)phenyl)pyrimidin-2-amine;
N-(4-(2-(diethylamino)ethoxy)phenyl)-5-(4-(difluoromethoxy)phenyl)pyrimidin-2-amine;
1-(2-(4-(5-(4-(difluoromethoxy)phenyl)pyrimidin-2-ylamino)phenoxy)ethyl)piperidine-4-carboxylic acid;
1-(4-(5-(4-(difluoromethoxy)phenyl)pyrimidin-2-ylamino)benzyl)piperidine-4-carboxylic acid;
1-(4-(5-(4-(trifluoromethoxy)phenyl)pyrimidin-2-ylamino)benzyl)piperidine-4-carboxylic acid;
1-(4-(5-(4-(difluoromethoxy)phenyl)pyrimidin-2-ylamino)phenethyl)piperidine-4-carboxylic acid;
N-(5-(5-(4-(difluoromethoxy)phenyl)pyrimidin-2-ylamino)-2-methylphenyl)-1-methylpiperidine-2-carboxamide;
N-(5-(5-(4-(difluoromethoxy)phenyl)pyrimidin-2-ylamino)-2-methylphenyl)-3-azabicyclo[3.1.0]hexane-2-carboxamide;
(1S,2R,5R)-N-(5-(5-(4-(difluoromethoxy)phenyl)pyrimidin-2-ylamino)-2-methylphenyl)-3-azabicyclo[3.1.0]hexane-2-carboxamide;
N-(5-(5-(4-(difluoromethoxy)phenyl)pyrimidin-2-ylamino)-2-methylphenyl)piperidine-2-carboxamide;
N-(5-(5-(4-(difluoromethoxy)phenyl)pyrimidin-2-ylamino)-2-methylphenyl)-5-oxopyrrolidine-2-carboxamide;
(R)-N-(5-(5-(4-(difluoromethoxy)phenyl)pyrimidin-2-ylamino)-2-methylphenyl)-5-oxopyrrolidine-2-carboxamide;
N-(5-(5-(4-(difluoromethoxy)phenyl)pyrimidin-2-ylamino)-2-methylphenyl)-6-oxopiperidine-3-carboxamide;
N-(5-(5-(4-(difluoromethoxy)phenyl)pyrimidin-2-ylamino)-2-methylphenyl)-6-fluoropyridine-3-carboxamide;
N-(5-(5-(4-(difluoromethoxy)phenyl)pyrimidin-2-ylamino)-2-methylphenyl)-1H-imidazole-5-carboxamide;
N-(2-methyl-5-(5-(4-(trifluoromethoxy)phenyl)pyrimidin-2-ylamino)phenyl)-5-oxopyrrolidine-2-carboxamide;
(S)-N-(2-methyl-5-(5-(4-(trifluoromethoxy)phenyl)pyrimidin-2-ylamino)phenyl)-5-oxopyrrolidine-2-carboxamide;
N-(5-(5-(4-(difluoromethoxy)phenyl)pyrimidin-2-ylamino)-2-methylphenyl)-1-cyclopropyl-5-oxopyrrolidine-3-carboxamide;
N-(5-(5-(4-(difluoromethoxy)phenyl)pyrimidin-2-ylamino)-2-methylphenyl)-1-ethyl-6-oxopiperidine-3-carboxamide;
2-(4-(5-(4-(difluoromethoxy)phenyl)pyrimidin-2-ylamino)phenyl)-N-(2-fluoroethyl)-3-hydroxypropanamide;
2-(4-(5-(4-(difluoromethoxy)phenyl)pyrimidin-2-ylamino)phenyl)-3-hydroxy-1-(4-hydroxypiperidin-1-yl)propan-1-one;
(R)-2-(4-(5-(4-(difluoromethoxy)phenyl)pyrimidin-2-ylamino)phenyl)-3-hydroxy-1-(4-hydroxypiperidin-1-yl)propan-1-one;
(S)-2-(4-(5-(4-(difluoromethoxy)phenyl)pyrimidin-2-ylamino)phenyl)-3-hydroxy-1-(4-hydroxypiperidin-1-yl)propan-1-one;
2-(4-(5-(4-(difluoromethoxy)phenyl)pyrimidin-2-ylamino)phenyl)-3-hydroxy-N-(2-hydroxypropyl)propanamide;
(R)-2-(4-(5-(4-(difluoromethoxy)phenyl)pyrimidin-2-ylamino)phenyl)-3-hydroxy-N-((R)-2-hydroxypropyl)propanamide;
(S)-2-(4-(5-(4-(difluoromethoxy)phenyl)pyrimidin-2-ylamino)phenyl)-3-hydroxy-N-((R)-2-hydroxypropyl)propanamide;
(R)-2-(4-(5-(4-(difluoromethoxy)phenyl)pyrimidin-2-ylamino)phenyl)-3-hydroxy-N-((S)-2-hydroxypropyl)propanamide;
(S)-2-(4-(5-(4-(difluoromethoxy)phenyl)pyrimidin-2-ylamino)phenyl)-3-hydroxy-N-((S)-2-hydroxypropyl)propanamide;
2-(4-(5-(4-(difluoromethoxy)phenyl)pyrimidin-2-ylamino)phenyl)-3-hydroxy-N-((S)-2-hydroxypropyl)propanamide;
2-(4-(5-(4-(difluoromethoxy)phenyl)pyrimidin-2-ylamino)phenyl)-3-hydroxy-N-(4-hydroxycyclohexyl)propanamide;
2-(4-(5-(4-(difluoromethoxy)phenyl)pyrimidin-2-ylamino)phenyl)-3-hydroxy-N-((1r,4r)-4-hydroxycyclohexyl)propanamide;
(R)-2-(4-(5-(4-(difluoromethoxy)phenyl)pyrimidin-2-ylamino)phenyl)-3-hydroxy-N-((1r,4R)-4-hydroxycyclohexyl)propanamide;
(S)-2-(4-(5-(4-(difluoromethoxy)phenyl)pyrimidin-2-ylamino)phenyl)-3-hydroxy-N-((1r,4R)-4-hydroxycyclohexyl)propanamide;
(R)-2-(4-(5-(4-(difluoromethoxy)phenyl)pyrimidin-2-ylamino)phenyl)-3-hydroxy-N-((1s,4S)-4-hydroxycyclohexyl)propanamide;
(S)-2-(4-(5-(4-(difluoromethoxy)phenyl)pyrimidin-2-ylamino)phenyl)-3-hydroxy-N-((1s,4S)-4-hydroxycyclohexyl)propanamide;
2-(4-(5-(4-(difluoromethoxy)phenyl)pyrimidin-2-ylamino)phenyl)-3-hydroxy-N-((1 s,4s)-4-hydroxycyclohexyl)propanamide;
2-(4-(5-(4-(difluoromethoxy)phenyl)pyrimidin-2-ylamino)phenyl)-3-hydroxy-1-(3-hydroxypiperidin-1-yl)propan-1-one;
2-(4-(5-(4-(difluoromethoxy)phenyl)pyrimidin-2-ylamino)phenyl)-3-hydroxy-1-((S)-3-hydroxypiperidin-1-yl)propan-1-one;
(R)-2-(4-(5-(4-(difluoromethoxy)phenyl)pyrimidin-2-ylamino)phenyl)-3-hydroxy-1-((S)-3-hydroxypiperidin-1-yl)propan-1-one;
(S)-2-(4-(5-(4-(difluoromethoxy)phenyl)pyrimidin-2-ylamino)phenyl)-3-hydroxy-1-((S)-3-hydroxypiperidin-1-yl)propan-1-one;
2-(4-(5-(4-(difluoromethoxy)phenyl)pyrimidin-2-ylamino)phenyl)-3-hydroxy-1-((R)-3-hydroxypiperidin-1-yl)propan-1-one;
(S)-2-(4-(5-(4-(difluoromethoxy)phenyl)pyrimidin-2-ylamino)phenyl)-3-hydroxy-1-((R)-3-hydroxypiperidin-1-yl)propan-1-one;
(R)-2-(4-(5-(4-(difluoromethoxy)phenyl)pyrimidin-2-ylamino)phenyl)-3-hydroxy-1-((R)-3-hydroxypiperidin-1-yl)propan-1-one;
2-(4-(5-(4-(difluoromethoxy)phenyl)pyrimidin-2-ylamino)phenyl)-3-hydroxy-N-(2-hydroxycyclopentyl)propanamide;
(R)-2-(4-(5-(4-(difluoromethoxy)phenyl)pyrimidin-2-ylamino)phenyl)-3-hydroxy-N-((1R,2R)-2-hydroxycyclopentyl)propanamide;
2-(4-(5-(4-(difluoromethoxy)phenyl)pyrimidin-2-ylamino)phenyl)-3-hydroxy-N-((1S,2R)-2-hydroxycyclopentyl)propanamide;

2-(4-(5-(4-(difluoromethoxy)phenyl)pyrimidin-2-ylamino)phenyl)-3-hydroxy-N-((1S,2S)-2-hydroxycyclopentyl)propanamide;

(S)-2-(4-(5-(4-(difluoromethoxy)phenyl)pyrimidin-2-ylamino)phenyl)-3-hydroxy-N-((1R,2R)-2-hydroxycyclopentyl)propanamide;

(S)-2-(4-(5-(4-(difluoromethoxy)phenyl)pyrimidin-2-ylamino)phenyl)-3-hydroxy-N-((1S,2S)-2-hydroxycyclopentyl)propanamide;

(S)-2-(4-(5-(4-(difluoromethoxy)phenyl)pyrimidin-2-ylamino)phenyl)-3-hydroxy-N-((1S,2R)-2-hydroxycyclopentyl)propanamide;

(R)-2-(4-(5-(4-(difluoromethoxy)phenyl)pyrimidin-2-ylamino)phenyl)-3-hydroxy-N-((1S,2S)-2-hydroxycyclopentyl)propanamide;

(R)-2-(4-(5-(4-(difluoromethoxy)phenyl)pyrimidin-2-ylamino)phenyl)-3-hydroxy-N-((1S,2R)-2-hydroxycyclopentyl)propanamide;

2-(4-(5-(4-(Difluoromethoxy)phenyl)pyrimidin-2-ylamino)phenyl)-1-(4-hydroxypiperidin-1-yl)prop-2-en-1-one;

2-(4-(5-(4-(difluoromethoxy)phenyl)pyrimidin-2-ylamino)phenyl)-1-(4-hydroxypiperidin-1-yl)ethanone;

2-(4-(5-(4-(difluoromethoxy)phenyl)pyrimidin-2-ylamino)phenyl)-3-hydroxy-1-(4-methylpiperazin-1-yl)propan-1-one;

(R)-2-(4-(5-(4-(difluoromethoxy)phenyl)pyrimidin-2-ylamino)phenyl)-3-hydroxy-1-(4-methylpiperazin-1-yl)propan-1-one;

(S)-2-(4-(5-(4-(difluoromethoxy)phenyl)pyrimidin-2-ylamino)phenyl)-3-hydroxy-1-(4-methylpiperazin-1-yl)propan-1-one;

2-(4-(5-(4-(difluoromethoxy)phenyl)pyrimidin-2-ylamino)phenyl)-3-hydroxy-1-(3-(trifluoromethyl)piperazin-1-yl)propan-1-one;

2-(4-(5-(4-(Difluoromethoxy)phenyl)pyrimidin-2-ylamino)phenyl)-1-(3-(trifluoromethyl)-4-methylpiperazin-1-yl)-3-hydroxypropan-1-one;

N1-(5-(5-(4-(difluoromethoxy)phenyl)pyrimidin-2-ylamino)-2-methylphenyl)piperidine-1,4-dicarboxamide;

N-(5-(5-(4-(difluoromethoxy)phenyl)pyrimidin-2-ylamino)-2-methylphenyl)-4-methylpiperazine-1-carboxamide;

N-(5-(5-(4-(difluoromethoxy)phenyl)pyrimidin-2-ylamino)-2-methylphenyl)-4-methanesulfonyl-piperazine-1-carboxamide;

N-(5-(5-(4-(difluoromethoxy)phenyl)pyrimidin-2-ylamino)-2-methylphenyl)-4-acetylpiperazine-1-carboxamide;

1-(5-(5-(4-(difluoromethoxy)phenyl)pyrimidin-2-ylamino)-2-methylphenyl)-3-(1,3-dimethyl-1H-pyrazol-5-yl)urea;

N-(5-(5-(4-(difluoromethoxy)phenyl)pyrimidin-2-ylamino)-2-methylphenyl)morpholine-4-carboxamide;

N-(5-(5-(4-(difluoromethoxy)phenyl)pyrimidin-2-ylamino)-2-methylphenyl)-4-(2-hydroxyethyl)piperazine-1-carboxamide;

N-(5-(5-(4-(difluoromethoxy)phenyl)pyrimidin-2-ylamino)-2-methylphenyl)-4,7-diazaspiro[2.5]octane-7-carboxamide;

N-(5-(5-(4-(difluoromethoxy)phenyl)pyrimidin-2-ylamino)-2-methylphenyl)-4-methyl-4,7-diazaspiro[2.5]octane-7-carboxamide;

N-(5-(5-(4-(difluoromethoxy)phenyl)pyrimidin-2-ylamino)-2-methylphenyl)-4-(2-hydroxyethyl)-4,7-diazaspiro[2.5]octane-7-carboxamide;

N-(5-(5-(4-(difluoromethoxy)phenyl)pyrimidin-2-ylamino)-2-methylphenyl)-3-(trifluoromethyl)piperazine-1-carboxamide;

N-(5-(5-(4-(difluoromethoxy)phenyl)pyrimidin-2-ylamino)-2-methylphenyl)-4-methyl-3-(trifluoromethyl)piperazine-1-carboxamide;

N-(5-(5-(4-(difluoromethoxy)phenyl)pyrimidin-2-ylamino)-2-methylphenyl)-4-methyl-3-oxopiperazine-1-carboxamide;

N-(5-(5-(4-(difluoromethoxy)phenyl)pyrimidin-2-ylamino)-2-methylphenyl)-4-(2-hydroxyethyl)-3-oxopiperazine-1-carboxamide;

1-(2-(3-(5-(4-(difluoromethoxy)phenyl)pyrimidin-2-ylamino)phenoxy)ethyl)piperidine-4-carboxylic acid;

1-(3-(5-(4-(difluoromethoxy)phenyl)pyrimidin-2-ylamino)phenethyl)piperidine-4-carboxylic acid;

1-(3-(5-(4-(difluoromethoxy)phenyl)pyrimidin-2-ylamino)benzyl)piperidine-4-carboxylic acid;

1-(2-(5-(5-(4-(difluoromethoxy)phenyl)pyrimidin-2-ylamino)-2-fluorophenoxy)ethyl)piperidine-4-carboxylic acid;

1-(5-(5-(4-(difluoromethoxy)phenyl)pyrimidin-2-ylamino)-2-methylphenethyl)piperidine-4-carboxylic acid;

4-(4-(5-(4-(Difluoromethoxy)phenyl)pyrimidin-2-ylamino)benzoyl)-1-methylpiperazin-2-one;

4-(4-(5-(4-(difluoromethoxy)phenyl)pyrimidin-2-ylamino)benzoyl)-1-(2-hydroxyethyl)piperazin-2-one;

4-(4-(5-(4-(difluoromethoxy)phenyl)pyrimidin-2-ylamino)benzoyl)piperazin-2-one;

(4-(5-(4-(difluoromethoxy)phenyl)pyrimidin-2-ylamino)phenyl)(3-(trifluoromethyl)piperazin-1-yl)methanone;

Methyl 1-(3-(5-(4-(difluoromethoxy)phenyl)pyrimidin-2-ylamino)phenethyl)piperidine-4-carboxylate;

1-(5-(5-(4-(difluoromethoxy)phenyl)pyrimidin-2-ylamino)-2-hydroxyphenethyl)piperidine-4-carboxylic acid;

1-(1-(4-(5-(4-(difluoromethoxy)phenyl)pyrimidin-2-ylamino)phenyl)ethyl)piperidine-4-carboxylic acid;

1-(4-(5-(4-(difluoromethoxy)phenyl)pyrimidin-2-ylamino)-2-methylbenzyl)piperidine-4-carboxylic acid;

1-(4-(5-(4-(difluoromethoxy)phenyl)pyrimidin-2-ylamino)-2-fluorobenzyl)piperidine-4-carboxylic acid;

1-(4-(5-(4-(difluoromethoxy)phenyl)pyrimidin-2-ylamino)-2-hydroxybenzyl)piperidine-4-carboxylic acid;

4-(3-(5-(4-(difluoromethoxy)phenyl)pyrimidin-2-ylamino)benzoyl)-1-(piperidin-4-yl)piperazin-2-one;

Isopropyl 4-(4-(3-(5-(4-(difluoromethoxy)phenyl)pyrimidin-2-ylamino)benzoyl)-2-oxopiperazin-1-yl)piperidine-1-carboxylate;

N-(1-(4-(5-(4-(difluoromethoxy)phenyl)pyrimidin-2-ylamino)phenyl)-2-hydroxyethyl)tetrahydro-2H-pyran-4-carboxamide;

N-(1-(4-(5-(4-(difluoromethoxy)phenyl)pyrimidin-2-ylamino)phenyl)-2-hydroxyethyl)-1-ethyl-6-oxopiperidine-3-carboxamide;

1-cyclopropyl-N-(1-(4-(5-(4-(difluoromethoxy)phenyl)pyrimidin-2-ylamino)phenyl)-2-hydroxyethyl)-5-oxopyrrolidine-3-carboxamide;

N-(1-(4-(5-(4-(difluoromethoxy)phenyl)pyrimidin-2-ylamino)phenyl)-2-hydroxyethyl)-3,5-dimethylisoxazole-4-carboxamide;

N-(1-(4-(5-(4-(difluoromethoxy)phenyl)pyrimidin-2-ylamino)phenyl)-2-hydroxyethyl)isoxazole-5-carboxamide;

N-(1-(4-(5-(4-(difluoromethoxy)phenyl)pyrimidin-2-ylamino)phenyl)-2-hydroxyethyl)-2-(3-methylisoxazol-5-yl)acetamide;

N-(1-(4-(5-(4-(difluoromethoxy)phenyl)pyrimidin-2-ylamino)phenyl)-2-hydroxyethyl)-2-(tetrahydro-2H-pyran-4-yl)acetamide; and N3-(1-(4-(5-(4-(difluoromethoxy)phenyl)pyrimidin-2-ylamino)phenyl)-2-hydroxyethyl)piperidine-1,3-dicarboxamide.

In another aspect, the present invention provides pharmaceutical compositions comprising a therapeutically effective amount of a compound having Formula (1), (2A) or (2B), and a pharmaceutically acceptable excipient.

In yet another aspect, the present invention provides methods for modulating kinase activity, comprising administering to a system or a subject in need thereof, a therapeutically effective amount of compound having Formula (1), (2A) or (2B), or pharmaceutically acceptable salts or pharmaceutical compositions thereof, thereby modulating said kinase activity.

In one embodiment, the invention provides methods for modulating c-kit, PDGFRα, PDGFRβ, CSF1R, Abl, BCR-Abl, CSK, JNK1, JNK2, p38, p70S6K, TGFβ, SRC, EGFR, trkB, FGFR3, Fes, Lck, Syk, RAF, MKK4, MKK6, SAPK2β, BRK, Fms, KDR, c-raf or b-raf kinases. In particular embodiments, the invention provides methods for modulating c-kit, PDGFRα or PDGFRβ; and more particularly, the invention provides methods wherein a compound having Formula (1), (2A) or (2B), or pharmaceutically acceptable salts or pharmaceutical compositions thereof, may directly contact c-kit, PDGFRα or PDGFRβ in vitro or in vivo.

The present invention also provides methods for treating a disease or condition wherein modulation of kinase activity can prevent, inhibit or ameliorate the pathology and/or symptomology of the disease or condition, comprising administering to a subject a therapeutically effective amount of a compound having Formula (1), (2A) or (2B), or pharmaceutically acceptable salts or pharmaceutical compositions thereof, and optionally in combination with a second therapeutic agent. Examples of therapeutic agents which may be used in combination with a compound of the invention include but are not limited to an anti-fibrotic agent, pirfenidone, tacrolimus, an anti-inflammatory agent, a corticosteroid, a cromolyn, a leukotriene antagonist, an IgE blocker, a bronchodilator, a $\beta_2$-agonist, xanthines, an anticholinergic, or a chemotherapeutic agent. When administered with a second therapeutic agent, the compound of Formula (1), (2A) or (2B), or pharmaceutically acceptable salts or pharmaceutical compositions thereof may be administered prior to, simultaneously with, or after the second therapeutic agent.

In one embodiment, the invention provides methods for treating a disease or condition modulated by c-kit, PDGFRα, PDGFRβ, CSF1R, Abl, BCR-Abl, CSK, JNK1, JNK2, p38, p70S6K, TGFβ, SRC, EGFR, trkB, FGFR3, Fes, Lck, Syk, RAF, MKK4, MKK6, SAPK2β, BRK, Fms, KDR, c-raf or b-raf kinases. In particular examples, the invention provides methods for treating a disease or condition modulated by PDGFRα, PDGFRβ or c-kit. In some examples, the invention provides methods for treating a disease or condition modulated by c-kit.

Examples of kinase mediated disease or conditions which may be mediated using the compounds and compositions of the invention include but are not limited to a mast-cell associated disease, an allergy disorder, irritable bowel syndrome (IBS), a fibrotic disease, a neoplastic disorder, an inflammatory disorder, an autoimmune disorder, a graft-versus-host disease, a metabolic syndrome, a CNS related disorder, a neurodegenerative disorder, a pain condition, a substance abuse disorder, a cancer, a cardiovascular disease, and a prion disease.

Examples of a mast cell associated disease which may be treated using compounds and compositions of the invention include but are not limited to allergic disorders (including asthma and atopic dermatitis), urticaria, acne and *Propionibacterium acnes*, Fibrodysplasia ossificans progressiva (FOP), inflammation and tissue destruction induced by exposure to chemical or biological weapons (such as anthrax and sulfur-mustard), cystic fibrosis; renal disease, inflammatory muscle disorders, HIV, type II diabetes, cerebral ischemia, mastocytosis, drug dependence and withdrawal symptoms, CNS disorders, preventing and minimizing hair loss, bacterial infections, interstitial cystitis, inflammatory bowel diseases (e.g., Crohn's disease, ulcerative colitis, indeterminate colitis, and infectious colitis), tumor angiogenesis, autoimmune diseases, inflammatory diseases, multiple sclerosis (MS), and bone loss.

Examples of allergy disorders which may be treated using the compounds and compositions of the invention include but are not limited to asthma, atopic dermatitis, allergic rhinitis, allergic sinusitis, anaphylactic syndrome, urticaria, angioedema, allergic contact dermatitis, erythema nodosum, erythema multiforme, cutaneous necrotizing venulitis, insect bite skin inflammation, and blood sucking parasite infestation.

Irritable bowel syndrome (IBS) is a functional gastrointestinal disorder characterized by abdominal pain and altered bowel habit. Pain is characteristically relieved by defecation and may be associated with increase or decrease in stool frequency, alterations in stool consistency, straining or urgency, a sensation of incomplete evacuation, passage of mucus or abdominal distention.

A fibrotic disease as used herein encompasses all conditions linked to or associated with the formation and deposition of extracellular matrix components, particularly in the internal organs, including the kidneys, heart, lungs, liver, skin and joints. Examples of fibrotic diseases which may be treated using the compounds and compositions of the invention include but are not limited to scleroderma, pulmonary fibrosis, idiopathic pulmonary fibrosis (IPF), primary pulmonary hypertension (e.g., pulmonary arterial hypertension (PPAH)), liver fibrosis, renal fibrosis, cardiac fibrosis, cirrhosis in liver, bone marrow fibrosis, hepatitis C(HCV) and non-alcoholic steatohepatitis (NASH).

Examples of neoplastic disorders which may be treated using the compounds and compositions of the invention include but are not limited to mastocytosis, gastrointestinal stromal tumor, small cell lung cancer, non-small cell lung cancer, acute myelocytic leukemia, acute lymphocytic leukemia, myelodyplastic syndrome, chronic myelogenous leukemia, colorectal carcinoma, gastric carcinoma, testicular cancer, glioblastoma and astrocytoma.

Examples of inflammatory disorders which may be treated using the compounds and compositions of the invention include but are not limited to rheumatoid arthritis, conjunctivitis, rheumatoid spondylitis, osteoarthritis and gouty arthritis.

Examples of autoimmune disorders which may be treated using the compounds and compositions of the invention include but are not limited to multiple sclerosis, psoriasis, intestine inflammatory disease, inflammatory bowel disease (IBD), ulcerative colitis, Crohn's disease, rheumatoid arthritis, polyarthritis, local or systemic scleroderma, systemic lupus erythematosus, discoid lupus erythematosis, cutaneous lupus, dermatomyositis, polymyositis, Sjogren's syndrome, nodular panarteritis, autoimmune enteropathy and proliferative glomerulonephritis.

Examples of graft-versus-host diseases which may be treated using the compounds and compositions of the invention include but are not limited to organ transplantation graft rejection, such as kidney transplantation, pancreas transplantation, liver transplantation, heart transplantation, lung transplantation, and bone marrow transplantation.

Examples of metabolic syndrome which may be treated using the compounds and compositions of the invention include but are not limited to type I diabetes, type II diabetes, and obesity.

Examples of CNS related disorders which may be treated using the compounds and compositions of the invention include but are not limited to depression, dysthymic disorder, cyclothymic disorder, anorexia, bulimia, premenstrual syndrome, post-menopause syndrome, mental slowing, loss of concentration, pessimistic worry, agitation, self-deprecation and decreased libido, an anxiety disorder, a psychiatric disorder and schizophrenia.

Examples of depression conditions which may be treated using the compounds and compositions of the invention include but are not limited to bipolar depression, severe or melancholic depression, atypical depression, refractory depression, and seasonal depression. Examples of anxiety disorders which may be treated using the compounds and compositions of the invention include but are not limited to anxiety associated with hyperventilation and cardiac arrhythmias, phobic disorders, obsessive-compulsive disorder, post-traumatic stress disorder, acute stress disorder, and generalized anxiety disorder. Examples of psychiatric disorders which may be treated using the compounds and compositions of the invention include but are not limited to panic attacks, including psychosis, delusional disorders, conversion disorders, phobias, mania, delirium, dissociative episodes including dissociative amnesia, dissociative fugue and dissociative suicidal behavior, self-neglect, violent or aggressive behavior, trauma, borderline personality, and acute psychosis such as schizophrenia, including paranoid schizophrenia, disorganized schizophrenia, catatonic schizophrenia, and undifferentiated schizophrenia.

Examples of neurodegenerative disorder which may be treated using the compounds and compositions of the invention include but are not limited to osteoarthritis, Alzheimer's disease, Parkinson's disease, Huntington's disease, the prion diseases, Motor Neuron Disease (MND), and Amyotrophic Lateral Sclerosis (ALS).

Examples of pain conditions which may be treated using the compounds and compositions of the invention include but are not limited to acute pain, postoperative pain, chronic pain, nociceptive pain, cancer pain, neuropathic pain and psychogenic pain syndrome.

Examples of substance use disorders which may be treated using the compounds and compositions of the invention include but are not limited to drug addiction, drug abuse, drug habituation, drug dependence, withdrawal syndrome and overdose.

Examples of cancers which may be treated using the compounds and compositions of the invention include but are not limited to glioma, melanoma, gastrointestinal stromal tumor (GIST), small cell lung cancer, colorectal cancer, and other solid tumors.

Examples of cardiovascular diseases which may be treated using the compounds and compositions of the invention include but are not limited to angina pectoris, myocardial infarction, congestive heart failure, cardiomyopathy, hypertension, arterial stenosis, and venous stenosis.

More particularly, the compounds of the invention may be used for the treatment and prevention of asthma, atopic dermatitis, urticaria, irritable bowel syndrome (IBS), or a fibrotic disease including but not limited to scleroderma, pulmonary fibrosis, idiopathic pulmonary fibrosis (IPF), primary pulmonary hypertension (PPH), primary pulmonary arterial hypertension (PPAH), idiopathic arterial hypertension (IPAH), liver fibrosis, renal fibrosis and cardiac fibrosis.

Furthermore, the present invention provides for the use of a compound having Formula (1), (2A) or (2B), or a pharmaceutically composition thereof, and optionally in combination with a second therapeutic agent, for the manufacture of a medicament for treating a disease or condition modulated by c-kit, PDGFRα, PDGFRβ, CSF1R, Abl, BCR-Abl, CSK, JNK1, JNK2, p38, p70S6K, TGFβ, SRC, EGFR, trkB, FGFR3, Fes, Lck, Syk, RAF, MKK4, MKK6, SAPK2β, BRK, Fms, KDR, c-raf or b-raf kinases; and more particularly, for the manufacture of a medicament for treating a disease or condition modulated by PDGFRα, PDGFRβ or c-kit.

In the above methods for using the compounds of the invention, a compound having Formula (1), (2A) or (2B) may be administered to a system comprising cells or tissues. In other embodiments, a compound having Formula (1), (2A) or (2B) may be administered to a human or animal subject.

Definitions

"Alkyl" refers to a moiety and as a structural element of other groups, for example halo-substituted-alkyl and alkoxy, and may be straight-chained or branched. An optionally substituted alkyl, alkenyl or alkynyl as used herein may be optionally halogenated (e.g., $CF_3$), or may have one or more carbons that is substituted or replaced with a heteroatom, such as NR, O or S (e.g., —OCH$_2$CH$_2$O—, alkylthiols, thioalkoxy, alkylamines, etc).

"Aryl" refers to a monocyclic or fused bicyclic aromatic ring containing carbon atoms. For example, aryl may be phenyl or naphthyl. "Arylene" means a divalent radical derived from an aryl group.

"Heteroaryl" as used herein is as defined for aryl above, where one or more of the ring members is a heteroatom. Examples of heteroaryls include but are not limited to pyridyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, tetrazolyl, pyrazolyl, thienyl, etc.

A "carbocyclic ring" as used herein refers to a saturated or partially unsaturated, monocyclic, fused bicyclic or bridged polycyclic ring containing carbon atoms, which may optionally be substituted, for example, with =O. Examples of carbocyclic rings include but are not limited to cyclopropyl, cyclobutyl, cyclopentyl, cyclohexyl, cyclopropylene, cyclohexanone, etc.

A "heterocyclic ring" as used herein is as defined for a carbocyclic ring above, wherein one or more ring carbons is a heteroatom. For example, a heterocyclic ring may contain N, O, S, —N=, —S—, —S(O), —S(O)$_2$—, or —NR— wherein R may be hydrogen, $C_{1-4}$alkyl or a protecting group. Examples of heterocyclic rings include but are not limited to morpholino, pyrrolidinyl, pyrrolidinyl-2-one, piperazinyl, piperidinyl, piperidinylone, 1,4-dioxa-8-aza-spiro[4.5]dec-8-yl, etc.

As used herein, an H atom in any substituent groups (e.g., CH$_2$) encompasses all suitable isotopic variations, e.g., H, $^2$H and $^3$H.

Unless otherwise indicated, when a substituent is deemed to be "optionally substituted," it is meant that the substituent is a group that may be substituted with one or more group(s) individually and independently selected from, for example, an optionally halogenated alkyl, alkenyl, alkynyl, alkoxy, alkylamine, alkylthio, alkynyl, amide, amino, including mono- and di-substituted amino groups, aryl, aryloxy, arylthio, carbonyl, carbocyclic, cyano, cycloalkyl, halogen, heteroalkyl, heteroalkenyl, heteroalkynyl, heteroaryl, heterocyclic, hydroxy, isocyanato, isothiocyanato, mercapto, nitro, O-carbamyl, N-carbamyl, O-thiocarbamyl, N-thiocarbamyl, C-amido, N-amido, S-sulfonamido, N-sulfonamido, C-carboxy, O-carboxy, perhaloalkyl, perfluoroalkyl, silyl, sulfonyl, thiocarbonyl, thiocyanato, trihalomethanesulfonyl, and the protected compounds thereof. The protecting groups that may form the protected compounds of the above substituents are known to those of skill in the art and may be found in references such as Greene and Wuts, Protective Groups in Organic Synthesis, 3$^{rd}$ Ed., John Wiley & Sons, New York, N.Y., 1999, and Kocienski, Protective Groups, Thieme Verlag, New York, N.Y., 1994, which are incorporated herein by reference in their entirety.

The terms "co-administration" or "combined administration" or the like as used herein are meant to encompass administration of the selected therapeutic agents to a single patient, and are intended to include treatment regimens in which the agents are not necessarily administered by the same route of administration or at the same time.

The term "pharmaceutical combination" as used herein refers to a product obtained from mixing or combining active ingredients, and includes both fixed and non-fixed combinations of the active ingredients. The term "fixed combination" means that the active ingredients, e.g. a compound of Formula (1) and a co-agent, are both administered to a patient simultaneously in the form of a single entity or dosage. The term "non-fixed combination" means that the active ingredients, e.g. a compound of Formula (1) and a co-agent, are both administered to a patient as separate entities either simultaneously, concurrently or sequentially with no specific time limits, wherein such administration provides therapeutically effective levels of the active ingredients in the body of the patient. The latter also applies to cocktail therapy, e.g. the administration of three or more active ingredients.

The term "therapeutically effective amount" means the amount of the subject compound that will elicit a biological or medical response in a cell, tissue, organ, system, animal or human that is being sought by the researcher, veterinarian, medical doctor or other clinician.

The term "administration" or "administering" of the subject compound means providing a compound of the invention and prodrugs thereof to a subject in need of treatment.

Unless otherwise stated for this invention, a kinase selected from c-kit, PDGFRα, PDGFRβ, CSF1R, Abl, BCR-Abl, CSK, JNK1, JNK2, p38, p70S6K, TGFβ, SRC, EGFR, trkB, FGFR3, Fes, Lck, Syk, RAF, MKK4, MKK6, SAPK2β, BRK, Fms, KDR, c-raf and b-raf refers to wild-type and mutant forms (i.e., having single or multiple amino acid changes from the wild-type sequence).

MODES OF CARRYING OUT THE INVENTION

The present invention provides compounds and pharmaceutical compositions thereof, which may be useful as protein kinase inhibitors.

In one aspect, the present invention provides compounds of Formula (1):

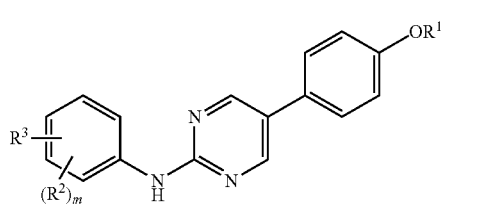

(1)

or a pharmaceutically acceptable salt thereof;

$R^1$ is a haloalkyl having 1-6 fluorine atoms;

$R^2$ is $C_{1-6}$ alkyl, $C_{2-6}$ alkenyl or $C_{2-6}$ alkynyl, each of which may be optionally substituted with halo, amino or hydroxyl groups; halo, cyano, nitro, $(CR_2)_kOR^7$, $(CR_2)_kO(CR_2)_{1-4}R^7$, $(CR_2)_kSR^7$, $(CR_2)_kNR^9R^{10}$, $(CR_2)_kC(O)O_{0-1}R^7$, $OC(O)R^7$, $(CR_2)_kC(S)R^7$, $(CR_2)_kC(O)NR^9R^{10}$, $(CR_2)_kC(O)NR(CR_2)_{0-6}C(O)O_{0-1}R^7$, $(CR_2)_kNRC(O)O_{0-1}R^7$, $(CR_2)_kS(O)_{1-2}NR^9R^{10}$, $(CR_2)_kS(O)_{1-2}R^8$, $(CR^2)_kNRS(O)_{1-2}R^8$ or $(CR_2)_kR^6$; or any two adjacent $R^2$ groups together may form an optionally substituted 5-8 membered carbocyclic, heterocyclic, aryl or heteroaryl ring;

$R^3$ is -L-$NR^4R^5$, —X—NR—C(O)$R^8$ or —X—NR—C(O)$NR^4R^5$ wherein L is —X—C(O), —X—OC(O), —(CR_2)_j, —SO_{0-2}(CR_2)_j, —O(CR_2)_{1-4}, or

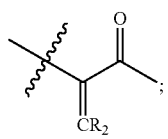

and X is $(CR_2)_j$ or $[C(R)(CR_2OR)]$;

$R^4$, $R^5$, $R^9$ and $R^{10}$ are independently H; $C_{1-6}$ alkyl, $C_{2-6}$ alkenyl or $C_{2-6}$ alkynyl, each of which may be optionally substituted with halo, amino, hydroxyl, alkoxy, cyano, carboxyl or $R^6$; $(CR_2)_kCN$, $(CR_2)_{1-6}NR^7R^7$, $(CR_2)_{1-6}OR^7$, $(CR_2)_kC(O)O_{0-1}R^7$, $(CR_2)_kC(O)NR^7R^7$ or $(CR_2)_k$—$R^6$;

$R^6$ is an optionally substituted $C_{3-7}$ cycloalkyl, $C_6$ aryl, or a 5-6 membered heteroaryl or 5-7 membered heterocyclic ring;

$R^7$ and $R^8$ are independently $(CR_2)_k$—$R^6$ or $C_{1-6}$ alkyl, $C_{2-6}$ alkenyl or $C_{2-6}$ alkynyl, each of which may be optionally substituted with halo, amino, amido, hydroxyl, alkoxy, cyano, carboxyl or $R^6$; or $R^7$ is H;

alternatively, $R^4$ and $R^5$ together with N in each $NR^4R^5$, $R^7$ and $R^7$ together with N in $NR^7R^7$ or $R^9$ and $R^{10}$ together with N in $NR^9R^{10}$ may form a 4-7 membered heterocyclic ring optionally substituted with 1-3 $R^{11}$ groups;

$R^{11}$ is $R^8$, $(CR_2)_k$—$OR^7$, $CO_2R^7$, $(CR_2)_k$—$C(O)$—$(CR_2)_k$—$R^8$, $(CR_2)_kC(O)NR^7R^7$, $(CR_2)_kC(O)NR(CR_2)_{0-6}C(O)O_{0-1}R^7$, $(CR_2)_kNRC(O)O_{0-1}R^7$, $(CR_2)_kS(O)_{1-2}NR^7R^7$, $(CR_2)_kS(O)_{1-2}R^8$ or $(CR_2)_kNRS(O)_{1-2}R^8$;

each R is H or $C_{1-6}$alkyl;

each k is 0-6; and j and m are independently 0-4;

provided $R^1$ is not trifluoromethoxy when $R^3$ is $C(O)NH_2$, $C(O)NR^{12}R^{13}$ or $SO_2NH(CH_2)_{2-3}NR^{14}R^{15}$; wherein $R^{12}$ and $R^{13}$ together form piperazinyl and $R^{14}$ and $R^{15}$ together form morpholinyl.

In one embodiment, the compounds have Formula (2A) or (2B):

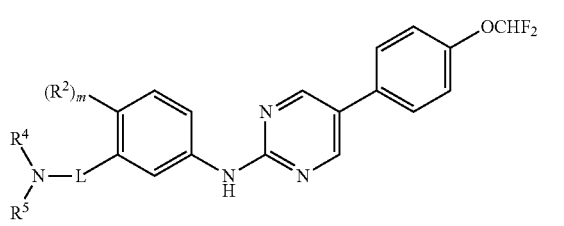

(2A)

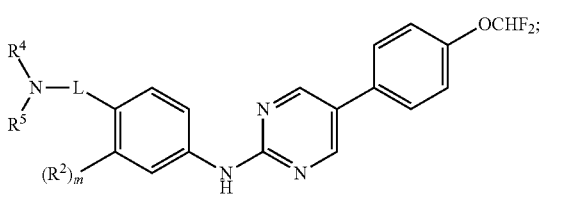

(2B)

wherein $R^4$ and $R^5$ together with N form a 5-6 membered heterocyclic ring optionally containing $NR^{16}$, O, S, =O or a double bond; wherein said heterocyclic ring is optionally substituted with 1-2 $R^{11}$ groups;

$R^{16}$ is H, $R^8$, —$(CR_2)_{1-4}CO_2R^7$, $(CR_2)_k$—$C(O)$—$(CR_2)_k$—$R^8$, $(CR_2)_kC(O)NR^7R^7$, $(CR_2)_kC(O)NR(CR_2)_{0-6}C(O)O_{0-1}R^7$, $(CR_2)_{1-4}NRC(O)O_{0-1}R^7$, $(CR_2)_kS(O)_{1-2}NR^7R^7$, $(CR_2)_kS(O)_{1-2}R^8$ or $(CR_2)_kNRS(O)_{1-2}R^8$; and $R^4$, $R^5$, $R^7$, $R^8$, $R^{11}$, R and k are as defined in Formula (1).

In each of the above formula, any asymmetric carbon atoms may be present in the (R)-, (S)- or (R,S)-configuration. The compounds may thus be present as mixtures of isomers or as pure isomers, for example, as pure enantiomers or diastereomers. The invention further encompasses possible tautomers of the inventive compounds.

The present invention also includes all suitable isotopic variations of the compounds of the invention, or pharmaceutically acceptable salts thereof. An isotopic variation of a compound of the invention or a pharmaceutically acceptable salt thereof is defined as one in which at least one atom is replaced by an atom having the same atomic number but an atomic mass different from the atomic mass usually found in nature. Examples of isotopes that may be incorporated into the compounds of the invention and pharmaceutically acceptable salts thereof include but are not limited to isotopes of hydrogen, carbon, nitrogen and oxygen such as $^2$H, $^3$H, $^{11}$C, $^{13}$C, $^{14}$C, $^{15}$N, $^{17}$O, $^{18}$O, $^{35}$S, $^{18}$F, $^{36}$Cl and $^{123}$I. Certain isotopic variations of the compounds of the invention and pharmaceutically acceptable salts thereof, for example, those in which a radioactive isotope such as $^3$H or $^{14}$C is incorporated, are useful in drug and/or substrate tissue distribution studies.

In particular examples, $^2$H, $^3$H and $^{14}$C isotopes may be used for their ease of preparation and detectability. In other examples, substitution with isotopes such as $^2$H may afford certain therapeutic advantages resulting from greater metabolic stability, such as increased in vivo half-life or reduced dosage requirements. Isotopic variations of the compounds of the invention or pharmaceutically acceptable salts thereof can generally be prepared by conventional procedures using appropriate isotopic variations of suitable reagents. Isotopic variations of the compounds have the potential to change a compound's metabolic fate and/or create small changes in physical properties such as hydrophobicity, and the like. Isotopic variation have the potential to enhance efficacy and safety, enhance bioavailability and half-life, alter protein binding, change biodistribution, increase the proportion of active metabolites and/or decrease the formation of reactive or toxic metabolites.

In each of the above formula, each optionally substituted moiety may be substituted with $C_{1-6}$ alkyl, $C_{2-6}$ alkenyl or $C_{3-6}$ alkynyl, each of which may be optionally halogenated or optionally having a carbon that may be replaced or substituted with N, S, O, or a combination thereof (for example, hydroxyl$C_1$-$C_8$alkyl, $C_1$-$C_8$alkoxy$C_1$-$C_8$alkyl); halo, amino, amidino, $C_{1-6}$ alkoxy; hydroxyl, methylenedioxy, carboxy; $C_{1-8}$ alkylcarbonyl, $C_{1-8}$ alkoxycarbonyl, carbamoyl, $C_{1-8}$ alkylcarbamoyl, sulfamoyl, cyano, oxo, nitro, or an optionally substituted carbocyclic ring, heterocyclic ring, aryl or heteroaryl as previously described.

Compounds having Formula (1), (2A) or (2B) in free form or in pharmaceutically acceptable salt form, may exhibit valuable pharmacological properties, for example, as indicated by the in vitro tests described in this application. The $IC_{50}$ value in those experiments is given as that concentration of the test compound in question that results in a cell count that is 50% lower than that obtained using the control without inhibitor. In general, compounds of the invention have $IC_{50}$ values from 1 nM to 10 µM. In some examples, compounds of the invention have $IC_{50}$ values from 0.01 µM to 5 µM. In other examples, compounds of the invention have $IC_{50}$ values from 0.01 µM to 1 µM, or more particularly from 1 nM to 1 µM. In yet other examples, compounds of the invention have $IC_{50}$ values of less than 1 nM or more than 10 µM. Formula (1), (2A) and (2B) may exhibit a percentage inhibition of greater than 50%, or in other embodiments, may exhibit a percentage inhibition greater than about 70%, against one or more of the following kinases at 10 µM: c-kit, PDGFRα, PDGFRβ, CSF1R, Abl, BCR-Abl, CSK, JNK1, JNK2, p38, p70S6K, TGFβ, SRC, EGFR, trkB, FGFR3, Fes, Lck, Syk, RAF, MKK4, MKK6, SAPK2β, BRK, Fms, KDR, c-raf or b-raf kinases.

The compounds of the invention may also be used for the treatment of a kinase-mediated condition or disease, such as diseases mediated by c-kit, PDGFRα, PDGFRβ, CSF1R, Abl, BCR-Abl, CSK, JNK1, JNK2, p38, p70S6K, TGFβ, SRC, EGFR, trkB, FGFR3, Fes, Lck, Syk, RAF, MKK4, MKK6, SAPK2β, BRK, Fms, KDR, c-raf or b-raf kinases. More particularly, the compounds of the invention may be used for the treatment and prevention of asthma, atopic dermatitis, urticaria, irritable bowel syndrome (IBS), or a fibrotic disease including but not limited to scleroderma, pulmonary fibrosis, idiopathic pulmonary fibrosis (IPF), primary pulmonary hypertension (PPH), primary pulmonary arterial hypertension (PPAH), idiopathic arterial hypertension (IPAH), liver fibrosis, renal fibrosis and cardiac fibrosis.

Pharmacology and Utility

Compounds of the invention are screened against the kinase panel (wild type and/or mutation thereof) and may modulate the activity of at least one panel kinase panel member. As such, compounds of the invention may be useful for treating diseases or disorders in which kinases contribute to the pathology and/or symptomology of the disease. Examples of kinases that may be inhibited by the compounds and compositions described herein and against which the methods described herein may be useful include, but are not limited to c-kit, PDGFRα, PDGFRβ, CSF1R, Abl, BCR-Abl, CSK, JNK1, JNK2, p38, p70S6K, TGFβ, SRC, EGFR, trkB, FGFR3, Fes, Lck, Syk, RAF, MKK4, MKK6, SAPK2β, BRK, Fms, KDR, c-raf or b-raf kinases.

c-Kit

Mast cells are tissue elements derived from a particular subset of hematopoietic stem cells that express CD34, c-kit and CD13 antigens. Mast cells are characterized by their heterogeneity, not only regarding tissue location and structure but also at the functional and histochemical levels. Immature mast cell progenitors circulate in the bloodstream and differentiate into various tissues. These differentiation and proliferation processes are under the influence of cytokines, one of importance being Stem Cell Factor (SCF), also termed the Kit ligand, Steel factor or Mast Cell Growth Factor. The Stem Cell Factor receptor is encoded by the protooncogene, c-kit, which is expressed in hematopoietic progenitor cells, mast cells, germ cells, interstitial cells of Cajal (ICC), and some human tumors, and is also expressed by non hematopoietic cells.

Tyrosine kinases are receptor type or non-receptor type proteins, which transfer the terminal phosphate of ATP to tyrosine residues of proteins thereby activating or inactivating signal transduction pathways. The Stem Cell Factor receptor, c-kit, is a Type III transmembrane receptor protein tyrosine kinase which initiates cell growth and proliferation signal transduction cascades in response to SCF binding. Ligation of c-kit receptor by SCF induces its dimerization followed by its transphorylation, leading to the recruitment and activation of various intracytoplasmic substrates. These activated substrates induce multiple intracellular signaling pathways responsible for cell proliferation and activation. These proteins are known to be involved in many cellular mechanisms, which in case of disruption, lead to disorders such as abnormal cell proliferation and migration, as well as inflammation. The compounds of the present invention may inhibit cellular processes involving SCF, such as inhibiting SCF receptor autophosphorylation and SCF-stimulated activation of MAPK kinase (mitogen-activated protein kinase).

The activity of the c-kit receptor protein tyrosine kinase is regulated in normal cells, and the normal functional activity of the c-kit gene product is important for the maintenance of normal hematopoeisis, melanogenesis, gametogenesis, and growth and differentiation of mast cells. In addition to its importance in normal cellular physiologic activities, c-kit plays a role in the biological aspects of certain human cancers, and unregulated c-kit kinase activity is implicated in the pathogenesis of human cancers, and in certain tumors types. Proliferation of tumor cell growth mediated by c-kit can occur by a specific mutation of the c-kit polypeptide that results in ligand independent activation or by autocrine stimulation of the receptor. In the former case, mutations that cause constitutive activation of c-kit kinase activity in the absence of SCF binding are implicated in malignant human cancers, including germ cell tumors, mast cell tumors, gastrointestinal stromal tumors, small-cell lung cancer, melanoma, breast cancer, acute myelogenous leukemia, neuroblastoma and mastocytosis.

Mast cells present in tissues of patients are implicated in or contribute to the genesis of diseases such as autoimmune diseases (multiple sclerosis, rheumatoid arthritis, inflammatory bowel diseases (IBD)), allergic diseases, tumor angiogenesis, inflammatory diseases, and interstitial cystitis. Allergic diseases include but are not limited to allergic rhinitis, allergic sinusitis, anaphylactic syndrome, urticaria, angioedema, atopic dermatitis, allergic contact dermatitis, erythema nodosum, erythema multiforme, cutaneous necrotizing venulitis, insect bite skin inflammation, and asthma. Asthma is characterized by airflow obstruction, bronchial hyper responsiveness and airway inflammation, and includes bronchial asthma and allergic asthma.

In these diseases, mast cells participate in the destruction of tissues by releasing a cocktail of different proteases and mediators such as histamine, neutral proteases, lipid-derived mediators (prostaglandins, thromboxanes and leucotrienes), and various cytokines (IL-1, IL-2, IL-3, IL-4, IL-5, IL-6, IL-8, TNF-A, GM-CSF, MIP-LA, MIP-1b, MIP-2 and IFN-y). Mast cell activation induces diverse effector responses, such as secretion of allergic mediators, proteases, chemokines such as MCP-1 and RANTES, leukotrienes, prostaglandins, neurotrophins, induction of cytokine gene transcription (IL-4, IL-5, IL-6, IL-13, TNFA and GM-CSF). These mediators contribute to creating the asthmatic phenotype by their effects on endothelial cells, smooth muscle cells and fibroblasts and on extracellular matrix, and by recruiting other inflammatory cells.

Mast cells may play a role in asthma as suggested by the humanized anti-IgE monoclonal antibody treatment. The rationale of anti-IgE therapy is to specifically target IgE with the result of inactivating free anti-IgE and halting further IgE production. In addition, since IgE levels are a major regulator of the level of expression of IgE receptor FceRI, one aim of this therapy is to decrease FceRI expression on mast cells and basophils, and, as a consequence, to decrease the capacity of these cells to be activated. The capacity of the anti-IgE therapy to decrease FceRI expression has been demonstrated on basophils. The decrease in FceRI expression on basophils is associated with a decrease in the capacity of basophils to secrete mediators upon activation.

C-kit inhibitors may also be used in the treatment of non-insulin-dependent diabetes mellitus (NLDDM), also known as type II diabetes, a chronic disease appearing when insulin is inefficient in promoting glucose uptake by cells, resulting in increased levels of glucose in the blood. This disease affects about 100 million people world-wide, 75% of which are obese at the time of diagnosis. Over many years, the failure of the glucose uptake regulation leads to the development of Type II diabetes, and the blood glucose level needs to be regulated with medicinal products. Ultimately, unregulated blood glucose level is responsible for blood vessels, kidney and eye damages, as well as cardiovascular diseases. This tissue damages contribute to mortality in diabetics.

In addition, the activation of mast cells by different stimuli such as stress, trauma, infection as well as neurotransmitters, may participate in the exacerbation of the chemical imbalance causing CNS disorders. More specifically, mast cell degranulation is stimulated by common neurotransmitters such as neurotensin, somatostatin, substance P and acetylcholine, by growth or survival factors, notably NGF, TGFβL Mast cells involved in the response to such stimulus can be brain mast cells but also other mast cells releasing the content of their granules in the blood stream that ultimately reach sensory, motor or brain neurons. Brain mast cells staining is CTMC staining-like but they show the secretory pattern of MMC, implying that they constitute a particular subset of mast cells presenting specificities.

Following mast cells activation, released granules liberate various factors capable of modulating and altering neurotransmission and neurons survival. Among such factors, serotonin is important since an increase of the level of free serotonin has been observed in depressed patients. Alternatively, the sudden burst of serotonin may be followed by a period of serotonin shortage, leading to pain and migraine. As a consequence, it is believed that mast cells exacerbate in autocrine or paracrine manner the deregulation of neurotransmission. For example, anxiety or stress-induced release of neurotransmitters such as serotonin activates mast cells, which in turn release the content of their granules, further contributing to the chemical imbalance in the brain leading to CNS disorders.

Other mediators released by mast cells can be categorized into vasoactive, nociceptive, proinflammatory and other neurotransmitters. Taken together, these factors are able to induce great disturbance in the activity of neurons, whether they are sensory, motor, or CNS neurons. In addition, patients afflicted with mastocytosis are more inclined to develop CNS disorders than the normal population. This can be explained by the presence of activating mutations in the c-kit receptor, which induce degranulation of mast cells and a burst of factors contributing to chemical imbalance and neurotransmission alteration.

In some cases, activated mast cells can also participate in the destruction of neuronal tissues by releasing a cocktail of different proteases and mediators categorized into three groups: preformed granule-associated mediators (histamine, proteoglycans, and neutral proteases), lipid-derived mediators (prostaglandins, thromboxanes and leucotrienes), and various cytokines (IL-1, IL-2, IL-3, IL-4, IL-5, IL-6, IL-8, TNF-A, GM-CSF, MIP-LA, MIP-1b, MIP-2 and IFN-y). The liberation by activated mast cells of mediators (TNF-A, histamine, leukotrienes, prostaglandins etc.) as well as proteases may i) induce inflammation and vasodilatation and ii) participate in the neuronal tissue destruction process Inhibition of c-kit activity reduces cellular proliferation, depleting the mast cells responsible for diseases and/or conditions, thereby suggesting a role for use of inhibitors of c-kit in the treatment of c-kit dependent diseases and/or conditions, such as CNS disorders.

Mast cells have also been identified to be involved in or to contribute to drug dependence and withdrawal symptoms. Drug dependence is the result of a phenomenon called tolerance, which is the need to increase the dose of the drug to maintain its full effect, and of physical dependence, which is the habituation of the body to a drug. When the intake of a drug is discontinued, individual may experience unpleasant withdrawal syndrome.

The activation of mast cells by different drugs, including, but not limited to, salicylic derivatives, morphine derivatives, opioids, heroin, amphetamines, alcohol, nicotine, analgesics, anesthetics, and anxyolitics results in the degranulation of mast cells, which participate in the exacerbation of the chemical imbalance responsible for drug habituation and withdrawal syndrome. Following mast cells activation, released granules liberate various factors capable of modulating and altering neurotransmission. Among such factors is morphine which is bound or stored in mast cells granules. Tobacco smoke also induces the release of mediators from canine mast cells and modulates prostaglandin production leading to asthma. In addition, patients afflicted with mastocytosis are more incline to develop substance use disorders than the normal population. This can be explained by the presence of activating mutations in the c-kit receptor, which induce degranulation of mast cells and a burst of factors contributing to chemical imbalance and neurotransmission alteration.

Presently, there is no available treatment that provides relief and help for individuals to withdraw from substance abuse disorders. C-kit inhibitors may be used for treating substance abuse disorders, particularly drug addiction, drug abuse, drug habituation, drug dependence, withdrawal syndrome and overdose, comprising administering a compound capable of depleting mast cells to a human in need of such treatment.

c-Kit has a substantial homology to the PDGF receptor and to the CSF-1 receptor (c-Fms). Investigations on various erythroid and myeloid cell lines indicate an expression of the c-Kit gene in early stages of differentiation (Andre et al., Oncogene 4 (1989), 1047-1049). Certain tumors such as glioblastoma cells likewise exhibit a pronounced expression of the c-Kit gene.

PDGF (Platelet-Derived Growth Factor)

PDGF (Platelet-derived Growth Factor) plays an important role both in normal growth and also in pathological cell proliferation. Compounds of the invention may inhibit PDGF receptor (PDGFR) activity, and may be used as an agent to treat non-malignant proliferative disorders, such as scleroderma and other fibrotic disorders, atherosclerosis, thrombosis or psoriasis. The compounds of the present invention may also be used as a tumor-inhibiting substance, for example in small cell lung cancer, gliomas, sarcomas, prostate tumors, and tumors of the colon, breast, and ovary.

In one embodiment, the compounds of the invention may be used for the treatment and prevention of a fibrotic disorder or disease, a condition linked to or associated with the formation and deposition of extracellular matrix components in the internal organs, including the kidneys, heart, lungs, liver, skin and joints. Various studies have implicated PDGFR as a central player in fibrotic responses to tissue injury, e.g.:

i) PDGF is upregulated in alveolar macrophages from patients with idiopathic pulmonary fibrosis (IPF);
 ii) PDGFRβ is one of the first genes upregulated after activation of hepatic stellate cells to become myofibroblasts, a central step in development of fibrosis in the liver;
 iii) PDGF and its receptors are significantly upregulated in scleroderma, and similarly upregulated in the process of renal fibrogenesis;
 iv) PDGF is induced by injury and/or pro-inflammatory cytokines, or in an autocrine fashion on myofibroblasts driving their proliferation, differentiation, and migration. These myofibroblasts then secrete extracellular matrix proteins and collagen leading to scarring and progressive organ damage. TGFβ secretion also contributes significantly to the production of collagen during fibrogenesis;
 v) A PDGF-C transgene induces the development of liver fibrosis in mice, while a soluble dominant-negative version of PDGFRβ prevents liver fibrosis in ratsl; and
 vi) Administration of PDGF-B to the kidney promoted signs of renal fibrogenesis in rats.

Fibrotic disorders or diseases which may be treated using the compounds of the invention include fibrotic lung diseases such as pulmonary fibrosis (or interstitial lung disease or interstitial pulmonary fibrosis), idiopathic pulmonary fibrosis, primary pulmonary hypertension, idiopathic pulmonary arterial hypertension, the fibrotic element of pneumoconiosis (which is associated with exposure to environmental hazards such as smoking, asbestos, cotton lint, stone dust, mine dust and other particles), pulmonary sarcoidosis, fibrosing alveolitis, the fibrotic or hypertrophic element of cystic fibrosis, chronic obstructive pulmonary disease, adult respiratory distress syndrome and emphysema. The compounds of the invention may also be used for the treatment and prevention of diseases that have as a manifestation fibrotic hypertrophy of the kidneys (renal fibrosis), liver (liver fibrosis), heart (cardiac fibrosis), prostate (e.g., benign prostatic hypertrophy (BPH)), pleura (e.g., pleurisy, pleural fibrosis), pancreas, and of the skin and/or muscle tissues such as scleroderma, eosinophilic fasciitis, discoid lesions associated with lupus or discoid lupus or surgical adhesions.

Other fibrotic disorders or diseases which may be treated using the compounds of the invention include but are not limited to systemic sclerosis, mixed connective tissue disease, fibrodysplasia, fibrocystic disease, sarcoidosis, myositis (e.g. polymyositis, primary idiopathic polymyositis, childhood polymyositis, dermatomyositis, childhood dermatomyositis, primary idiopathic dermatomyositis in adults, inclusion body myositis, polymyositis or dermatomyositis associated with malignant tumors); diseases that have as a manifestation fibrotic vascular intimal hypertrophy, such as vasculitis (including coronary artery vasculitis), polyarteritis nodosa or temporal arteritis; diseases that have as a manifestation fibrotic hypertrophy of nerve tissue such as cerebrosclerosis, annular sclerosis. diffuse sclerosis and lobar sclerosis; and diseases that have as a manifestation fibrotic hypertrophy or fibrosis of the bowel wall, such as inflammatory bowel disease, including Crohn's disease.

Furthermore, the compounds of the present invention may also be useful for the protection of stem cells, for example to combat the hemotoxic effect of chemotherapeutic agents, such as 5-fluorouracil; and may also be useful for the treatment of asthma and hypereosinophilia. Compounds of the invention may especially be used for the treatment of diseases which respond to an inhibition of the PDGF receptor kinase.

Compounds of the present invention may also exhibit useful effects in the treatment of disorders arising as a result of transplantation, for example, allogenic transplantation, especially tissue rejection, such as obliterative bronchiolitis (OB), i.e. a chronic rejection of allogenic lung transplants. In contrast to patients without OB, those with OB often show an elevated PDGF concentration in bronchoalveolar lavage fluids.

Compounds of the present invention may also be effective against diseases associated with vascular smooth-muscle cell migration and proliferation (where PDGF and PDGFR often also play a role), such as restenosis and atherosclerosis. These effects and the consequences thereof for the proliferation or migration of vascular smooth-muscle cells in vitro and in vivo may be demonstrated by administration of the compounds of the present invention, and also by investigating its effect on the thickening of the vascular intima following mechanical injury in vivo.

CSF1R (FMS)

The protein encoded by this gene is the receptor for colony stimulating factor 1, a cytokine which controls the production, differentiation, and function of macrophages. CSFR1 mediates most if not all of the biological effects of this cytokine. The encoded protein is a tyrosine kinase transmembrane receptor and member of the CSF1/PDGF receptor family of tyrosine-protein kinases. Mutations in this gene have been associated with a predisposition to myeloid malignancy. (See e.g., Casas et al., Leuk. Lymphoma 2003 44:1935-41).

Abl, Trk, Syk, Ras, Raf, MAPK, TGFβ, FGFR3, c-Src, SAPK, Lck, Fes, Csk

Abelson tyrosine kinase (i.e. Abl, c-Abl) is involved in the regulation of the cell cycle, in the cellular response to genotoxic stress, and in the transmission of information about the cellular environment through integrin signaling. The Abl protein appears to serve a complex role as a cellular module that integrates signals from various extracellular and intracellular sources and that influences decisions in regard to cell cycle and apoptosis. Abelson tyrosine kinase includes sub-types derivatives such as the chimeric fusion (oncoprotein) BCR-Abl with deregulated tyrosine kinase activity or the v-Abl.

The fusion protein BCR-Abl is a result of a reciprocal translocation that fuses the Abl proto-oncogene with the Bcr gene. BCR-Abl is then capable of transforming B-cells through the increase of mitogenic activity. This increase results in a reduction of sensitivity to apoptosis, as well as altering the adhesion and homing of CML progenitor cells.

BCR-Abl is important in the pathogenesis of 95% of chronic myelogenous leukemia (CML) and 10% of acute lymphocytic leukemia. STI-571 (GLEEVEC®) is an inhibitor of the oncogenic BCR-Abl tyrosine kinase and is used for the treatment of chronic myeloid leukemia (CML). However, some patients in the blast crisis stage of CML are resistant to STI-571 due to mutations in the BCR-Abl kinase. Over 22 mutations have been reported to date, such as G250E, E255V, T315I, F317L and M351T.

Compounds of the present invention may inhibit abl kinase, for example, v-abl kinase. The compounds of the present invention may also inhibit wild-type BCR-Abl kinase and mutations of BCR-Abl kinase, and thus may be suitable for the treatment of Bcr-abl-positive cancer and tumor diseases, such as leukemias (especially chronic myeloid leukemia and acute lymphoblastic leukemia, where especially apoptotic mechanisms of action are found). Compounds of the present invention may also be effective against leukemic stem cells, and may be potentially useful for the purification of these cells in vitro after removal of said cells (for example, bone marrow removal), and reimplantation of the cells once they have been cleared of cancer cells (for example, reimplantation of purified bone marrow cells).

The trk family of neurotrophin receptors (trkA, trkB, trkC) promotes the survival, growth and differentiation of the neuronal and non-neuronal tissues. The TrkB protein is expressed in neuroendocrine-type cells in the small intestine and colon, in the alpha cells of the pancreas, in the monocytes and macrophages of the lymph nodes and of the spleen, and in the granular layers of the epidermis (Shibayama and Koizumi, 1996). Expression of the TrkB protein has been associated with an unfavorable progression of Wilms tumors and of neuroblastomas. Moreover, TrkB is expressed in cancerous prostate cells but not in normal cells. The signaling pathway downstream of the trk receptors involves the cascade of MAPK activation through the Shc, activated Ras, ERK-1 and ERK-2 genes, and the PLC-gammal transduction pathway (Sugimoto et al., 2001).

Syk is a tyrosine kinase that plays an important role in mast cell degranulation and eosinophil activation. Accordingly, Syk kinase is implicated in various allergic disorders, particularly asthma. It has been shown that Syk binds to the phosphorylated gamma chain of the FceR1 receptor via N-terminal SH2 domains and is important for downstream signaling.

The Ras-Raf-MEK-ERK signaling pathway mediates cellular response to growth signals. Ras is mutated to an oncogenic form in ~15% of human cancer. The Raf family belongs to the serine/threonine protein kinase and includes three members, A-Raf, B-Raf and c-Raf (or Raf-1). B-Raf may have a prominent role in the formation of certain tumors with no requirement for an activated Ras allele (Nature 417: 949-954 (2002)). B-Raf mutations have been detected in a large percentage of malignant melanomas.

Existing medical treatments for melanoma are limited in their effectiveness, especially for late stage melanomas. The compounds of the present invention also inhibit cellular processes involving b-Raf kinase, providing a new therapeutic opportunity for treatment of human cancers, especially for melanoma.

Mitogen-activated protein kinases (MAPKs) are members of conserved signal transduction pathways that activate transcription factors, translation factors and other target molecules in response to a variety of extracellular signals. MAPKs are activated by phosphorylation at a dual phosphorylation motif having the sequence Thr-X-Tyr by mitogen-activated protein kinase kinases (MKKs). In higher eukaryotes, the physiological role of MAPK signaling has been correlated with cellular events such as proliferation, oncogenesis, development and differentiation. Accordingly, the ability to regulate signal transduction via these pathways (particularly via MKK4 and MKK6) could lead to the development of treatments and preventive therapies for human diseases associated with MAPK signaling, such as inflammatory diseases, autoimmune diseases and cancer.

Multiple forms of p38 MAPK ($\alpha$, $\beta$, $\gamma$, $\delta$), each encoded by a separate gene, form part of a kinase cascade involved in the response of cells to a variety of stimuli, including osmotic stress, UV light and cytokine mediated events. These four isoforms of p38 are thought to regulate different aspects of intracellular signaling. Its activation is part of a cascade of signaling events that lead to the synthesis and production of pro-inflammatory cytokines like TNF$\alpha$. P38 functions by phosphorylating downstream substrates that include other kinases and transcription factors. Agents that inhibit p38 kinase have been shown to block the production of cytokines including but not limited to TNF$\alpha$, IL-6, IL-8 and IL-1$\beta$.

Peripheral blood monocytes (PBMCs) have been shown to express and secrete pro-inflammatory cytokines when stimulated with lipopolysaccharide (LPS) in vitro. P38 inhibitors efficiently block this effect when PBMCs are pretreated with such compounds prior to stimulation with LPS. P38 inhibitors are efficacious in animal models of inflammatory disease. The destructive effects of many disease states are caused by the over production of pro-inflammatory cytokines. The ability of p38 inhibitors to regulate this overproduction makes them useful as disease modifying agents.

Molecules that block p38 function have been shown to be effective in inhibiting bone resorption, inflammation, and other immune and inflammation-based pathologies. Thus, a safe and effective p38 inhibitor would provide a means to treat debilitating diseases that can be regulated by modulation of p38 signaling. Therefore, compounds of the invention that inhibit p38 activity are useful for the treatment of inflammation, osteoarthritis, rheumatoid arthritis, cancer, autoimmune diseases, and for the treatment of other cytokine mediated diseases.

Transforming growth factor-beta (TGF$\beta$) denotes a superfamily of proteins that includes, for example, TGF$\beta$1, TGF$\beta$2, and TGF$\beta$3, which are pleotropic modulators of cell growth and differentiation, embryonic and bone development, extracellular matrix formation, hematopoiesis, immune and inflammatory responses. The members of the TGF$\beta$ family initiate intracellular signaling pathways leading ultimately to the expression of genes that regulate the cell cycle, control proliferative responses, or relate to extracellular matrix proteins that mediate outside-in cell signaling, cell adhesion, migration and intercellular communication.

Consequently, compounds of the invention that are inhibitors of the TGF$\beta$ intracellular signaling pathway are useful therapeutics for fibroproliferative diseases, including kidney disorders associated with unregulated TGF$\beta$ activity and excessive fibrosis including glomerulonephritis (GN), such as mesangial proliferative GN, immune GN, and crescentic GN. Other renal conditions include diabetic nephropathy, renal interstitial fibrosis, renal fibrosis in transplant patients receiving cyclosporin, and HIV-associated nephropathy. Collagen vascular disorders include progressive systemic sclerosis, polymyositis, scleroderma, dermatomyositis, eosinophilic fascitis, morphea, or those associated with the occurrence of Raynaud's syndrome. Lung fibroses resulting from excessive TGF$\beta$ activity include adult respiratory distress syndrome, COPD, idiopathic pulmonary fibrosis, and interstitial pulmonary fibrosis often associated with autoimmune disorders, such as systemic lupus erythematosus and scleroderma, chemical contact, or allergies. Another autoimmune disorder associated with fibroproliferative characteristics is rheumatoid arthritis. Fibroproliferative conditions can be associated with surgical eye procedures. Such procedures include retinal reattachment surgery accompanying proliferative vitreoretinopathy, cataract extraction with intraocular lens implantation, and post glaucoma drainage surgery.

Fibroblast growth factor receptor 3 was shown to exert a negative regulatory effect on bone growth and an inhibition of chondrocyte proliferation. Thanatophoric dysplasia is caused by different mutations in fibroblast growth factor receptor 3. One mutation, TDII FGFR3, has a constitutive tyrosine kinase activity which activates the transcription factor Stat1, leading to expression of a cell-cycle inhibitor, growth arrest and abnormal bone development (Su et al., Nature, 1997, 386, 288-292). FGFR3 is also often expressed in multiple myeloma-type cancers.

The kinase, c-Src, transmits oncogenic signals of many receptors. For example, over-expression of EGFR or HER2/ neu in tumors leads to the constitutive activation of c-src, which is characteristic for the malignant cell but absent from the normal cell. On the other hand, mice deficient in the expression of c-src exhibit an osteopetrotic phenotype, indicating a key participation of c-src in osteoclast function and a possible involvement in related disorders.

The family of human ribosomal S6 protein kinases consists of at least 8 members (RSK1, RSK2, RSK3, RSK4, MSK1, MSK2, p70S6K and p70S6 Kb). Ribosomal protein S6 protein kinases play important pleotropic functions; among them is a key role in the regulation of mRNA translation during protein biosynthesis (Eur. J. Biochem 2000 November; 267 (21): 6321-30, Exp Cell Res. Nov. 25, 1999; 253 (1):100-9, Mol Cell Endocrinol. May 25, 1999; 151(1-2):65-77). The phosphorylation of the S6 ribosomal protein by p70S6 has also been implicated in the regulation of cell motility (Immunol. Cell Biol. 2000 August; 78(4):447-51) and cell growth (Prog. Nucleic Acid Res. Mol. Biol., 2000; 65:101-27), and hence, may be important in tumor metastasis, the immune response and tissue repair as well as other disease conditions.

The SAPK's (also called "jun N-terminal kinases" or "JNK's") are a family of protein kinases that represent the penultimate step in signal transduction pathways that result in activation of the c-jun transcription factor and expression of genes regulated by c-jun. In particular, c-jun is involved in the transcription of genes that encode proteins involved in the repair of DNA that is damaged due to genotoxic insults. Agents that inhibit SAPK activity in a cell prevent DNA repair and sensitize the cell to those cancer therapeutic modalities that act by inducing DNA damage.

Lck plays a role in T-cell signaling. Mice that lack the Lck gene have a poor ability to develop thymocytes. The function of Lck as a positive activator of T-cell signaling suggests that Lck inhibitors may be useful for treating autoimmune disease such as rheumatoid arthritis.

Fes is strongly expressed in myeloid hematopoietic cells and is implicated in both differentiation and survival signaling pathways in myeloid leukocytes. CSK is implicated in cancers, particularly colorectal and breast cancers.

In accordance with the foregoing, the present invention further provides a method for preventing or treating any of the diseases or disorders described above in a subject in need of such treatment, which method comprises administering to said subject a therapeutically effective amount (See, "Administration and Pharmaceutical Compositions," infra) of a compound of Formula (1), (2A), (2B) or (C), or a pharmaceutically acceptable salt thereof. For any of the above uses, the required dosage will vary depending on the mode of administration, the particular condition to be treated and the effect desired.

Administration and Pharmaceutical Compositions

A pharmaceutical composition, as used herein, refers to a mixture of a compound of the invention with other chemical components, such as carriers, stabilizers, diluents, dispersing agents, suspending agents, thickening agents, and/or excipients. The pharmaceutical composition facilitates administration of the compound to an organism. Pharmaceutical compositions containing a compound of the invention may be administered in therapeutically effective amounts as pharmaceutical compositions by any conventional form and route known in the art including, but not limited to: intravenous, oral, rectal, aerosol, parenteral, ophthalmic, pulmonary, transdermal, vaginal, otic, nasal, and topical administration.

One may administer the compound in a local rather than systemic manner, for example, via injection of the compound directly into an organ, often in a depot or sustained release formulation. Furthermore, one may administer pharmaceutical composition containing a compound of the invention in a targeted drug delivery system, for example, in a liposome coated with organ-specific antibody. The liposomes will be targeted to and taken up selectively by the organ. In addition, pharmaceutical compositions containing a compound of the invention may be provided in the form of a rapid release formulation, in the form of an extended release formulation, or in the form of an intermediate release formulation.

For oral administration, a compound of the invention may be formulated readily by combining the active compounds with pharmaceutically acceptable carriers or excipients well known in the art. Such carriers enable the compounds described herein to be formulated as tablets, powders, pills, dragees, capsules, liquids, gels, syrups, elixirs, slurries, suspensions and the like, for oral ingestion by a patient to be treated.

Pharmaceutical preparations for oral use may be obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Dragee cores may be provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which may be used orally include push-fit capsules made of gelatin, as well as soft, sealed capsules made of gelatin and a plasticizer, such as glycerol or sorbitol. The push-fit capsules may contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

For buccal or sublingual administration, the compositions may take the form of tablets, lozenges, or gels formulated in conventional manner. Parental injections may involve bolus injection or continuous infusion. The pharmaceutical composition of a compound of the invention may be in a form suitable for parenteral injection as a sterile suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

The compounds of the invention may be administered topically and may be formulated into a variety of topically administrable compositions, such as solutions, suspensions, lotions, gels, pastes, medicated sticks, balms, creams or ointments. Such pharmaceutical compounds may contain solubilizers, stabilizers, tonicity enhancing agents, buffers and preservatives.

Formulations suitable for transdermal administration may employ transdermal delivery devices and transdermal delivery patches, and may be lipophilic emulsions or buffered, aqueous solutions, dissolved and/or dispersed in a polymer or an adhesive. Such patches may be constructed for continuous, pulsatile, or on demand delivery of pharmaceutical agents. Still further, transdermal delivery of the compounds of the invention may be accomplished by means of iontophoretic patches and the like. Additionally, transdermal patches may provide controlled delivery of the compounds of the invention. The rate of absorption may be slowed by using rate-controlling membranes or by trapping the compound within a polymer matrix or gel. Conversely, absorption enhancers may be used to increase absorption. An absorption enhancer or carrier may include absorbable pharmaceutically acceptable solvents to assist passage through the skin. For example, transdermal devices are in the form of a bandage comprising a backing member, a reservoir containing the compound optionally with carriers, optionally a rate controlling bather to deliver the compound to the skin of the host at a controlled and predetermined rate over a prolonged period of time, and means to secure the device to the skin.

For administration by inhalation, the compounds of the invention may be in a form as an aerosol, a mist or a powder. Pharmaceutical compositions of the compounds of the invention may be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges, such as, by way of example only, gelatin for use in an inhaler or insufflator may be formulated containing a powder mix of the compound and a suitable powder base such as lactose or starch.

The compounds of the invention may also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

Pharmaceutical compositions may be formulated in conventional manner using one or more physiologically acceptable carriers comprising excipients and auxiliaries which facilitate processing of the active compounds into preparations which may be used pharmaceutically. Proper formulation is dependent upon the route of administration chosen. Any of the well-known techniques, carriers, and excipients may be used as suitable and as understood in the art. Pharmaceutical compositions comprising a compound of the invention may be manufactured in a conventional manner, such as, by way of example only, by means of conventional mixing, dissolving, granulating, dragee-making, levigating, emulsifying, encapsulating, entrapping or compression processes.

The pharmaceutical compositions will include at least one pharmaceutically acceptable carrier, diluent or excipient and a compound of Formula (1), (2A) or (2B) described herein as an active ingredient in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. In some situations, compounds may exist as tautomers. All tautomers are included within the scope of the compounds presented herein. Additionally, the compounds described herein may exist in unsolvated as well as solvated forms with pharmaceutically acceptable solvents such as water, ethanol, and the like. The solvated forms of the compounds presented herein are also considered to be disclosed herein. In addition, the pharmaceutical compositions may include other medicinal or pharmaceutical agents, carriers, adjuvants, such as preserving, stabilizing, wetting or emulsifying agents, solution promoters, salts for regulating the osmotic pressure, and/or buffers. In addition, the pharmaceutical compositions may also contain other therapeutically valuable substances.

Methods for the preparation of compositions comprising the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The compositions may be in liquid solutions or suspensions, solid forms suitable for solution or suspension in a liquid prior to use, or as emulsions. These compositions may also contain minor amounts of nontoxic, auxiliary substances, such as wetting or emulsifying agents, pH buffering agents, and so forth.

A summary of pharmaceutical compositions described herein may be found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins1999), herein incorporated by reference in their entirety.

Methods of Administration and Treatment Methods

The compositions containing the compound(s) described herein may be administered for prophylactic and/or therapeutic treatments. In therapeutic applications, the compositions are administered to a patient already suffering from a disease or condition, in an amount sufficient to cure or at least partially arrest the symptoms of the disease or condition. It is considered well within the skill of the art for one to determine such therapeutically effective amounts by routine experimentation (including, but not limited to, a dose escalation clinical trial).

The compounds of the invention may be used in combination with a second therapeutic agent. For example, if one of the side effects experienced by a patient upon receiving one of the compounds herein is inflammation, the compounds of the invention may be administered with in combination with an anti-inflammatory agent. The therapeutic effectiveness of a compound described herein may also be enhanced by administration of an adjuvant. When the compounds of the invention are administered in conjunction with other therapies, dosages of the co-administered compounds will vary depending on the type of co-drug employed, on the specific drug employed, on the disease or condition being treated and so forth. In addition, when co-administered with one or more biologically active agents, the compounds of the invention may be administered either simultaneously with the biologically active agent(s), or sequentially. The administration of a compound of the invention in combination with a second therapeutic agent may have an additive or synergistic effect.

In some examples, the compounds of the invention may be used in combination with an anti-fibrotic agent; e.g., an agent that interferes with or modulates the progression of a fibrotic disease such as scleroderma, pulmonary fibrosis, idiopathic pulmonary fibrosis (IPF), primary pulmonary hypertension (PPH), primary pulmonary arterial hypertension (PPAH), idiopathic arterial hypertension (IPAH), liver fibrosis, renal fibrosis and cardiac fibrosis. Examples of anti-fibrotic agents which may be used in combination with a compound of the invention include but are not limited to pirfenidone (Nakazoto et al., Eur. J. Pharmacol. 446:177-185 (2002), tacrolimus (Nagano et al., Eur. Respir. J. 27: 460-469 (2006) or 5-chloro-2-{(1E)-3-[2-(4-methoxybenzoyl)-4-methyl-1H-pyrrol-1-yl]prop-1-en-1-yl}-N-(methylsulfonyl)benzamide (SMP-534) (Sugaru et al., Am. J. Nephrology 26:50-58 (2006)). The compounds of the invention may also be used in combination with an anti-inflammatory agent, including, but not limited to, corticosteroids and cromolyns, leukotriene antagonists, and IgE blockers such as omalizumab. In other examples, the compounds of the invention may be used in combination with a medication for treating asthma; e.g., bronchodilators such as $\beta_2$-agonists, xanthines (e.g. methylxanthines) and anticholinerigcs; and an anti-inflammatory agent as described above.

The compounds of the invention may also be used in combination with a chemotherapeutic agent to treat a cell proliferative disorder, including but not limited to, lymphoma, osteosarcoma, melanoma, or a tumor of breast, renal, prostate, colorectal, thyroid, ovarian, pancreatic, neuronal, lung, uterine or gastrointestinal tumor. Examples of chemotherapeutic agents which may be used in the compositions and methods of the invention include but are not limited to anthracyclines, alkylating agents (e.g., mitomycin C), alkyl sulfonates, aziridines, ethylenimines, methylmelamines, nitrogen mustards, nitrosoureas, antibiotics, antimetabolites, folic acid analogs (e.g., dihydrofolate reductase inhibitors such as methotrexate), purine analogs, pyrimidine analogs, enzymes, podophyllotoxins, platinum-containing agents, interferons, and interleukins. Particular examples of known chemotherapeutic agents which may be used in the compositions and methods of the invention include, but are not limited to, busulfan, improsulfan, piposulfan, benzodepa, carboquone, meturedepa, uredepa, altretamine, triethylenemelamine, triethylenephosphoramide, triethylenethiophosphoramide, trimethylolomelamine, chlorambucil, chlornaphazine, cyclophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimustine, dacarbazine, mannomustine, mitobronitol, mitolactol, pipobroman, aclacinomycins, actinomycin F(1), anthramycin, azaserine, bleomycin, cactinomycin, carubicin, carzinophilin, chromomycin, dactinomycin, daunorubicin, daunomycin, 6-diazo-5-oxo-1-norleucine, doxorubicin, epirubicin, mitomycin C, mycophenolic acid, nogalamycin, olivomycin, peplomycin, plicamycin, porfiromycin, puromycin, streptonigrin, streptozocin, tubercidin, ubenimex, zinostatin, zorubicin, denopterin, methotrexate, pteropterin, trimeterxate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, fluorouracil, tegafur, L-asparaginase, pulmozyme, aceglatone, aldophosphamide glycoside, aminolevulinic acid, amsacrine, bestrabucil, bisantrene, carboplatin, cisplatin, defofamide, demecolcine, diaziquone, elformithine, elliptinium acetate, etoglucid, etoposide, flutamide, gallium nitrate, hydroxyurea, interferon-alpha, interferon-beta, interferon-gamma, interleukin-2, lentinan, lonidamine, mitoguazone, mitoxantrone, mopidamol, nitracrine, pentostatin, phenamet, pirarubicin, podophyllinic acid, 2-ethylhydrazide, procarbazine, razoxane, sizofuran, spirogermanium, paclitaxel, tamoxifen, teniposide, tenuazonic acid, triaziquone, 2,2',2''-trichlorotriethylamine, urethane, vinblastine, vincristine, and vindesine.

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

Toxicity and therapeutic efficacy of such therapeutic regimens may be determined by standard pharmaceutical procedures in cell cultures or experimental animals, including, but not limited to, for determining the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. The data obtained from cell culture assays and animal studies may be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

Processes for Making Compounds of the Invention

General procedures for preparing compounds of the invention are described in the Examples, infra. In the reactions described, reactive functional groups, for example hydroxy, amino, imino, thio or carboxy groups, where these are desired in the final product, may be protected to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

A compound of the invention may be prepared as a pharmaceutically acceptable acid addition salt by reacting the free base form of the compound with a pharmaceutically acceptable inorganic or organic acid. Alternatively, a pharmaceutically acceptable base addition salt of a compound of the invention may be prepared by reacting the free acid form of the compound with a pharmaceutically acceptable inorganic or organic base. Alternatively, the salt forms of the compounds of the invention may be prepared using salts of the starting materials or intermediates.

The free acid or free base forms of the compounds of the invention may be prepared from the corresponding base addition salt or acid addition salt form, respectively. For example, a compound of the invention in an acid addition salt form may be converted to the corresponding free base by treating with a suitable base (e.g., ammonium hydroxide solution, sodium hydroxide, and the like). A compound of the invention in a base addition salt form may be converted to the corresponding free acid by treating with a suitable acid (e.g., hydrochloric acid, etc.).

Compounds of the invention in unoxidized form may be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention may be prepared by methods known to those of ordinary skill in the art (e.g., for further details see Saulnier et al., (1994), Bioorganic and Medicinal Chemistry Letters, Vol. 4, p. 1985). For example, appropriate prodrugs may be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention may be made by means known to those of ordinary skill in the art. A detailed description of techniques applicable to the creation of protecting groups and their removal can be found in T. W. Greene, "Protecting Groups in Organic Chemistry", 3$^{rd}$ edition, John Wiley and Sons, Inc., 1999.

Compounds of the present invention may be conveniently prepared or formed during the process of the invention, as solvates (e.g., hydrates). Hydrates of compounds of the present invention may be conveniently prepared by recrystallization from an aqueous/organic solvent mixture, using organic solvents such as dioxin, tetrahydrofuran or methanol.

Compounds of the invention may be prepared as their individual stereoisomers by reacting a racemic mixture of the compound with an optically active resolving agent to form a pair of diastereoisomeric compounds, separating the diastereomers and recovering the optically pure enantiomers. Resolution of enantiomers may be carried out using covalent diastereomeric derivatives of the compounds of the invention, or by using dissociable complexes (e.g., crystalline diastereomeric salts). Diastereomers have distinct physical properties (e.g., melting points, boiling points, solubility, reactivity, etc.) and may be readily separated by taking advantage of these dissimilarities. The diastereomers may be separated by chromatography, or by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

In summary, compounds having Formula (1), (2A) or (2B) may be made by a process which involves:

(a) general procedures as described in the Examples (infra); and
(b) optionally converting a compound of the invention into a pharmaceutically acceptable salt;
(c) optionally converting a salt form of a compound of the invention to a non-salt form;
(d) optionally converting an unoxidized form of a compound of the invention into a pharmaceutically acceptable N-oxide;
(e) optionally converting an N-oxide form of a compound of the invention to its unoxidized form;
(f) optionally resolving an individual isomer of a compound of the invention from a mixture of isomers;
(g) optionally converting a non-derivatized compound of the invention into a pharmaceutically acceptable prodrug derivative; and
(h) optionally converting a prodrug derivative of a compound of the invention to its non-derivatized form.

Insofar as the production of the starting materials is not particularly described, the compounds are known or may be prepared analogously to methods known in the art or as disclosed in the Examples hereinafter. One of skill in the art will appreciate that the above transformations are only representative of methods for preparation of the compounds of the present invention, and that other well known methods can similarly be used.

The following examples are offered to illustrate but not to limit the invention.

PREPARATION OF INTERMEDIATES

Synthesis of (5-bromo-pyrimidin-2-yl)-[4-(2-diethylamino-ethoxy)-phenyl-amine 5

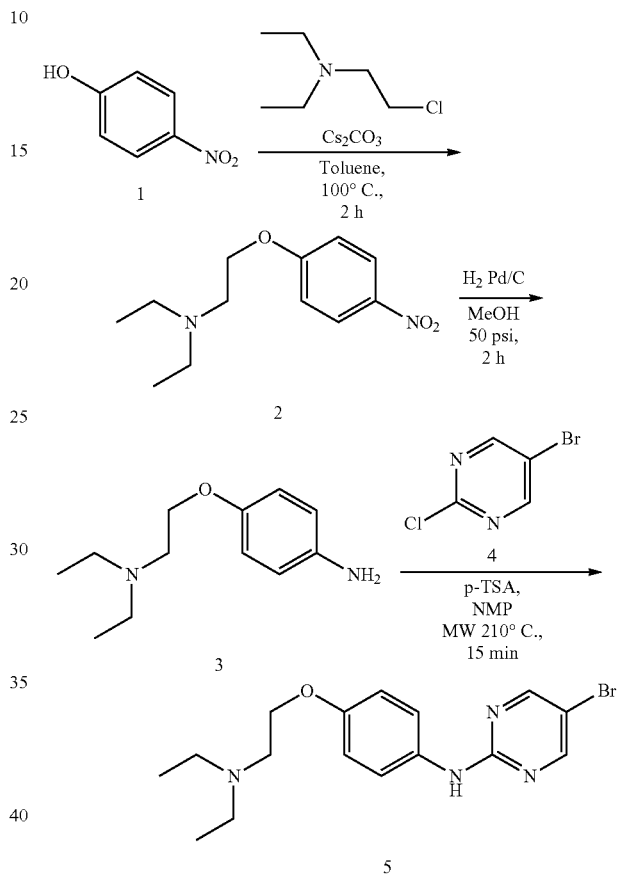

To a solution of 4-nitro-phenol 1 (36.0 mmol) in toluene (40 mL) is added cesium carbonate (53.8 mmol) and (2-chloro-ethyl)-diethyl-amine hydrochloride (28.7 mmol). The reaction mixture is heated at 100° C. for 2 h then cooled to rt. The solid is filtered under vacuum and washed with warm toluene. The filtrate is concentrated to afford diethyl-[2-(4-nitro-phenoxy)-ethyl]-amine 2 and used in the next step without further purification. $^1$H NMR (400 MHz, CDCl$_3$) δ 8.10-8.08 (m, 2H), 6.86-6.84 (m, 2H), 4.05 (t, J=4.0 Hz, 2H), 2.81 (t, J=4.0 Hz), 2.55 (q, J=8.0 Hz, 4H), 0.98 (t, J=8.0 Hz, 6H). MS (m/z) (M+1)$^+$: 239.3.

To a solution of diethyl-[2-(4-nitro-phenoxy)-ethyl]-amine 2 (14.0 mmol) in MeOH (20 mL), in a Parr pressure bottle, is added Pd (10% on carbon, 50% wet, 10% weight). The suspension is shaken at 50 psi of H$_2$ for 2 h. The reaction mixture is filtered through celite. The solvent is removed and the residue is dissolved in MeOH (20 mL) and treated with HCl (1 eq of a 4N solution in dioxane) to afford 4-(2-diethylamino-ethoxy)-phenylamine 3 as hydrochloride salt. $^1$H NMR (400 MHz, d6-DMSO) δ 6.98-6.91 (m, 4H), 4.30 (t, J=4.0 Hz, 2H), 3.47 (t, J=4.0 Hz), 3.20 (m, 4H), 1.24 (t, J=8.0 Hz, 6H). MS (m/z) (M+1)$^+$: 209.3.

A dry flask charged with 4-(2-diethylamino-ethoxy)-phenylamine 3 (6.1 mmol), p-TSA (6.1 mmol), 5-bromo-2-chloropyrimidine 4 (6.1 mmol) in NMP (5 mL) is heated in a microwave oven at 210° C. for 15 min. The reaction mixture is diluted with water and extracted with EtOAc (5×70 mL). The organic layer is washed with water, brine, dried over Na$_2$SO$_4$, and concentrated. Purification by silica chromatography (DCM:MeOH:NH$_4$OH=95:5:0.1) affords 5-bromopyrimidin-2-yl)-[4-(2-diethylamino-ethoxy)-phenyl-amine 5. $^1$H NMR (400 MHz, CDCl$_3$) δ 8.37 (s, 2H), 7.43-7.40 (m, 2H), 7.02 (s, 1H), 6.91-6.89 (m, 2H), 4.06 (t, J=4.0 Hz, 2H), 2.90 (t, J=4.0 Hz, 2H), 2.67 (q, J=8.0 Hz, 4H), 1.09 (t, J=8.0 Hz, 6H). MS (m/z) (M+1)$^+$: 366.1.

Synthesis of 2-(4-(difluoromethoxy)phenyl)-4,4,5,5-tetramethyl-1,3,2-dioxaborolane 7

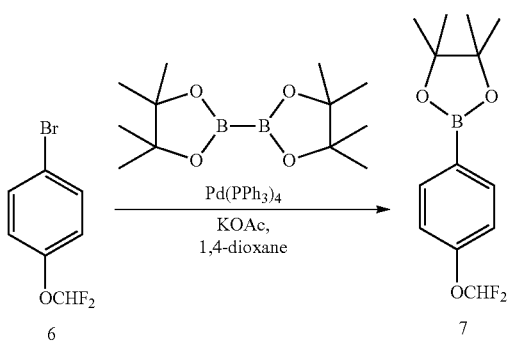

Bromo-4-(difluoromethoxy)benzene 6 (2.23 g, 10 mmol), potassium acetate (30.0 mmol), 4,4,5,5-tetramethyl-2-(4,4,5,5-tetramethyl-1,3,2-dioxaborolan-2-yl)-1,3,2-dioxaborolane (11.0 mmol) and Pd(PPh$_3$)$_4$ (0.5 mmol) are added to a 40-mL Schlenk flask equipped with a stir bar. The flask is evacuated and backfilled with nitrogen several times. 1,4-Dioxane (10 mL) is added by syringe. The Schlenk flask is sealed and heated at 150° C. for 20 min in a microwave oven. After the reaction is complete, the solvent is removed under vacuum. The residue is dissolved in DCM (200 mL) and washed with water. The organic phase is dried with anhydrous Na$_2$SO$_4$, filtered and concentrated to yield a crude product. Purification by silica gel column chromatography (EtOAc:hexanes, gradient from 0% to 20%) affords 2-(4-(difluoromethoxy)phenyl)-4,4,5,5-tetramethyl-1,3,2-dioxaborolane 7. $^1$H NMR (400 MHz, CDCl$_3$) δ 7.74 (d, J=8.4 Hz, 2H), 7.02 (d, J=8.4 Hz, 2H), 6.48 (t, J=73.6 Hz, 1H), 1.27 (s, 12H). MS (m/z) (M+1)$^+$: 271.1.

Synthesis of sodium 1-(2-(4-(5-bromopyrimidin-2-ylamino)phenoxy)ethyl)piperidine-4-carboxylate 13

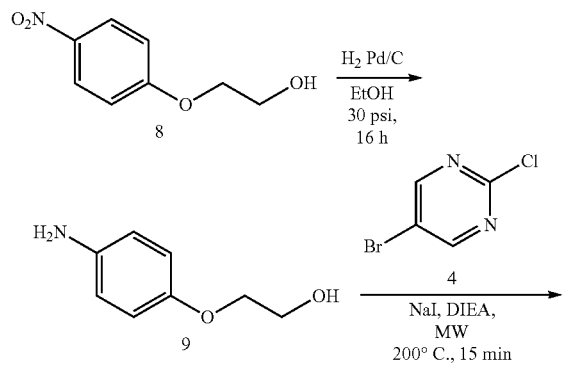

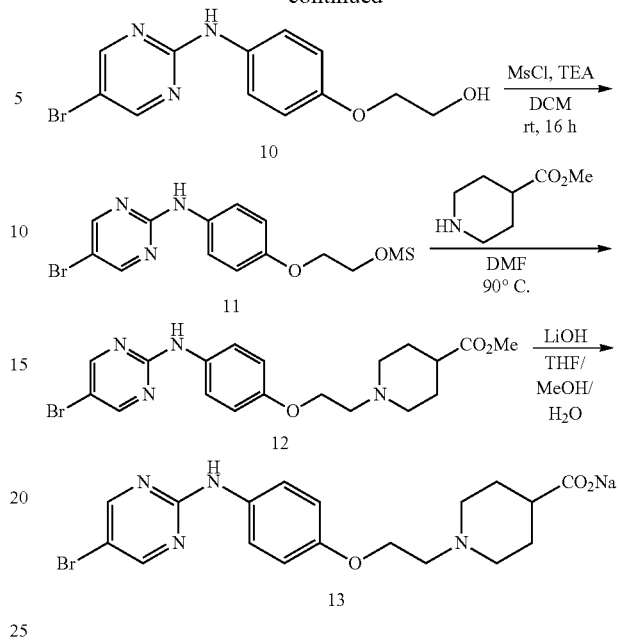

2-(4-Nitrophenoxy)ethanol 8 (109 mmol) and Pd/C (10% wt.) are suspended in EtOH (50 mL) and allowed to absorb 30 psi of hydrogen in a Parr shaker. The mixture is shaken at rt for 16 h. After filtration and concentration, 2-(4-aminophenoxy)ethanol 9 is obtained as a light pink colored solid and used in the next step without purification. MS (m/z) (M+1)$^+$: 154.1.

A mixture of 2-(4-aminophenoxy)ethanol 9 (70 mmol), 5-bromo-2-chloropyrimidine 4 (70 mmol), sodium iodide (70 mmol), and diisopropylethylamine (140 mmol) is heated at 200° C. for 15 min in a microwave oven. The reaction mixture is poured into water (300 mL). After filtration, the solid is washed with a mixture of H$_2$O:MeOH=1:1 (100 mL) and dried under vacuum for 12 h to give the product 10 as a tannish solid which is used in the next step without purification. MS (m/z) (M+1)$^+$: 310.2, 312.2.

2-(4-(5-Bromopyrimidin-2-ylamino)phenoxy)ethanol 10 (26.6 mmol) is dissolved in DCM (50 mL) followed by addition of MsCl (32 mmol). The reaction vessel is chilled in an ice-water bath and triethylamine (53.3 mmol) is added slowly. The mixture is stirred at rt for 16 h. The solvent is removed and the residue is triturated with water (300 mL). The solid is filtered and dried under vacuum for 12 h to give 2-(4-(5-Bromopyrimidin-2-ylamino)phenoxy)ethyl methanesulfonate 11 as off-white solid. $^1$H NMR (400 MHz, d6-DMSO) δ 9.71 (s, 1H), 8.54 (s, 2H), 7.59 (d, J=9.2 Hz, 2H), 6.93 (d, J=9.2 Hz, 2H), 4.52 (m, 2H), 4.22 (m, 2H), 3.24 (s, 3H). MS (m/z) (M+1)$^+$: 388.0, 340.0.

2-(4-(5-Bromopyrimidin-2-ylamino)phenoxy)ethyl methanesulfonate 11 (1.55 mmol) and methyl isonipecotate (3.10 mmol) are dissolved in DMF (5 mL) and stirred at 90° C. for 12 h. After the reaction is completed, 2M Na$_2$CO$_3$ (20 mL) is added and the resulting mixture is extracted with EtOAc (50 mL). The organic layer is separated and concentrated to give crude methyl 1-(2-(4-(5-bromopyrimidin-2-ylamino)phenoxy)ethyl)piperidine-4-carboxylate 12. MS (m/z) (M+1)$^+$: 435.1, 437.1.

The crude 12 is suspended in a THF/MeOH/H$_2$O solution (3:2:1, 10 mL) with 6N aq. LiOH (9.3 mmol) and stirred at rt for 2 h. The solvent is removed under vacuum to give an aqueous solution. To the above aqueous solution, 1N NaOH (2.0 mL) is added and the precipitate is filtered and dried to yield sodium 1-(2-(4-(5-bromopyrimidin-2-ylamino)phenoxy)ethyl)piperidine-4-carboxylate 13. $^1$H NMR (400 MHz, d6-DMSO) δ 9.67 (s, 1H), 8.52 (s, 2H), 7.54 (d, J=8.8 Hz, 2H), 6.88 (d, J=8.8 Hz, 2H), 4.01 (t, J=6.0 Hz, 2H), 2.83

(m, 2H), 2.61 (m, 2H), 1.98 (m, 2H), 1.60-1.81 (m, 3H), 1.42-1.58 (m, 2H). MS (m/z) (M+1)+: 421.1, 423.1.

Synthesis of 1-(4-(5-bromopyrimidin-2-ylamino) benzyl)piperidine-4-carboxylic acid 17

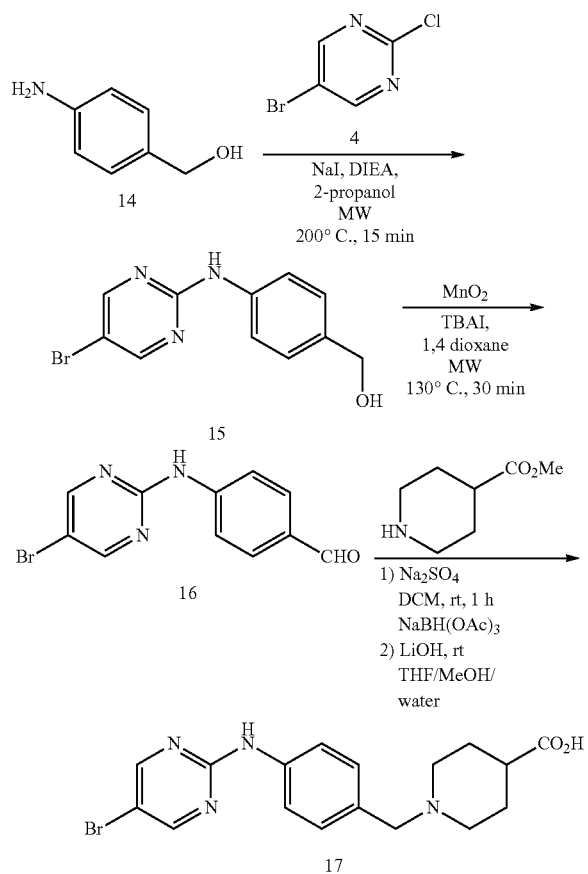

To a solution of 4-aminobenzyl alcohol 14 (8.12 mmol) and 5-bromo-2-chloro-pyrimidine 4 (9.74 mmol) in 2-propanol (20 mL) is added sodium iodide (8.12 mmol) and diisopropylethylamine (16.2 mmol). The reaction mixture is heated in the microwave oven at 200° C. for 15 min. Purification by silica gel chromatography with hexane:EtOAc=7:3 affords [4-(5-bromo-pyrimidin-2-ylamino)-phenyl]-methanol 15. $^1$H NMR (400 MHz, CDCl$_3$) δ 8.36 (s, 2H), 7.49 (d, J=8.8 Hz, 2H), 7.28 (d, J=8.4 Hz, 2H) 7.07 (bs, 1H), 4.60 (s, 2H). MS (m/z) (M+1)+: 280.3, 282.3.

To a solution of [4-(5-bromo-pyrimidin-2-ylamino)-phenyl]-methanol 15 (0.94 mmol) in dioxane (2 mL) is added manganese (IV) oxide (4.7 mmol) and TBAI (0.06 mmol). The reaction mixture is heated in a microwave oven at 130° C. for 30 min. Purification by silica gel chromatography using hexane:EtOAc=1:1 affords 4-[5-(4-methoxy-phenyl)-pyrimidin-2-ylamino]-benzaldehyde 16. $^1$H NMR (400 MHz, d6-DMSO) δ 10.45 (s, 1H), 9.85 (s, 1H), 8.72 (s, 2H), 7.96 (d, J=8.4 Hz, 2H), 7.85 (d, J=8.4 Hz, 2H). MS (m/z) (M+1)+: 278.0, 280.0.

A mixture of 4-(5-bromopyrimidin-2-ylamino)benzaldehyde 16 (5.0 mmol), isonipecotic acid methyl ester (10 mmol) and Na$_2$SO$_4$ (excess) in DCM:MeOH:DMSO (4:1:0.2 v/v, 26 mL) is stirred at rt for 1 h. Then NaBH(OAc)$_3$ (15.0 mmol) is added and stirred for 12 h. The reaction mixture is quenched with 1 N HCl (1 ml). After filtration, all solvents are removed under vacuum. To the residue is added 6 N LiOH (2.5 mL) and THF:MeOH:water (3:2:1, 6 mL). The mixture is stirred for 1 h and quenched by 12 N HCl (5 mL). After concentration, EtOH:MeCN (1:1 v/v, 100 mL) is added. Inorganic solid is filtered off. The yellow filtrate is concentrated and filtered to give the HCl salt of 1-(4-(5-bromopyrimidin-2-ylamino)benzyl)piperidine-4-carboxylic acid 17 as a yellow solid precipitate. $^1$H NMR (400 MHz, d6-DMSO) δ 10.07 (s, 1H), 8.63 (s, 2H), 7.76 (d, J=8.4 Hz, 2H), 7.48 (d, J=7.6 Hz, 2H), 4.17 (s, 2H), 3.10-3.40 (m, 2H), 2.89 (m, 2H), 1.67-2.06 (m, 5H). MS (m/z) (M+1)+: 391.1, 393.1.

Synthesis of 1-(4-(5-bromopyrimidin-2-ylamino) phenethyl)piperidine-4-carboxylic acid 21

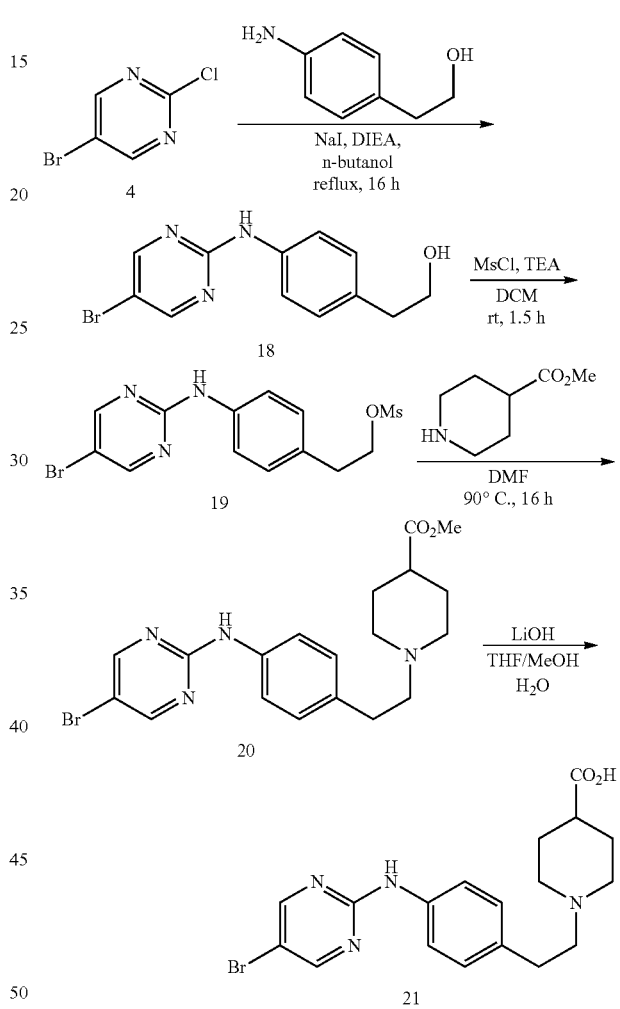

A mixture of 2-(4-aminophenyl)ethanol (0.72 mol), 5-bromo-2-chloropyrimidine 4 (0.72 mol), sodium iodide (0.72 mol), and diisopropylethylamine (1.45 mol) in n-butanol (400 mL) is heated at reflux for 16 h. The reaction is cooled to rt and the mixture is diluted with water. The light yellow solid that precipitates is filtered to give 2-(4-(5-bromopyrimidin-2-ylamino)phenyl)ethanol 18. $^1$H NMR (300 MHz, d6-DMSO) δ 9.72 (s, 1H), 8.52 (s, 2H), 7.55 (m, 2H), 7.09 (d, 2H), 4.64 (m, 1H), 3.52 (m, 2H), 2.65 (m, 2H). MS (m/z) (M+1)+: 294.1, 296.1.

To a solution of 2-(4-(5-bromopyrimidin-2-ylamino)phenyl)ethanol 18 (6.22 mmol) in DCM (30 mL) is added triethylamine (9.33 mmol) and methanesulfonyl chloride (7.47 mmol). The reaction mixture is stirred at rt for 1.5 h. The reaction is diluted with H$_2$O (10 mL) and washed with Na$_2$CO$_3$ solution (3×10 mL). The organic layer is washed with brine, dried over MgSO$_4$ and concentrated to afford 4-(5-bromopyrimidin-2-ylamino)phenethyl methanesulfonate 19. $^1$H NMR (400 MHz, CD$_2$Cl$_2$) δ 8.36 (s, 2H), 7.65 (bs, 1H), 7.49 (d, J=8.8 Hz, 2H), 7.14 (d, J=8.4 Hz, 2H), 4.31 (t, J=6.8 Hz, 2H), 2.95 (t, J=6.8 Hz, 2H), 2.79 (s, 3H). MS (m/z) (M+1)$^+$: 372.0, 374.0.

The reaction mixture of 4-(5-bromopyrimidin-2-ylamino) phenethyl methanesulfonate 19 (1.55 mmol) and methyl isonipecotate (3.10 mmol) in DMF (5 mL) is stirred at 90° C. for 12 h. After the reaction is complete, Na$_2$CO$_3$ (2.0 M, 20 mL) is added and the resulting mixture is extracted with EtOAc (50 mL). The organic layer is separated and concentrated to give crude methyl 1-(4-(5-bromopyrimidin-2-ylamino)phenethyl)piperidine-4-carboxylate 20. MS (m/z) (M+1)$^+$: 419.1.

Crude methyl 1-(4-(5-bromopyrimidin-2-ylamino)phenethyl)piperidine-4-carboxylate 20 is suspended in THF/MeOH/H$_2$O (3:2:1, 10 mL) and 6N LiOH (9.3 mmol) and stirred at rt for 2 h. After neutralization to pH 6 by addition of HCl (1N), the solvent is removed under vacuum to give a solid which is dissolved in THF (20 mL). To the above suspension, excess Na$_2$SO$_4$ is added and filtered. The filtrate is concentrated to yield 1-(4-(5-bromopyrimidin-2-ylamino)phenethyl)piperidine-4-carboxylic acid 21. $^1$H NMR (400 MHz, d6-DMSO) δ 9.87 (s, 1H), 9.39 (bs, 1H), 8.59 (s, 2H), 7.66 (d, J=8.4 Hz, 2H), 7.20 (d, J=8.4 Hz, 2H), 3.58-3.64 (m, 2H), 3.48-3.28 (m, 1H), 3.22-3.27 (m, 2H), 2.88-3.03 (m, 4H), 2.05-2.15 (m, 2H), 1.66-1.80 (m, 2H). MS (m/z) (M+1)$^+$: 405.1, 407.1.

Synthesis of 2-(4-(5-(4-(difluoromethoxy)phenyl) pyrimidin-2-ylamino)phenyl)-3-hydroxypropanoic acid 26

2-(4-Aminophenyl)acetic acid (4.56 mmol), 5-bromo-2-chloropyrimidine 4 (3.26 mmol), and p-TSA (0.842 mmol) are heated at reflux in 1,4-dioxane (10 mL) and DMSO (2 mL) for 16 h. The mixture is poured onto water and extracted with EtOAc. Concentration of the organic phase gives 2-(4-(5-Bromopyrimidin-2-ylamino)phenyl)acetic acid 22 as a yellow solid. $^1$H NMR (400 MHz, d6-DMSO) δ 9.84 (s, 1H), 8.58 (s, 2H), 7.61 (d, J=8.4 Hz, 2H), 7.17 (d, J=8.4 Hz, 2H), 3.50 (s, 2H). MS (m/z) (M+1)$^+$: 308.0, 310.0.

2-(4-(5-Bromopyrimidin-2-ylamino)phenyl)acetic acid 22 (5.0 mmol) and HATU (6.0 mmol) are dissolved in dry DMF (10 mL) and stirred for 10 min. Then N,O-dimethylhydroxylamine (7.5 mmol) and diisopropylethylamine (15.0 mmol) are added to the solution. The reaction mixture is stirred for 1 h at rt. After the reaction is complete, the reaction mixture is added dropwise into water (100 mL). The precipitate is filtered and dried to yield 2-(4-(5-bromopyrimidin-2-ylamino) phenyl)-N-methoxy-N-methylacetamide 23. $^1$H NMR (400 MHz, d6-DMSO) δ 9.82 (s, 1H), 8.58 (s, 2H), 7.61 (d, J=8.4 Hz, 2H), 7.15 (d, J=8.4 Hz, 2H), 3.67 (s, 3H), 3.34 (s, 2H), 3.10 (s, 3H). MS (m/z) (M+1)$^+$: 351.0, 353.0.

2-(4-(5-Bromopyrimidin-2-ylamino)phenyl)-N-methoxy-N-methylacetamide 23 (2.0 mmol), paraformaldehyde (6.0 mmol) and sodium ethoxide (12.0 mmol) are dissolved in DMSO (10 mL). The reaction mixture is stirred at rt for 1 h. Then a solution of KOH (12.0 mmol) in H$_2$O (5.0 mL) and EtOH (5.0 mL) is added. The reaction mixture is heated at 50° C. for 5 h. After the reaction is completed, the reaction mixture is washed with DCM (50 mL). The aqueous phase is acidified to pH ~5 and extracted with DCM (2×50 mL). The organic layer is separated, dried and concentrated to yield-

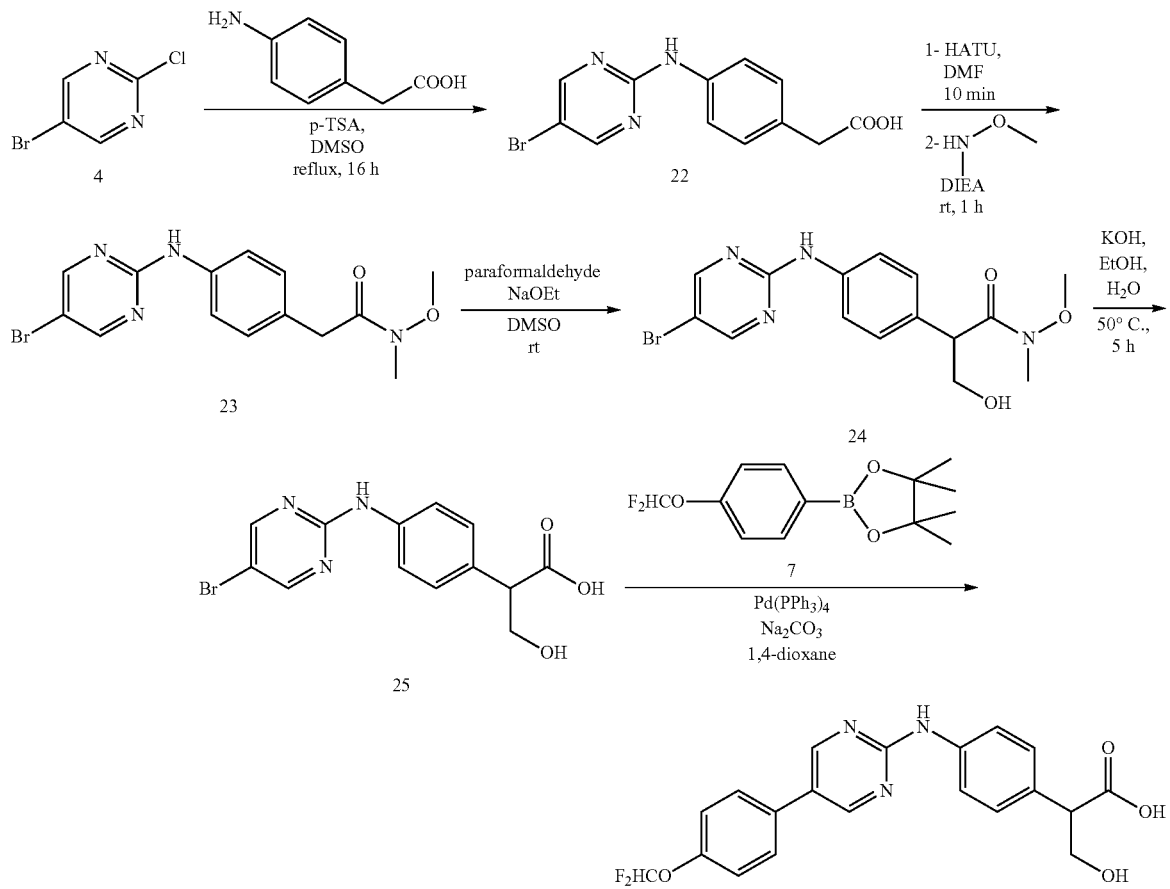

2-(4-(5-bromopyrimidin-2-ylamino)phenyl)-3-hydroxypropanoic acid 25, which is used in the next step without further purification. $^1$H NMR (400 MHz, d6-DMSO) δ 12.30 (bs, 1H), 9.84 (s, 1H), 8.57 (s, 2H), 7.61 (d, J=8.4 Hz, 2H), 7.21 (d, J=8.4 Hz, 2H), 3.90 (t, J=8.8 Hz, 1H), 3.49-3.61 (m, 2H), 3.35 (bs, 1H). MS (m/z) (M+1)$^+$: 338.0, 340.0.

To a solution of 2-(4-(5-bromopyrimidin-2-ylamino)phenyl)-3-hydroxypropanoic acid 25 (0.5 mmol) in 1,4-dioxane (2 mL) is added 2-(4-(difluoromethoxy)phenyl)-4,4,5,5-tetramethyl-1,3,2-dioxaborolane 7 (0.5 mmol), Na$_2$CO$_3$ (1.5 mmol of a 3.0 M aq. solution) and Pd(PPh$_3$)$_4$ (0.025 mmol). The reaction is evacuated and backfilled with nitrogen twice then heated at 150° C. for 10 min. The reaction mixture is diluted with water (10 mL). The aqueous layer is washed with DCM (2×50 mL) and acidified to pH 5 using aqueous HCl (1 N). The resulting mixture is extracted with DCM (2×50 mL). The organic layer is separated, dried over Na$_2$SO$_4$ and concentrated to yield a crude 2-(4-(5-(4-(difluoromethoxy)phenyl)pyrimidin-2-ylamino)phenyl)-3-hydroxypropanoic acid 26 which is used without further purification. $^1$H NMR (400 MHz, d6-DMSO) δ 9.65 (s, 1H), 8.79 (s, 2H), 7.76 (d, J=8.8 Hz, 2H), 7.60 (d, J=8.4 Hz, 2H), 7.30 (s, 1H), 7.27 (d, J=8.8 Hz, 2H), 7.17 (d, J=8.4 Hz, 2H), 3.60-3.70 (m, 2H), 3.50-3.58 (m, 2H), 3.20-3.26 (m, 2H). MS (m/z) (M+1)$^+$: 402.1.

Synthesis of -(5-(4-(difluoromethoxy)phenyl)pyrimidin-2-yl)-4-methylbenzene-1,3-diamine 29a

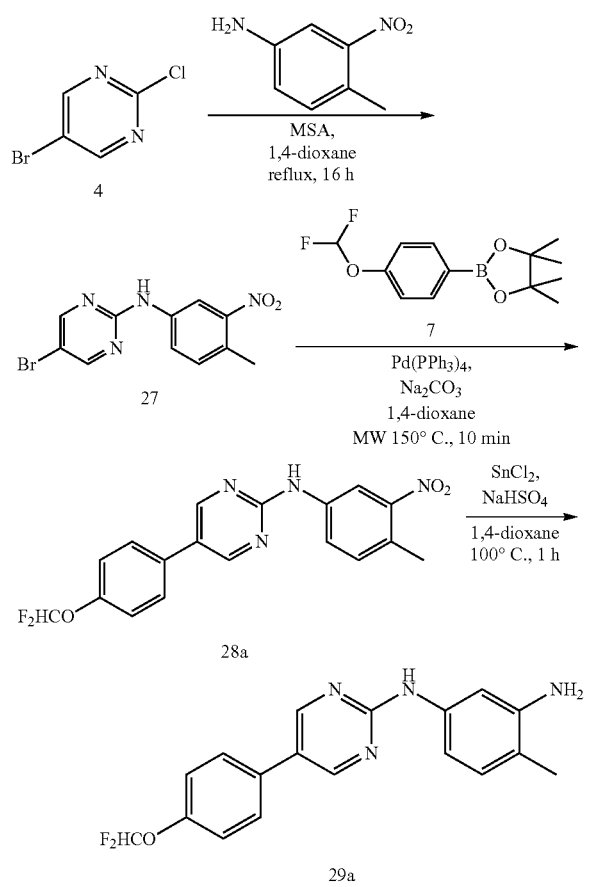

5-Bromo-2-chloropyrimidine 4 (50 mmol), 4-methyl-3-nitroaniline (60 mmol) and methylsulphonic acid (15 mmol) are heated at reflux in 1,4-dioxane (100 mL) for 16 h. The mixture is poured into water, filtered and dried under vacuum to give 5-bromo-N-(4-methyl-3-nitrophenyl)pyrimidin-2-amine 27 as a yellow solid. $^1$H NMR (400 MHz, d6-DMSO) δ 10.25 (s, 1H), 8.68 (s, 2H), 8.49 (d, J=2.0 Hz, 1H), 7.86 (dd, J=2.4, 8.4 Hz, 1H), 7.41 (d, J=8.4 Hz, 1H), 2.46 (s, 3H). MS (m/z) (M+1)$^+$: 309.0, 311.0.

To a solution of 5-bromo-N-(4-methyl-3-nitrophenyl)pyrimidin-2-amine 27 (0.5 mmol) in 1,4-dioxane (2.0 mL) is added 2-(4-(difluoromethoxy)phenyl)-4,4,5,5-tetramethyl-1,3,2-dioxaborolane 7 (0.5 mmol), Na$_2$CO$_3$ (1.5 mmol of a 3.0 M aq. solution) and Pd(PPh$_3$)$_4$ (0.025 mmol). The reaction is evacuated and backfilled with nitrogen twice then heated in the microwave oven at 150° C. for 10 min. The reaction mixture is diluted with water (10 mL) and extracted with DCM (2×50 mL). The organic layer is separated, dried over Na$_2$SO$_4$ and concentrated. Purification by preparative HPLC (ACN gradient 10-70%) affords 4-(difluoromethoxy)phenyl)-N-(4-methyl-3-nitrophenyl)pyrimidin-2-amine 28a. $^1$H NMR (400 MHz, d6-DMSO) δ 10.23 (s, 1H), 8.92 (s, 2H), 8.66 (d, J=2.4 Hz, 1H), 7.93 (dd, J=2.4, 8.4 Hz, 1H), 7.82 (d, J=8.4 Hz, 2H), 7.43 (d, J=8.4 Hz, 1H), 7.31 (t, J=74.0 Hz, 1H), 7.29 (d, J=8.4 Hz, 2H), 2.47 (s, 3H). MS (m/z) (M+1)$^+$: 373.1.

A suspension of 5-(4-(difluoromethoxy)phenyl)-N-(4-methyl-3-nitrophenyl)pyrimidin-2-amine 28a (1.5 mmol) and SnCl$_2$.2H$_2$O (4.5 mmol) in 1N NaHSO$_4$ (50 mL) and 1,4-dioxane (50 mL) is heated at 100° C. for 1 h. The solvent is removed under vacuum and the residue dissolved in 5% NaOH and extracted with DCM (3×50 mL). The organic layer is washed with 5% NaOH (1×50 mL), water (1×50 mL), brine, dried over Na$_2$SO$_4$ and concentrated to afford N1-(5-(4-(difluoromethoxy)phenyl)pyrimidin-2-yl)-4-methylbenzene-1,3-diamine 29a which is used without further purification. $^1$H NMR (400 MHz, d6-DMSO) δ 9.44 (s, 1H), 8.76 (s, 2H), 7.76 (d, J=8.4 Hz, 2H), 7.27 (d, J=8.8 Hz, 2H), 7.30 (t, J=74.4 Hz, 1H), 7.07 (d, J=2.0 Hz, 1H), 6.90 (dd, J=2.0, 8.0 Hz, 1H), 6.82 (d, J=8.4 Hz, 1H), 4.95 (bs, 2H), 2.02 (s, 3H). MS (m/z) (M+1)$^+$: 343.1.

Synthesis of 4-methyl-N1-(5-(4-(trifluoromethoxy)phenyl)pyrimidin-2-yl)benzene-1,3-diamine 29b

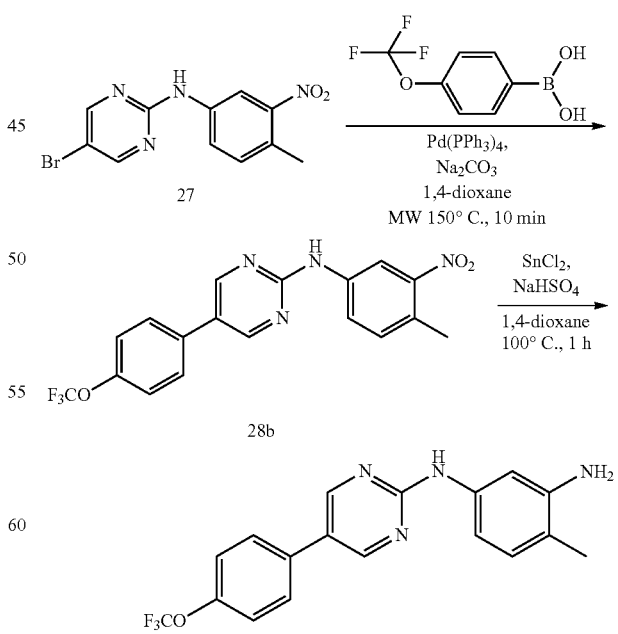

To a solution of 5-bromo-N-(4-methyl-3-nitrophenyl)pyrimidin-2-amine 27 (9.7 mmol) in 1,4-dioxane (29 mL) is added 4-(trifluoromethoxy)phenylboronic acid (10.7 mmol), $Na_2CO_3$ (29.2 mmol of 1.8 M aq. solution) and $Pd(PPh_3)_4$ (1.46 mmol). The reaction is evacuated and backfilled with nitrogen twice then heated at 100° C. for 12 h. The reaction mixture is diluted with water (20 mL) and extracted with EtOAc (2×50 mL). The organic layer is separated, dried over $Na_2SO_4$ and concentrated. Purification by preparative HPLC (ACN gradient 10-70%) affords N-(4-methyl-3-nitrophenyl)-5-(4-(trifluoromethoxy)phenyl)pyrimidin-2-amine 28b. MS (m/z) (M+1)$^+$: 390.1.

N-(4-methyl-3-nitrophenyl)-5-(4-(trifluoromethoxy)phenyl)pyrimidin-2-amine 28b (7.53 mmol) and $SnCl_2.2H_2O$ (33.2 mmol) are suspended in 6N HCl (40 mL). The mixture is heated at 100° C. for 3 h. The reaction vessel is chilled in an ice-water bath and 5% NaOH is added. The organic layer is extracted with EtOAc (3×50 mL), washed with brine (1×50 mL), dried over $Na_2SO_4$ and concentrated to afford 4-methyl-N1-(5-(4-(trifluoromethoxy)phenyl)pyrimidin-2-yl)benzene-1,3-diamine 29b which is used without further purification. $^1$H NMR (400 MHz, d6-DMSO) δ 9.54 (s, 1H), 8.84 (s, 2H), 7.88 (d, J=8.8 Hz, 2H), 7.51 (d, J=8.0 Hz, 2H), 7.12 (d, J=2.4 Hz, 1H), 6.94 (dd, J=2.0 and 8.0 Hz, 1H), 6.88 (d, J=8.4 Hz, 1H), 4.83 (bs, 2H), 2.07 (s, 3H). MS (m/z) (M+1)$^+$: 361.1.

Synthesis of
2-chloro-5-(4-(difluoromethoxy)phenyl)pyrimidine
30

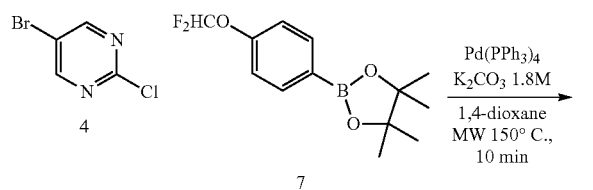

To a solution of 5-bromo-2-chloropyrimidine 4 (7.7 mmol) in 1,4-dioxane (1.5 mL) is added 2-(4-(difluoromethoxy)phenyl)-4,4,5,5-tetramethyl-1,3,2-dioxaborolane 7 (8.9 mmol), 1.8M $K_2CO_3$ aq. (16.2 mmol) and $Pd(PPh_3)_4$ (0.38 mmol). The reaction is evacuated and backfilled with nitrogen twice then heated at 150° C. for 10 min under microwave. After this time, the reaction mixture is diluted with a saturated solution of $NH_4Cl$ and extracted with DCM (3×50 mL). The organic layer is washed with brine, dried over $Na_2SO_4$ and concentrated. Purification by short silica gel chromatography using a hexane:EtOAc=3:1 mixture affords 2-chloro-5-(4-(difluoromethoxy)phenyl)pyrimidine 30. $^1$HNMR (400 MHz, $CDCl_3$) δ 8.73 (s, 2H), 7.47-7.52 (m, 2H), 7.20-7.24 (m, 2H), 6.52 (t, J=72 Hz, 1H). MS (m/z) (M+1)$^+$: 257.0.

Synthesis of 2-(4-(5-(4-(difluoromethoxy)phenyl)pyrimidin-2-ylamino)phenyl)-3-hydroxypropanoic acid 26

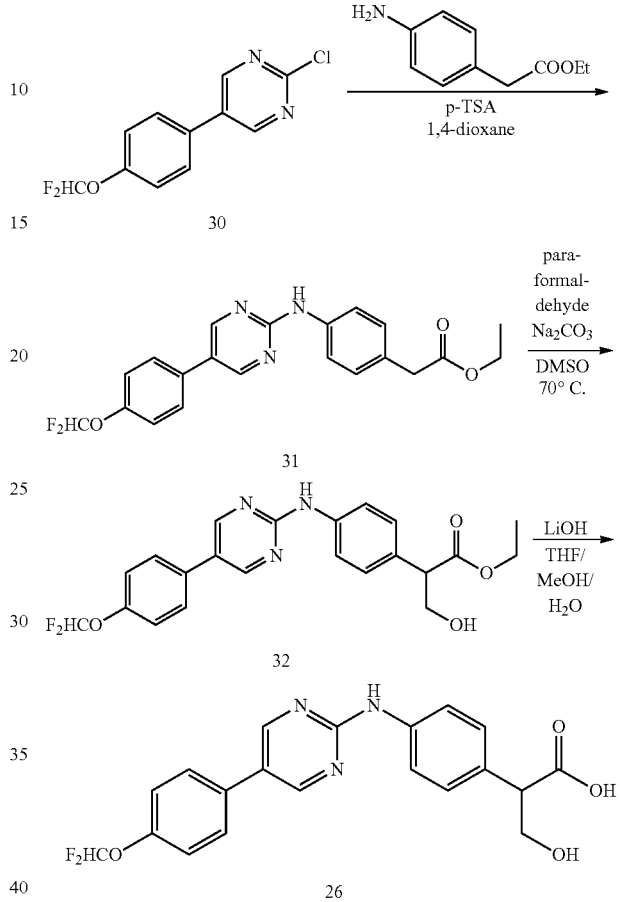

A mixture of ethyl 2-(4-aminophenyl)acetate (8 mmol), 2-chloro-5-(4-(difluoromethoxy)phenyl)pyrimidine 30 (4 mmol), and p-TSA (2 mmol) in 1,4-dioxane (4 mL) are heated at reflux for 4 h. The mixture is poured onto 1 N HCl. The solid is filtered, washed with 1 N HCl and dried to afford ethyl 2-(4-(5-(4-(difluoromethoxy)phenyl)pyrimidin-2-ylamino)phenyl)acetate 31 as a yellow solid. $^1$H NMR (400 MHz, $CDCl_3$) δ 8.57 (s, 2H), 7.92 (s, 1H), 7.54 (d, J=8.5 Hz, 2H), 7.43 (d, J=8.6 Hz, 2H), 7.23 (d, J=8.6 Hz, 2H), 7.18 (d, J=9.1 Hz, 2H), 6.49 (t, J=73.5 Hz, 1H), 4.09 (q, J=7.1 Hz, 2H), 3.54 (s, 2H), 1.19 (t, J=7.1 Hz, 3H). MS (m/z) (M+1)$^+$: 400.1.

Ethyl 2-(4-(5-(4-(difluoromethoxy)phenyl)pyrimidin-2-ylamino)phenyl)acetate 31 (1 mmol) and paraformaldehyde (5 mmol.) are dissolved in dry DMSO (0.2-0.5M) and heated at 70° C. in the presence of $Na_2CO_3$ (5 mmol.) for 2-6 h until greater than 50% conversion is achieved by LC/MS monitoring. The mixture is diluted with EtOAc and washed with water. After concentration, the residue is purified by silica gel chromatography to yield ethyl 2-(4-(5-(4-(difluoromethoxy)phenyl)pyrimidin-2-ylamino)phenyl)-3-hydroxypropanoate 32. MS (m/z) (M+1)$^+$: 432.1.

To a solution of ethyl 2-(4-(5-(4-(difluoromethoxy)phenyl)pyrimidin-2-ylamino)phenyl)-3-hydroxypropanoate 32 (1 mmol) in THF:MeOH:water (3:2:1 v/v) is added 6 N LiOH (3 mmol). The reaction mixture is stirred at rt for 1 h until complete by LC/MS and diluted with water. The aqueous layer is washed with DCM (2×30 mL) and acidified to pH=5 using aqueous 1N HCl. The resulting mixture is extracted with DCM (3×50 mL). The organic layer is separated, dried over Na$_2$SO$_4$ and concentrated to yield a crude product, which upon crystallization from water yield 2-(4-(5-(4-(difluoromethoxy)phenyl)pyrimidin-2-ylamino)phenyl)-3-hydroxypropanoic acid, 26 as off white solid. $^1$H NMR (400 MHz, d6-DMSO) δ 9.65 (s, 1H), 8.79 (s, 2H), 7.76 (d, J=8.8 Hz, 2H), 7.60 (d, J=8.4 Hz, 2H), 7.30 (s, 1H), 7.27 (d, J=8.8 Hz, 2H), 7.17 (d, J=8.4 Hz, 2H), 3.60-3.70 (m, 2H), 3.50-3.58 (m, 2H), 3.20-3.26 (m, 2H). MS (m/z) (M+1)$^+$: 402.1.

Chiral HPLC separation using a (R,R)-WelkO-1 column and hexane:ethanol:methanol=75:12.5:12.5 0.1% diethylamine as gradient affords the two enantiomers 26a (first peak eluted) and 26b (second peak eluted). The enantiomer 26a is arbitrarily assigned the R configuration whereas enantiomer 26b is arbitrarily assigned the S configuration.

Synthesis of 2-(trifluoromethyl)piperazine 35a

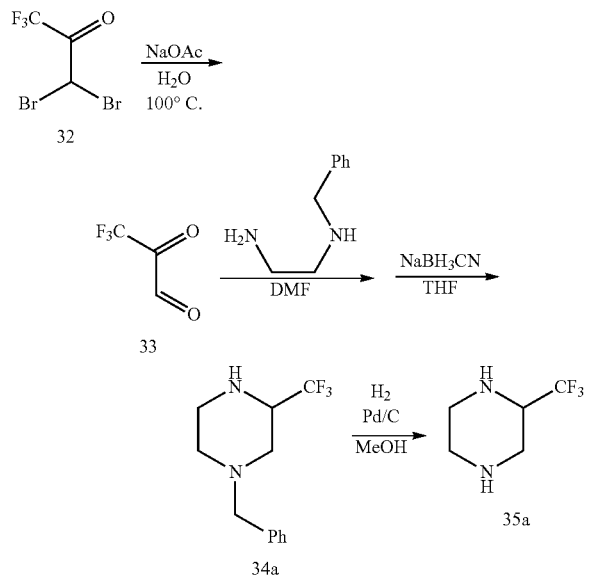

A mixture of 3,3-dibromo-1,1,1-trifluoropropan-2-one 32 (38.4 mmol) and NaOAc (153.7 mmol) in H$_2$O (50 mL) is heated at 100° C. for 12 h. Extraction of aqueous mixture with EtOAc (2×50 mL) and concentration of organic phase affords a crude oil. To the above residue is added DMF (30 mL), and the solution is cooled to 0° C. Then a solution of N1-benzylethane-1,2-diamine (2.3 mL) in DMF (15 mL) is added. The resulting reaction mixture is stirred at rt for 12 h. Solvent is removed under vacuum to afford a residue which is dissolved in THF (15 mL) and citrate buffer (30 mL), followed by addition of 1M NaBH$_3$CN (25 mL). The mixture is stirred at rt for 12 h. The organic solvent is removed under vacuum and the resulting residue is basified to pH=8 by addition of 1N NaOH. Extraction of aqueous solution with DCM (2×50 mL) and concentration of the organic phase yield a crude oil which is purified by silica gel chromatography using a hexane:EtOAc=3:1 to afford 1-benzyl-3-(trifluoromethyl)piperazine 34a. $^1$H NMR (400 MHz, d2-DCM) δ 7.37-7.25 (m, 5H), 3.57 (d, 2H), 3.35-3.45 (m, 1H), 3.05-3.10 (m, 1H), 2.87-3.00 (m, 2H), 2.74-2.80 (m, 1H), 2.10-2.18 (m, 2H), 1.74 (s, 1H). MS (m/z) (M+1)$^+$: 245.1.

1-Benzyl-3-(trifluoromethyl)piperazine 34a (4.1 mmol) is dissolved in MeOH (50 mL) followed by addition of AcOH (2.0 mL) and 5% mol of Pd/C. The flask is charged with a hydrogen balloon and stirred for 12 h. The mixture is filtered over celite and the filtrate is concentrated to afford 2-(trifluoromethyl)piperazine 35a, which is used without further purification. MS (m/z) (M+1)$^+$: 155.1.

Synthesis of Ethyl 2-(trifluoromethyl)piperazine-1-carboxylate 35b

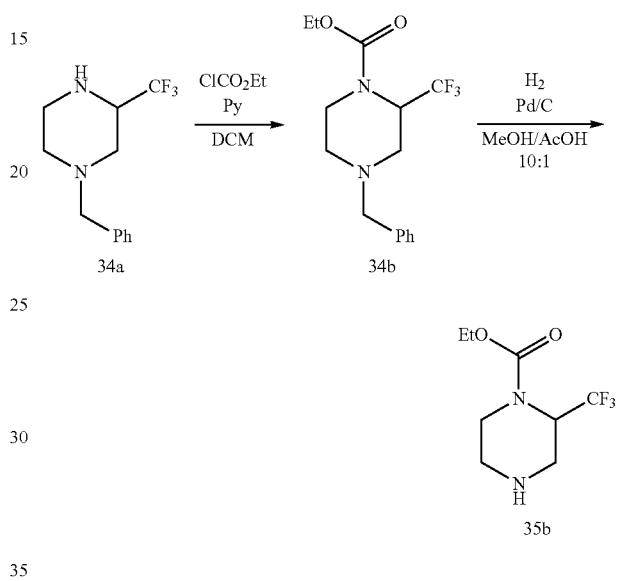

To a solution of 1-benzyl-3-(trifluoromethyl)piperazine 34a (1.0 mmol) and pyridine (1.1 mmol) in DCM (5 mL), is added ethyl chloroformate (1.1 mmol). The resulting mixture is stirred at rt for 1 h. After the reaction is complete, the reaction mixture is diluted with DCM (15 mL) and washed with water. The organic layer is separated, dried over Na$_2$SO$_4$, filtered, and concentrated to afford ethyl 4-benzyl-2-(trifluoromethyl)piperazine-1-carboxylate 34b, which is used without purification. MS (m/z) (M+1)$^+$: 317.1.

Ethyl 4-benzyl-2-(trifluoromethyl)piperazine-1-carboxylate 34b (1.0 mmol) is dissolved in MeOH (10 mL) followed by addition of AcOH (1.0 mL) and 5% mol of Pd/C. The flask is charged with a hydrogen balloon and stirred for 12 h. The mixture is filtered over celite and the filtrate is concentrated to afford 2-(trifluoromethyl)piperazine 1-carboxylate 35b, which is used without further purification. MS (m/z) (M+1)$^+$: 227.1.

Preparation of Final Compounds

Type A Compounds

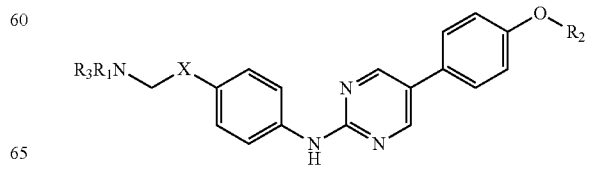

Example A1

N-(4-(2-(diethylamino)ethoxy)phenyl)-5-(4-(trifluoromethoxy)phenyl)pyrimidin-2-amine

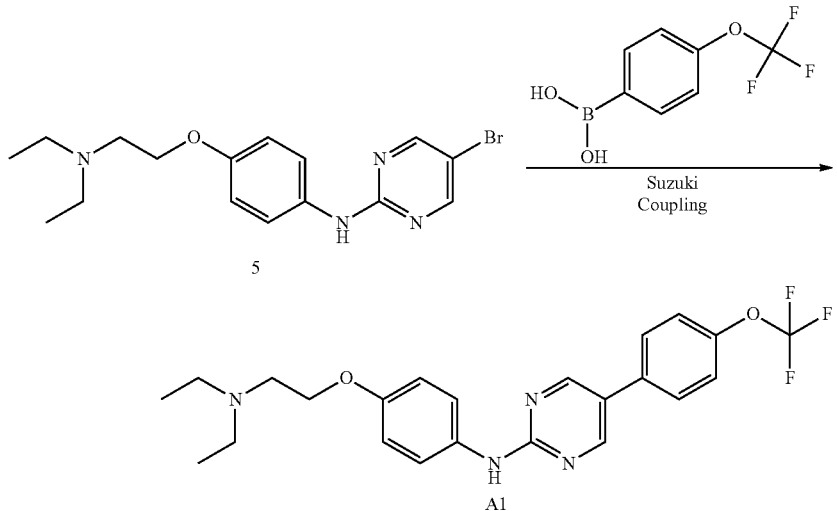

To a solution of (5-bromo-pyrimidin-2-yl)-[4-(2-diethylamino-ethoxy)-phenyl-amine 5 (0.5 mmol) in 1,4-dioxane (2.0 mL) is added 4-(trifluoromethoxy)phenylboronic acid (0.5 mmol), 3M Na₂CO₃ (1.5 mmol) and Pd(PPh₃)₄ (0.025 mmol). The reaction is evacuated and backfilled with nitrogen twice then heated at 150° C. for 10 min. Purification by preparative HPLC (ACN gradient 10-70%) affords N-(4-(2-(diethylamino)ethoxy)phenyl)-5-(4-(trifluoromethoxy)phenyl)pyrimidin-2-amine A1. MS (m/z) (M+1)$^+$: 447.2.

Example A2

N-(4-(2-(diethylamino)ethoxy)phenyl)-5-(4-(difluoromethoxy)phenyl)pyrimidin-2-amine To a solution of (5-bromo-pyrimidin-2-yl)-[4-(2-diethylamino-ethoxy)-phenyl-amine 5 (0.5 mmol) in 1,4-dioxane (2.0 mL) is added 2-(4-(difluoromethoxy)phenyl)-4,4,5,5-tetramethyl-1,3,2-dioxaborolane 7 (0.5 mmol), 3M Na₂CO₃ (1.5 mmo) and Pd(PPh₃)₄ (0.025 mmol). The reaction is evacuated and backfilled with nitrogen twice then heated at 150° C. for 10 min. Purification by preparative HPLC (ACN gradient 10-70%) affords N-(4-(2-(diethylamino)ethoxy)phenyl)-5-(4-(difluoromethoxy)phenyl)pyrimidin-2-amine A2. $^1$H NMR (400 MHz, d6-DMSO) δ 9.68 (s, 1H), 8.78 (s, 2H), 7.76 (d, J=8.8 Hz, 2H), 7.71 (d, J=9.2 Hz, 2H), 7.28 (t, J=74.0 Hz, 1H), 7.27 (d, J=8.4 Hz, 2H), 6.98 (d, J=8.8 Hz, 1H), 4.28 (t, J=4.8 Hz, 2H), 3.51 (m, 2H), 3.23 (m, 4H), 1.24 (t, J=7.2 Hz, 6H). MS (m/z) (M+1)$^+$: 429.2.

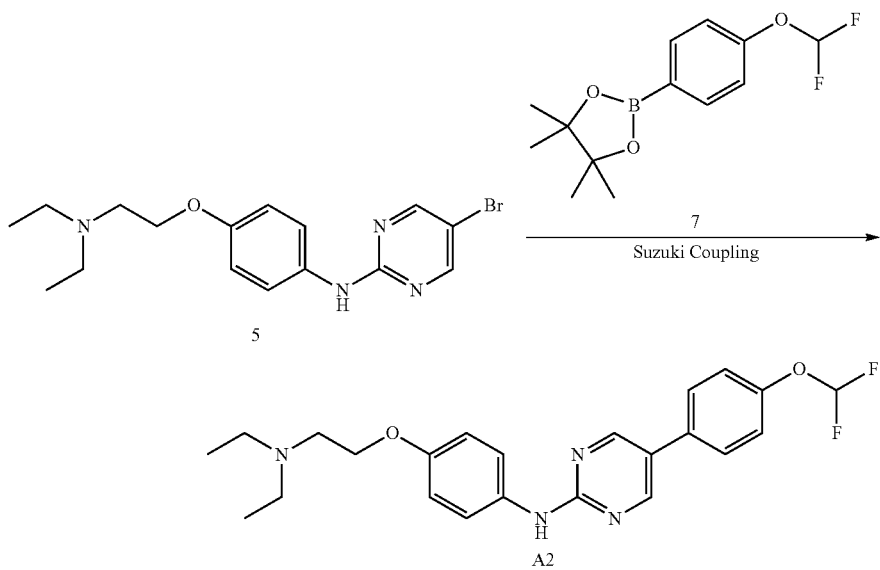

Example A3

1-(2-(4-(5-(4-(difluoromethoxy)phenyl)pyrimidin-2-ylamino)phenoxy)ethyl)piperidine-4-carboxylic acid

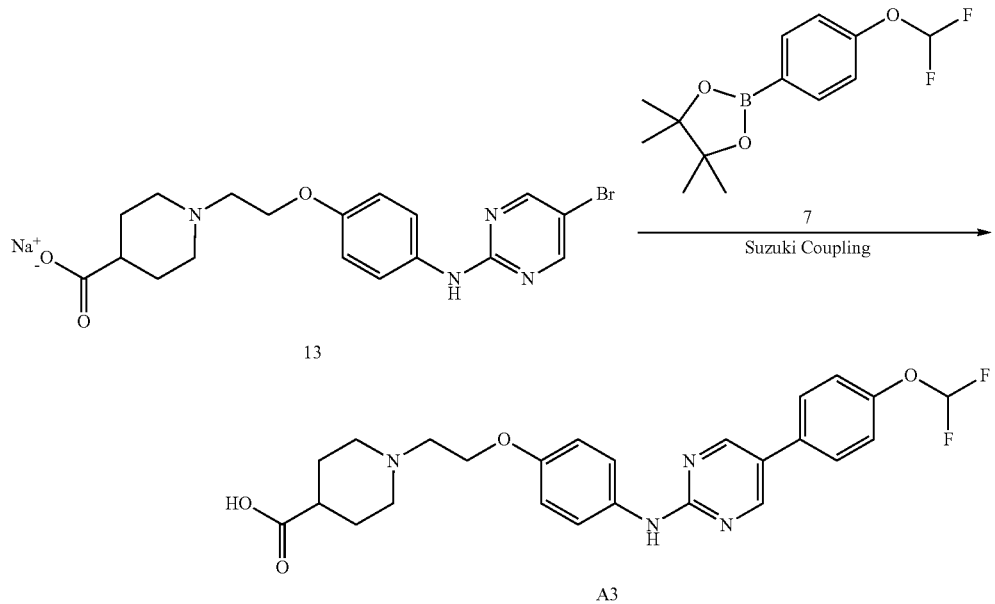

To a solution of sodium 1-(2-(4-(5-bromopyrimidin-2-ylamino)phenoxy)ethyl)piperidine-4-carboxylate 13 (0.05 mmol) in 1,4-dioxane (1.0 mL) is added 2-(4-(difluoromethoxy)phenyl)-4,4,5,5-tetramethyl-1,3,2-dioxaborolane 7 (0.05 mmol), 3M Na$_2$CO$_3$ (0.15 mmol) and Pd(PPh$_3$)$_4$ (0.0025 mmol). The reaction is evacuated and backfilled with nitrogen twice then heated at 150° C. for 10 min. Purification by prep-HPLC (ACN gradient 10-70%) affords 1-(2-(4-(5-(4-(difluoromethoxy)phenyl)pyrimidin-2-ylamino)phenoxy)ethyl)piperidine-4-carboxylic acid A3. $^1$H NMR (400 MHz, d6-DMSO) δ 9.68 (s, 1H), 8.78 (s, 2H), 7.76 (d, J=8.8 Hz, 2H), 7.71 (d, J=9.2 Hz, 2H), 7.28 (t, J=74.0 Hz, 1H), 7.27 (d, J=8.4 Hz, 2H), 6.98 (d, J=8.8 Hz, 1H), 4.28 (t, J=4.8 Hz, 2H), 3.51 (m, 2H), 3.23 (m, 4H), 1.24 (t, J=7.2, 6H). MS (m/z) (M+1)$^+$: 485.2.

Example A4

1-(4-(5-(4-(difluoromethoxy)phenyl)pyrimidin-2-ylamino)benzyl)piperidine-4-carboxylic acid

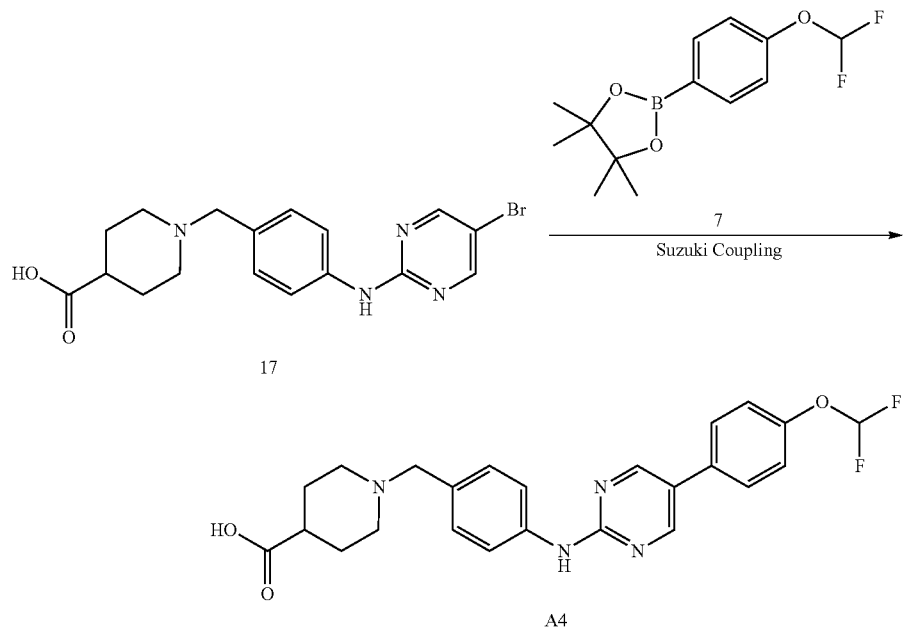

To a solution of 1-(4-(5-bromopyrimidin-2-ylamino)benzyl)piperidine-4-carboxylic acid 17 (0.05 mmol) in 1,4-dioxane (1.0 mL) is added 2-(4-(difluoromethoxy)phenyl)-4,4,5,5-tetramethyl-1,3,2-dioxaborolane 7 (0.05 mmol), 3M Na$_2$CO$_3$ (0.15 mmol) and Pd(PPh$_3$)$_4$ (0.0025 mmol). The reaction is evacuated and backfilled with nitrogen twice then heated at 150° C. for 10 min. Purification by preparative HPLC (ACN gradient 10-70%) affords 1-(4-(5-(4-(difluoromethoxy)phenyl)pyrimidin-2-ylamino)benzyl)piperidine-4-carboxylic acid A4. $^1$H NMR (400 MHz, d4-MeOH) δ 8.64 (s, 2H), 7.78 (d, J=8.8 Hz, 2H), 7.56 (d, J=8.8 Hz, 2H), 7.32 (d, J=8.8 Hz, 2H), 7.16 (d, J=8.8 Hz, 2H), 6.78 (t, J=74.0 Hz, 1H), 4.11 (s, 2H), 3.31 (m, 2H), 2.92 (m, 2H), 2.36 (m, 1H), 2.02 (m, 2H), 1.81 (m, 2H). MS (m/z) (M+1)$^+$: 455.2.

Example A5

1-(4-(5-(4-(trifluoromethoxy)phenyl)pyrimidin-2-ylamino)benzyl)piperidine-4-carboxylic acid

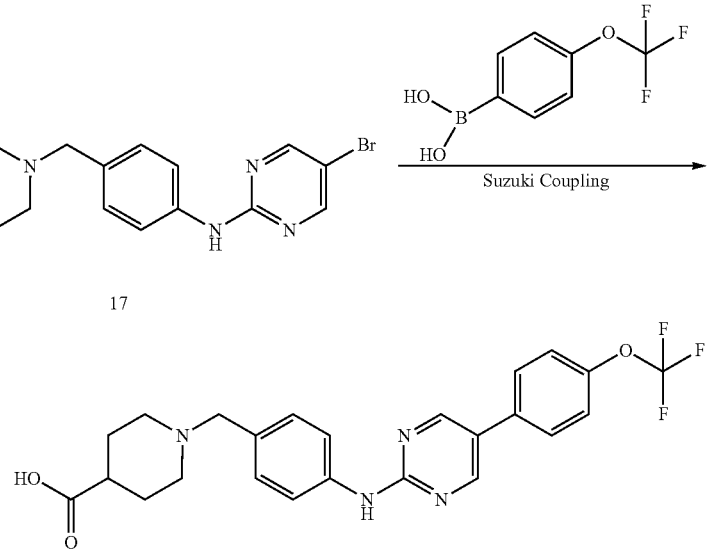

To a solution of 1-(4-(5-bromopyrimidin-2-ylamino)benzyl)piperidine-4-carboxylic acid 17 (0.05 mmol) in 1,4-dioxane (1.0 mL) is added 4-(trifluoromethoxy)phenylboronic acid (0.05 mmol), 3M Na$_2$CO$_3$ (0.15 mmol) and Pd(PPh$_3$)$_4$ (0.0025 mmol). The reaction is evacuated and backfilled with nitrogen twice then heated at 150° C. for 10 min. Purification by preparative HPLC (ACN gradient 10-70%) affords 1-(4-(5-(4-(trifluoromethoxy)phenyl)pyrimidin-2-ylamino)benzyl)piperidine-4-carboxylic acid A5. $^1$H NMR (400 MHz, d6-DMSO) δ 10.06 (s, 1H), 8.89 (s, 2H), 7.88 (M, 4H), 7.48 (d, J=8.4 Hz, 2H), 7.42 (d, J=8.0 Hz, 2H), 4.23 (s, 2H), 2.95 (m, 1H), 2.51 (m, 4H), 2.09 (m, 2H), 1.71 (m, 2H). MS (m/z) (M+1)$^+$: 473.2.

Example A6

1-(4-(5-(4-(difluoromethoxy)phenyl)pyrimidin-2-ylamino)phenethyl)piperidine-4-carboxylic acid

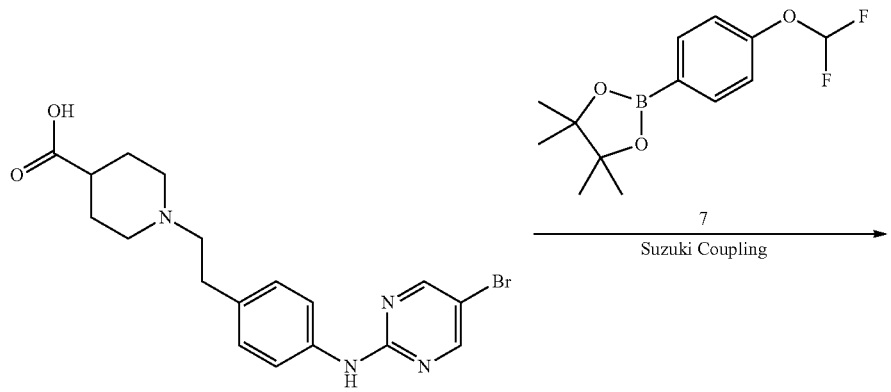

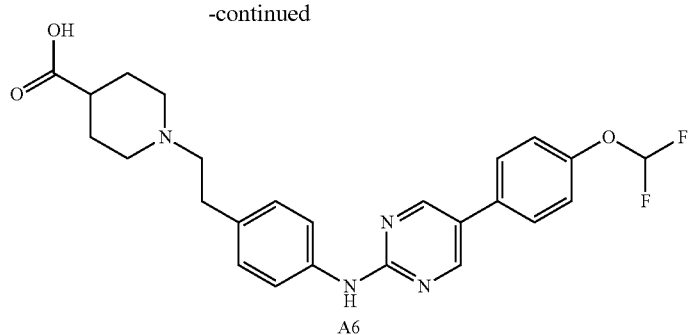

A6

To a solution of 1-(4-(5-bromopyrimidin-2-ylamino)phenethyl)piperidine-4-carboxylic acid 21 (0.05 mmol) in 1,4-dioxane (1.0 mL) is added 2-(4-(difluoromethoxy)phenyl)-4,4,5,5-tetramethyl-1,3,2-dioxaborolane 7 (0.05 mmol), 3M Na$_2$CO$_3$ (0.15 mmol) and Pd(PPh$_3$)$_4$ (0.0025 mmol). The reaction is evacuated and backfilled with nitrogen twice then heated in a microwave oven at 150° C. for 10 min. Purification by preparative HPLC (ACN gradient 10-70%) affords 1-(4-(5-(4-(difluoromethoxy)phenyl)pyrimidin-2-ylamino)phenethyl)piperidine-4-carboxylic acid A6. MS (m/z) (M+1)$^+$: 469.2.

Type B Compounds

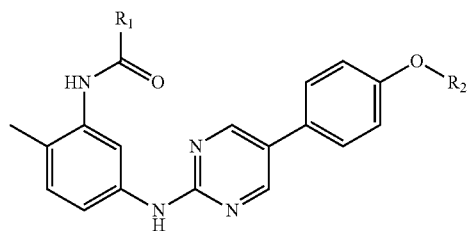

B

Example B1

N-(5-(5-(4-(difluoromethoxy)phenyl)pyrimidin-2-ylamino)-2-methylphenyl)-1-methylpiperidine-2-carboxamide

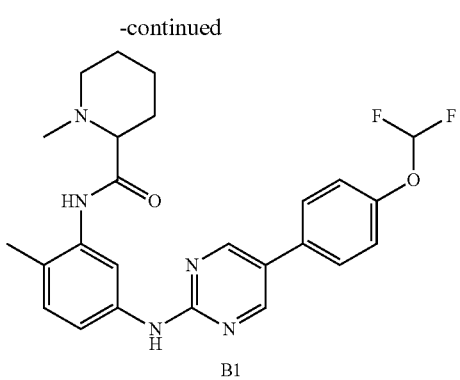

B1

N1-(5-(4-(difluoromethoxy)phenyl)pyrimidin-2-yl)-4-methylbenzene-1,3-diamine 29a (0.1 mmol), 1-methylpiperidine-2-carboxylic acid (0.1 mmol) and HATU (0.15 mmol) are dissolved in dry DMF (0.5 mL) at rt. Diisopropylethylamine (0.50 mmol) is added to the solution. The reaction mixture is stirred for 1 h at rt. HPLC purification affords the target compound B1 as a TFA salt. MS (m/z) (M+1)$^+$: 468.2.

Example B4

(R)-N-(5-(5-(4-(difluoromethoxy)phenyl)pyrimidin-2-ylamino)-2-methylphenyl)-5-oxopyrrolidine-2-carboxamide

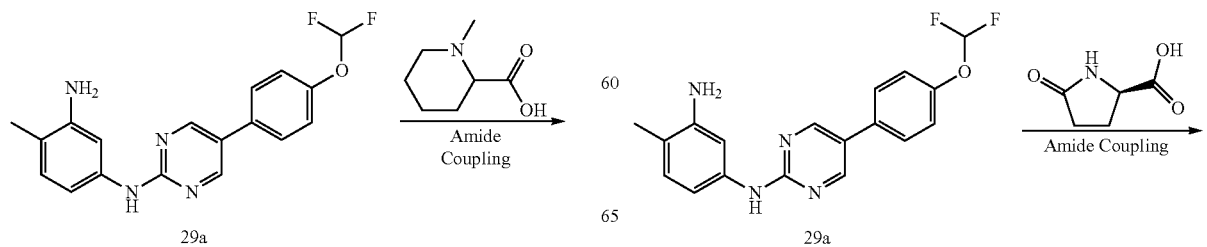

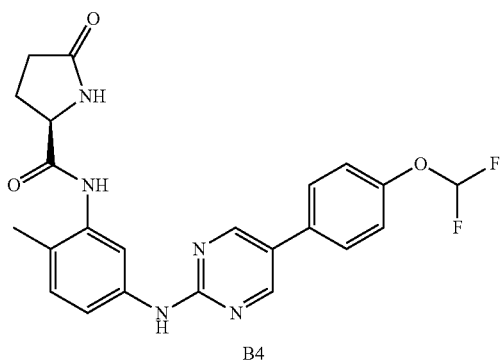

B4

Similar to the preparation of B1. $^1$H NMR (400 MHz, d6-DMSO) δ 9.76 (s, 1H), 9.47 (s, 1H), 8.81 (s, 2H), 7.95 (s, 1H), 7.77 (m, 3H), 7.55 (dd, J=2.0, 8.8 Hz, 1H), 7.29 (t, J=74.4 Hz, 1H), 7.27 (d, J=9.2 Hz, 2H), 7.13 (d, J=8.4 Hz, 1H), 4.26 (m, 1H), 2.40 (m, 2H), 2.14 (s, 3H), 2.04 (m, 2H). MS (m/z) (M+1)$^+$: 454.2.

Example B5

N-(5-(5-(4-(difluoromethoxy)phenyl)pyrimidin-2-ylamino)-2-methylphenyl)-6-oxopiperidine-3-carboxamide

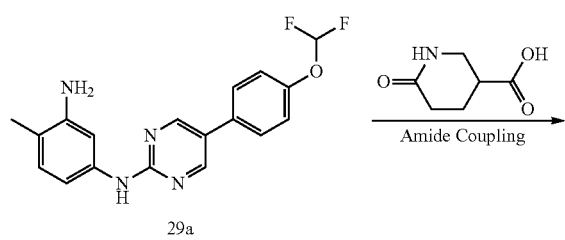

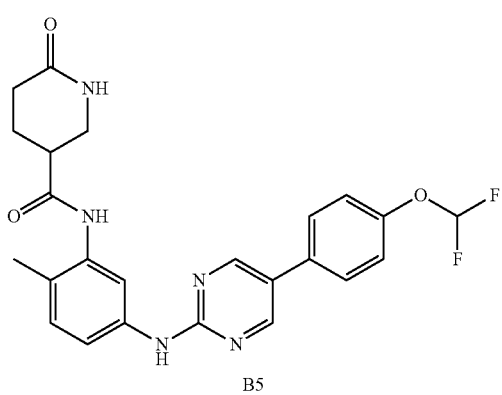

B5

Similar to the preparation of B1. $^1$H NMR (400 MHz, d6-DMSO) δ 9.75 (s, 1H), 9.50 (s, 1H), 8.81 (s, 2H), 7.78 (d, J=8.8 Hz, 2H), 7.74 (d, J=2.0 Hz, 1H), 7.56 (m, 2H), 7.30 (t, J=74.0 Hz, 1H), 7.28 (d, J=8.4 Hz, 2H), 7.13 (d, J=8.4 Hz, 1H), 3.34 (m, 2H), 2.86 (m, 1H), 2.25 (m, 2H), 2.12 (s, 3H), 2.03 (m, 1H), 1.92 (m, 1H). MS (m/z) (M+1)$^+$: 468.2.

Example B6

N-(5-(5-(4-(difluoromethoxy)phenyl)pyrimidin-2-ylamino)-2-methylphenyl)-6-fluoropyridine-3-carboxamide

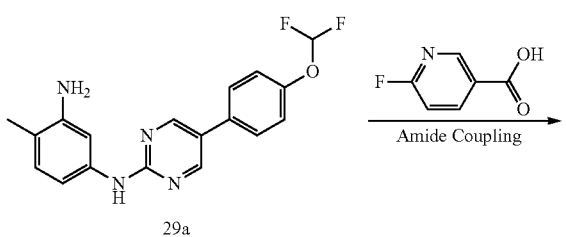

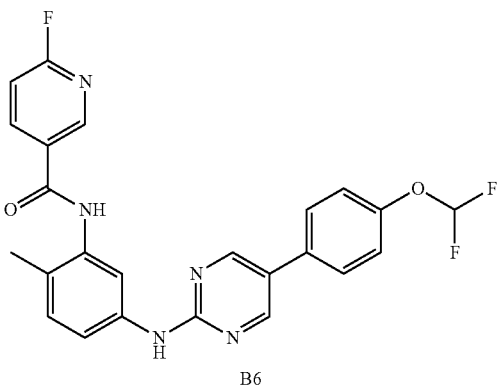

B6

Similar to the preparation of B1. $^1$H NMR (400 MHz, d6-DMSO) δ 10.21 (s, 1H), 9.85 (s, 1H), 8.88 (s, 1H), 8.55 (m, 1H), 7.86 (s, 1H), 7.79 (d, J=8.8 Hz, 2H), 7.64 (dd, J=2.0, 8.4 Hz, 1H), 7.40 (dd, J=2.4, 8.4 Hz, 1H), 7.31 (t, J=74.0 Hz, 1H), 7.30 (d, J=8.0 Hz, 2H), 7.24 (d, J=8.4 Hz, 1H), 2.21 (s, 3H). MS (m/z) (M+1)$^+$: 466.1.

Example B7

N-(5-(5-(4-(difluoromethoxy)phenyl)pyrimidin-2-ylamino)-2-methylphenyl)-1H-imidazole-5-carboxamide

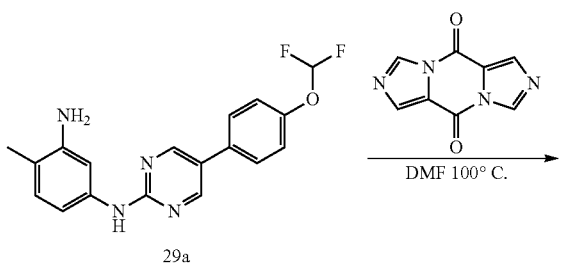

-continued

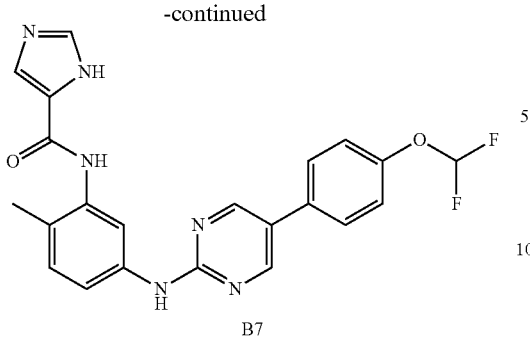

B7

N1-(5-(4-(difluoromethoxy)phenyl)pyrimidin-2-yl)-4-methylbenzene-1,3-diamine 29a (0.1 mmol) and 5H,10H-diimidazo[1,5-a:1',5'-d]pyrazine-5,10-dione (0.1 mmol) in dry DMF (0.5 mL) are heated at 110° C. for 24 h. HPLC purification affords the target compound B7 as a TFA salt. $^1$H NMR (400 MHz, d6-DMSO) δ 9.80 (s, 2H), 8.81 (s, 2H), 8.44 (s, 1H), 8.04 (s, 2H), 7.77 (d, J=8.8 Hz, 2H), 7.57 (m, 1H), 7.28 (t, J=74.0 Hz, 1H), 7.27 (d, J=8.4 Hz, 2H), 7.19 (d, J=8.4 Hz, 1H), 2.20 (s, 3H). MS (m/z) (M+1)$^+$: 437.2.

Example B8

(S)-N-(2-methyl-5-(5-(4-(trifluoromethoxy)phenyl)pyrimidin-2-ylamino)phenyl)-5-oxopyrrolidine-2-carboxamide

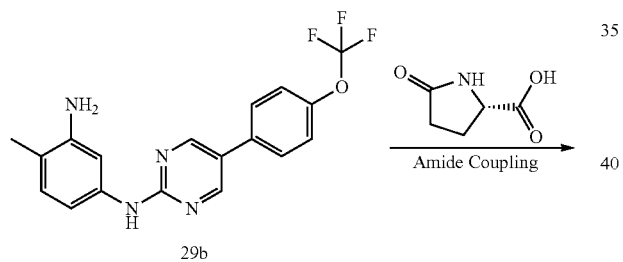

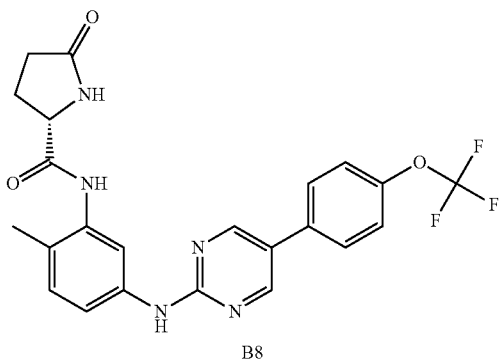

B8

4-Methyl-N1-(5-(4-(trifluoromethoxy)phenyl)pyrimidin-2-yl)benzene-1,3-diamine 29b (0.1 mmol), (S)-5-oxopyrrolidine-2-carboxylic acid (0.1 mmol) and HATU (0.15 mmol) are dissolved in dry DMF (0.5 mL) at rt. Diisopropylethylamine (0.50 mmol) is added to the solution and the reaction mixture is stirred for 1 h at rt. HPLC purification affords the target compound B8 as a TFA salt. MS (m/z) (M+1)$^+$: 473.1.

Example B9

N-(5-(5-(4-(difluoromethoxy)phenyl)pyrimidin-2-ylamino)-2-methylphenyl)-1-cyclopropyl-5-oxopyrrolidine-3-carboxamide

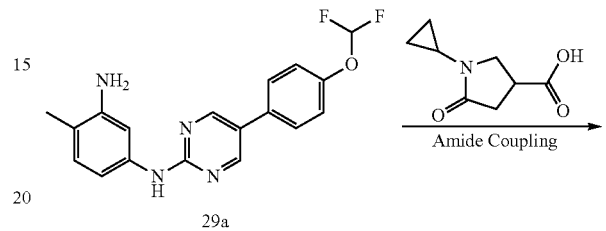

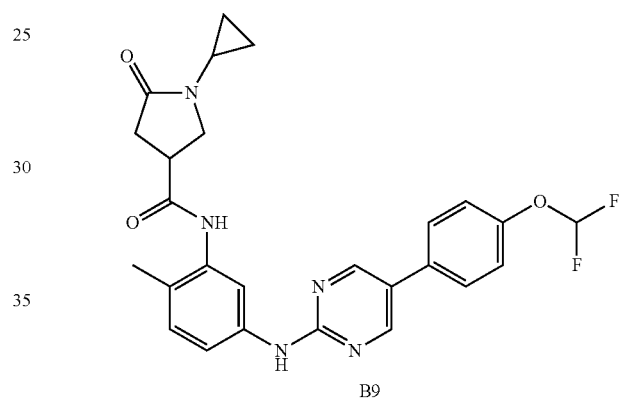

B9

Similar to the preparation of B1. $^1$H NMR (400 MHz, d4-MeOD) δ 8.84 (s, 2H), 7.71 (m, 3H), 7.36 (s, 2H), 7.29 (d, J=8.0 Hz, 2H), 6.91 (t, J=74.0 Hz, 1H), 3.52-3.56 (m, 2H), 3.46 (m, 1H), 2.74 (m, 2H), 2.64 (m, 1H), 2.29 (s, 3H), 0.77 (m, 4H). MS (m/z) (M+1)$^+$: 494.2.

Example B10

N-(5-(5-(4-(difluoromethoxy)phenyl)pyrimidin-2-ylamino)-2-methylphenyl)-1-ethyl-6-oxopiperidine-3-carboxamide

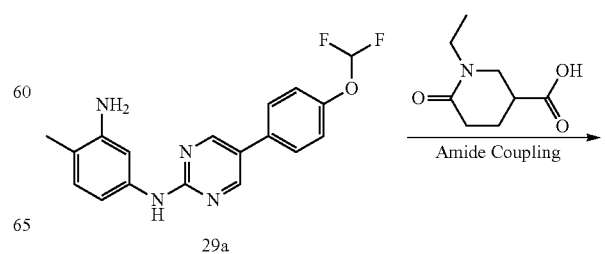

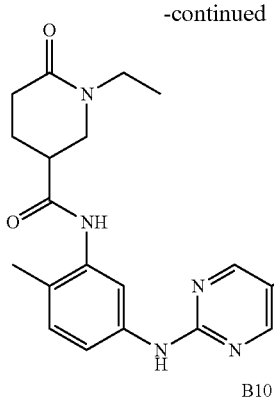

B10

Similar to the preparation of B1. $^1$H NMR (400 MHz, d6-DMSO) δ 9.75 (s, 1H), 9.52 (s, 1H), 8.79 (s, 2H), 7.76 (m, 3H), 7.55 (m, 1H), 7.28 (d, J=8.0 Hz, 2H), 7.27 (t, J=74.0 Hz, 1H), 7.13 (d, J=8.0 Hz, 1H), 3.2-3.5 (m, 2H), 2.9-3.0 (m, 1H), 2.5 (m, 2H), 2.3 (m, 2H), 2.13 (s, 3H), 1.80-2.08 (m, 2H), 1.05 (t, J=6.8 Hz, 3H). MS (m/z) (M+1)$^+$: 496.2.

Type C Compounds

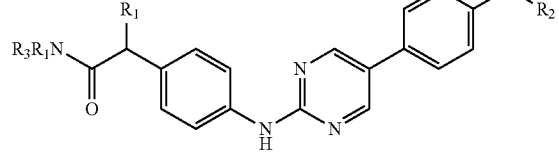

C

Example C1

2-(4-(5-(4-(difluoromethoxy)phenyl) pyrimidin-2-ylamino)phenyl)-N-(2-fluoroethyl)-3-hydroxypropanamide

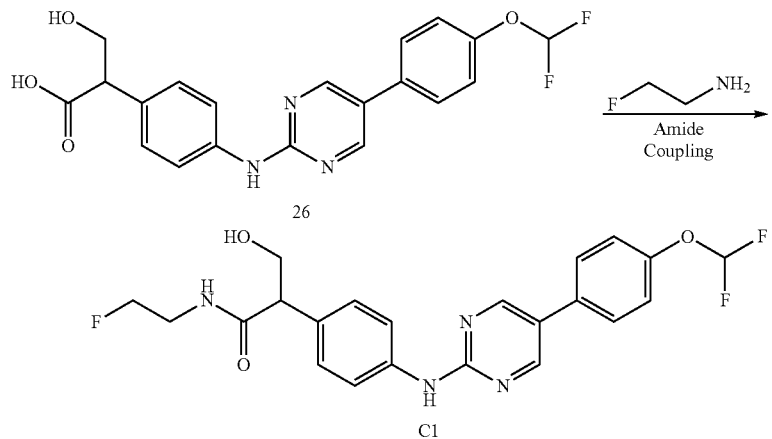

2-(4-(5-(4-(Difluoromethoxy)phenyl)pyrimidin-2-ylamino)phenyl)-3-hydroxypropanoic acid 26 (0.1 mmol), 2-fluoroethanamine (0.1 mmol) and HATU (0.15 mmol) are dissolved in dry DMF (0.5 mL) at rt. Diisopropylethylamine (0.50 mmol) is added to the solution. The reaction mixture is stirred for 1 h at rt. HPLC purification (ACN gradient 10-90%) affords 2-(4-(5-(4-(difluoromethoxy)phenyl)pyrimidin-2-ylamino)phenyl)-N-(2-fluoroethyl)-3-hydroxypropanamide C1 as a TFA salt. MS (m/z) (M+1)$^+$: 447.2.

Example C2

2-(4-(5-(4-(difluoromethoxy)phenyl)pyrimidin-2-ylamino)phenyl)-3-hydroxy-1-(4-hydroxypiperidin-1-yl)propan-1-one

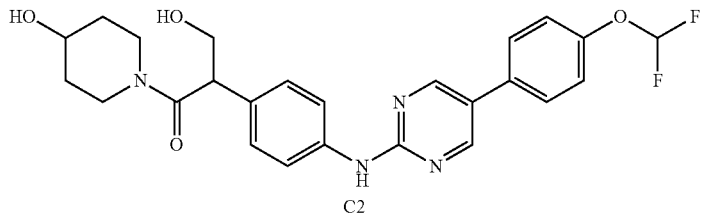

C2

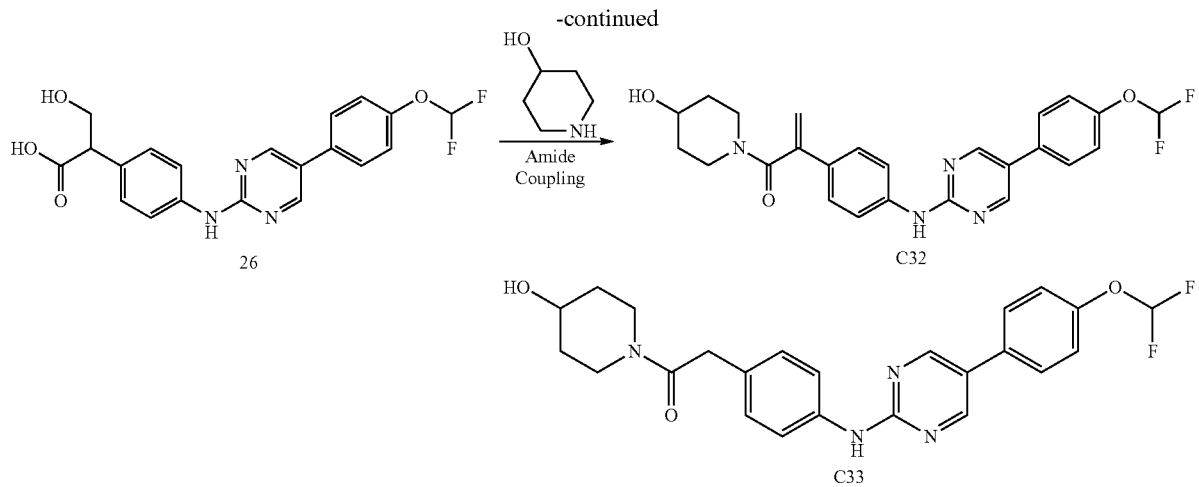

Similar to the preparation of C1. $^1$H NMR (400 MHz, d4-MeOH) δ 8.88 (d, J=2.8 Hz, 2H), 7.73 (d, J=8.4 Hz, 2H), 7.59 (t, J=8.8 Hz, 2H), 7.43 (m, 2H), 7.31 (d, J=8.4 Hz, 2H), 6.92 (t, J=74.0 Hz, 1H), 4.20 (m, 2H), 4.13 (m, 1H), 3.80 (m, 2H), 3.70 (m, 2H), 1.56 (m, 2H), 1.50 (m, 2H), 1.28 (m, 1H). MS (m/z) (M+1)$^+$: 485.2.

Example C3

(R)-2-(4-(5-(4-(difluoromethoxy)phenyl) pyrimidin-2-ylamino)phenyl)-3-hydroxy-1-(4-hydroxypiperidin-1-yl)propan-1-one

Example C4

(S)-2-(4-(5-(4-(difluoromethoxy)phenyl)pyrimidin-2-ylamino)phenyl)-3-hydroxy-1-(4-hydroxypiperidin-1-yl)propan-1-one

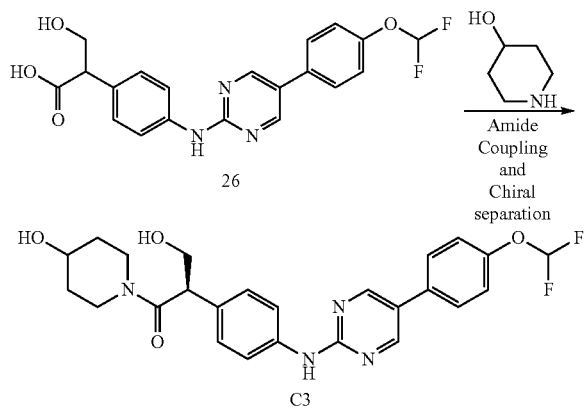

Similar to the preparation of C1. Chiral separation on (R,R)-WelkO-1 column and hexane:isopropanol=70:30 as gradient affords the two enantiomers C3 (first peak eluted) and C4 (second peak eluted). C3 is arbitrarily assigned the R configuration. $^1$H NMR (400 MHz, d4-MeOH) δ 8.88 (d, J=2.8 Hz, 2H), 7.73 (d, J=8.4 Hz, 2H), 7.59 (t, J=8.8 Hz, 2H), 7.43 (m, 2H), 7.31 (d, J=8.4 Hz, 2H), 6.92 (t, J=74.0 Hz, 1H), 4.20 (m, 2H), 4.13 (m, 1H), 3.80 (m, 2H), 3.70 (m, 2H), 1.56 (m, 2H), 1.50 (m, 2H), 1.28 (m, 1H). MS (m/z) (M+1)$^+$: 485.2.

C4 is arbitrarily assigned the S configuration. $^1$H NMR (400 MHz, d4-MeOH) δ 8.88 (d, J=2.8 Hz, 2H), 7.73 (d, J=8.4 Hz, 2H), 7.59 (t, J=8.8 Hz, 2H), 7.43 (m, 2H), 7.31 (d, J=8.4 Hz, 2H), 6.92 (t, J=74.0 Hz, 1H), 4.20 (m, 2H), 4.13 (m, 1H), 3.80 (m, 2H), 3.70 (m, 2H), 1.56 (m, 2H), 1.50 (m, 2H), 1.28 (m, 1H). MS (m/z) (M+1)$^+$: 485.2.

Example C5

(R)-2-(4-(5-(4-(difluoromethoxy)phenyl) pyrimidin-2-ylamino)phenyl)-3-hydroxy-N-((R)-2-hydroxypropyl)propanamide

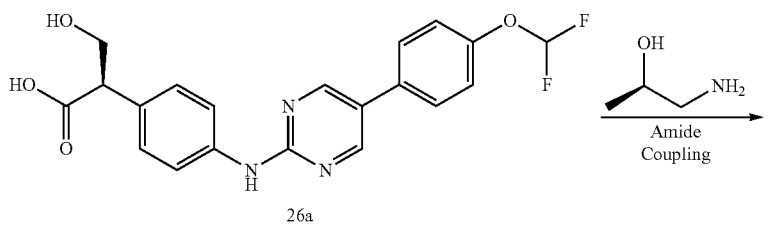

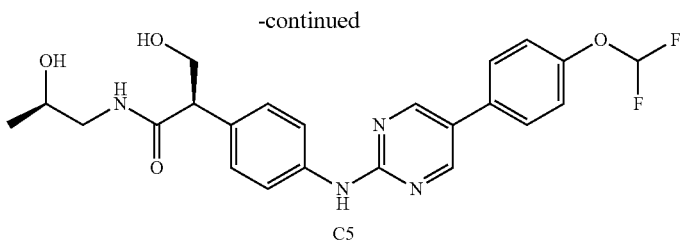

2-(4-(5-(4-(Difluoromethoxy)phenyl)pyrimidin-2-ylamino)phenyl)-3-hydroxypropanoic acid 26a (0.1 mmol), (R)-1-aminopropan-2-ol (0.1 mmol) and HATU (0.12 mmol) are dissolved in dry DMF (0.5 mL) at rt. Diisopropylethylamine (0.40 mmol) is added and the reaction mixture is stirred for 1 h at rt. HPLC purification (ACN gradient 10-70%) affords (R)-2-(4-(5-(4-(difluoromethoxy)phenyl)pyrimidin-2-ylamino)phenyl)-3-hydroxy-N-((R)-2-hydroxypropyl)propanamide C5 as a TFA salt. $^1$H NMR (400 MHz, d6-DMSO) δ 9.73 (s, 1H), 8.80 (s, 2H), 7.92 (t, J=8.0 Hz, 1H), 7.77 (m, 2H), 7.30 (t, J=74.0 Hz, 1H), 7.28 (m, 2H), 7.22 (m, 2H), 7.45 (t, J=4.0 Hz, 1H), 3.91 (m, 1H), 3.59 (m, 2H), 3.40 (quint., J=8.0 Hz, 1H), 0.95 (d, J=8.0 Hz, 3H). MS (m/z) (M+1)$^+$: 459.2.

Example C6

(S)-2-(4-(5-(4-(difluoromethoxy)phenyl)pyrimidin-2-ylamino)phenyl)-3-hydroxy-N-((R)-2-hydroxypropyl)propanamide

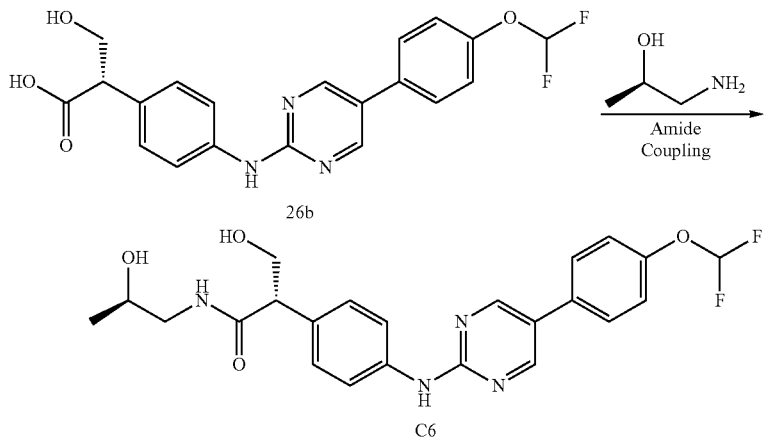

2-(4-(5-(4-(Difluoromethoxy)phenyl)pyrimidin-2-ylamino)phenyl)-3-hydroxypropanoic acid 26b (0.1 mmol), (R)-1-aminopropan-2-ol (0.1 mmol) and HATU (0.12 mmol) are dissolved in dry DMF (0.5 mL) at rt. Diisopropylethylamine (0.40 mmol) is added to the solution. The reaction mixture is stirred for 1 h at rt. HPLC purification (ACN gradient 10-70%) affords (R)-2-(4-(5-(4-(difluoromethoxy)phenyl)pyrimidin-2-ylamino)phenyl)-3-hydroxy-N-((R)-2-hydroxypropyl)propanamide C6 as a TFA salt. $^1$H NMR (400 MHz, d6-DMSO) δ 9.72 (s, 1H), 8.80 (s, 2H), 7.93 (m, 1H), 7.76 (d, J=8.8 Hz, 2H), 7.66 (d, J=8.4 Hz, 2H), 7.28 (t, J=72.0 Hz, 1H), 7.27 (d, J=8.4 Hz, 2H), 7.23 (d, J=8.4 Hz, 2H), 3.93 (m, 1H), 3.61 (m, 1H), 2.99 (m, 2H), 2.51 (m, 2H), 0.95 (d, J=6.0 Hz, 3H). MS (m/z) (M+1)$^+$: 459.1.

Example C7

(R)-2-(4-(5-(4-(difluoromethoxy)phenyl) pyrimidin-2-ylamino)phenyl)-3-hydroxy-N-((S)-2-hydroxypropyl)propanamide

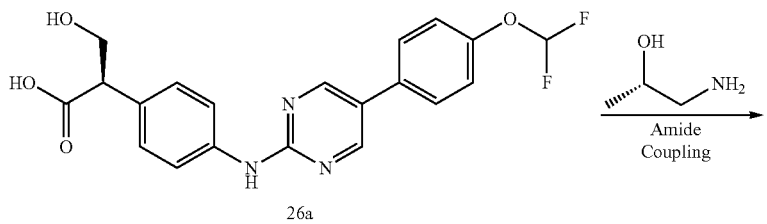

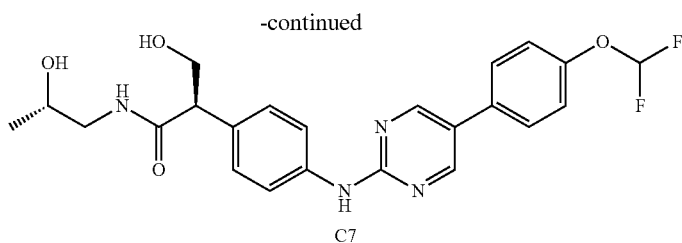

C7

Similar to the preparation of C5. $^1$H NMR (400 MHz, d4-MeOH) δ 8.69 (s, 2H), 7.67 (m, 4H), 7.31 (d, J=8.0 Hz, 2H), 7.27 (d, J=8.0 Hz, 2H), 6.88 (t, J=76.0 Hz, 1H), 4.62 (s, 1H), 4.14 (m, 1H), 3.83 (m, 1H), 3.70 (m, 2H), 3.26 (dd J=8.0, 12.0 hz, 1H), 3.10 (dd, J=8.0, 12.0 Hz, 1H), 1.09 (d, J=4.0 Hz, 3H). MS (m/z) (M+1)$^+$: 459.1.

Example C8

(S)-2-(4-(5-(4-(difluoromethoxy)phenyl)pyrimidin-2-ylamino)phenyl)-3-hydroxy-N-((S)-2-hydroxypropyl)propanamide

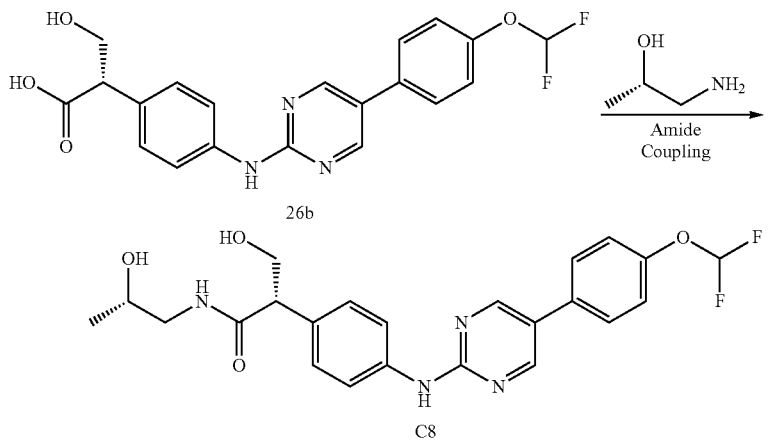

Similar to the preparation of C6. $^1$H NMR (400 MHz, d6-DMSO) δ 9.72 (s, 1H), 8.80 (s, 2H), 7.93 (m, 1H), 7.77 (d, J=8.0 Hz, 1H), 7.71 (d, J=8.0 Hz, 2H), 7.61 (d, J=8.0 Hz, 2H), 7.23 (t, J=76 Hz, 1H), 7.21 (d, J=8 Hz, 2H), 7.16 (d, J=8.4 Hz, 2H), 3.84 (m, 1H), 3.42 (m, 3H), 3.28 (m, 1H), 1.72 (m, 3H), 1.02 (m, 6H). MS (m/z) (M+1)$^+$: 459.1.

Example C9

2-(4-(5-(4-(difluoromethoxy)phenyl) pyrimidin-2-ylamino)phenyl)-3-hydroxy-N-((S)-2-hydroxypropyl)propanamide

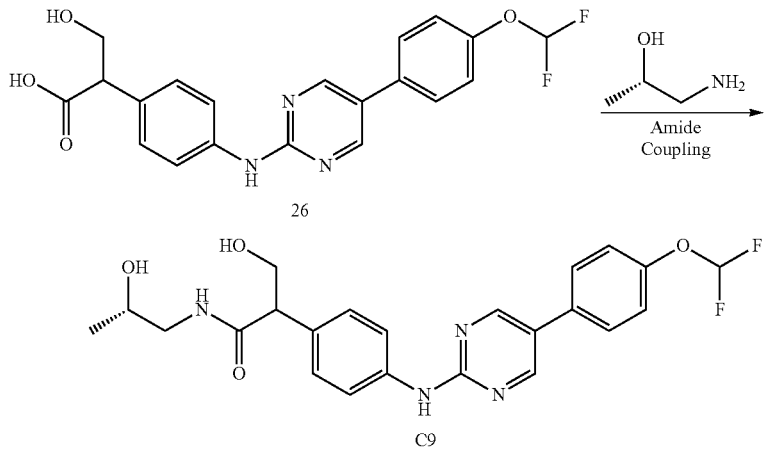

Similar to the preparation of C1. ¹H NMR (400 MHz, d6-DMSO) δ 9.70 (s, 1H), 8.79 (s, 2H), 8.13 (s, 1H), 7.93 (d, J=2.1 Hz, 2H), 7.77 (d, J=8.5 Hz, 2H), 7.66 (d, J=8.4 Hz, 2H), 7.28 (d, J=8 Hz, 2H), 7.26 (t, J=75 Hz, 1H), 7.23 (d, J=8.4 Hz, 2H), 3.92 (dt, J=8.7, 2.5 Hz, 1H), 3.0 (m, 2H), 2.5 (m, 5H), 2.07 (s, 1H), 0.96 (t, J=5.7 Hz, 3H). MS (m/z) (M+1)⁺: 459.1.

Example C11

(R)-2-(4-(5-(4-(difluoromethoxy)phenyl) pyrimidin-2-ylamino)phenyl)-3-hydroxy-N-((1r,4R)-4-hydroxycyclohexyl)propanamide

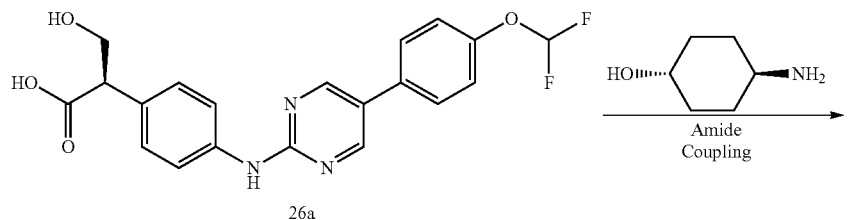

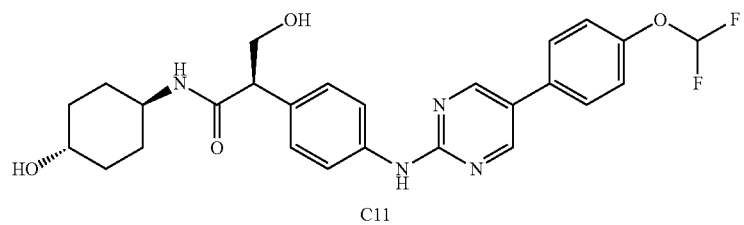

Similar to the preparation of C5. ¹H NMR (400 MHz, d6-DMSO) δ 9.73 (s, 1H), 8.80 (s, 2H), 7.93 (m, 1H), 7.77 (d, J=8.4 Hz, 2H), 7.66 (d, J=8.4 Hz, 2H), 7.29 (t, J=76.0 Hz, 1H), 7.27 (d, J=8 Hz, 2H), 7.23 (d, J=8.4 Hz, 2H), 3.93 (m, 1H), 3.59 (m, 1H), 3.0 (m, 2H), 2.51 (m, 2H), 0.97 (d, J=6 Hz, 3H). MS (m/z) (M+1)⁺: 499.1.

Example C12

(S)-2-(4-(5-(4-(difluoromethoxy)phenyl) pyrimidin-2-ylamino)phenyl)-3-hydroxy-N-((1r,4R)-4-hydroxycyclohexyl)propanamide

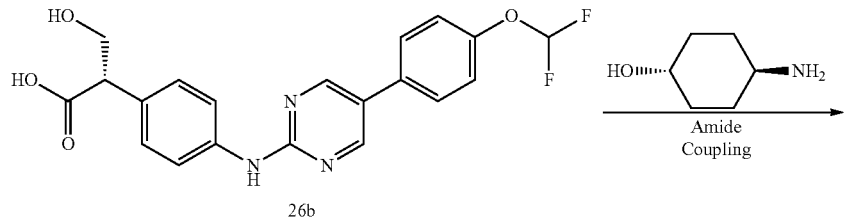

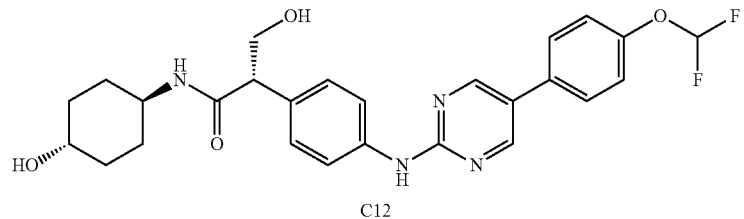

Similar to the preparation of C6. ¹H NMR (400 MHz, d6-DMSO) δ 9.72 (s, 1H), 8.80 (s, 2H), 8.14 (s, 1H), 7.79 (m, 3H), 7.66 (d, J=8.4 Hz, 2H), 7.29 (d, J=7.6 Hz, 2H), 7.27 (t, J=79.6 Hz, 1H), 7.21 (d, J=8.4 Hz, 2H), 3.91 (m, 1H), 2.51 (m, 4H), 1.76 (m, 2H), 1.62 (m, 1H), 1.19 (m, 5H). MS (m/z) (M+1)⁺: 499.2.

Example C13

(R)-2-(4-(5-(4-(difluoromethoxy)phenyl) pyrimidin-2-ylamino)phenyl)-3-hydroxy-N-((1s,4S)-4-hydroxycyclohexyl)propanamide

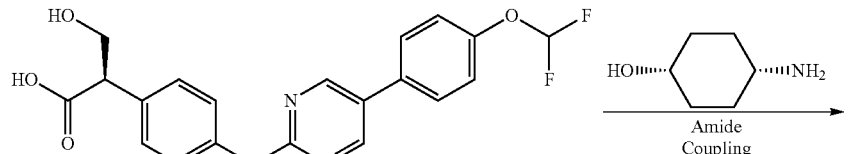

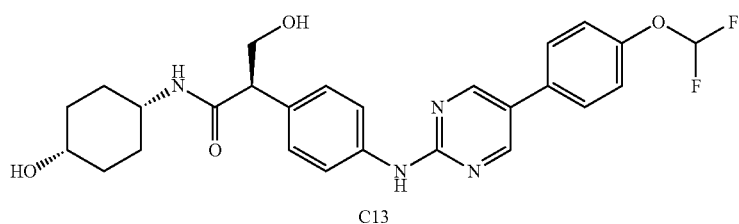

Similar to the preparation of C5. $^1$H NMR (400 MHz, d6-DMSO) δ 9.74 (s, 1H), 8.81 (s, 2H), 7.84 (m, 1H), 7.78 (m, 2H), 7.68 (m, 2H), 7.30 (t, J=76.0 Hz, 1H), 7.27 (d, J=8 Hz, 2H), 7.23 (d, J=8.4 Hz, 2H), 4.73 (t, J=4.0 Hz, 1H), 4.37 (d, J=4.0 Hz, 1H), 3.93 (m, 1H), 3.65 (bm, 1H), 3.58 (m, 2H), 3.48 (m, 1H), 1.62 (m, 2H), 1.38 (m, 8H). MS (m/z) (M+1)$^+$: 499.1.

Example C14

(S)-2-(4-(5-(4-(difluoromethoxy)phenyl)pyrimidin-2-ylamino)phenyl)-3-hydroxy-N-((1s,4S)-4-hydroxycyclohexyl)propanamide

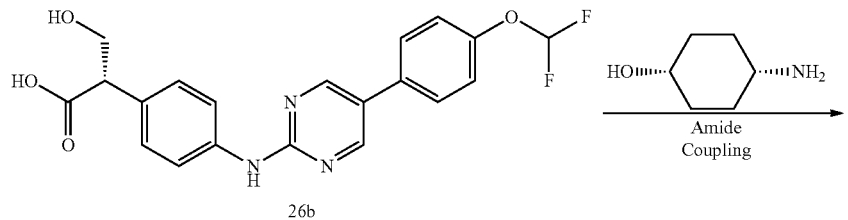

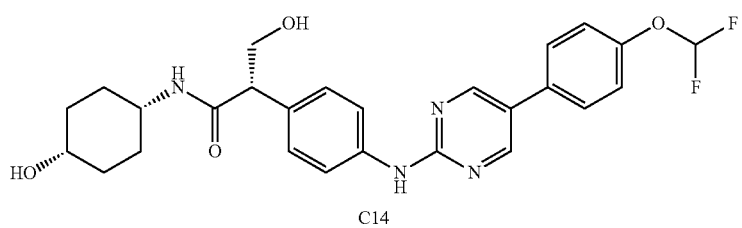

Similar to the preparation of C6. $^1$H NMR (400 MHz, d6-DMSO) δ 9.72 (s, 1H), 8.8 (s, 2H), 7.83 (d, J=7.6 Hz, 1H), 7.77 (d, J=8.8 Hz, 2H), 7.66 (d, J=8.4 Hz, 2H), 7.27 (d, J=7.6 Hz, 2H), 7.26 (t, J=79.6 Hz, 1H), 7.22 (d, J=8.4 Hz, 2H), 3.91 (m, 1H), 3.58 (m, 1H), 2.51 (m, 4H), 1.59 (m, 2H), 1.46 (m, 5H). MS (m/z) (M+1)$^+$: 499.2.

Example C15

2-(4-(5-(4-(difluoromethoxy)phenyl)pyrimidin-2-ylamino)phenyl)-3-hydroxy-N-((1s,4s)-4-hydroxycyclohexyl)propanamide

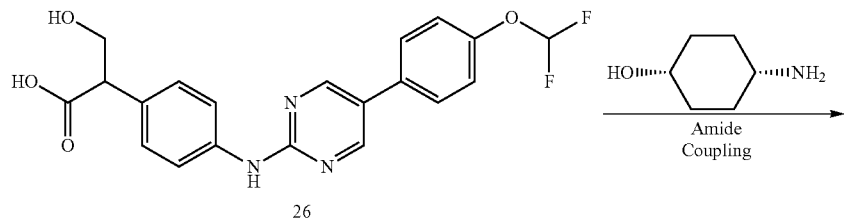

26

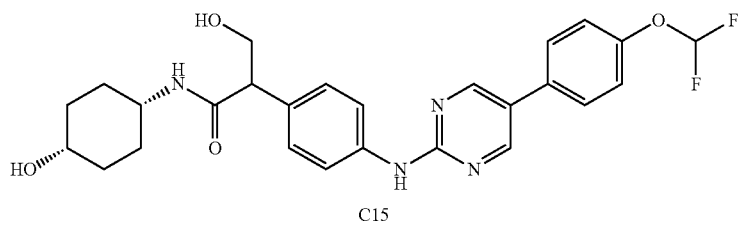

C15

Similar to the preparation of C1. $^1$H NMR (400 MHz, d6-DMSO) δ 9.72 (s, 1H), 8.8 (s, 2H), 7.77 (d, J=8.5 Hz, 2H), 7.66 (d, J=8.4 Hz, 2H), 7.29 (d, J=74 Hz, 1H), 7.28 (d, J=8.5 Hz, 2H), 7.22 (d, J=8.4 Hz, 2H), 3.91 (t, J=9 Hz, 1H), 3.6 (m, 2H), 2.51 (m, 3H), 1.46 (m, 9H). MS (m/z) (M+1)$^+$: 499.4.

Example C18

(R)-2-(4-(5-(4-(difluoromethoxy)phenyl)pyrimidin-2-ylamino)phenyl)-3-hydroxy-1-((S)-3-hydroxypiperidin-1-yl)propan-1-one

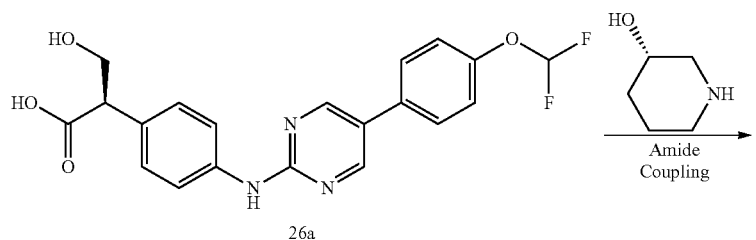

26a

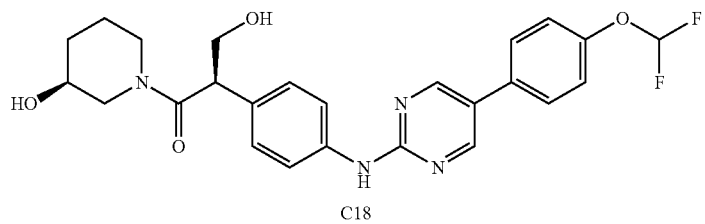

C18

Similar to the preparation of C5. $^1$H NMR (400 MHz, d6-DMSO) δ 9.75 (s, 1H), 8.82 (s, 2H), 7.77 (d, J=8.0 Hz, 2H), 7.70 (m, 2H), 7.28 (t, J=70.0 Hz, 1H), 7.27 (m, 4H), 4.32 (m, 1H), 4.20 (m, 1H), 3.95 (m, 2H), 3.74 (m, 1H), 2.91 (m, 1H), 1.90 (m, 2H), 1.68 (m, 1H), 1.41 (m, 2H). MS (m/z) (M+1)$^+$: 485.1.

Example C19

(S)-2-(4-(5-(4-(difluoromethoxy)phenyl)pyrimidin-2-ylamino)phenyl)-3-hydroxy-1-((S)-3-hydroxypiperidin-1-yl)propan-1-one

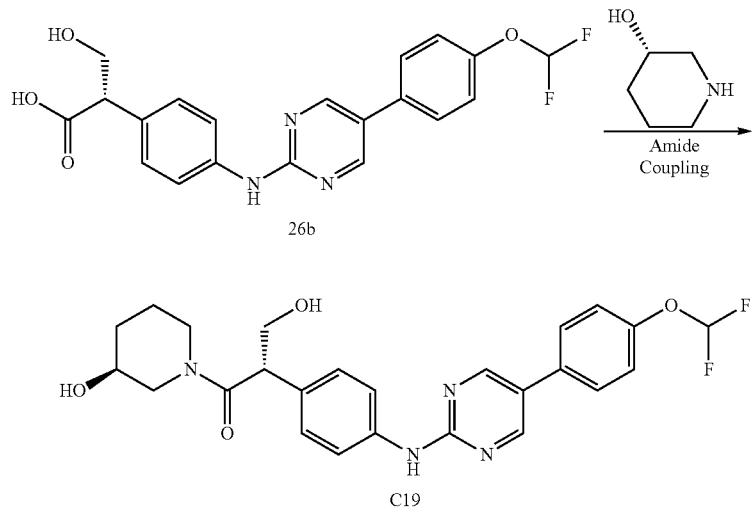

Similar to the preparation of C6. $^1$H NMR (400 MHz, d6-DMSO) δ 9.76 (d, J=10.8 Hz, 1H), 8.82 (s, 2H), 7.77 (d, J=7.6 Hz, 2H), 7.71 (m, 2H), 7.28 (t, J=67.6 Hz, 1H), 7.27 (d, J=6.8 Hz, 2H), 3.95 (m, 2H), 2.92 (m, 1H), 2.55 (m, 6H), 2.53 (m, 2H), 1.68 (m, 1H), 1.37 (m, 2H). MS (m/z) (M+1)$^+$: 485.1.

Example C21

(S)-2-(4-(5-(4-(difluoromethoxy)phenyl)pyrimidin-2-ylamino)phenyl)-3-hydroxy-1-((R)-3-hydroxypiperidin-1-yl)propan-1-one

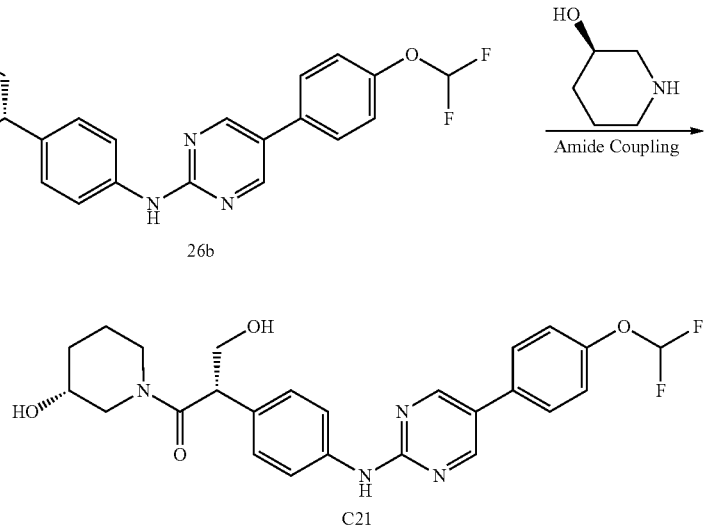

Similar to the preparation of C6. $^1$H NMR (400 MHz, d6-DMSO) δ 9.77 (s, 1H), 8.82 (s, 2H), 7.77 (d, J=8.8 Hz, 2H), 7.71 (m, 2H), 7.28 (t, J=68 Hz, 1H), 7.27 (d, J=6.4 Hz, 2H), 7.18 (d, J=8.4 Hz, 2H), 3.95 (m, 2H), 2.92 (m, 1H), 2.55 (m, 6H), 2.53 (m, 2H), 1.68 (m, 1H), 1.37 (m, 2H). MS (m/z) (M+1)$^+$: 485.1.

Example C22

(R)-2-(4-(5-(4-(difluoromethoxy)phenyl)pyrimidin-2-ylamino)phenyl)-3-hydroxy-1-((R)-3-hydroxypiperidin-1-yl)propan-1-one

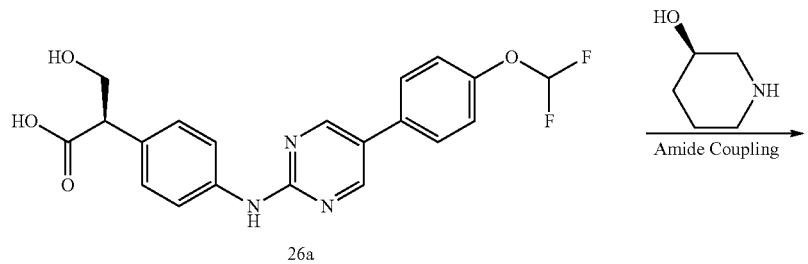

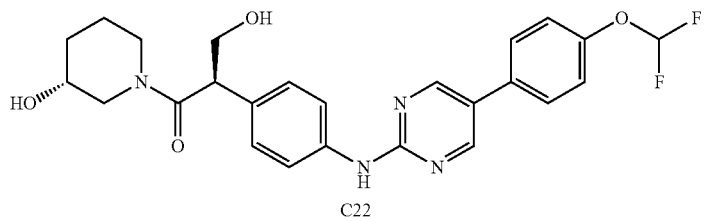

Similar to the preparation of C5. ¹H NMR (400 MHz, d4-MeOH) δ 8.68 (s, 2H), 7.58 (m, 4H), 7.22 (m, 4H), 6.79 (t, J=72.0 Hz, 1H), 4.20 (m, 1H), 4.01 (m, 2H), 3.93 (m, 1H), 3.59 (bm, 2H), 3.38 (m, 1H), 3.33 (m, 1H), 3.06 (m, 1H), 2.72 (m, 1H), 2.64 (m, 1H). MS (m/z) (M+1)$^+$: 485.1.

Example C24

(R)-2-(4-(5-(4-(difluoromethoxy)phenyl) pyrimidin-2-ylamino)phenyl)-3-hydroxy-N-((1R,2R)-2-hydroxycyclopentyl)propanamide

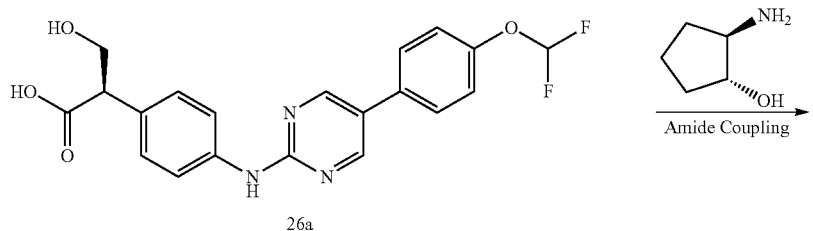

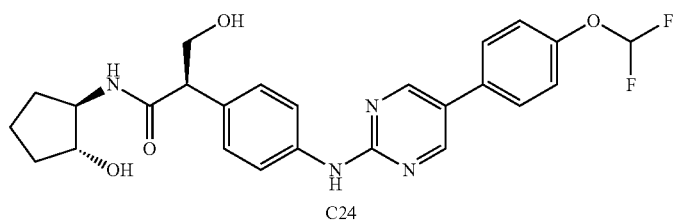

Similar to the preparation of C5. ¹H NMR (400 MHz, d6-DMSO) δ 9.71 (s, 1H), 8.79 (s, 2H), 7.09 (d, J=6.8 Hz, 1H), 7.77 (d, J=8.0 Hz, 2H), 7.67 (d, J=8.0 Hz, 2H), 7.28 (t, J=71.6 Hz, 1H), 7.26 (d, J=8.0 Hz, 2H), 7.22 (d, J=8.0 Hz, 2H), 3.92 (m, 1H), 3.85 (m, 1H), 3.75 (m, 1H), 1.88 (m, 1H), 1.78 (m, 1H), 1.53 (m, 2H), 1.43 (m, 1H), 1.24 (m, 2H). MS (m/z) (M+1)$^+$: 485.1.

Example C27

(S)-2-(4-(5-(4-(difluoromethoxy)phenyl) pyrimidin-2-ylamino)phenyl)-3-hydroxy-N-((1R,2R)-2-hydroxycyclopentyl)propanamide

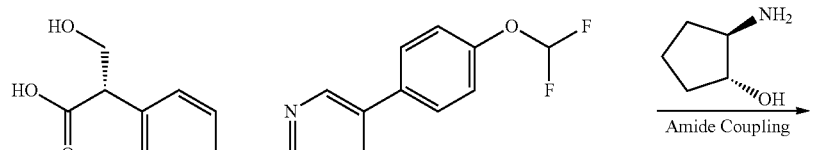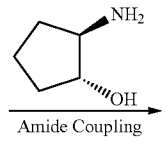

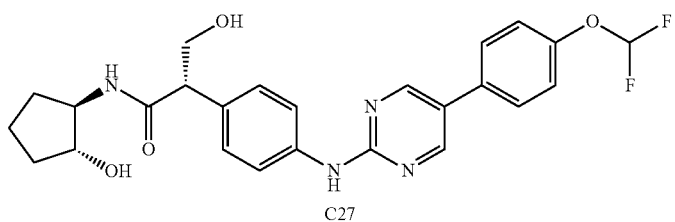

Similar to the preparation of C6. $^1$H NMR (400 MHz, d6-DMSO) δ 9.72 (s, 1H), 8.8 (s, 2H), 7.89 (d, J=6.8 Hz, 1H), 7.77 (d, J=8.4 Hz, 2H), 7.66 (d, J=8.4 Hz, 2H), 7.29 (t, J=74.4 Hz, 1H) 7.27 (d, J=7.2 Hz, 2H), 7.22 (d, J=8.4 Hz, 2H), 3.91 (m, 1H), 3.73 (m, 2H), 1.99 (m, 3H), 1.65 (m, 3H), 1.38 (m, 2H). MS (m/z) (M+1)$^+$: 485.1.

Example C28

(S)-2-(4-(5-(4-(difluoromethoxy)phenyl) pyrimidin-2-ylamino)phenyl)-3-hydroxy-N-((1S,2S)-2-hydroxycyclopentyl)propanamide

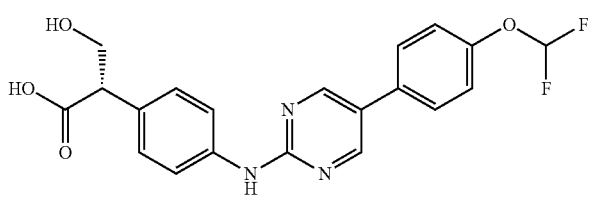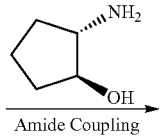

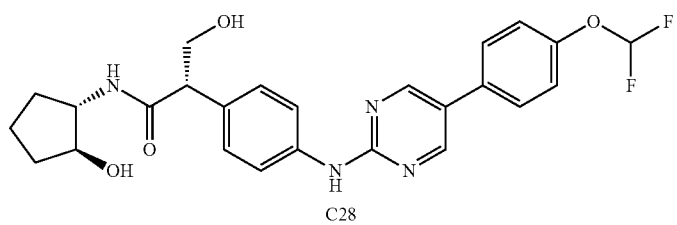

Similar to the preparation of C6. $^1$H NMR (400 MHz, d6-DMSO) δ 9.72 (s, 1H), 8.8 (s, 2H), 7.89 (d, J=6.8 Hz, 1H), 7.77 (d, J=8.4 Hz, 2H), 7.66 (d, J=8.4 Hz, 2H), 7.29 (t, J=74.4 Hz, 1H) 7.27 (d, J=7.2 Hz, 2H), 7.22 (d, J=8.4 Hz, 2H), 3.89 (m, 2H), 3.74 (m, 1H), 1.99 (m, 2H), 1.87 (m, 1H), 1.79 (m, 1H), 1.57 (m, 2H), 1.43 (m, 1H), 1.19 (m, 1H). MS (m/z) (M+1)$^+$: 485.2.

Example C29

(S)-2-(4-(5-(4-(difluoromethoxy)phenyl)pyrimidin-2-ylamino)phenyl)-3-hydroxy-N-((1S,2R)-2-hydroxycyclopentyl)propanamide

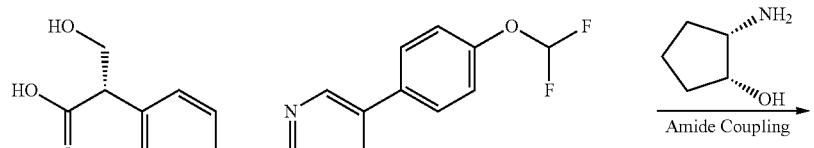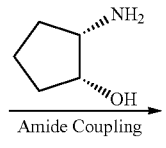

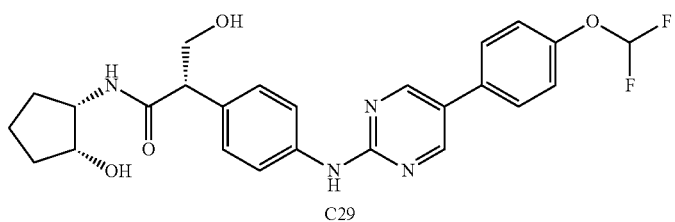

Similar to the preparation of C6. ¹H NMR (400 MHz, d6-DMSO) δ 9.72 (s, 1H), 8.8 (s, 2H), 7.89 (d, J=6.8 Hz, 1H), 7.77 (d, J=8.4 Hz, 2H), 7.66 (d, J=8.4 Hz, 2H), 7.29 (t, J=74.4 Hz, 1H) 7.27 (d, J=7.2 Hz, 2H), 7.22 (d, J=8.4 Hz, 2H), 3.97 (m, 2H), 3.80 (m, 1H), 1.99 (s, 2H), 1.71 (m, 3H), 1.54 (m, 1H), 1.41 (m, 2H). MS (m/z) (M+1)⁺: 485.1.

Example C30

(R)-2-(4-(5-(4-(difluoromethoxy)phenyl)pyrimidin-2-ylamino)phenyl)-3-hydroxy-N-((1S,2S)-2-hydroxycyclopentyl)propanamide

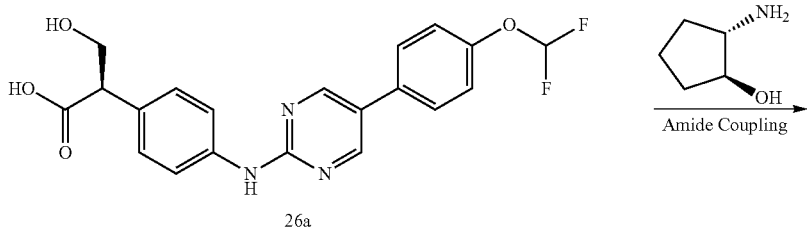

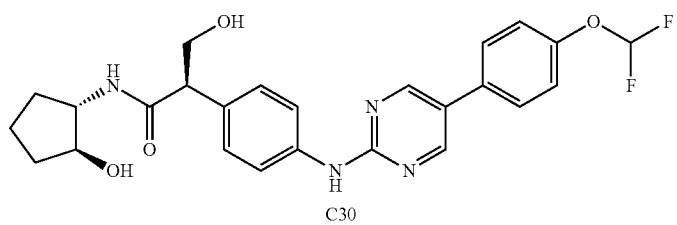

Similar to the preparation of C5. ¹H NMR (400 MHz, d4-MeOH) δ 8.68 (s, 2H), 7.56 (m, 4H), 7.22 (m, 4H), 6.77 (t, J=72.0 Hz, 1H), 4.01 (m, 1H), 3.84 (m, 1H), 3.81 (m, 1H), 3.57 (m, 2H),), 2.01 (m, 1H), 1.74 (m, 1H), 1.69 (m, 2H), 1.44 (m, 2H). MS (m/z) (M+1)⁺: 485.1.

Example C31

(R)-2-(4-(5-(4-(difluoromethoxy)phenyl)pyrimidin-2-ylamino)phenyl)-3-hydroxy-N-((1S,2R)-2-hydroxycyclopentyl)propanamide

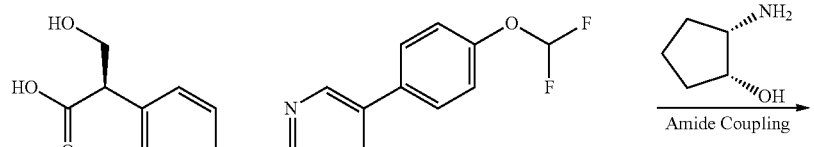

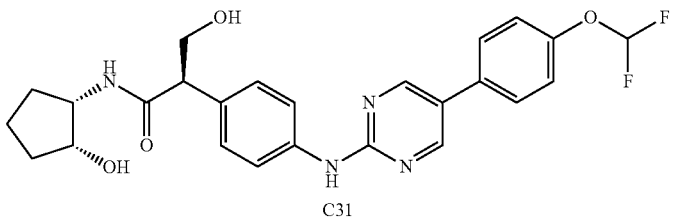

Similar to the preparation of C5. ¹H NMR (400 MHz, d6-DMSO) δ 9.71 (s, 1H), 8.80 (s, 2H), 7.78 (d, J=8.4 Hz, 2H), 7.67 (d, J=8.4 Hz, 2H), 7.53 (d, J=7.2 Hz, 1H), 7.27 (t, J=65.6 Hz, 1H) 7.26 (m, 4H), 3.90 (m, 4H), 3.65 (m, 1H), 1.79 (m, 1H), 1.70 (m, 2H), 1.52 (m, 3H). MS (m/z) (M+1)⁺: 485.2.

Example C32

2-(4-(5-(4-(Difluoromethoxy)phenyl)pyrimidin-2-ylamino)phenyl)-1-(4-hydroxypiperidin-1-yl)prop-2-en-1-one 2-(4-(5-(4-(Difluoromethoxy)phenyl)pyrimidin-2-ylamino)phenyl)-1-(4-hydroxypiperidin-1-yl)prop-2-en-1-one C32 is obtained as a minor side product during the preparation of Example C2. ¹H NMR (400 MHz, d6-DMSO) δ 9.97 (s, 1H), 8.85 (s, 2H), 7.2 (m, 4H), 7.35 (m, 4H), 7.29 (t, J=74.0 Hz, 1H), 5.70 (s, 1H), 5.11 (s, 1H), 4.06 (m, 1H), 3.70 (m, 1H), 3.15 (m, 2H), 1.78 (m, 1H), 1.58 (m, 1H), 1.35 (m, 1H), 1.16 (m, 1H). MS (m/z) (M+1)⁺: 467.2.

Example C33

2-(4-(5-(4-(difluoromethoxy)phenyl) pyrimidin-2-ylamino)phenyl)-1-(4-hydroxypiperidin-1-yl)ethanone 2-(4-(5-(4-(Difluoromethoxy)phenyl)pyrimidin-2-ylamino)phenyl)-1-(4-hydroxypiperidin-1-yl)ethanone C33 is obtained as a minor side product during the preparation of Example C2. ¹H NMR (400 MHz, d6-DMSO) δ 9.76 (s, 1H), 8.81 (s, 2H), 7.77 (d, J=8.2 Hz, 2H), 7.72 (d, J=8.1 Hz, 2H), 7.29 (t, J=71 Hz, 1H), 7.28 (d, J=7.4 Hz, 2H), 7.15 (d, J=8.1 Hz, 2H), 3.94 (dd, J=6.2, 4.1 Hz, 1H), 3.73 (dd, J=8.4, 5.3 Hz, 1H), 3.64 (m, 2H), 3.15 (dd, J=10.6, 8.6 Hz, 1H), 2.97 (m, 1H), 1.62 (m, 2H), 1.2 (m, 4H). MS (m/z) (M+1)⁺: 455.2.

Example C35

(R)-2-(4-(5-(4-(difluoromethoxy)phenyl) pyrimidin-2-ylamino)phenyl)-3-hydroxy-1-(4-methylpiperazin-1-yl)propan-1-one

Example C36

(S)-2-(4-(5-(4-(difluoromethoxy)phenyl) pyrimidin-2-ylamino)phenyl)-3-hydroxy-1-(4-methylpiperazin-1-yl)propan-1-one

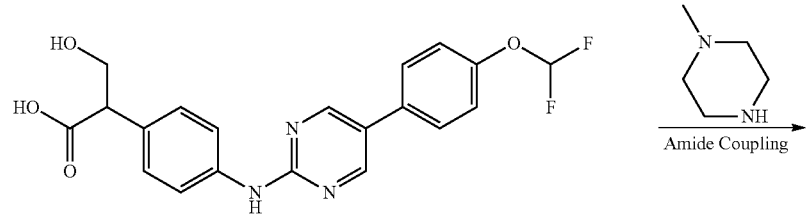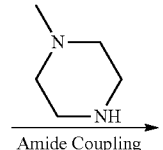

-continued

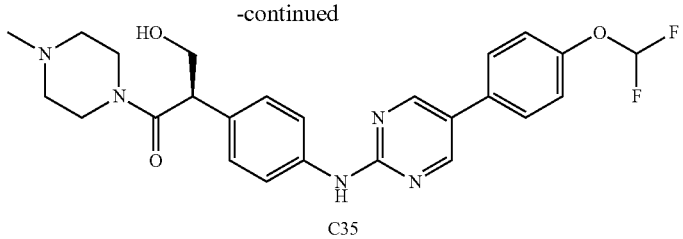

C35

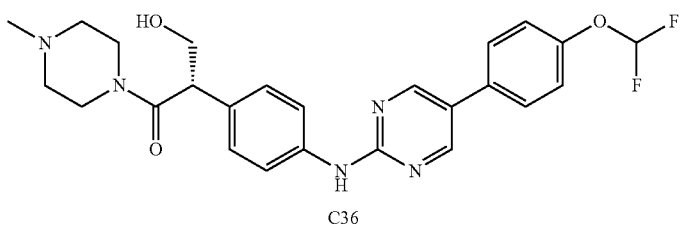

C36

Similar to the preparation of C1. Chiral HPLC separation on (R,R)-WelkO-1 column and hexane:isopropanol=70:30 as gradient affords the two enantiomers C35 (first peak eluted) and C36 (second peak eluted). C35 is arbitrarily assigned the R configuration. ¹H NMR (400 MHz, d6-DMSO) δ 9.80 (s, 1H), 8.81 (s, 2H), 7.77 (d, J=8.8 Hz, 2H), 7.72 (d, J=8.0 Hz, 2H), 7.1-7.5 (m, 5H), 4.09 (s, 1H), 3.96 (t, J=8.8 Hz, 1H), 2.7-2.9 (m, 2H), 2.55 (m, 4H), 2.51 (m, 4H), 2.07 (s, 3H). MS (m/z) (M+1)⁺: 484.2.

C36 is arbitrarily assigned the S configuration. ¹H NMR (400 MHz, d6-DMSO) δ 9.80 (s, 1H), 8.81 (s, 2H), 7.77 (d, J=8.8 Hz, 2H), 7.72 (d, J=8.0 Hz, 2H), 7.1-7.5 (m, 5H), 4.09 (s, 1H), 3.96 (t, J=8.8 Hz, 1H), 2.7-2.9 (m, 2H), 2.55 (m, 4H), 2.51 (m, 4H), 2.07 (s, 3H). MS (m/z) (M+1)⁺: 484.2.

Example C38

2-(4-(5-(4-(Difluoromethoxy)phenyl)pyrimidin-2-ylamino)phenyl)-1-(3-(trifluoromethyl)-4-methylpiperazin-1-yl)-3-hydroxypropan-1-one

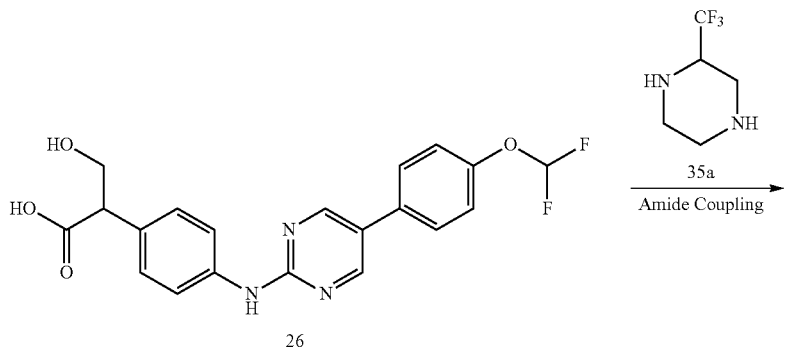

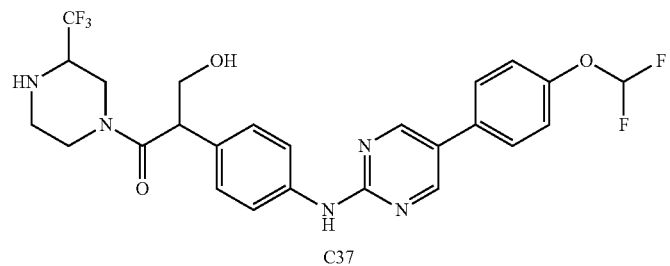

C37

HCHO, Na₂SO₄
NaHB(OAc)₃
rt, 12 h

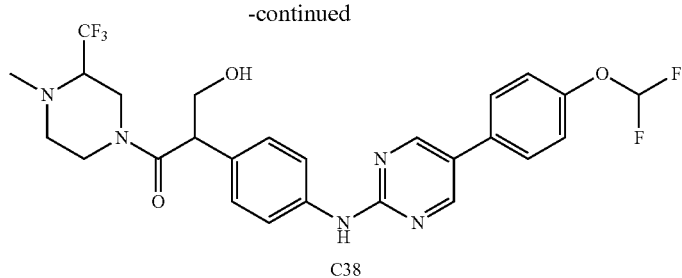

C38

A solution of 2-(4-(5-(4-(difluoromethoxy)phenyl)pyrimidin-2-ylamino)phenyl)-1-(3-(trifluoromethyl)piperazin-1-yl)-3-hydroxypropan-1-one C37 (prepared as described for C1, 0.05 mmol), HCHO (0.15 mmol, 30% aqueous) and anhydrous $Na_2SO_4$ (1.5 mmol) in DCM (2 mL) is stirred at rt for 30 min. Then $NaHB(OAc)_3$ (0.3 mmol) is added and the resulting mixture is stirred for 12 h. Purification by prep-HPLC (ACN gradient 10-70%) affords 2-(4-(5-(4-(difluoromethoxy)phenyl)pyrimidin-2-ylamino)phenyl)-1-(3-(trifluoromethyl)-4-methylpiperazin-1-yl)-3-hydroxypropan-1-one C38. MS (m/z) (M+1)$^+$: 552.2.

Type D Compounds

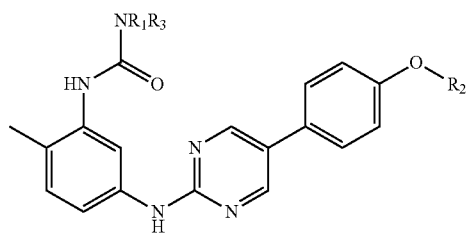

D

Example D1

N1-(5-(5-(4-(difluoromethoxy)phenyl)pyrimidin-2-ylamino)-2-methylphenyl)piperidine-1,4-dicarboxamide

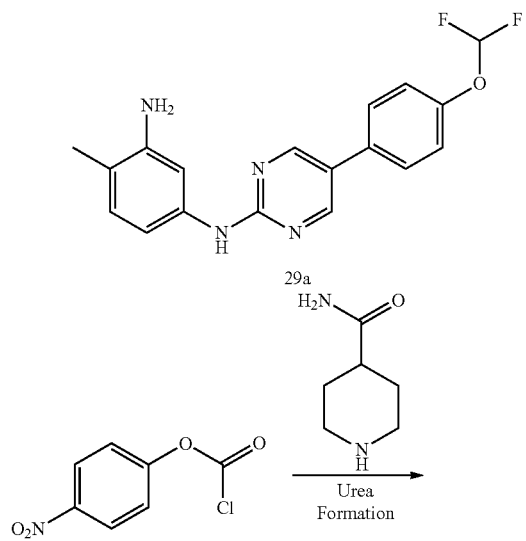

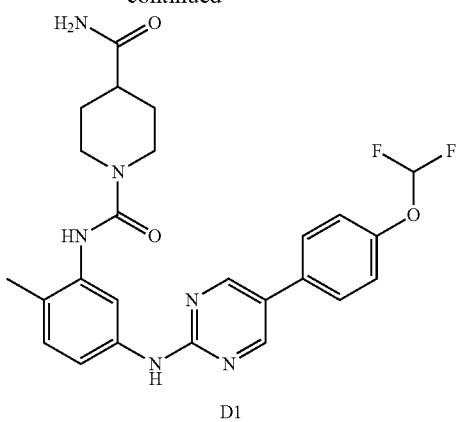

D1

N1-(5-(4-(difluoromethoxy)phenyl)pyrimidin-2-yl)-4-methylbenzene-1,3-diamine 29a (0.1 mmol), 4-nitrophenyl chloroformate (0.12 mmol) and pyridine (0.24 mmol) in dry DCM (0.5 mL) are stirred at rt for 10 min. Then piperidine-4-carboxamide (0.12 mmol) is added and the reaction mixture is stirred for 2 h. HPLC purification affords the target compound D1 as the TFA salt. $^1$H NMR (400 MHz, d6-DMSO) δ 9.68 (s, 1H), 8.81 (s, 2H), 8.05 (s, 1H), 7.77 (d, J=8.8 Hz, 2H), 7.62 (s, 1H), 7.48 (m, 1H), 7.26 (m, 4H), 7.08 (d, J=8.4 Hz, 1H), 6.80 (s, 1H), 4.09 (m, 2H), 2.81 (t, J=12.4 Hz, 2H), 2.32 (m, 1H), 2.10 (s, 3H), 1.70 (m, 2H), 1.48 (m, 2H). MS (m/z) (M+1)$^+$: 497.2.

Example D2

N-(5-(5-(4-(difluoromethoxy)phenyl)pyrimidin-2-ylamino)-2-methylphenyl)-4-methylpiperazine-1-carboxamide

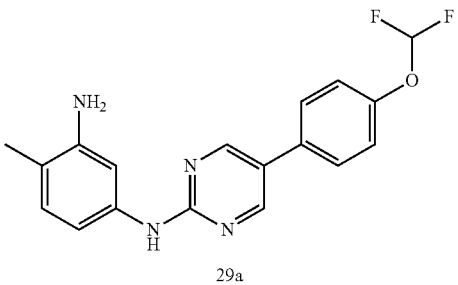

29a

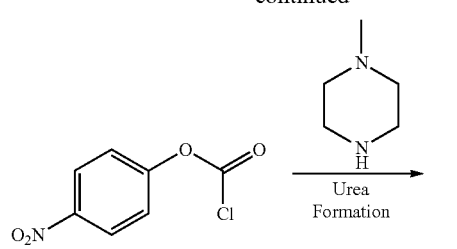

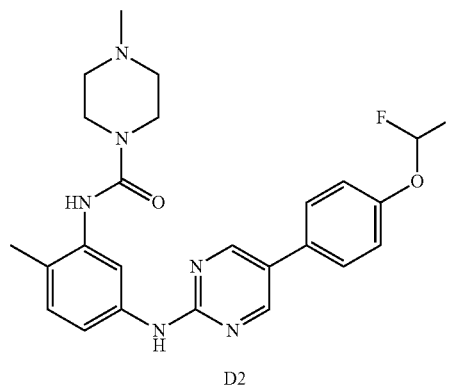

Similar to the preparation of D1. $^1$H NMR (400 MHz, d6-DMSO) δ 9.74 (s, 1H), 8.80 (s, 2H), 8.37 (s, 1H), 7.77 (d, J=8.8 Hz, 2H), 7.64 (s, 1H), 7.49 (d, J=8.4 Hz, 1H), 7.29 (s, 2H), 7.27 (t, J=74.0 Hz, 1H), 7.11 (d, J=8.0 Hz, 1H), 2.86 (s, 3H), 2.51 (m, 4H), 2.54 (m, 4H), 2.11 (s, 3H). MS (m/z) (M+1)$^+$: 469.2.

Example D3

N-(5-(5-(4-(difluoromethoxy)phenyl)pyrimidin-2-ylamino)-2-methylphenyl)-4-methanesulfonyl-piperazine-1-carboxamide

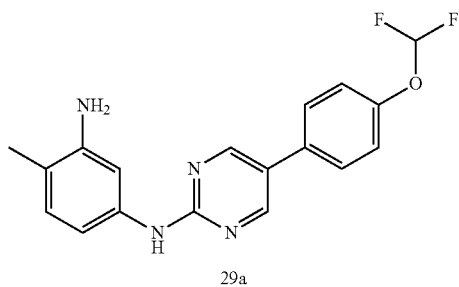

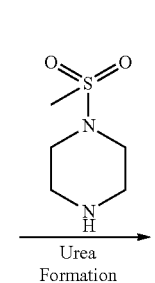

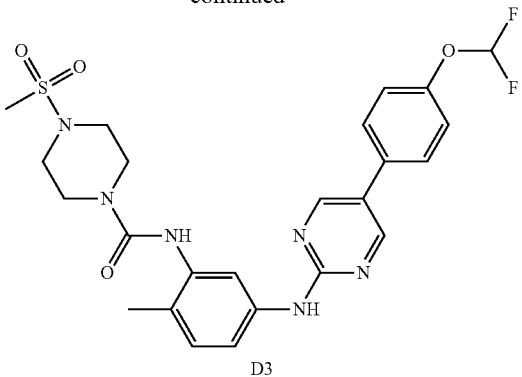

Similar to the preparation of D1. $^1$H NMR (400 MHz, d6-DMSO) δ 9.70 (s, 1H), 8.80 (s, 2H), 8.25 (s, 1H), 7.76 (d, J=8.4 Hz, 2H), 7.62 (s, 1H), 7.49 (d, J=8.0 Hz, 1H), 7.28 (t, J=74.0 Hz, 1H), 7.27 (d, J=8.4 Hz, 2H), 7.10 (d, J=8.4 Hz, 1H), 3.56 (m, 4H), 3.15 (m, 4H), 2.92 (s, 3H), 2.10 (s, 3H). MS (m/z) (M+1)$^+$: 533.2.

Example D4

N-(5-(5-(4-(difluoromethoxy)phenyl)pyrimidin-2-ylamino)-2-methylphenyl)-4-acetylpiperazine-1-carboxamide

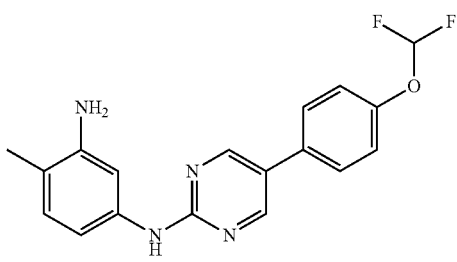

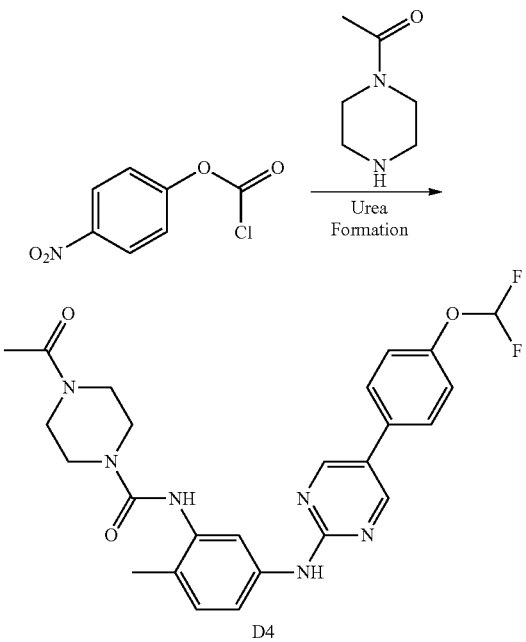

Similar to the preparation of D1. $^1$H NMR (400 MHz, d6-DMSO) δ 9.69 (s, 1H), 8.80 (s, 2H), 8.18 (s, 1H), 7.76 (d, J=8.4 Hz, 2H), 7.63 (s, 1H), 7.49 (d, J=8.0 Hz, 1H), 7.28 (d, J=8.0 Hz, 2H), 7.27 (t, J=74.0 Hz, 1H), 7.09 (d, J=8.0 Hz, 1H), 3.56 (m, 4H), 3.35 (m, 4H), 2.10 (s, 3H), 2.04 (s, 3H). MS (m/z) (M+1)$^+$: 497.2.

Example D7

N-(5-(5-(4-(difluoromethoxy)phenyl)pyrimidin-2-ylamino)-2-methylphenyl)-4-(2-hydroxyethyl)piperazine-1-carboxamide

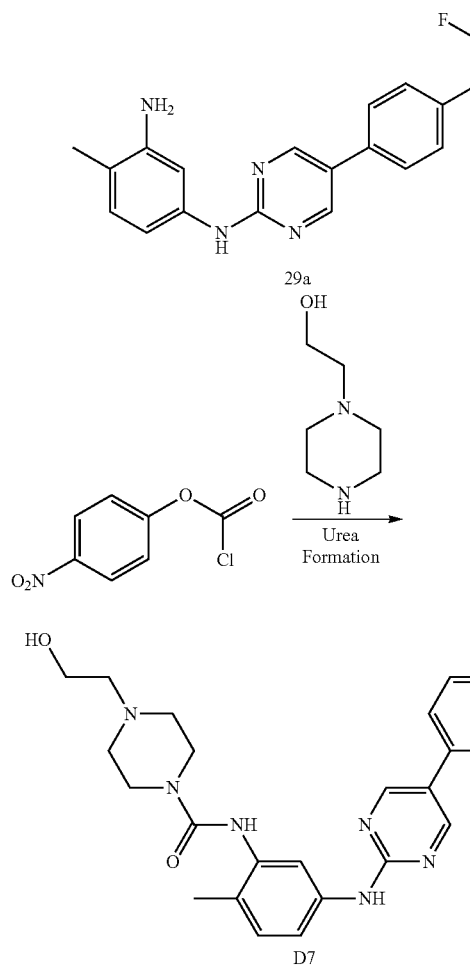

Similar to the preparation of D1. $^1$H NMR (400 MHz, d6-DMSO) δ 9.72 (s, 1H), 8.8 (s, 2H), 8.4 (s, 1H), 7.76 (d, J=8.6 Hz, 2H), 7.64 (m, 1H), 7.28 (m, 2H), 7.2 (t, J=50 Hz, 1H), 7.1 (m, 2H), 3.8 (t, J=4.9 Hz, 2H), 3.24 (t, J=5 Hz, 2H), 2.51 (m, 8H), 2.11 (s, 3H). MS (m/z) (M+1)$^+$: 499.2.

Example D8

N-(5-(5-(4-(difluoromethoxy)phenyl)pyrimidin-2-ylamino)-2-methylphenyl)-4,7-diazaspiro[2.5]octane-7-carboxamide

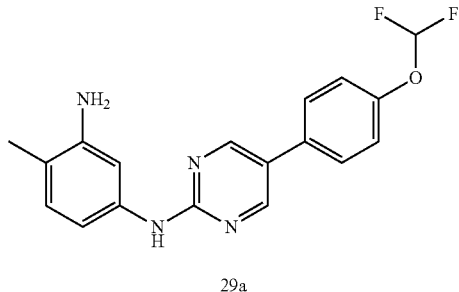

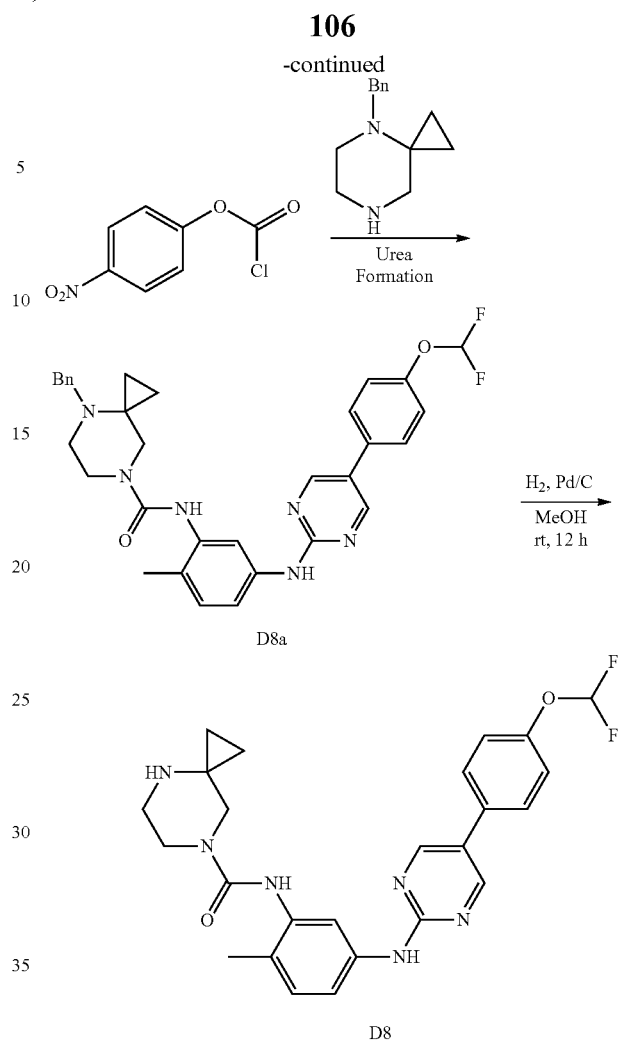

N-(5-(5-(4-(difluoromethoxy)phenyl)pyrimidin-2-ylamino)-2-methylphenyl)-4-(phenylmethyl)-4,7-diazaspiro[2.5]octane-7-carboxamide D8a (prepared as described for D1; 0.2 mmol) is dissolved in 10 mL MeOH followed by addition of 5% mol of Pd/C (10% in weight). The flask is charged with a hydrogen balloon for 12 h stiffing. The mixture is filtered over a celite pad and the filtrate is concentrated to afford N-(5-(5-(4-(difluoromethoxy)phenyl)pyrimidin-2-ylamino)-2-methylphenyl)-4,7-diazaspiro[2.5]octane-7-carboxamide D8, which is used without further purification. MS (m/z) (M+1)$^+$: 523.1.

Example D9

N-(5-(5-(4-(difluoromethoxy)phenyl)pyrimidin-2-ylamino)-2-methylphenyl)-4-methyl-4,7-diazaspiro[2.5]octane-7-carboxamide

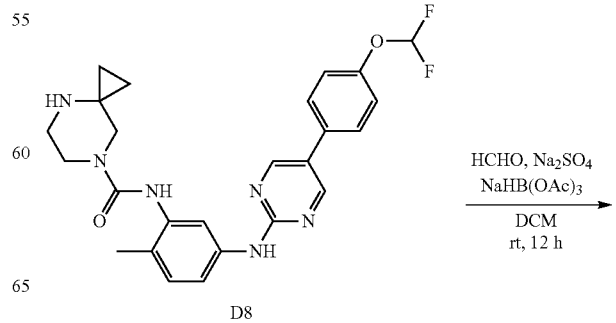

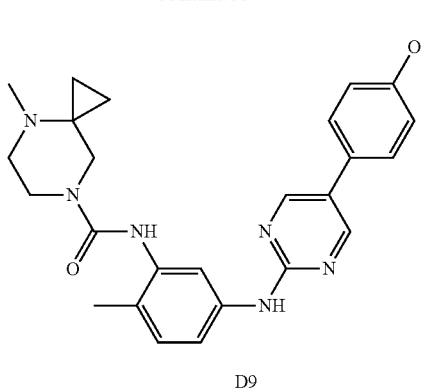

D9

A solution of N-(5-(5-(4-(difluoromethoxy)phenyl)pyrimidin-2-ylamino)-2-methylphenyl)-4,7-diazaspiro[2.5]octane-7-carboxamide D8 (0.05 mmol), HCHO (0.15 mmol, 30% aqueous) and anhydrous Na$_2$SO$_4$ (1.5 mmol) in DCM (2 mL) is stirred at rt for 30 min. Then NaHB(OAc)$_3$ (0.3 mmol) is added and the resulting mixture is stirred for 12 h. Purification by prep-HPLC (ACN gradient 10-70%) affords N-(5-(5-(4-(difluoromethoxy)phenyl)pyrimidin-2-ylamino)-2-methylphenyl)-4-methyl-4,7-diazaspiro[2.5]octane-7-carboxamide D9. $^1$H NMR (400 MHz, d6-DMSO) δ 9.67 (s, 1H), 8.79 (s, 2H), 7.98 (s, 1H), 7.76 (d, J=8.4 Hz, 2H), 7.60 (s, 1H), 7.48 (d, J=8.4 Hz, 1H), 7.27 (d, J=8.4 Hz, 2H), 7.26 (t, J=76.0 Hz, 1H), 7.08 (d, J=8.4 Hz, 1H), 2.78 (m, 2H), 2.51 (m, 4H), 2.31 (s, 3H), 2.10 (s, 3H), 0.62 (m, 2H), 0.50 (m, 2H). MS (m/z) (M+1)$^+$: 537.1.

Example D10

N-(5-(5-(4-(difluoromethoxy)phenyl)pyrimidin-2-ylamino)-2-methylphenyl)-4-(2-hydroxyethyl)-4,7-diazaspiro[2,5]octane-7-carboxamide

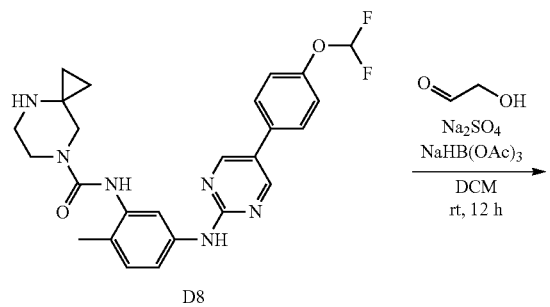

D8

A solution of N-(5-(5-(4-(difluoromethoxy)phenyl)pyrimidin-2-ylamino)-2-methylphenyl)-4,7-diazaspiro[2.5]octane-7-carboxamide D8 (0.05 mmol), 2-hydroxyacetaldehyde (0.6 mmol) and anhydrous Na$_2$SO$_4$ (1.5 mmol) in DCM (2 mL) is stirred at rt for 30 min. Then NaHB(OAc)$_3$ (0.3 mmol) is added and the resulting mixture is stirred for 12 h. Purification by prep-HPLC (ACN gradient 10-70%) affords N-(5-(5-(4-(difluoromethoxy)phenyl)pyrimidin-2-ylamino)-2-methylphenyl)-4-(2-hydroxyethyl)-4,7-diazaspiro[2.5]octane-7-carboxamide D10. $^1$H NMR (400 MHz, d6-DMSO) δ 9.67 (s, 1H), 8.79 (s, 2H), 7.95 (s, 1H), 7.76 (d, J=8.4 Hz, 2H), 7.60 (s, 1H), 7.48 (d, J=8.4 Hz, 1H), 7.27 (d, J=8.4 Hz, 2H), 7.26 (t, J=76.0 Hz, 1H), 7.08 (d, J=8.4 Hz, 1H), 2.89 (m, 2H), 2.77 (m, 2H), 2.54 (m, 2H), 2.51 (m, 4H), 2.10 (s, 3H), 0.50-0.62 (m, 4H). MS (m/z) (M+1)$^+$: 525.2.

Example D11

N-(5-(5-(4-(difluoromethoxy)phenyl)pyrimidin-2-ylamino)-2-methylphenyl)-3-(trifluoromethyl)piperazine-1-carboxamide

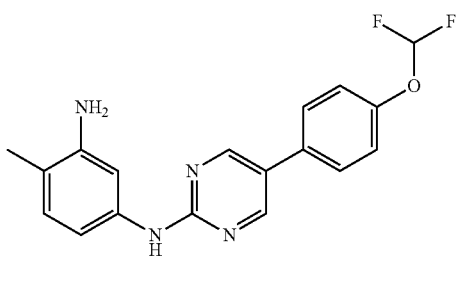

29a

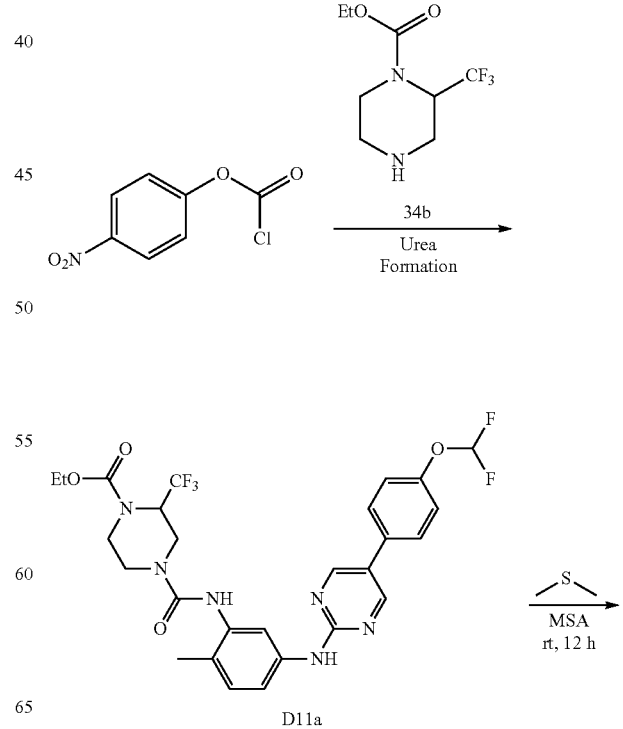

D11a

-continued

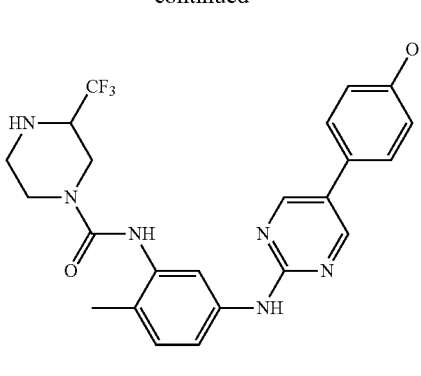

D11

N1-(5-(4-(difluoromethoxy)phenyl)pyrimidin-2-yl)-4-methylbenzene-1,3-diamine 29a (0.4 mmol), 4-nitrophenyl chloroformate (0.48 mmol) and pyridine (0.8 mmol) in dry DCM (2 mL) are stirred at rt for 10 min. Then ethyl 2-(trifluoromethyl)piperazine-1-carboxylate 34b (0.48 mmol) is added and the reaction mixture is stirred for 2 h. After the reaction is complete, the mixture is diluted with 20 mL of DCM and washed with water. The organic layer is separated, dried over Na$_2$SO$_4$, filtered and concentrated under vacuum to afford a residue D11a. To this residue is added dimethylsulfide (1.2 mmol) and methanesulfonic acid (1.0 mL) and the resulting mixture is stirred at rt for 12 h. HPLC purification (ACN gradient 10-70%) affords D11 as a TFA salt. $^1$H NMR (400 MHz, d6-DMSO) δ 9.73 (s, 1H), 8.80 (s, 2H), 8.43 (s, 1H), 7.76 (d, J=8.4 Hz, 2H), 7.64 (s, 1H), 7.50 (d, J=8.0 Hz, 1H), 7.29 (d, J=8.4 Hz, 2H), 7.28 (t, J=74.0 Hz, 1H), 7.11 (d, J=8.4 Hz, 1H), 4.27 (m, 1H), 4.02 (m, 1H), 3.17 (m, 1H), 3.0 (s, 1H), 2.51 (m, 4H), 2.11 (s, 3H). MS (m/z) (M+1)$^+$: 523.2.

Example D12
N-(5-(5-(4-(difluoromethoxy)phenyl) pyrimidin-2-ylamino)-2-methylphenyl)-4-methyl-3-(trifluoromethyl)piperazine-1-carboxamide

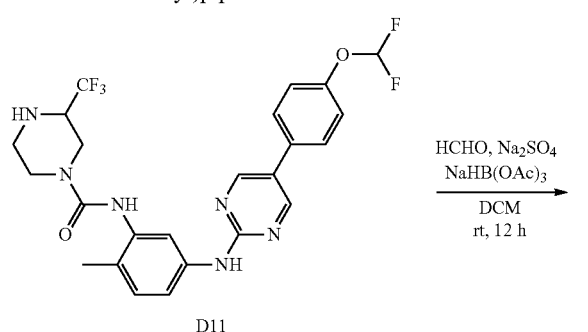

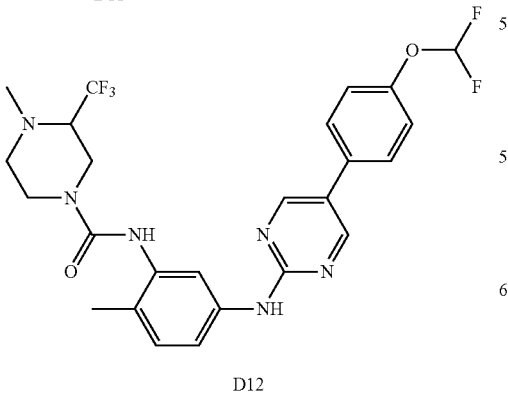

D12

A solution of N-(5-(5-(4-(difluoromethoxy)phenyl)pyrimidin-2-ylamino)-2-methylphenyl)-3-(trifluoromethyl)piperazine-1-carboxamide D11 (0.05 mmol), HCHO (0.15 mmol, 30% aqueous) and anhydrous Na$_2$SO$_4$ (1.5 mmol) in DCM (2 mL) is stirred at rt for 30 min. Then NaHB(OAc)$_3$ (0.3 mmol) is added and the resulting mixture is stirred for 12 h. Purification by prep-HPLC (ACN gradient 10-70%) affords N-(5-(5-(4-(Difluoromethoxy)phenyl)pyrimidin-2-ylamino)-2-methylphenyl)-3-(trifluoromethyl)-4-methylpiperazine-1-carboxamide D12 as a TFA salt. $^1$H NMR (400 MHz, d6-DMSO) δ 9.69 (s, 1H), 8.80 (s, 2H), 8.15 (s, 1H), 7.76 (d, J=8.8 Hz, 2H), 7.61 (s, 1H), 7.50 (d, J=8.0 Hz, 1H), 7.28 (t, J=74.0 Hz, 1H), 7.27 (d, J=8.8 Hz, 2H), 7.09 (d, J=8.4 Hz, 1H), 3.68 (m, 1H), 3.54 (m, 1H), 2.88 (m, 1H), 2.51 (m, 4H), 2.47 (s, 1H), 2.09 (s, 3H). MS (m/z) (M+1)$^+$: 537.2.

Example D13
N-(5-(5-(4-(difluoromethoxy)phenyl)pyrimidin-2-ylamino)-2-methylphenyl)-4-methyl-3-oxopiperazine-1-carboxamide

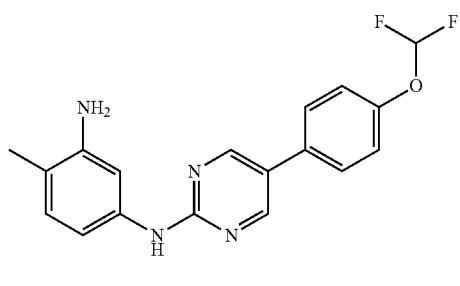

29a

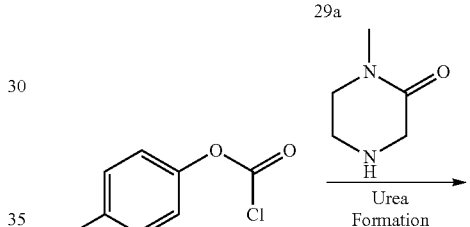

Urea Formation

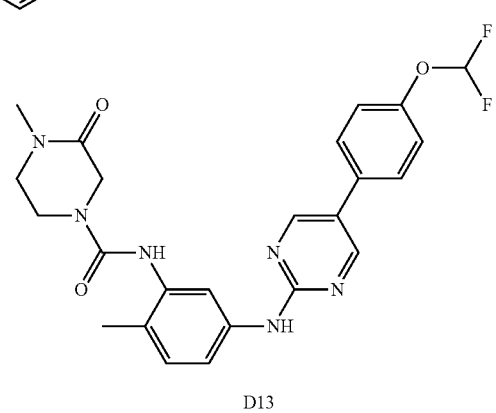

D13

Similar to the preparation of D1. $^1$H NMR (400 MHz, d6-DMSO) δ 9.70 (s, 1H), 8.80 (s, 2H), 8.21 (s, 1H), 7.76 (d, J=8.4 Hz, 2H), 7.65 (s, 1H), 7.50 (d, J=8.0 Hz, 1H), 7.28 (t, J=74.0 Hz, 1H), 7.27 (d, J=8.4 Hz, 2H), 7.10 (d, J=8.4 Hz, 1H), 4.06 (s, 2H), 2.89 (s, 3H), 2.51 (m, 4H), 2.10 (s, 3H). MS (m/z) (M+1)$^+$: 483.2.

Type E Compounds

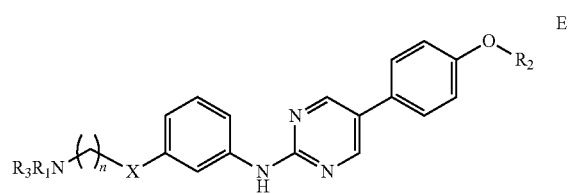

E

Example E1

1-(2-(3-(5-(4-(difluoromethoxy)phenyl)pyrimidin-2-ylamino)phenoxy)ethyl)piperidine-4-carboxylic acid

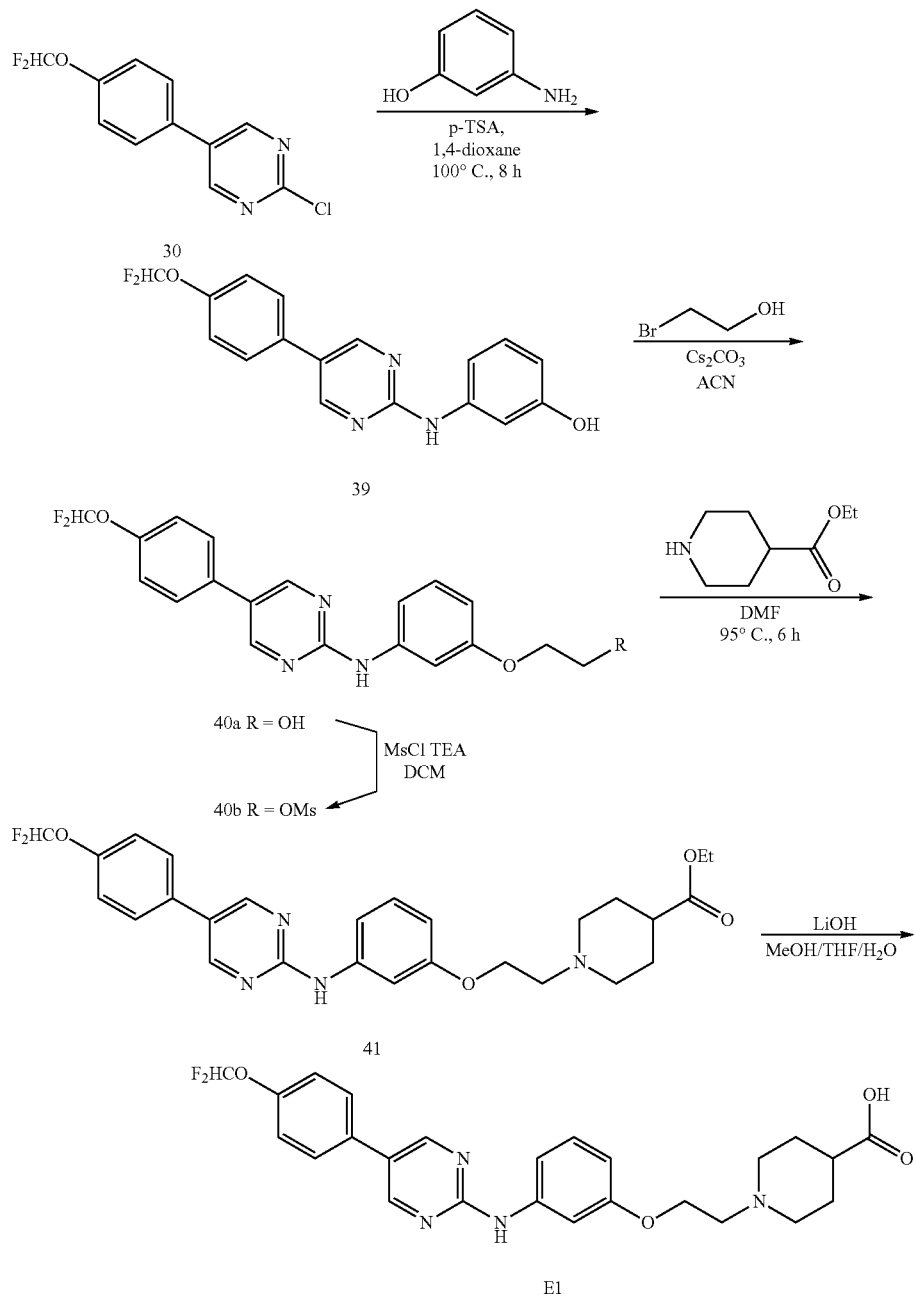

To a mixture of 2-chloro-5-(4-(difluoromethoxy)phenyl)pyrimidine 30 (3.2 mmol) and 3-aminophenol (6.42 mmol) in 1,4-dioxane (5 mL) is added p-TSA (5.4 mmol). The reaction mixture is heated at 100° C. for 12 h. After this time, the reaction is diluted with a 2M solution of $Na_2CO_3$ and extracted with DCM (3×50 mL). The organic layer is washed with brine, dried over $Na_2SO_4$, and concentrated. Purification by short $SiO_2$ chromatography using a DCM:EtOAc=7:3 as eluant affords (3-(5-(4-(difluoromethoxy)phenyl)pyrimidin-2-ylamino)phenol 39. MS (m/z) (M+1)$^+$: 330.1.

A solution of 3-(5-(4-(difluoromethoxy)phenyl)pyrimidin-2-ylamino)phenol 39 (1.2 mmol), 2-bromoethanol (1.4 mmol) and cesium carbonate (1.6 mmol) in acetonitrile (10 mL) is heated to 85° C. for 12 h then cooled to rt. The reaction is evaporated to dryness then re-dissolved in DCM. The organic mixture is washed with water and brine then dried over magnesium sulfate, filtered and reduced to dryness. Purification by silica gel chromatography with hexane: EtOAc=1:1 as eluant affords 2-(3-(5-(4-(difluoromethoxy)

phenyl)pyrimidin-2-ylamino)phenoxy)ethanol 40a as white solid. MS (m/z) (M+1)⁺: 373.8.

To a solution of 2-(3-(5-(4-(difluoromethoxy)phenyl)pyrimidin-2-ylamino)phenoxy)ethanol 40 (0.4 mmol) in DCM (15 mL) is added triethyl amine (0.4 mmol) and methanesulfonyl chloride (0.4 mmol). The reaction mixture is stirred at rt for 12 h then washed with brine and dried over magnesium sulfate, filtered and reduced to dryness. The resulting crude 2-(3-(5-(4-(Difluoromethoxy)phenyl)pyrimidin-2-ylamino)phenoxy)ethyl methanesulfonate 40b as tan solid is used without further purification.

2-(3-(5-(4-(Difluoromethoxy)phenyl)pyrimidin-2-ylamino)phenoxy)ethyl methanesulfonate 40b (0.4 mmol), ethyl piperidine-4-carboxylate (0.9 mmol) are dissolved in DMF (3 mL) and heated to 95° C. for 6 h then cooled to rt. The reaction mixture is partitioned with EtOAC and water. The organic layer is washed with water, brine, dried over magnesium sulfate, filtered, and reduced to dryness. The crude product is triturated with MeOH and filtered to yield ethyl 1-(2-(3-(5-(4-(difluoromethoxy)phenyl)pyrimidin-2-ylamino)phenoxy)ethyl)piperidine-4-carboxylate 41 as white solid. MS (m/z) (M+1)⁺: 513.2.

To ethyl 1-(2-(3-(5-(4-(difluoromethoxy)phenyl)pyrimidin-2-ylamino)phenoxy)ethyl)piperidine-4-carboxylate 41 (78 umol) is added THF (3 mL), MeOH (2 mL) and 3M lithium hydroxide (0.5 mmol). The reaction mixture is stirred at rt for 6 h until complete as detected by LCMS. Subsequently the organic solvents are evaporated and the reaction mixture is diluted with water (5 mL) and neutralized with 3M HCl (0.5 mmol). The resulting precipitate is filtered, washed with water and air dried to yield 1-(2-(3-(5-(4-(difluoromethoxy)phenyl)pyrimidin-2-ylamino)phenoxy)ethyl)piperidine-4-carboxylic acid E1 as white solid. ¹H NMR (400 MHz, d6-DMSO) δ 12.12 (s, 1H), 9.79 (s, 1H), 8.85 (s, 2H), 7.78 (d, J=8.0 Hz, 2H), 7.52 (bs, 1H), 7.34 (bd, J=8.0 Hz, 1H), 7.31 (t, J=74.0 Hz, 1H), 7.28 (d, J=8.0 Hz, 1H), 7.18 (t, J=8.0 Hz, 1H), 6.56 (bd, J=8.0 Hz, 1H) 4.05 (m, 2H), 2.88 (m, 2H), 2.67 (m, 2H), 2.20 (m, 1H), 2.09 (m, 2H), 1.78 (m, 2H), 1.57 (m, 2H). MS (m/z) (M+1)⁺: 484.2.

Example E2

1-(3-(5-(4-(difluoromethoxy)phenyl)pyrimidin-2-ylamino)phenethyl)piperidine-4-carboxylic acid

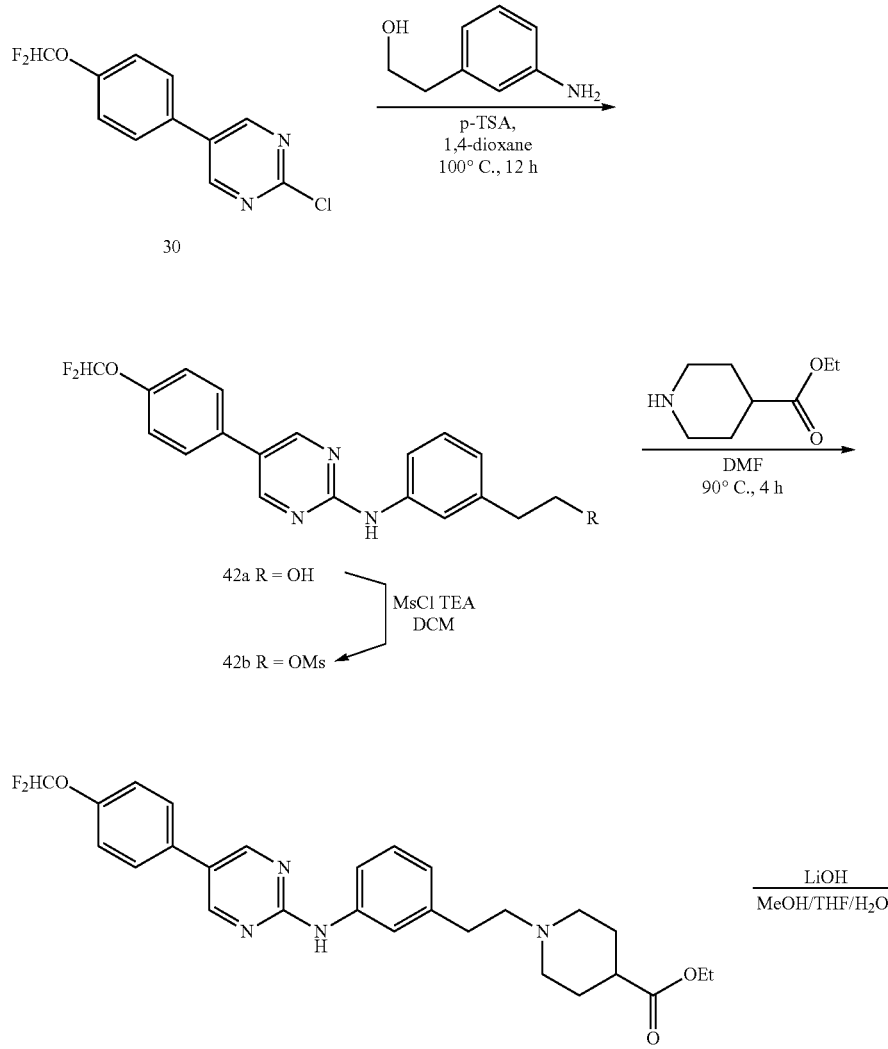

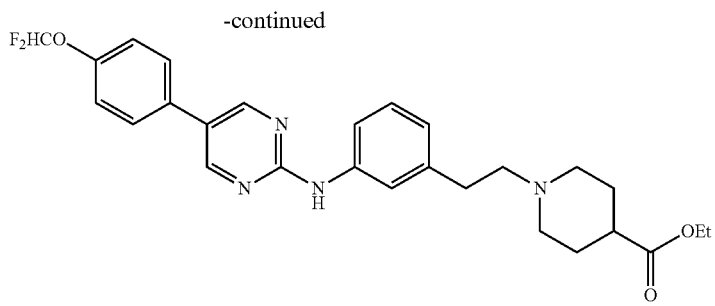

E2

A solution of 2-(3-aminophenyl)ethanol (1.8 mmol), 2-chloro-5-(4-difluoromethoxy-phenyl)-pyrimidine 30 (1.8 mmol) and p-TSA (1.8 mmol) in dioxane (10 mL) is heated at 100° C. for 12 h then cooled to rt. The reaction mixture is slowly added to water (100 mL) with stirring. The resulting precipitate is collected by filtration, washed with water and air dried. The crude precipitate of 2-(3-(5-(4-(difluoromethoxy)phenyl)pyrimidin-2-ylamino)phenyl)ethanol 42a is used without further purification. MS (m/z) (M+1)$^+$: 357.9.

To a solution of 2-(3-(5-(4-(difluoromethoxy)phenyl)pyrimidin-2-ylamino)phenyl)ethanol 42a (0.7 mmol) in DCM (20 mL) is added triethyl amine (0.8 mmol) and methanesulfonyl chloride (0.8 mmol). The reaction mixture is stirred at rt for 12 h then washed with brine and dried over magnesium sulfate, filtered, and reduced to dryness. The resulting 3-(5-(4-(difluoromethoxy)phenyl)pyrimidin-2-ylamino) phenethyl methanesulfonate 42b as crude tan solid, is used without further purification.

3-(5-(4-(Difluoromethoxy)phenyl)pyrimidin-2-ylamino) phenethyl methanesulfonate 42b (0.7 mmol) and ethyl piperidine-4-carboxylate (1.7 mmol) are dissolved in DMF (6 mL) and heated to 95° C. for 6 h then cooled to rt. The reaction mixture is partitioned with EtOAc and water. The organic layer is washed with water, brine, dried over magnesium sulfate, filtered and reduced to dryness. The crude material is purified by column chromatography on silica with hexane:EtOAc=1:1 to 100% EtOAc as eluant to yield ethyl 1-(3-(5-(4-(difluoromethoxy)phenyl)pyrimidin-2-ylamino)phenethyl)piperidine-4-carboxylate 43 as clear crystalline solid. MS (m/z) (M+1)$^+$: 497.2.

To ethyl 1-(3-(5-(4-(difluoromethoxy)phenyl)pyrimidin-2-ylamino)phenethyl)piperidine-4-carboxylate 43 (0.3 mmol) is added THF (3 mL), MeOH (2 mL) and 3.0M lithium hydroxide (1.8 mmol). The reaction mixture is stirred at rt for 6 h until complete as detected by LCMS. Subsequently the organic solvents are evaporated and the reaction mixture is diluted with water (10 mL) then neutralized with 3M HCl (1.8 mmol). The resulting precipitate is filtered, washed with water and air dried to yield E2 as white solid. $^1$H NMR (400 MHz, d6-DMSO) δ 9.75 (s, 1H), 8.83 (s, 2H), 7.78 (d, J=8.0 Hz, 2H), 7.65 (m, 2H), 7.31 (t, J=74.0 Hz, 1H), 7.28 (d, J=8.0 Hz, 2H), 7.21 (t, J=8.0 Hz, 1H), 6.83 (d, J=7.2 Hz, 1H), 2.71 (m, 2H), 2.21 (m, 1H), 2.03 (m, 2H), 1.81 (m, 2H), 1.58 (m, 2H). MS (m/z) (M+1)$^+$: 468.2.

Example E3

1-(3-(5-(4-(difluoromethoxy)phenyl)pyrimidin-2-ylamino)benzyl)piperidine-4-carboxylic acid

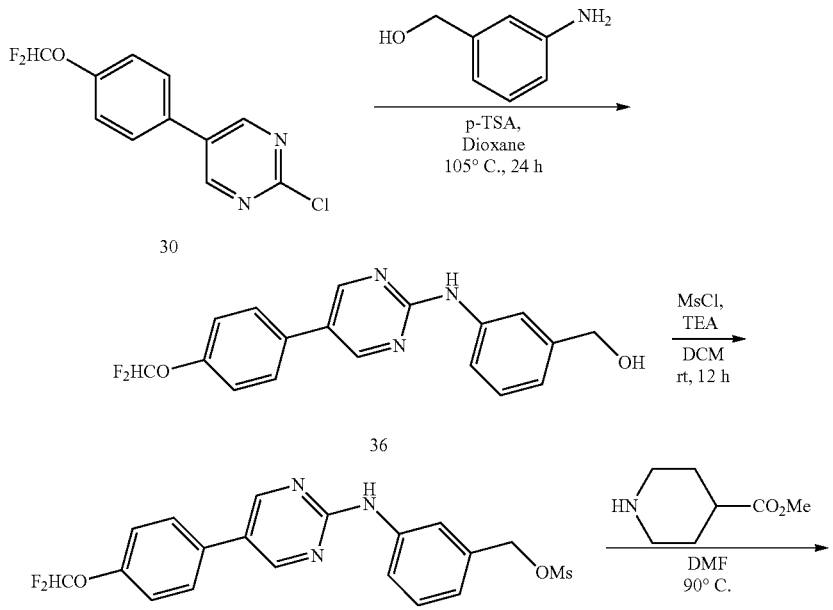

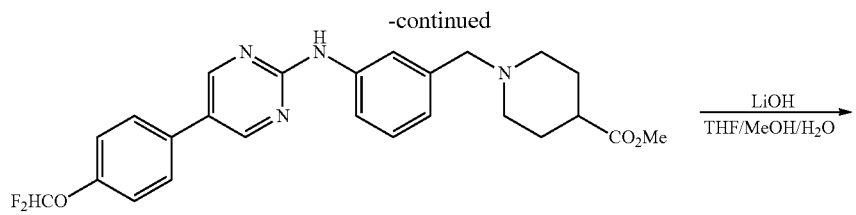

38

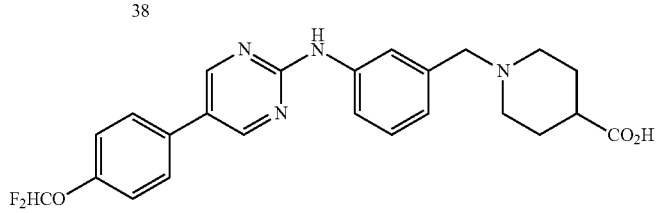

E3

To a mixture of 2-chloro-5-(4-(difluoromethoxy)phenyl)pyrimidine 30 (0.40 mmol) and (3-aminophenyl)methanol (0.40 mmol) in 1,4-dioxane (0.5 mL) is added p-TSA (0.4 mmol). The reaction mixture is heated at 105° C. for 2 days. After this time, the reaction mixture is diluted with a solution of 2M $Na_2CO_3$ (30 mL) and extracted with DCM (3×30 mL). The organic layer is washed with brine, dried over $Na_2SO_4$ and concentrated. Purification by short silica gel chromatography using a hexane:EtOAc=1:2 affords (3-(5-(4-(difluoromethoxy)phenyl)pyrimidin-2-ylamino)phenyl)methanol 36. $^1$H NMR (400 MHz, d4-MeOH) δ 8.56 (s, 2H), 7.65 (m, 1H), 7.48-7.52 (m, 1H), 7.42-7.46 (m, 2H), 7.29 (t, J=8 Hz, 1H), 7.15-7.18 (m, 3H), 6.99-7.03 (m, 1H), 6.49 (t, J=73.6 Hz, 1H), 4.67 (s, 2H). MS (m/z) (M+1)$^+$ 344.1.

To a solution of (3-(5-(4-(difluoromethoxy)phenyl)pyrimidin-2-ylamino)phenyl)methanol 36 (6.22 mmol) in DCM (30 mL) is added triethylamine (9.33 mmol) and methanesulfonyl chloride (7.47 mmol). The reaction mixture is stirred at rt for 1.5 h. The reaction is diluted with $H_2O$ (10 mL) and washed with $Na_2CO_3$ solution (3×20 mL). The organic layer is washed with brine, dried over $MgSO_4$ and concentrated to afford 3-(5-(4-(difluoromethoxy)phenyl)pyrimidin-2-ylamino)benzyl methanesulfonate 37. MS (m/z) (M+1)$^+$ 422.1.

To a solution of 3-(5-(4-(difluoromethoxy)phenyl)pyrimidin-2-ylamino)benzyl methanesulfonate 37 (0.050 mmol) in anhydrous DMF (1 mL) is added methyl piperidine-4-carboxylate (0.10 mmol) and the solution is heated at 100° C. for 8 h. After the reaction is complete, the mixture is diluted with THF:MeOH:$H_2O$ (3:2:1, 5 mL). To the reaction mixture is added 6N LiOH (0.30 mmol). The reaction is stirred at rt for 1 h. Purification by preparative LC/MS affords 1-(3-(5 (4-(difluoromethoxy)phenyl)pyrimidin-2-ylamino)benzyl)piperidine-4-carboxylic acid E3. $^1$H NMR (400 MHz, d4-MeOH) δ 8.64 (s, 2H), 7.78 (d, J=8.8 Hz, 2H), 7.56 (d, J=8.8 Hz, 2H), 7.32 (d, J=8.8 Hz, 2H), 7.16 (d, J=8.8 Hz, 2H), 6.78 (t, J=74.0 Hz, 1H), 4.11 (s, 2H), 3.31 (m, 2H), 2.92 (m, 2H), 2.36 (m, 1H), 2.02 (m, 2H), 1.81 (m, 2H). MS (m/z) (M+1)$^+$: 455.2.

Type F Compounds

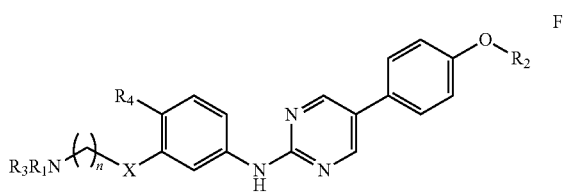

Example F1

1-(2-(5-(5-(4-(difluoromethoxy)phenyl)pyrimidin-2-ylamino)-2-fluorophenoxy)ethyl)piperidine-4-carboxylic acid

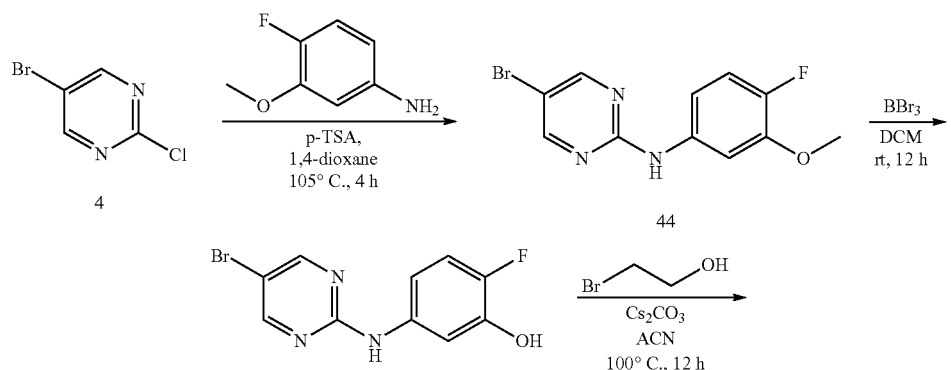

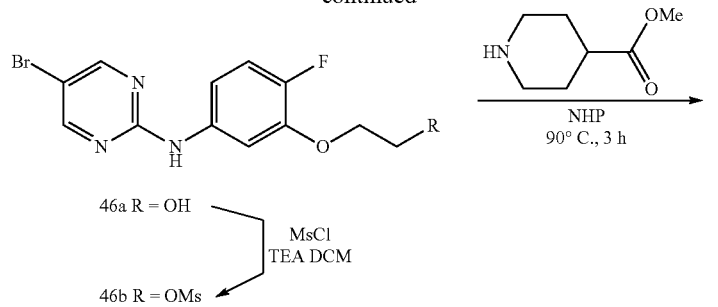

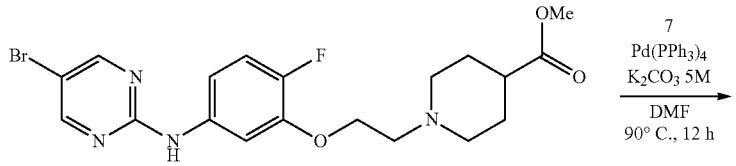

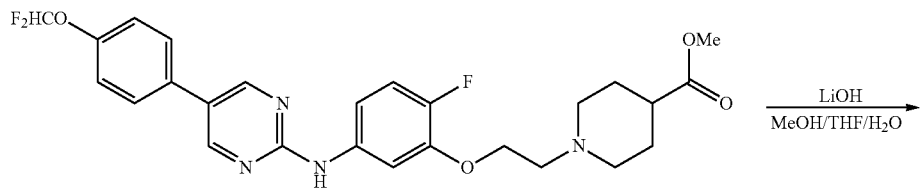

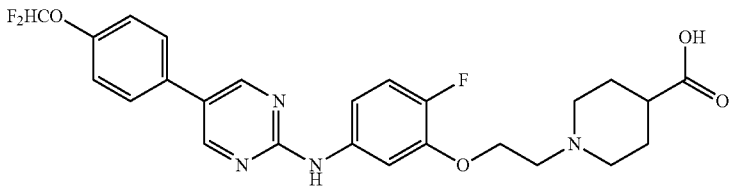

F1

To a mixture of -5-bromo 2-chloropyrimidine 4 (1.1 mmol) and 4-fluoro-3-methoxyaniline (1.1 mmol) in 5 mL of 1,4-dioxane is added p-TSA (1.0 mmol). The reaction mixture is heated at 105° C. for 4 h. After this time, the reaction mixture is diluted with a 2M Na$_2$CO$_3$ solution and extracted with DCM (3×50 mL). The organic layer is washed with brine, dried over Na$_2$SO$_4$ and concentrated. Purification prep HPLC (ACN gradient 20-70%) 5-bromo-N-(4-fluoro-3-methoxyphenyl)pyrimidin-2-amine 44 as brown solid. MS (m/z) (M+1)$^+$: 299.1.

To a solution of 5-bromo-N-(4-fluoro-3-methoxyphenyl)pyrimidin-2-amine 44 (0.25 mmol) in 3 mL of anhydrous DCM at 0° C. is added BBr$_3$ (1.27 mmol) drop wise. The reaction mixture is stirred at rt for 12 h. After this time the reaction mixture is diluted with a 2M solution of Na$_2$CO$_3$ and extracted with DCM (2×20 mL). The organic layer is washed with brine, dried over Na$_2$SO$_4$ and concentrated to afford 5-(5-bromopyrimidin-2-ylamino)-2-fluorophenol 45 as brownish solid which is used without further purification. MS (m/z) (M+1)$^+$: 286.2.

A solution of 5-(5-bromopyrimidin-2-ylamino)-2-fluorophenol 45 (0.25 mmol), 2-bromoethanol (0.28 mmol) and cesium carbonate (0.36 mmol) in acetonitrile (3 mL) is heated to 100° C. for 12 h. The reaction is evaporated to dryness then re-dissolved in DCM. The organic mixture is washed with water and brine then dried over magnesium sulfate, filtered and reduced to dryness to yield 2-(5-(5-bromopyrimidin-2-ylamino)-2-fluorophenoxy)ethanol 46a as a brown solid which is used without further purification. MS (m/z) (M+1)$^+$: 329.2.

To a solution of 2-(5-(5-bromopyrimidin-2-ylamino)-2-fluorophenoxy)ethanol 46a (0.24 mmol) in DCM (15 mL) is added triethylamine (0.24 mmol) and methanesulfonyl chloride (0.24 mmol). The reaction mixture is stirred at rt for 12 h then washed with brine and dried over magnesium sulfate, filtered and reduced to dryness. The resulting tan solid of 2-(5-(5-bromopyrimidin-2-ylamino)-2-fluorophenoxy)ethyl methanesulfonate 46b is used without further purification. MS (m/z) (M+1)$^+$: 407.1.

2-(5-(5-bromopyrimidin-2-ylamino)-2-fluorophenoxy)ethyl methanesulfonate 46b (0.24 mmol) and methyl piperidine-4-carboxylate (0.48 mmol) are dissolved in NMP (2 mL) and heated to 90° C. for 3 h. The reaction mixture is cooled to rt and diluted with water and extracted with EtOAc (2×30 mL). The organic layer is washed with water, brine, dried over sodium sulfate, and concentrated to dryness. The crude product is purified by short SiO$_2$ chromatography using DCM:hexane=9:1 as eluant to yield methyl 1-(2-(5-(5-bromopyrimidin-2-ylamino)-2-fluorophenoxy)ethyl)piperidine-4-carboxylate 47 as light brown solid. MS (m/z) (M+1)$^+$: 454.1.

To a solution of methyl 1-(2-(5-(5-bromopyrimidin-2-ylamino)-2-fluorophenoxy)ethyl)piperidine-4-carboxylate 47 (0.24 mmol) in 1,4-dioxane (2.0 mL) is added 2-(4-(difluoromethoxy)phenyl)-4,4,5,5-tetramethyl-1,3,2-dioxaborolane 7 (0.28 mmol), 1.8M K$_2$CO$_3$ (0.5 mmol) and Pd(PPh$_3$)$_4$ (0.017 mmol). The reaction is evacuated and backfilled with nitrogen twice then heated at 90° C. for 12 h. The reaction mixture is cooled to rt, diluted with water (10 mL) and extracted with DCM (2×20 mL). The organic layer is separated, dried over Na$_2$SO$_4$ and concentrated. Purification by preparative HPLC (ACN gradient 20-70%) affords methyl 1-(2-(5-(5-(4-(difluoromethoxy)phenyl)pyrimidin-2-ylamino)-2-fluorophenoxy)ethyl)piperidine-4-carboxylate 48 as white solid. MS (m/z) (M+1)$^+$: 517.1.

To methyl 1-(2-(5-(5-(4-(difluoromethoxy)phenyl)pyrimidin-2-ylamino)-2-fluorophenoxy)ethyl)piperidine-4-carboxylate 48 (0.072 mmol) is added THF (1 mL), MeOH (0.8 mL) and 6M lithium hydroxide (0.42 mmol). The reaction mixture is stirred at rt for 6 h until complete by LCMS. The organic solvents are evaporated and the reaction mixture is diluted with water and neutralized with 6M HCl (0.42 mmol). The resulting precipitate is filtered, washed with water and air dried to yield F1 as white solid. $^1$H NMR (400 MHz, d6-DMSO) δ 9.88 (s, 1H), 8.85 (s, 2H), 7.79 (m, 2H), 7.71 (dd, J=8.0, 12.0 Hz, 1H), 7.46 (m, 1H), 7.31 (m, 2H), 7.29 (t, J=69.0 Hz, 1H), 7.23 (d, J=8.0 Hz, 1H), 7.20 (d, J=8.0 Hz, 1H), 4.41 (m, 2H), 3.58 (m, 6H), 3.14 (m, 2H), 2.12 (m, 2H), 1.77 (m, 1H). MS (m/z) (M+1)$^+$: 503.2.

Example F2

1-(5-(5-(4-(difluoromethoxy)phenyl)pyrimidin-2-ylamino)-2-methylphenethyl)piperidine-4-carboxylic acid

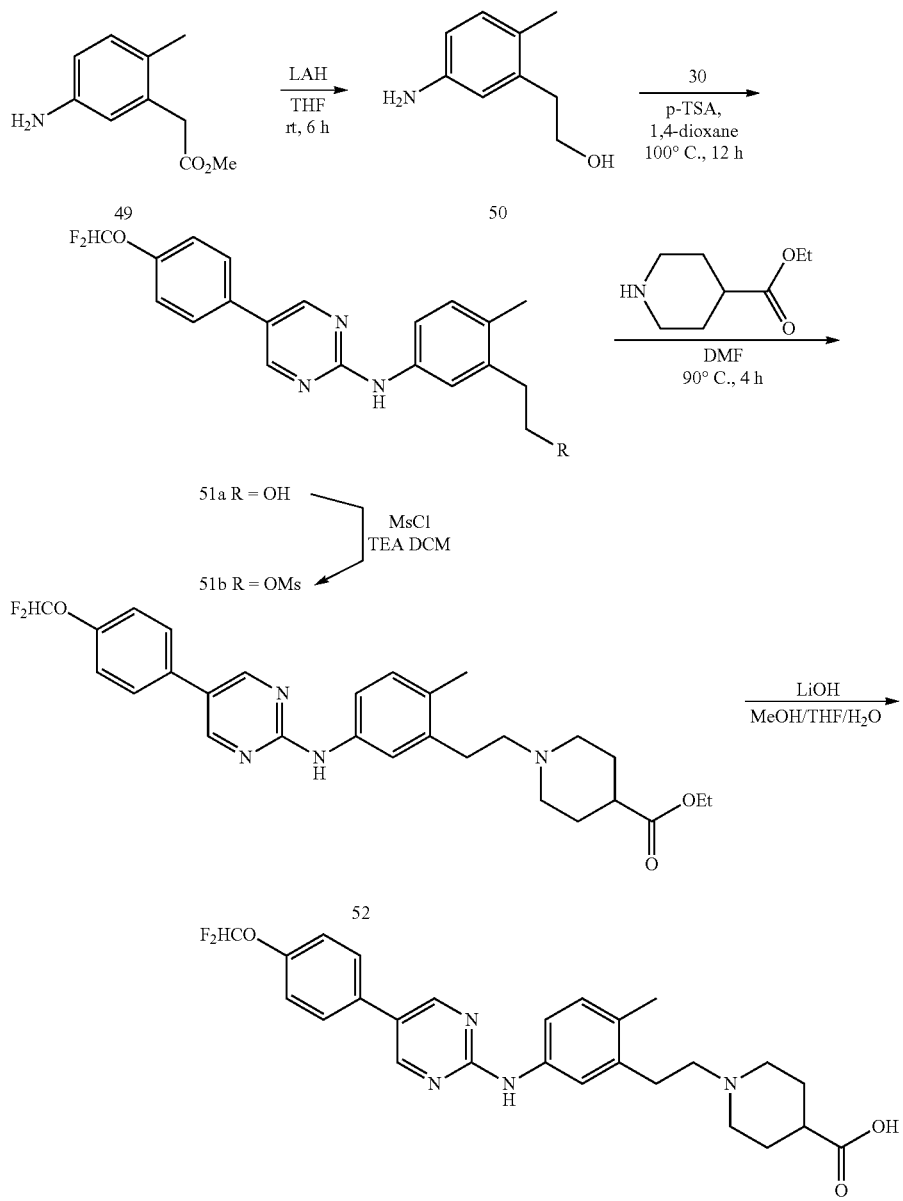

To a solution of (5-amino-2-methyl-phenyl)-acetic acid methyl ester 49 (1.4 mmol) in THF (7 mL) at 0° C. is added 1M lithium aluminum hydride THF solution (1.4 mmol). The reaction is stirred at rt for 6 h and subsequently quenched with ice water and partitioned with ethyl acetate. The organic layer is washed with brine, dried over magnesium sulfate, filtered and reduced to dryness to yield 2-(amino-2-methylphenyl) ethanol 50 as tan crystalline solid, which is used without further purification.

A solution of 2-chloro-5-(4-difluoromethoxy-phenyl)-pyrimidine 30 (1.3 mmol), 2-(5-Amino-2-methyl-phenyl)-ethanol 50 (1.3 mmol) and p-TSA (0.24 g, 1.3 mmol) in dioxane (10 mL) is heated at 100° C. for 12 h then cooled to rt. The reaction mixture is slowly added to water (100 mL) with stirring. The resulting precipitate is collected by filtration, washed with water and air dried. The crude precipitate is purified by column chromatography on silica with hexanes: EtOAc=1:1 as eluant to yield 2-{5-[5-(4-difluoromethoxy-phenyl)-pyrimidin-2-ylamino]-2-methyl-phenyl}-ethanol 51a as solid. MS (m/z) (M+1)$^+$: 372.3.

To a solution of 2-{5-[5-(4-difluoromethoxy-phenyl)-pyrimidin-2-ylamino]-2-methyl-phenyl}-ethanol 51a (0.8 mmol) in DCM (25 mL) is added triethyl amine (1.0 mmol) and methanesulfonyl chloride (0.9 mmol). The reaction mixture is stirred at rt for 12 h then washed with brine and dried over magnesium sulfate, filtered and reduced to dryness. The resulting 5-(5-(4-(difluoromethoxy)phenyl)pyrimidin-2-ylamino)-2-methylphenethyl methanesulfonate 51b as clear amber oil is used without further purification. MS (m/z) (M+1)$^+$: 450.1.

5-(5-(4-(Difluoromethoxy)phenyl)pyrimidin-2-ylamino)-2-methylphenethyl methanesulfonate 51b (0.9 mmol), ethyl piperidine-4-carboxylate (2.2 mmol) are dissolved in DMF (10 mL) and heated to 90° C. for 4 h then cooled to rt. The reaction mixture is partitioned with EtOAc and water. The organic layer is washed with water, brine, dried over magnesium sulfate, filtered and reduced to dryness. The crude material is purified by column chromatography on silica with hexane:EtOAc=1:1 to 100% EtOAc as eluant to yield ethyl 1-(5-(5-(4-(difluoromethoxy)phenyl)pyrimidin-2-ylamino)-2-methylphenethyl)piperidine-4-carboxylate 52 as clear viscous oil. MS (m/z) (M+1)$^+$: 511.2.

To ethyl 1-(5-(5-(4-(difluoromethoxy)phenyl)pyrimidin-2-ylamino)-2-methylphenethyl)piperidine-4-carboxylate 52 (0.6 mmol) is added THF (3 mL), MeOH (2 mL) and 3M lithium hydroxide (7.3 mmol). The reaction mixture is stirred at rt for 6 h until complete as detected by LCMS. Subsequently, the organic solvents are evaporated and the reaction mixture is diluted with water (10 mL) then neutralized with 3M HCl (7.3 mmol). The resulting precipitate is filtered, washed with water and air dried. The crude precipitate is purified by preparative LCMS to yield 1-(5-(5-(4-(difluoromethoxy)phenyl)pyrimidin-2-ylamino)-2-methylphenethyl)piperidine-4-carboxylic acid F2 as white solid. $^1$H NMR (400 MHz, d6-DMSO) δ 9.69 (s, 1H), 8.79 (s, 2H), 7.75 (d, J=8.0 Hz, 2H), 7.60 (bd, J=8.0 Hz, 1H), 7.56 (bs, 1H), 7.46 (s, 1H), 7.28 (d, J=8.0 Hz, 2H), 7.12 (d, J=8.0 Hz, 1H), 3.19 (m, 1H), 2.96 (m, 2H), 2.27 (s, 3H), 2.10 (m, 2H), 1.75 (m, 2H). MS (m/z) (M+1)$^+$: 483.2.

Type G Compounds

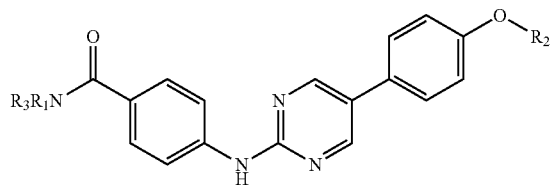

Example G1

4-(4-(5-(4-(Difluoromethoxy)phenyl) pyrimidin-2-ylamino)benzoyl)-1-methylpiperazin-2-one

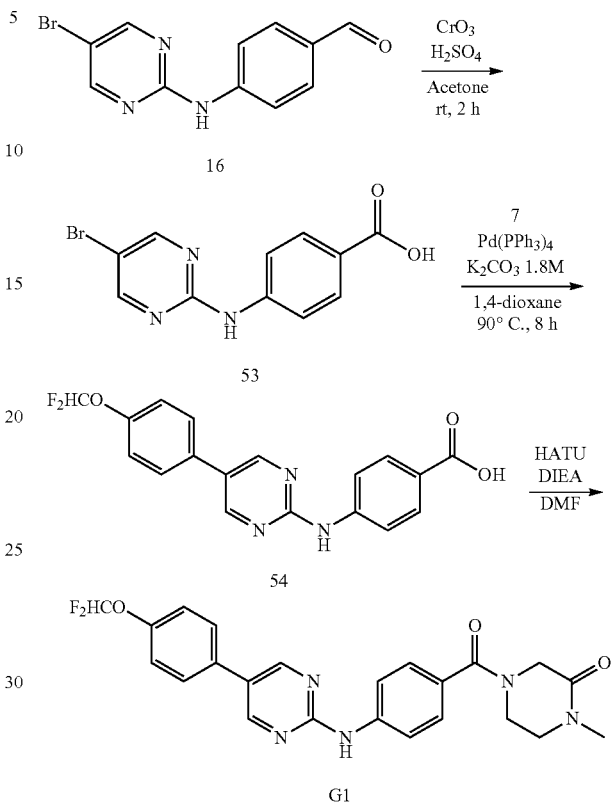

To a solution of 4-(5-bromopyrimidin-2-ylamino)benzaldehyde 16 (1.26 mmol) in acetone (5 mL) is added Jones' reagent (3.0 mmol of a 4M solution) portionwise until complete conversion as detected by LCMS. Isopropanol (10 mL) is added and the reaction mixture is stirred at rt for 1 h, then the solvent is removed under vacuum. The green residue is re-dissolved in water and partitioned with ethyl acetate. The organic layer is washed with water, brine, dried over sodium sulfate, filtered and reduced to dryness to afford 4-(5-bromopyrimidin-2-ylamino)benzoic acid 53 as yellow solid which is used without further purification. MS (m/z) (M+1)$^+$: 295.1.

To 4-(5-bromopyrimidin-2-ylamino)benzoic acid 53 (0.25 mmol) in 1,4-dioxane (2.0 mL) is added 2-(4-(difluoromethoxy)phenyl)-4,4,5,5-tetramethyl-1,3,2-dioxaborolane 7 (0.28 mmol), 1.8M K$_2$CO$_3$ (0.5 mmol) and Pd(PPh$_3$)$_4$ (0.017 mmol). The reaction is evacuated and backfilled with nitrogen twice then heated at 90° C. for 8 h. The reaction mixture is diluted with water (10 mL) neutralized with 2M HCl and extracted with DCM (3×20 mL). Purification by preparative HPLC (ACN gradient 20-70%) affords 4-(5-(4-(difluoromethoxy)phenyl)pyrimidin-2-ylamino)benzoic acid 54 as white solid. MS (m/z) (M+1)$^+$: 358.2.

4-(5-(4-(difluoromethoxy)phenyl)pyrimidin-2-ylamino) benzoic acid 54 (0.022 mmol), HATU (0.027 mmol) and 1-methylpiperazin-2-one (0.022 mmol) are dissolved in dry DMF (0.5 mL) at rt. Diisopropylethylamine (0.06 mmol) is added to the solution. The reaction mixture is stirred for 1 h at rt. HPLC purification affords 4-(4-(5-(4-(difluoromethoxy) phenyl)pyrimidin-2-ylamino)benzoyl)-1-methylpiperazin-2-one G1 as a TFA salt. $^1$H NMR (400 MHz, d6-DMSO) δ 10.1 (s, 1H), 8.87 (s, 2H), 7.90 (d, J=8.4 Hz, 2H), 7.79 (d, J=8.7 Hz, 2H), 7.43 (d, J=8.4 Hz, 2H), 7.29 (d, J=8.0 Hz, 2H), 7.12 (t, J=51.2 Hz, 1H), 4.1 (s, 2H), 2.87 (s, 3H), 2.55 (m, 4H). MS (m/z) (M+1)$^+$: 454.2.

Example G2

4-(4-(5-(4-(difluoromethoxy)phenyl)pyrimidin-2-ylamino)benzoyl)-1-(2-hydroxyethyl)piperazin-2-one

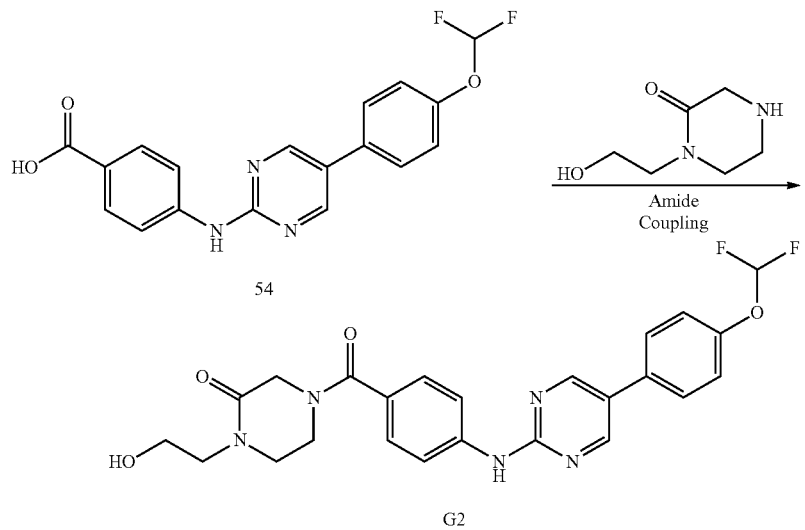

Similar to the preparation of G1. $^1$H NMR (400 MHz, d6-DMSO) δ 10.1 (s, 1H), 8.87 (s, 2H), 7.90 (d, J=8.4 Hz, 2H), 7.79 (d, J=8.4 Hz, 2H), 7.44 (d, J=8.4 Hz, 2H), 7.29 (d, J=8.4 Hz, 2H), 7.2 (t, J=50.2 Hz, 1H), 4.1 (s, 2H), 2.55 (m, 6H), 2.51 (m, 4H). MS (m/z) (M+1)$^+$: 484.1.

Example G3

4-(4-(5-(4-(difluoromethoxy)phenyl)pyrimidin-2-ylamino)benzoyl)piperazin-2-one

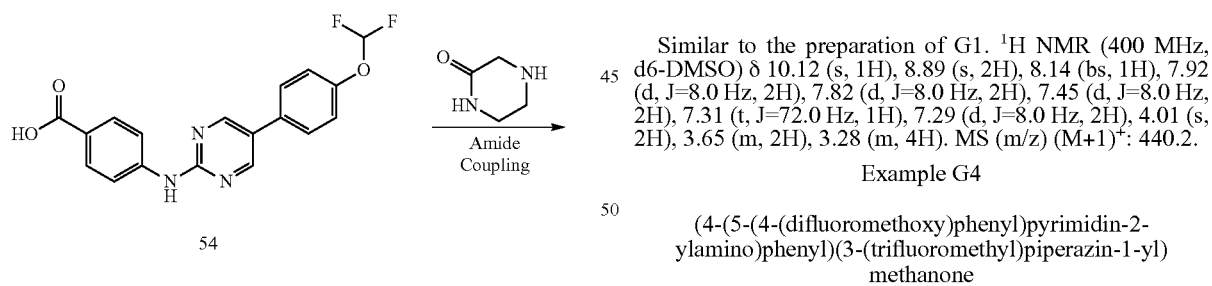

Similar to the preparation of G1. $^1$H NMR (400 MHz, d6-DMSO) δ 10.12 (s, 1H), 8.89 (s, 2H), 8.14 (bs, 1H), 7.92 (d, J=8.0 Hz, 2H), 7.82 (d, J=8.0 Hz, 2H), 7.45 (d, J=8.0 Hz, 2H), 7.31 (t, J=72.0 Hz, 1H), 7.29 (d, J=8.0 Hz, 2H), 4.01 (s, 2H), 3.65 (m, 2H), 3.28 (m, 4H). MS (m/z) (M+1)$^+$: 440.2.

Example G4

(4-(5-(4-(difluoromethoxy)phenyl)pyrimidin-2-ylamino)phenyl)(3-(trifluoromethyl)piperazin-1-yl)methanone

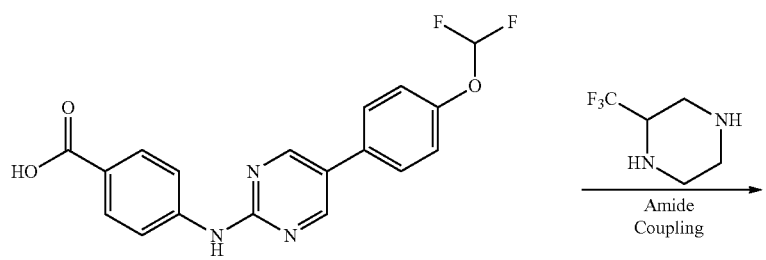

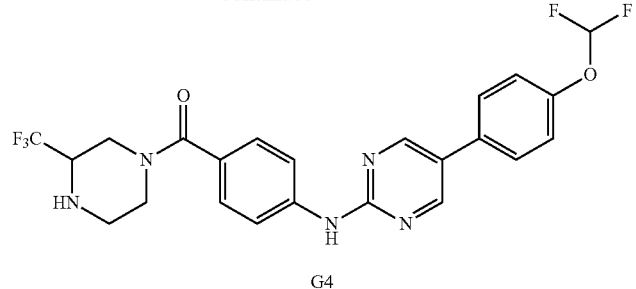

G4

Similar to the preparation of G1. $^1$H NMR (400 MHz, d6-DMSO) δ 10.13 (s, 1H), 8.89 (s, 2H), 7.93 (d, J=8.0 Hz, 2H), 7.82 (d, J=8.0 Hz, 2H), 7.44 (d, J=8.0 Hz, 2H), 7.31 (t, J=76.0 Hz, 1H), 7.29 (d, J=8.0 Hz, 2H), 4.01 (bs, 4H), 3.30 (bs, 2H), 3.28 (bs, 2H). MS (m/z) (M+1)$^+$: 494.2.

Table 1 describes representative compounds of the invention, prepared following the procedures described above. Compounds in Table 1 have an activity of <1 μM in c-kit Mo7e assay and/or PDGFR TG-HA-VSMC assay.

TABLE 1

| Example No. | Structure | MS [M + 1]$^+$ |
|---|---|---|
| A1 | 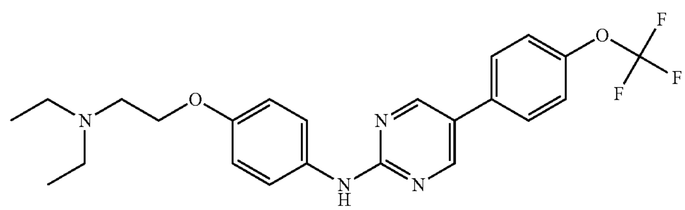 | 447.2 |
| A2 | 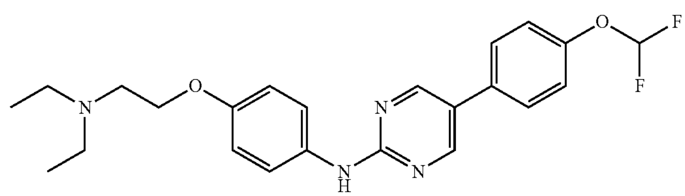 | 429.2 |
| A3 | 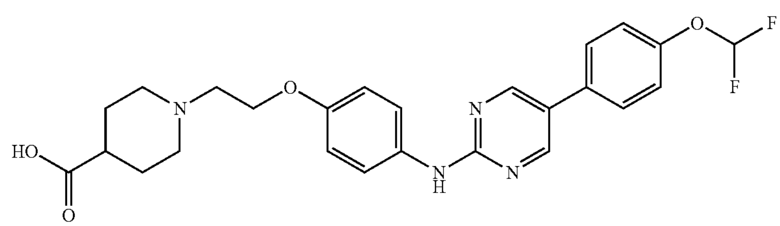 | 485.2 |
| A4 | 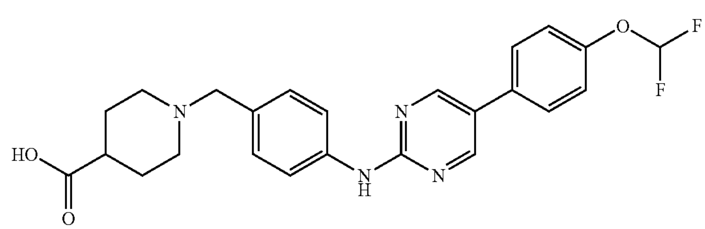 | 455.2 |

TABLE 1-continued

| Example No. | Structure | MS [M + 1]+ |
|---|---|---|
| A5 | 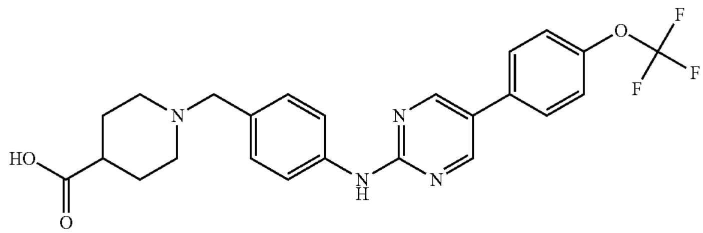 | 473.2 |
| A6 | 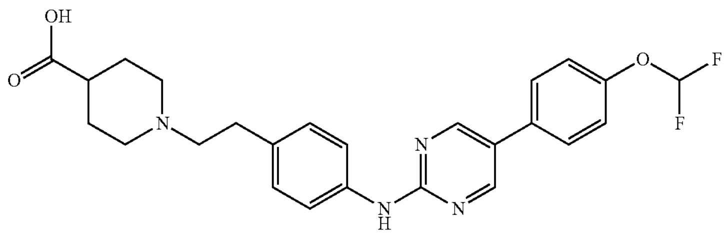 | 469.2 |
| B1 | 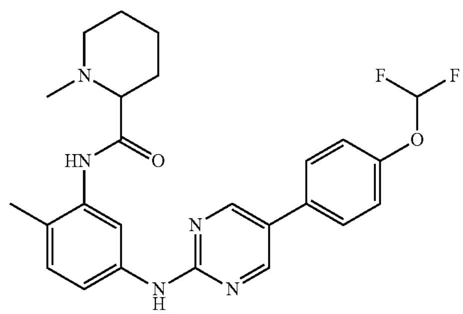 | 468.2 |
| B2 | 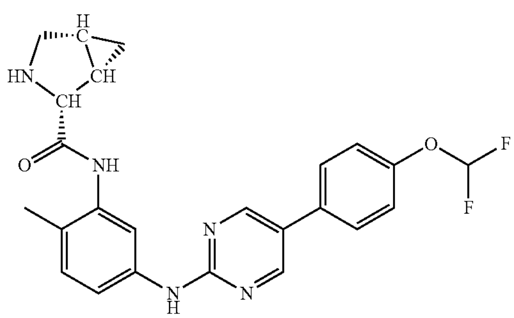 | 452.2 |
| B3 | 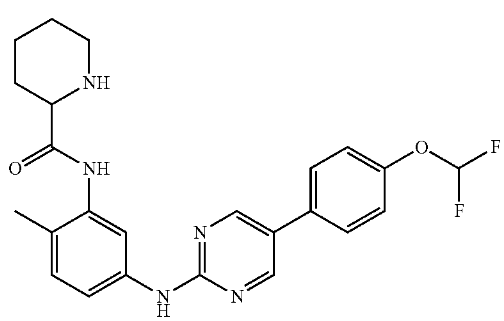 | 454.2 |

TABLE 1-continued
| Example No. | Structure | MS [M + 1]+ |
|---|---|---|
| B4 | 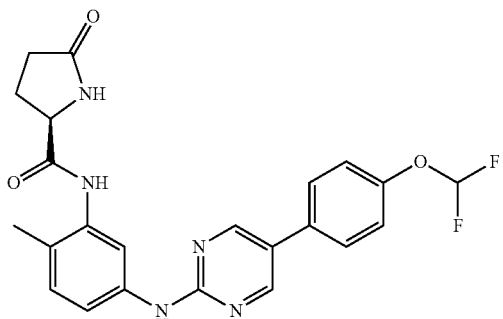 | 454.2 |
| B5 | 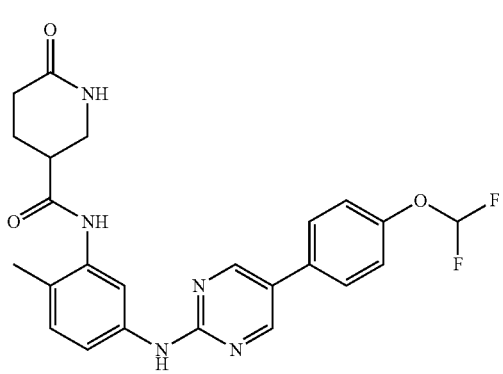 | 468.2 |
| B6 | 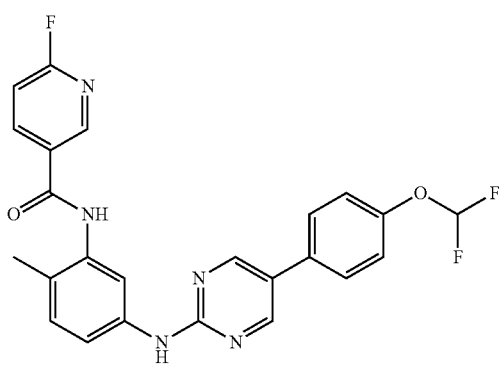 | 466.1 |
| B7 | 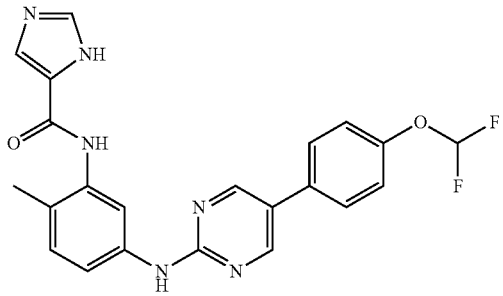 | 437.2 |

TABLE 1-continued

| Example No. | Structure | MS [M + 1]+ |
|---|---|---|
| B8 | 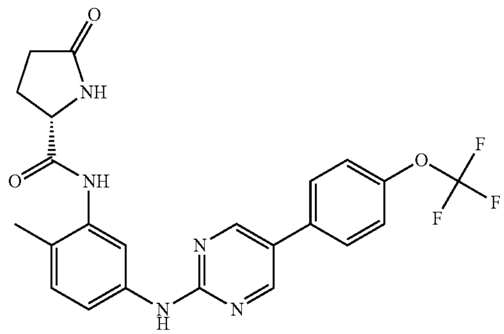 | 472.2 |
| B9 | 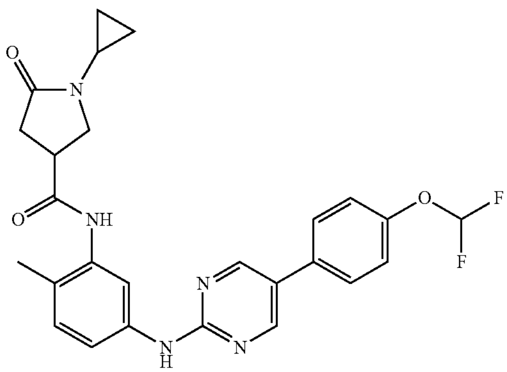 | 494.1 |
| B10 | 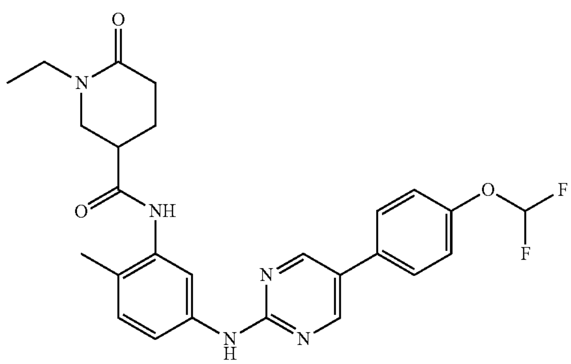 | 496.2 |
| C1 | 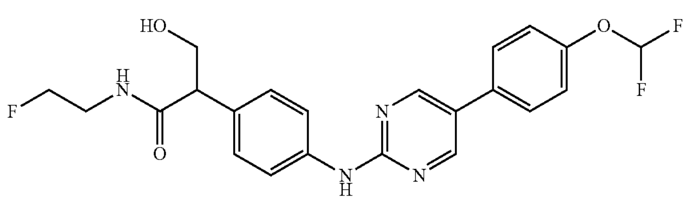 | 447.2 |
| C2 | 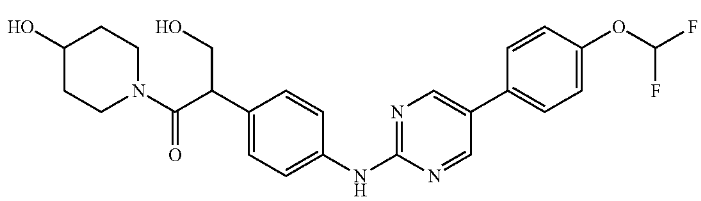 | 485.2 |

TABLE 1-continued

| Example No. | Structure | MS [M + 1]+ |
|---|---|---|
| C3 | 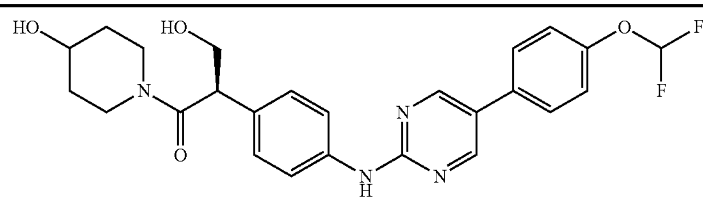 | 485.1 |
| C4 | 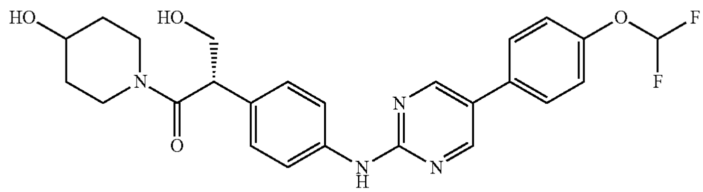 | 485.1 |
| C5 | 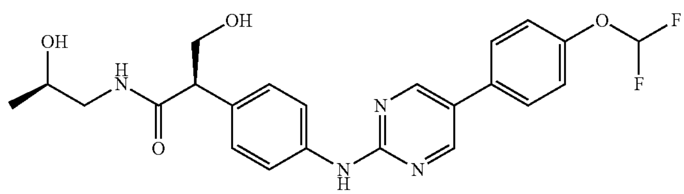 | 459.1 |
| C6 | 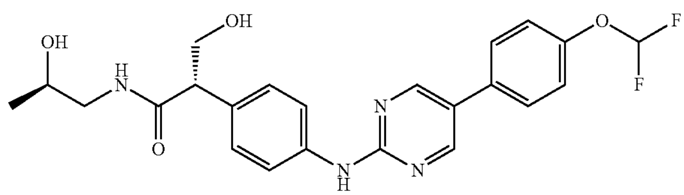 | 459.1 |
| C7 | 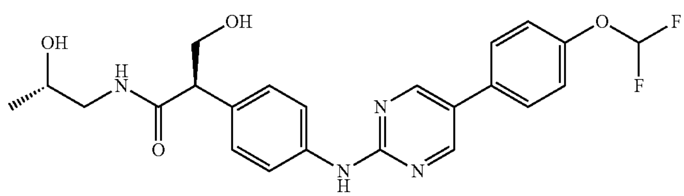 | 459.1 |
| C8 | 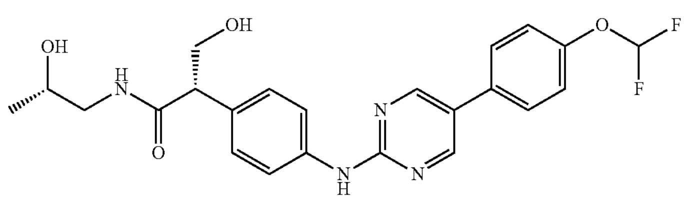 | 459.1 |
| C9 | 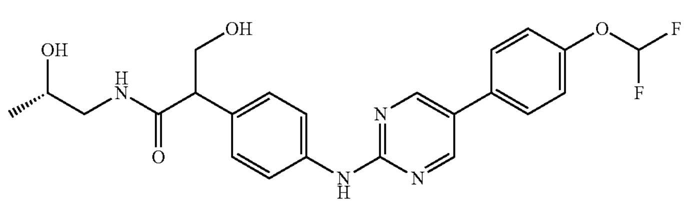 | 459.2 |
| C10 | 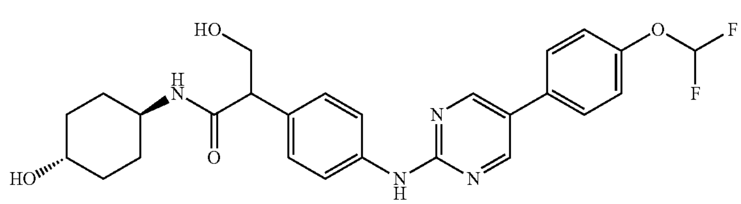 | 499.2 |

TABLE 1-continued

| Example No. | Structure | MS [M + 1]+ |
|---|---|---|
| C11 | 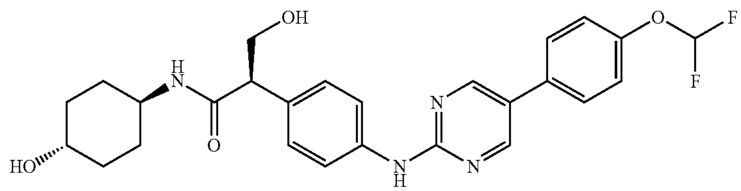 | 499.1 |
| C12 | 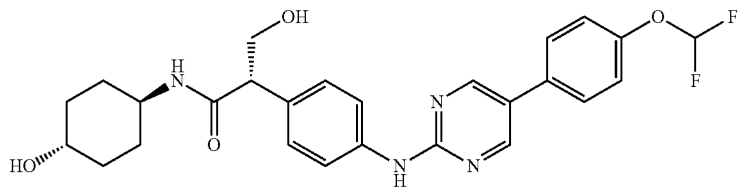 | 499.2 |
| C13 | 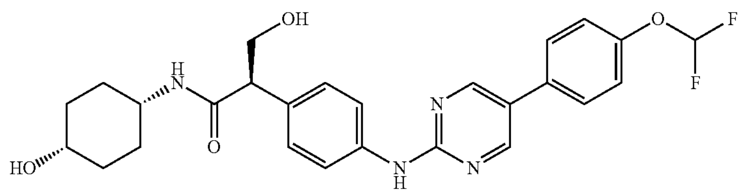 | 499.1 |
| C14 | 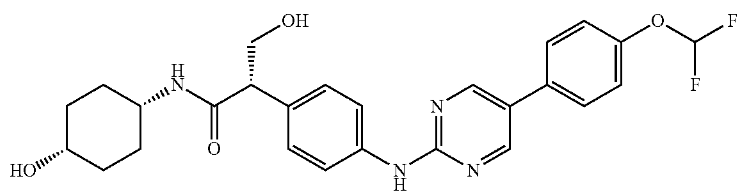 | 499.2 |
| C15 | 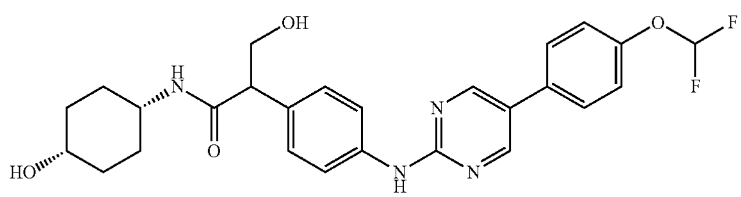 | 499.2 |
| C16 | 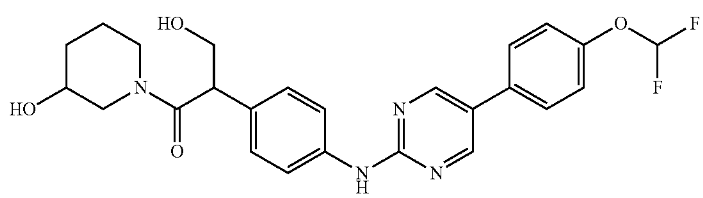 | 485.2 |
| C17 | 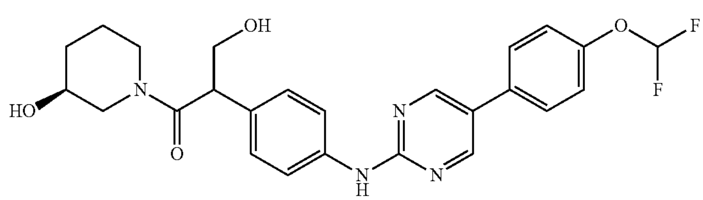 | 485.2 |
| C18 | 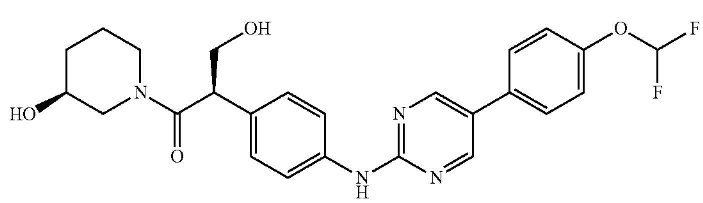 | 485.1 |

TABLE 1-continued

| Example No. | Structure | MS [M + 1]+ |
|---|---|---|
| C19 | 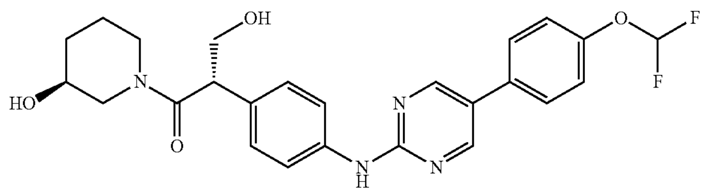 | 485.1 |
| C20 | 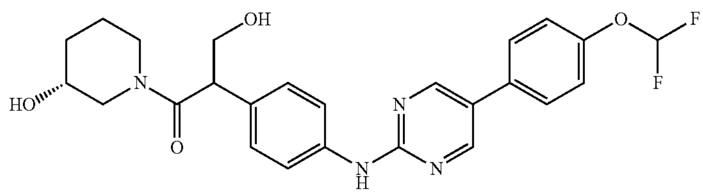 | 485.2 |
| C21 | 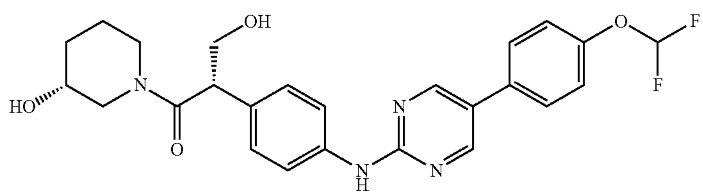 | 485.1 |
| C22 | 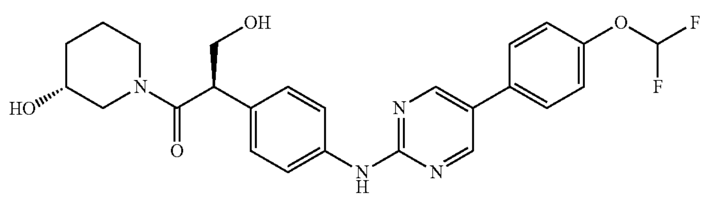 | 485.2 |
| C23 | 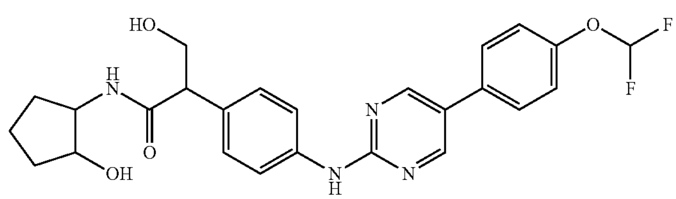 | 485.2 |
| C24 | 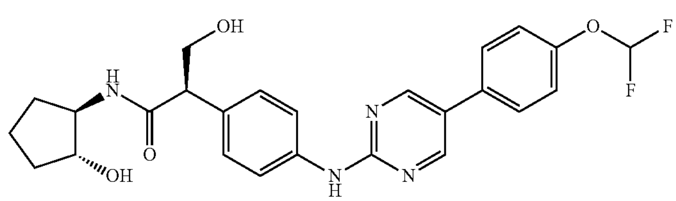 | 485.1 |
| C25 | 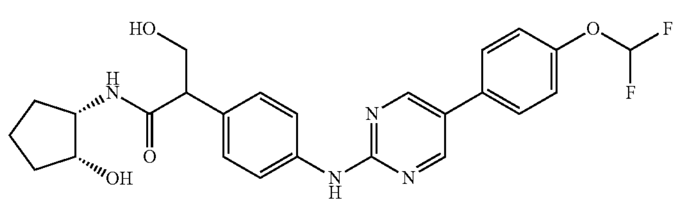 | 485.2 |

TABLE 1-continued

| Example No. | Structure | MS [M + 1]+ |
|---|---|---|
| C26 | 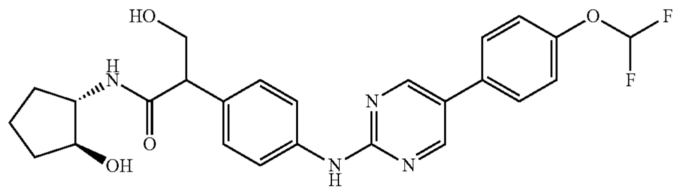 | 485.2 |
| C27 | 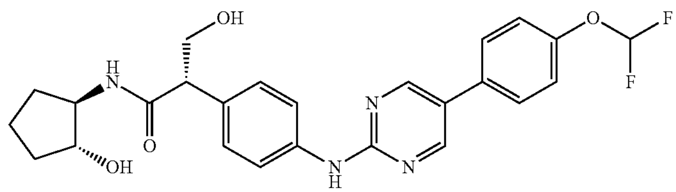 | 485.1 |
| C28 | 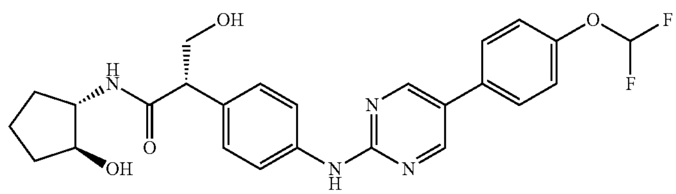 | 485.1 |
| C29 | 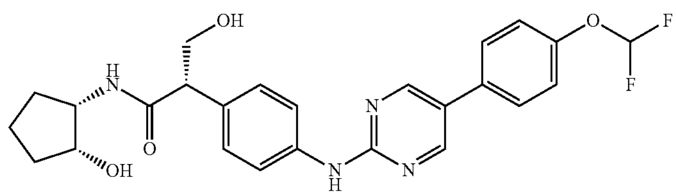 | 485.2 |
| C30 | 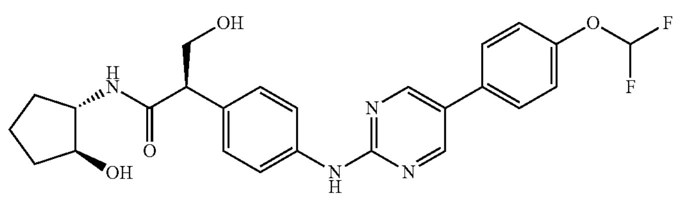 | 485.1 |
| C31 | 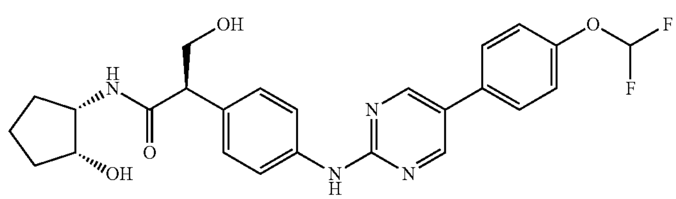 | 485.2 |
| C32 | 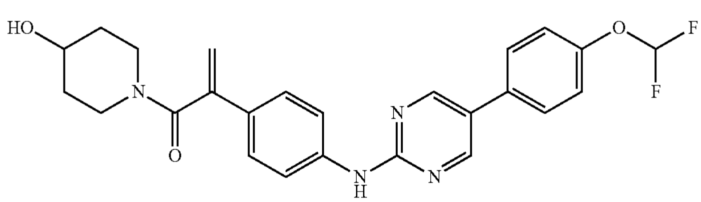 | 467.2 |
| C33 | 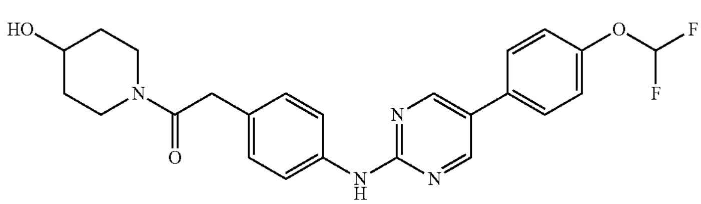 | 455.1 |

TABLE 1-continued

| Example No. | Structure | MS [M + 1]+ |
|---|---|---|
| C34 | 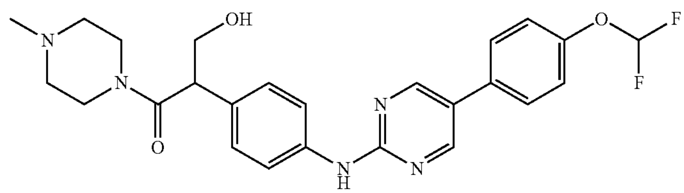 | 484.4 |
| C35 | 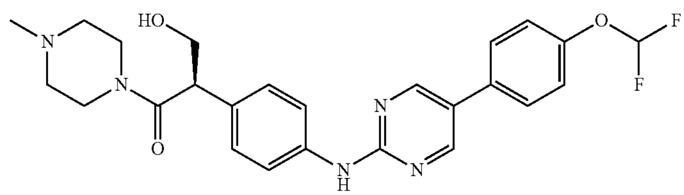 | 484.1 |
| C36 | 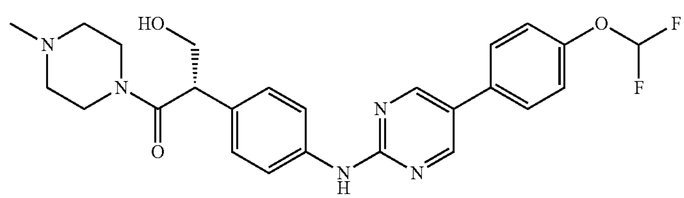 | 484.2 |
| C37 | 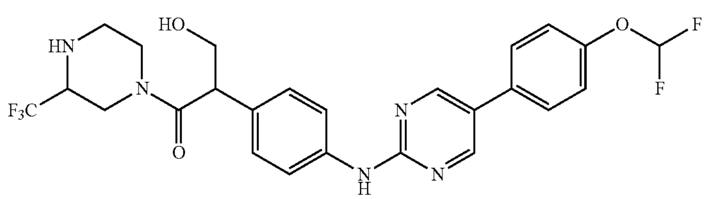 | 538.1 |
| C38 | 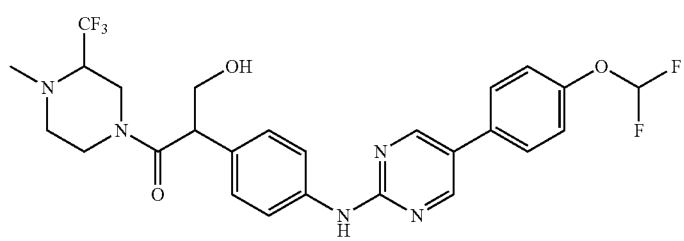 | 552.1 |
| D1 | 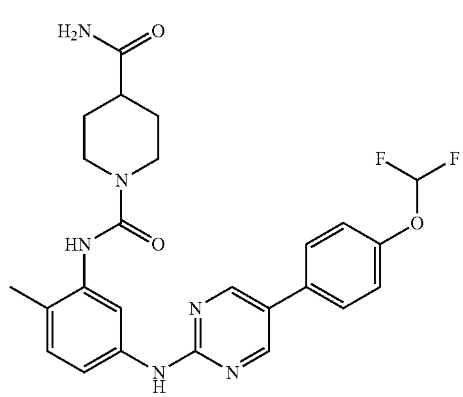 | 497.2 |

TABLE 1-continued

| Example No. | Structure | MS [M + 1]+ |
|---|---|---|
| D2 | 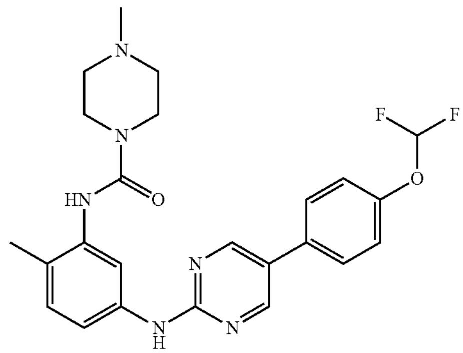 | 469.2 |
| D3 | 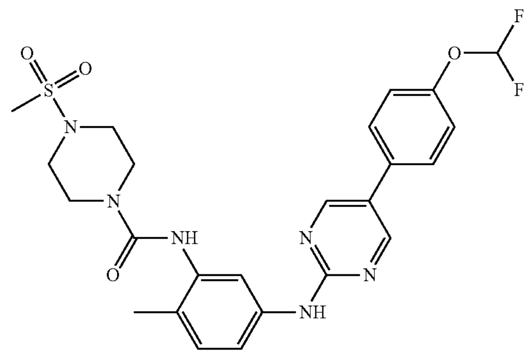 | 533.2 |
| D4 | 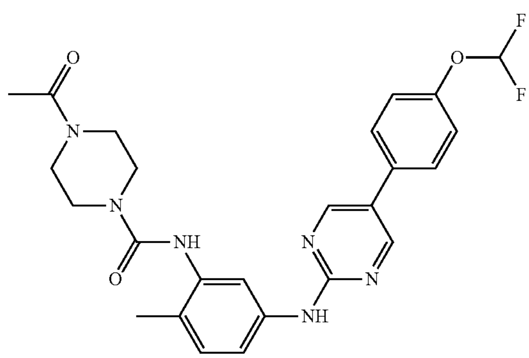 | 497.2 |
| D5 | 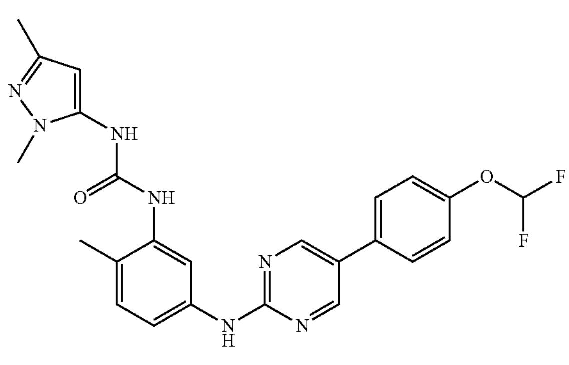 | 480.2 |

TABLE 1-continued

| Example No. | Structure | MS [M + 1]+ |
|---|---|---|
| D6 | 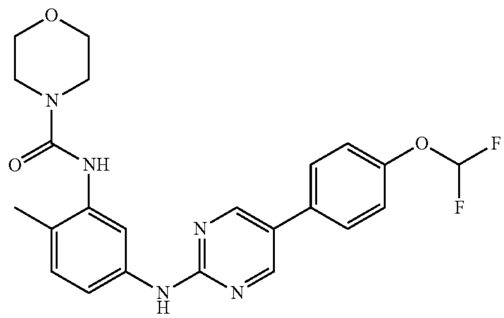 | 456.2 |
| D7 | 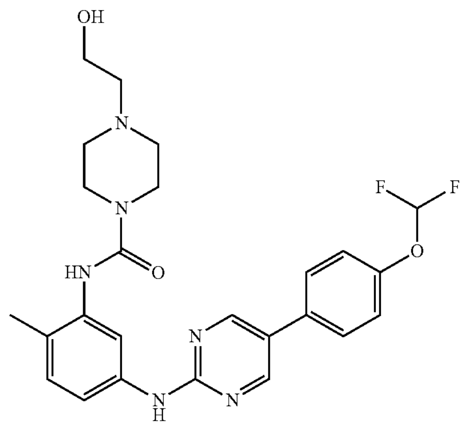 | 499.2 |
| D8 | 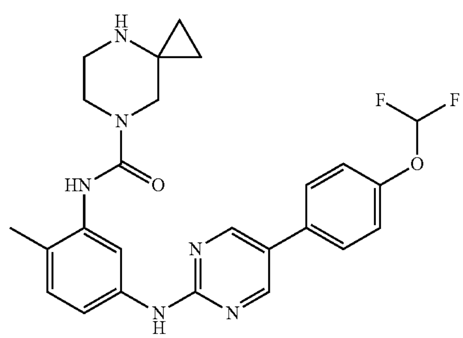 | 481.2 |
| D9 | 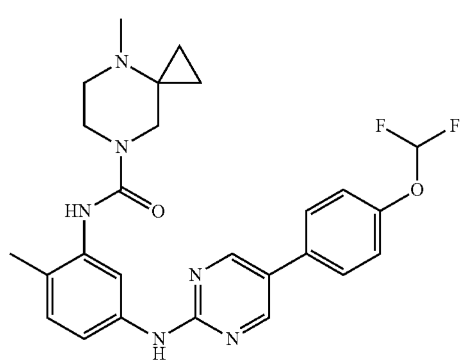 | 495.2 |

TABLE 1-continued
| Example No. | Structure | MS [M + 1]+ |
|---|---|---|
| D10 | 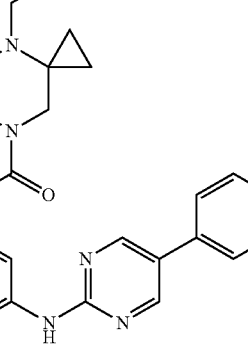 | 524.56 |
| D11 | 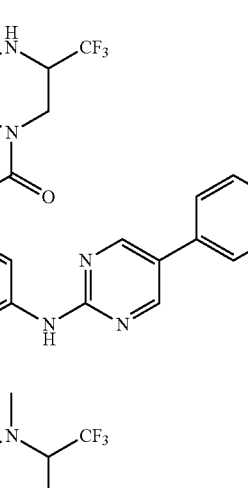 | 522.47 |
| D12 | 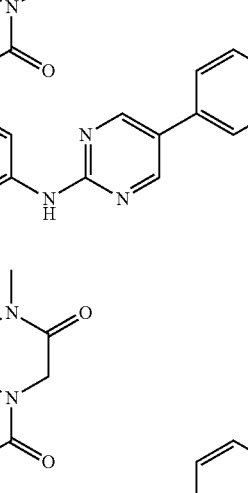 | 536.50 |
| D13 | 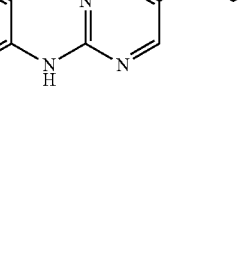 | 483.2 |

TABLE 1-continued

| Example No. | Structure | MS [M + 1]+ |
|---|---|---|
| D14 | 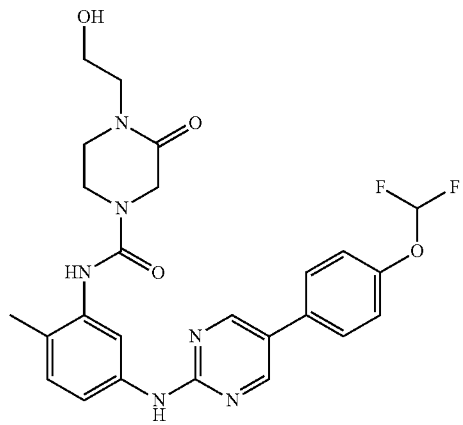 | 513.1 |
| E1 | 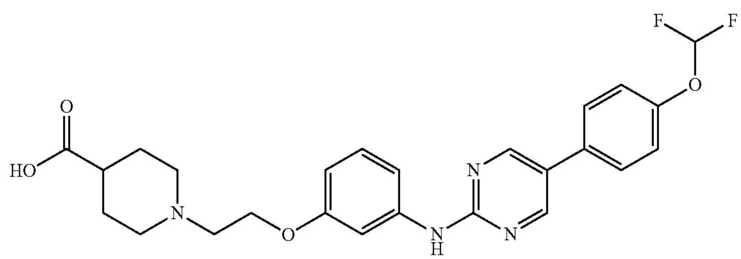 | 485.2 |
| E2 | 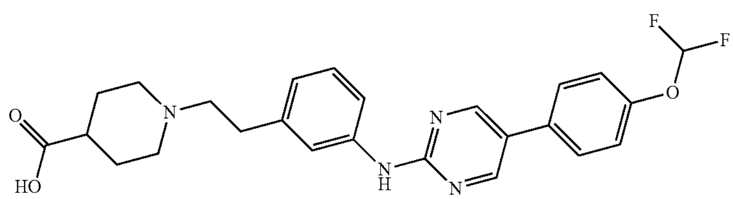 | 469.2 |
| E3 | 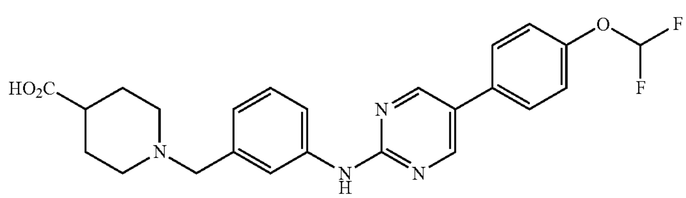 | 455.1 |
| F1 | 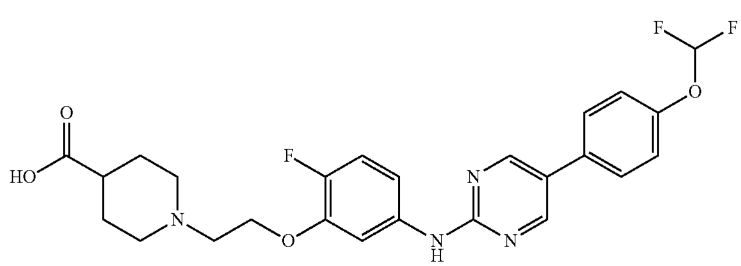 | 503.2 |
| F2 | 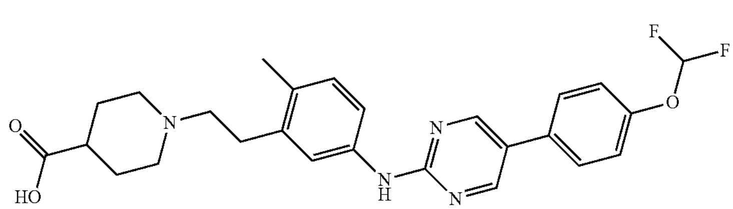 | 483.2 |

TABLE 1-continued

| Example No. | Structure | MS [M + 1]+ |
|---|---|---|
| G1 | 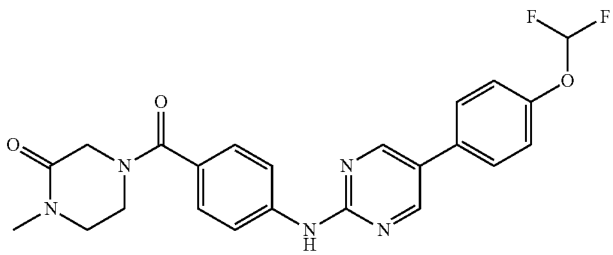 | 454.2 |
| G2 | 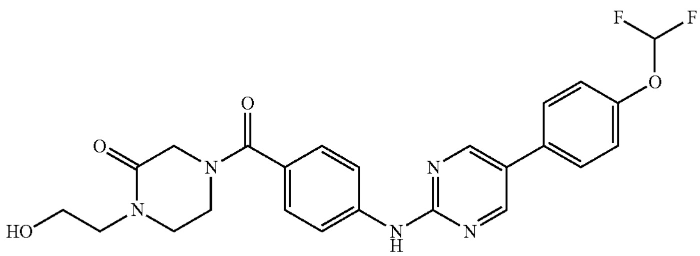 | 485.2 |
| G3 | 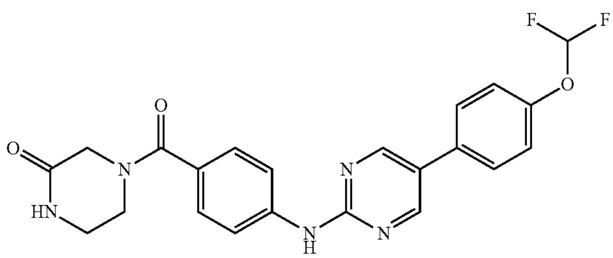 | 439.4 |
| G4 | 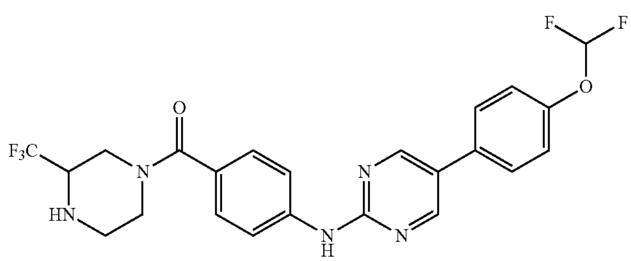 | 495.1 |

TABLE 1-continued

| Example No. | Structure | MS [M + 1]+ |
|---|---|---|

TABLE 1-continued

| Example No. | Structure | MS [M + 1]+ |
|---|---|---|
| | | |

Assays

Compounds of the present invention are assayed to measure their capacity to selectively inhibit the proliferation of wild type Ba/F3 cells and Ba/F3 cells transformed with Tel c-kit kinase and Tel PDGFR fused tyrosine kinases. In addition, compounds of the invention may selectively inhibit SCF dependent proliferation in Mo7e cells. Further, compounds are assayed to measure their capacity to inhibit Abl, ARG, BCR-Abl, BRK, EphB, Fms, Fyn, KDR, c-Kit, LCK, PDGF-R, b-Raf, c-Raf, SAPK2, Src, Tie2 and TrkB kinases.

Proliferation Assay: BaF3 Library—Bright glo Readout Protocol

Compounds are tested for their ability to inhibit the proliferation of wt Ba/F3 cells and Ba/F3 cells transformed with Tel fused tyrosine kinases. Untransformed Ba/F3 cells are maintained in media containing recombinant IL3. Cells are plated into 384 well TC plates at 5,000 cells in 50 ul media per well and test compound at 0.06 nM to 10 µM is added. The cells are then incubated for 48 hours at 37° C., 5% $CO_2$. After incubating the cells, 25 µL of BRIGHT GLO® (Promega) is added to each well following manufacturer's instructions and the plates are read using Analyst GT—Luminescence mode—50000 integration time in RLU. $IC_{50}$ values are determined from a dose response curve.

Mo7e Assay

The compounds described herein are tested for inhibition of SCF dependent proliferation using Mo7e cells which endogenously express c-kit in a 96 well format. Two-fold serially diluted test compounds (Cmax=10 µM) are evaluated for their antiproliferative activity of Mo7e cells stimulated with human recombinant SCF. After 48 hours of incubation at 37° C., cell viability is measured by using a MTT colorimetric assay from Promega.

c-Kit HTRF Protocol

An aliquot (5 µL) of a 2x concentration of c-kit enzyme mix 25 ng c-kit (5 ng/µL) and 2 µM of Biotin-EEEPQYEE-IPIYLELLP-$NH_2$ peptide in kinase buffer (20 mM Tris pH 7.5, 10 mM $MgCl_2$, 0.01% BSA, 0.1% Brij35, 1 mM DTT, 5% glycerol, 0.05 mM $Na_3VO_4$) is added to each well of a 384 proxiplate (Packard). Each well of the last row of the proxiplate has 5 µL of c-kit enzyme mix without c-kit to ascertain the background level. Compounds of the invention are added to each well and the plates are incubated for 30 minutes at room temperature. 2xATP (40 µM) in kinase buffer (5 µL) is added to each well and the plate is incubated at room temperature for 3 hours. Detection mix (50% KF, 40% kinase buffer, 10% EDTA, 1:100 diluted Mab PT66-K (cat# 61T66KLB) and 1:100 diluted Streptavidin-XL (cat#611SAXLB)0 (10 µL) is added to each well and the plates are further incubated for 1 to 2 hours at room temperature. The HTRF signal is then read on a detector.

Human TG-HA-VSMC Proliferation Assay

Human TG-HA-VSMC cells (ATCC) are grown in DMEM supplemented with 10% FBS to 80-90% confluence prior to resuspending in DMEM supplemented with 1% FBS and 30 ng/mL recombinant human PDGF-BB at 6e4 cells/mL. Cells are then aliquoted into 384 well plates at 50 uL/well, incubated for 20 h at 37° C., then treated with 0.5 µL of 100x compounds for 48 h at 37° C. After the treatment, 25 µL of CellTiter-Glo is added to each well for 15 min, then the plates are read on the CLIPR (Molecular Devices).

PDGFRα/β Lance Assay Protocol

An aliquot (2.5 µL) of a 2x concentration of PDGFRβ peptide and ATP mix (4 µM biotin-βA-βA-βA-AEEEEYVFIEAKKK peptide, 20 µM ATP in assay buffer (20 mM Hepes, 54 mM $MgCl_2$, 0.01% BSA, 0.05% Tween-20, 1 mM DTT, 10% glycerol, 50 µM $Na_3VO_4$)) is added to each well of a 384 proxiplate (Packard). The plates are centrifuged and compounds of the invention (50 nL) are added to each well via a pintool dispenser. To each well is added (2.5 µL) of a 2x concentration of enzyme mix (PDGFRα at 4.5 ng/µL (cat# PV4117) or PDGFRβ at 1.5 ng/µL (cat# PV3591) in assay buffer) or assay buffer alone without PDGFRα/β enzyme. The plates are incubated for 1.5 hours at room temperature. Detection mix (5 µL; 50% 1M KF, 40% kinase buffer, 10% EDTA, 1:100 diluted Mab PT66-K (cat# 61T66KLB) and 1:100 diluted Streptavidin-XL (cat# 611SAXLB) is added to each well and the proxiplate is incubated for 1 hour at room temperature before reading the HTRF signal on a detector.

Ba/F3 FL FLT3 Proliferation Assay

The murine cell line used is the Ba/F3 murine pro-B cell line that over expresses full length FLT3 construct. These cells are maintained in RPMI 1640/10% fetal bovine serum (RPMI/FBS) supplemented with penicillin 50 µg/mL, streptomycin 50 µg/mL and L-glutamine 200 mM with the addition of murine recombinant IL3. Ba/F3 full length FLT3 cells undergo IL3 starvation for 16 hours and then plated into 384 well TC plates at 5,000 cells in 25 uL media per well and test compound at 0.06 nM to 10 µM is added. After the compound addition FLT3 ligand or IL3 for cytotoxicity control are added in 25 ul media per well at the appropriate concentrations. The cells are then incubated for 48 hours at 37° C., 5% $CO_2$. After incubating the cells, 25 µL of BRIGHT GLO® (Promega) is added to each well following manufacturer's instructions and the plates are read using Analyst GT—Luminescence mode—50000 integration time in RLU.

Inhibition of Cellular BCR-Abl Dependent Proliferation (High Throughput Method)

The murine cell line used is the 32D hemopoietic progenitor cell line transformed with BCR-Abl cDNA (32D-p210). These cells are maintained in RPMI/10% fetal calf serum (RPMI/FCS) supplemented with penicillin 50 µg/mL, streptomycin 50 µg/mL and L-glutamine 200 mM. Untransformed 32D cells are similarly maintained with the addition of 15% of WEHI conditioned medium as a source of IL3.

50 µL of a 32D or 32D-p210 cells suspension are plated in Greiner 384 well microplates (black) at a density of 5000 cells per well. 50 nL of test compound (1 mM in DMSO stock solution) is added to each well (STI571 is included as a positive control). The cells are incubated for 72 hours at 37° C., 5% $CO_2$. 10 µL of a 60% Alamar Blue solution (Tek diagnostics) is added to each well and the cells are incubated for an additional 24 hours. The fluorescence intensity (Excitation at 530 nm, Emission at 580 nm) is quantified using the Acquest™ system (Molecular Devices).

Inhibition of Cellular BCR-Abl Dependent Proliferation 32D-p210 cells are plated into 96 well TC plates at a density of 15,000 cells per well. 50 µL of two fold serial dilutions of the test compound ($C_{max}$ is 40 µM) are added to each well (STI571 is included as a positive control). After incubating the cells for 48 hours at 37° C., 5% $CO_2$, 15 µL of MTT (Promega) is added to each well and the cells are incubated for an additional 5 hours. The optical density at 570 nm is quantified spectrophotometrically and $IC_{50}$ values are determined from a dose response curve.

Effect on Cell Cycle Distribution 32D and 32D-p210 cells are plated into 6 well TC plates at $2.5 \times 10^6$ cells per well in 5 mL of medium and a test compound at 1 or 10 µM is added (STI571 is included as a control). The cells are then incubated for 24 or 48 hours at 37° C., 5% $CO_2$. 2 mL of cell suspension is washed with PBS, fixed in 70% EtOH for 1 hour and treated with PBS/EDTA/RNase A for 30 minutes. Propidium iodide (Cf=10 µg/ml) is added and the fluorescence intensity is quantified by flow cytometry on the FACScalibur™ system (BD Biosciences). Test compounds of the present invention demonstrate an apoptotic effect on the 32D-p210 cells but do not induce apoptosis in the 32D parental cells.

Effect on Cellular BCR-Abl Autophosphorylation

BCR-Abl autophosphorylation is quantified with capture ELISA using a c-abl specific capture antibody and an antiphosphotyrosine antibody. 32D-p210 cells are plated in 96 well TC plates at $2 \times 10^5$ cells per well in 50 µL of medium.

50 µL of two fold serial dilutions of test compounds ($C_{max}$ is 10 µM) are added to each well (STI571 is included as a positive control). The cells are incubated for 90 minutes at 37° C., 5% $CO_2$. The cells are then treated for 1 hour on ice with 150 µL of lysis buffer (50 mM Tris-HCl, pH 7.4, 150 mM NaCl, 5 mM EDTA, 1 mM EGTA and 1% NP-40) containing protease and phosphatase inhibitors. 50 µL of cell lysate is added to 96 well optiplates previously coated with anti-abl specific antibody and blocked. The plates are incubated for 4 hours at 4° C. After washing with TBS-Tween 20 buffer, 50 µL of alkaline-phosphatase conjugated anti-phosphotyrosine antibody is added and the plate is further incubated overnight at 4° C. After washing with TBS-Tween 20 buffer, 90 µL of a luminescent substrate are added and the luminescence is quantified using the Acquest™ system (Molecular Devices). Test compounds of the invention that inhibit the proliferation of the BCR-Abl expressing cells, inhibit the cellular BCR-Abl autophosphorylation in a dose-dependent manner.

Effect on Proliferation of Cells Expressing Mutant Forms of Bcr-abl

Compounds of the invention are tested for their antiproliferative effect on Ba/F3 cells expressing either wild type or the mutant forms of BCR-Abl (G250E, E255V, T315I, F317L, M351T) that confers resistance or diminished sensitivity to STI571. The antiproliferative effect of these compounds on the mutant-BCR-Abl expressing cells and on the non transformed cells are tested at 10, 3.3, 1.1 and 0.37 µM as described above (in media lacking IL3). The $IC_{50}$ values of the compounds lacking toxicity on the untransformed cells are determined from the dose response curves obtained as describe above.

FGFR3 (Enzymatic Assay)

Kinase activity assay with purified FGFR3 (Upstate) is carried out in a final volume of 10 µL containing 0.25 µg/mL of enzyme in kinase buffer (30 mM Tris-HCl pH 7.5, 15 mM $MgCl_2$, 4.5 mM $MnCl_2$, 15 µM $Na_3VO_4$ and 50 µg/mL BSA), and substrates (5 µg/mL biotin-poly-EY(Glu, Tyr) (CIS-US, Inc.) and 3 µM ATP). Two solutions are made: the first solution of 5 µL containing the FGFR3 enzyme in kinase buffer is first dispensed into 384-format ProxiPlate® (Perkin-Elmer) followed by adding 50 nL of compounds dissolved in DMSO. A 5 µL of second solution containing the substrate (poly-EY) and ATP in kinase buffer is then added to each wells. The reactions are incubated at room temperature for one hour, stopped by adding 10 µL of HTRF detection mixture, which contains 30 mM Tris-HCl pH7.5, 0.5 M KF, 50 mM ETDA, 0.2 mg/mL BSA, 15 µg/mL streptavidin-XL665 (CIS-US, Inc.) and 150 ng/mL cryptate conjugated anti-phosphotyrosine antibody (CIS-US, Inc.). After one hour of room temperature incubation to allow for streptavidin-biotin interaction, time resolved florescent signals are read on Analyst GT (Molecular Devices Corp.). $IC_{50}$ values are calculated by linear regression analysis of the percentage inhibition of each compound at 12 concentrations (1:3 dilution from 50 µM to 0.28 nM). In this assay, compounds of the invention have an $IC_{50}$ in the range of 10 nM to 2 µM.

FGFR3 (Cellular Assay)

Compounds of the invention are tested for their ability to inhibit transformed Ba/F3-TEL-FGFR3 cells proliferation, which is depended on FGFR3 cellular kinase activity. Ba/F3-TEL-FGFR3 are cultured up to 800,000 cells/mL in suspension, with RPMI 1640 supplemented with 10% fetal bovine serum as the culture medium. Cells are dispensed into 384-well format plate at 5000 cell/well in 50 µL culture medium. Compounds of the invention are dissolved and diluted in dimethylsufoxide (DMSO). Twelve points 1:3 serial dilutions are made into DMSO to create concentrations gradient ranging typically from 10 mM to 0.05 µM. Cells are added with 50 nL of diluted compounds and incubated for 48 hours in cell culture incubator. AlamarBlue® (TREK Diagnostic Systems), which can be used to monitor the reducing environment created by proliferating cells, are added to cells at final concentration of 10%. After an additional four hours of incubation in a 37° C. cell culture incubator, fluorescence signals from reduced AlamarBlue® (Excitation at 530 nm, Emission at 580 nm) are quantified on Analyst GT (Molecular Devices Corp.). $IC_{50}$ values are calculated by linear regression analysis of the percentage inhibition of each compound at 12 concentrations.

b-Raf—Enzymatic Assay

Compounds of the invention are tested for their ability to inhibit the activity of b-Raf. The assay is carried out in 384-well MaxiSorp plates (NUNC) with black walls and clear bottom. The substrate, IκBα is diluted in DPBS (1:750) and 15 µL is added to each well. The plates are incubated at 4° C. overnight and washed 3 times with TBST (25 mM Tris, pH 8.0, 150 mM NaCl and 0.05% Tween-20) using the EMBLA plate washer. Plates are blocked by Superblock (15 µL/well) for 3 hours at room temperature, washed 3 times with TBST and pat-dried. Assay buffer containing 20 µM ATP (10A) is added to each well followed by 100 nL or 500 nL of compound. B-Raf is diluted in the assay buffer (1 µL into 25 µL) and 10 µL of diluted b-Raf is added to each well (0.4 µg/well). The plates are incubated at room temperature for 2.5 hours. The kinase reaction is stopped by washing the plates 6 times with TBST. Phosph-IκBα (Ser32/36) antibody is diluted in Superblock (1:10,000) and 15 µL is added to each well. The plates are incubated at 4° C. overnight and washed 6 times with TBST. AP-conjugated goat-anti-mouse IgG is diluted in Superblock (1:1,500) and 15 µL is added to each well. Plates are incubated at room temperature for 1 hour and washed 6 times with TBST. 15 µL of fluorescent Attophos AP substrate (Promega) is added to each well and plates are incubated at room temperature for 15 minutes. Plates are read on Acquest or Analyst GT using a Fluorescence Intensity Program (Excitation 455 nm, Emission 580 nm).

b-Raf—Cellular Assay

Compounds of the invention are tested in A375 cells for their ability to inhibit phosphorylation of MEK. A375 cell line (ATCC) is derived from a human melanoma patient and it has a V599E mutation on the B-Raf gene. The levels of phosphorylated MEK are elevated due to the mutation of B-Raf. Sub-confluent to confluent A375 cells are incubated with compounds for 2 hours at 37° C. in serum free medium. Cells are then washed once with cold PBS and lysed with the lysis buffer containing 1% Triton X100. After centrifugation, the supernatants are subjected to SDS-PAGE, and then transferred to nitrocellulose membranes. The membranes are then subjected to western blotting with anti-phospho-MEK antibody (ser217/221) (Cell Signaling). The amount of phosphorylated MEK is monitored by the density of phospho-MEK bands on the nitrocellulose membranes.

Upstate KinaseProfiler™—Radio-Enzymatic Filter Binding Assay

Compounds of the invention are assessed for their ability to inhibit individual members of the kinase panel. The compounds are tested in duplicates at a final concentration of 10 µM following this generic protocol. Kinase buffer (2.5 µL, 10×—containing $MnCl_2$ when required), active kinase (0.001-0.01 Units; 2.5 µL), specific or Poly(Glu-4-Tyr) peptide (5-500 µM or 0.01 mg/ml) in kinase buffer and kinase buffer (50 µM; 5 µL) are mixed in an eppendorf on ice. A Mg/ATP mix (10 µL; 67.5 (or 33.75) mM $MgCl_2$, 450 (or 225) µM ATP and 1 µCi/µl [γ-$^{32}$P]-ATP (3000Ci/mmol)) is added and the reaction is incubated at about 30° C. for about 10 minutes. The reaction mixture is spotted (20 µL) onto a 2 cm×2 cm P81 (phosphocellulose, for positively charged peptide substrates) or Whatman No. 1 (for Poly (Glu-4-Tyr) peptide substrate) paper square. The assay squares are washed 4 times, for 5 minutes each, with 0.75% phosphoric acid and washed once with acetone for 5 minutes. The assay squares are transferred to a scintillation vial, 5 ml scintillation cocktail are added and $^{32}$P incorporation (cpm) to the peptide substrate is quantified with a Beckman scintillation counter. Percentage inhibition is calculated for each reaction.

*****

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

The invention claimed is:

1. A compound of Formula (1):

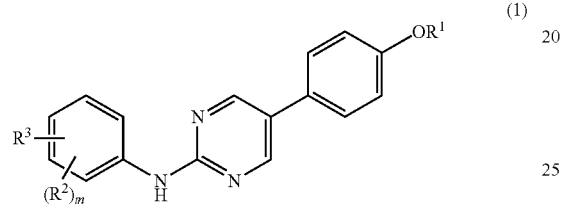

or a pharmaceutically acceptable salt thereof;
wherein:

$R^1$ is a haloalkyl having 1-6 fluorine atoms;

$R^2$ is $C_{1-6}$ alkyl, $C_{2-6}$ alkenyl or $C_{2-6}$ alkynyl, each of which may be optionally substituted with halo, amino or hydroxyl groups; halo, cyano, nitro, $(CR_2)_kOR^7$, $(CR_2)_kO(CR_2)_{1-4}R^7$, $(CR_2)_kSR^7$, $(CR_2)_kNR^9R^{10}$, $(CR_2)_kC(O)O_{0-1}R^7$, $OC(O)R^7$, $(CR_2)_kC(S)R^7$, $(CR_2)_kC(O)NR^9R^{10}$, $(CR_2)_kC(O)NR(CR_2)_{0-6}C(O)O_{0-1}R^7$, $(CR_2)_kNRC(O)O_{0-1}R^7$, $(CR_2)_kS(O)_{1-2}NR^9R^{10}$, $(CR_2)_kS(O)_{1-2}R^8$, $(CR_2)_kNRS(O)_{1-2}R^8$ or $(CR_2)_kR^6$; or any two adjacent $R^2$ groups together may form an optionally substituted 5-8 membered carbocyclic, heterocyclic, aryl or heteroaryl ring;

$R^3$ is selected from the group consisting of

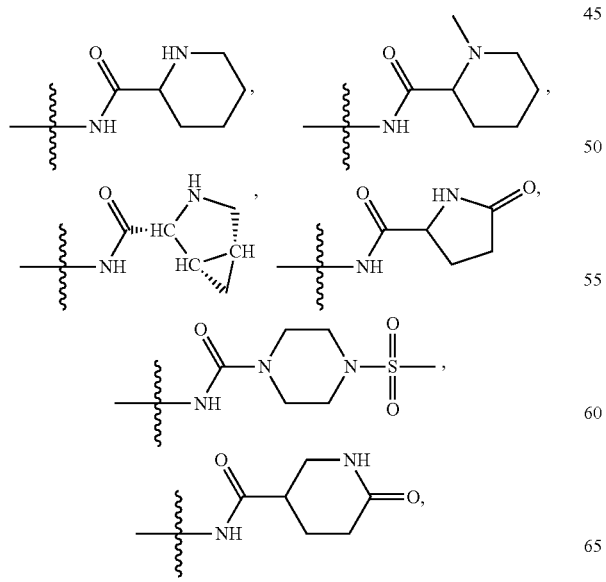

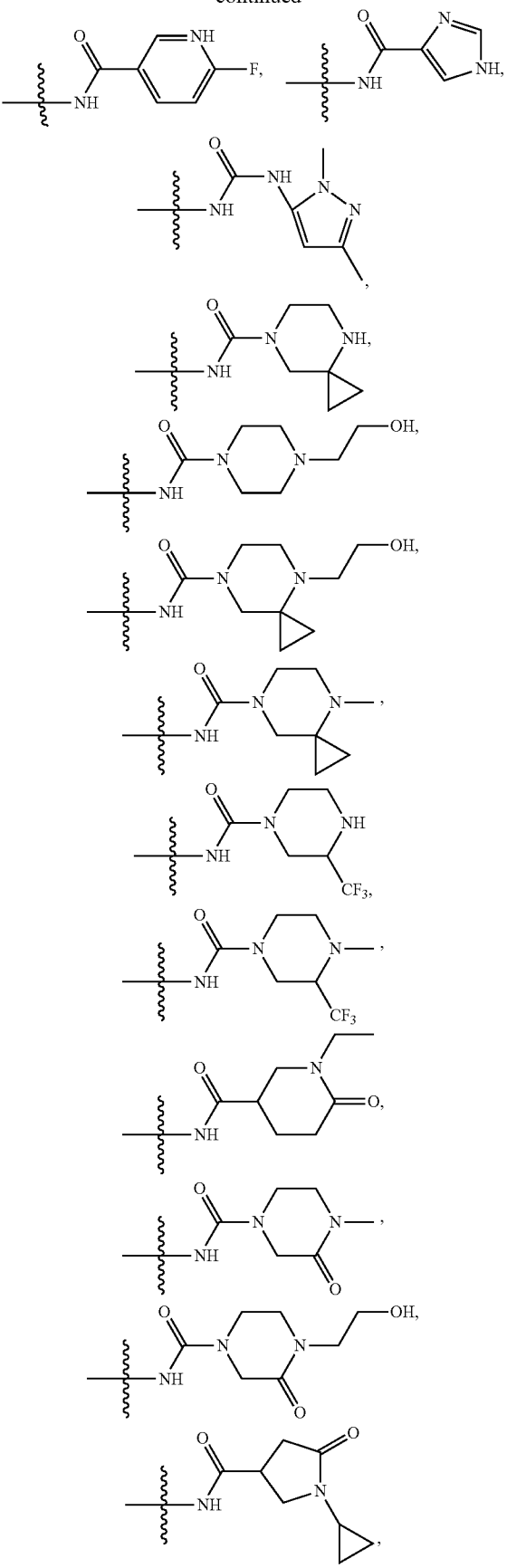

-continued

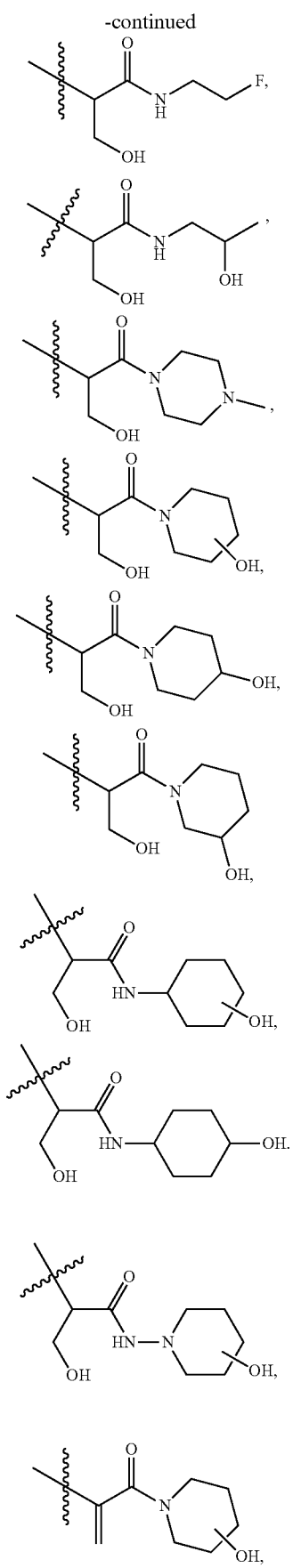

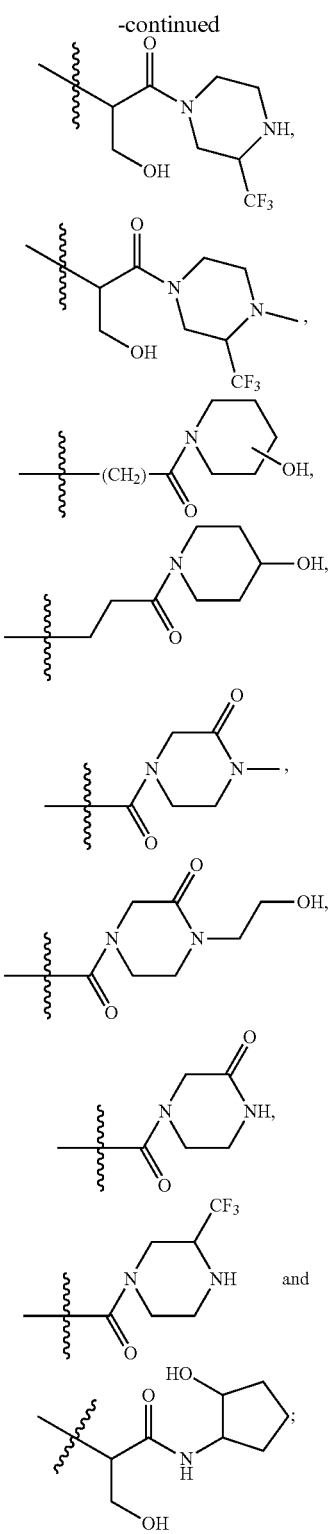

$R^9$ and $R^{10}$ are independently H, $C_{1-6}$ alkyl, $C_{2-6}$ alkenyl or $C_{2-6}$ alkynyl, each of which may be optionally substituted with halo, amino, hydroxyl, alkoxy, cyano, carboxyl or $R^6$; $(CR_2)_k CN$, $(CR_2)_{1-6} NR^7 R^7$, $(CR_2)_{1-6} OR^7$, $(CR_2)_k C(O)O_{0-1} R^7$, $(CR_2)_k C(O) NR^7 R^7$ or $(CR_2)_k$—$R^6$;

$R^6$ is an optionally substituted $C_{3-7}$ cycloalkyl, $C_{6-10}$ aryl, or a 5-10 membered heteroaryl or 5-7 membered heterocyclic ring;

$R^7$ and $R^8$ are independently $(CR_2)_k$—$R^6$ or $C_{1-6}$ alkyl, $C_{2-6}$ alkenyl or $C_{2-6}$ alkynyl, each of which may be optionally substituted with halo, amino, amido, or hydroxyl, alkoxy, cyano, carboxyl or $R^6$;
or $R^7$ is H;
each R is H or $C_{1-6}$alkyl;
each k is 0-6; and
j and m are independently 0-4.

2. The compound of claim 1, wherein $R^1$ is —$CHF_2$, —$CF_3$, —$CH_2CF_3$, —$CF_2CH_3$, or —$CH_2CF_3$.

3. The compound of claim 2, wherein $R^1$ is —$CHF_2$.

4. The compound of claim 1, wherein $R^2$ if present, is halo, $C_{1-6}$ alkyl, $C_{1-6}$ alkoxy, hydroxy or $CO_2R^7$ and $R^7$ is H or $C_{1-6}$ alkyl.

5. The compound of claim 1, wherein said compound is selected from the group consisting of:
- N-(5-(5-(4-(difluoromethoxy)phenyl)pyrimidin-2-ylamino)-2-methylphenyl)-1-methylpiperidine-2-carboxamide;
- N-(5-(5-(4-(difluoromethoxy)phenyl)pyrimidin-2-ylamino)-2-methylphenyl)-3-azabicyclo[3.1.0]hexane-2-carboxamide;
- (1S,2R,5R)-N-(5-(5-(4-(difluoromethoxy)phenyl)pyrimidin-2-ylamino)-2-methylphenyl)-3-azabicyclo[3.1.0]hexane-2-carboxamide;
- N-(5-(5-(4-(difluoromethoxy)phenyl)pyrimidin-2-ylamino)-2-methylphenyl)piperidine-2-carboxamide;
- N-(5-(5-(4-(difluoromethoxy)phenyl)pyrimidin-2-ylamino)-2-methylphenyl)-5-oxopyrrolidine-2-carboxamide;
- (R)-N-(5-(5-(4-(difluoromethoxy)phenyl)pyrimidin-2-ylamino)-2-methylphenyl)-5-oxopyrrolidine-2-carboxamide;
- N-(5-(5-(4-(difluoromethoxy)phenyl)pyrimidin-2-ylamino)-2-methylphenyl)-6-oxopiperidine-3-carboxamide;
- N-(5-(5-(4-(difluoromethoxy)phenyl)pyrimidin-2-ylamino)-2-methylphenyl)-6-fluoropyridine-3-carboxamide;
- N-(5-(5-(4-(difluoromethoxy)phenyl)pyrimidin-2-ylamino)-2-methylphenyl)-1H-imidazole-5-carboxamide;
- N-(2-methyl-5-(5-(4-(trifluoromethoxy)phenyl)pyrimidin-2-ylamino)phenyl)-5-oxopyrrolidine-2-carboxamide;
- (S)-N-(2-methyl-5-(5-(4-(trifluoromethoxy)phenyl)pyrimidin-2-ylamino)phenyl)-5-oxopyrrolidine-2-carboxamide;
- N-(5-(5-(4-(difluoromethoxy)phenyl)pyrimidin-2-ylamino)-2-methylphenyl)-1-cyclopropyl-5-oxopyrrolidine-3-carboxamide;
- N-(5-(5-(4-(difluoromethoxy)phenyl)pyrimidin-2-ylamino)-2-methylphenyl)-1-ethyl-6-oxopiperidine-3-carboxamide;
- 2-(4-(5-(4-(difluoromethoxy)phenyl)pyrimidin-2-ylamino)phenyl)-N-(2-fluoroethyl)-3-hydroxypropanamide;
- 2-(4-(5-(4-(difluoromethoxy)phenyl)pyrimidin-2-ylamino)phenyl)-3-hydroxy-1-(4-hydroxypiperidin-1-yl)propan-1-one;
- (R)-2-(4-(5-(4-(difluoromethoxy)phenyl)pyrimidin-2-ylamino)phenyl)-3-hydroxy-1-(4-hydroxypiperidin-1-yl)propan-1-one;
- (S)-2-(4-(5-(4-(difluoromethoxy)phenyl)pyrimidin-2-ylamino)phenyl)-3-hydroxy-1-(4-hydroxypiperidin-1-yl)propan-1-one;
- 2-(4-(5-(4-(difluoromethoxy)phenyl)pyrimidin-2-ylamino)phenyl)-3-hydroxy-N-(2-hydroxypropyl)propanamide;
- (R)-2-(4-(5-(4-(difluoromethoxy)phenyl)pyrimidin-2-ylamino)phenyl)-3-hydroxy-N-((R)-2-hydroxypropyl)propanamide;
- (S)-2-(4-(5-(4-(difluoromethoxy)phenyl)pyrimidin-2-ylamino)phenyl)-3-hydroxy-N-((R)-2-hydroxypropyl)propanamide;
- (R)-2-(4-(5-(4-(difluoromethoxy)phenyl)pyrimidin-2-ylamino)phenyl)-3-hydroxy-N-((S)-2-hydroxypropyl)propanamide;
- (S)-2-(4-(5-(4-(difluoromethoxy)phenyl)pyrimidin-2-ylamino)phenyl)-3-hydroxy-N-((S)-2-hydroxypropyl)propanamide;
- 2-(4-(5-(4-(difluoromethoxy)phenyl)pyrimidin-2-ylamino)phenyl)-3-hydroxy-N-((S)-2-hydroxypropyl)propanamide;
- 2-(4-(5-(4-(difluoromethoxy)phenyl)pyrimidin-2-ylamino)phenyl)-3-hydroxy-N-(4-hydroxycyclohexyl)propanamide;
- 2-(4-(5-(4-(difluoromethoxy)phenyl)pyrimidin-2-ylamino)phenyl)-3-hydroxy-N-((1r,4r)-4-hydroxycyclohexyl)propanamide;
- (R)-2-(4-(5-(4-(difluoromethoxy)phenyl)pyrimidin-2-ylamino)phenyl)-3-hydroxy-N-((1r,4R)-4-hydroxycyclohexyl)propanamide;
- (S)-2-(4-(5-(4-(difluoromethoxy)phenyl)pyrimidin-2-ylamino)phenyl)-3-hydroxy-N-((1r,4R)-4-hydroxycyclohexyl)propanamide;
- (R)-2-(4-(5-(4-(difluoromethoxy)phenyl)pyrimidin-2-ylamino)phenyl)-3-hydroxy-N-((1s,4S)-4-hydroxycyclohexyl)propanamide;
- (S)-2-(4-(5-(4-(difluoromethoxy)phenyl)pyrimidin-2-ylamino)phenyl)-3-hydroxy-N-((1s,4S)-4-hydroxycyclohexyl)propanamide;
- 2-(4-(5-(4-(difluoromethoxy)phenyl)pyrimidin-2-ylamino)phenyl)-3-hydroxy-N-((1s,4s)-4-hydroxycyclohexyl)propanamide;
- 2-(4-(5-(4-(difluoromethoxy)phenyl)pyrimidin-2-ylamino)phenyl)-3-hydroxy-1-(3-hydroxypiperidin-1-yl)propan-1-one;
- 2-(4-(5-(4-(difluoromethoxy)phenyl)pyrimidin-2-ylamino)phenyl)-3-hydroxy-1-((S)-3-hydroxypiperidin-1-yl)propan-1-one;
- (R)-2-(4-(5-(4-(difluoromethoxy)phenyl)pyrimidin-2-ylamino)phenyl)-3-hydroxy-1-((S)-3-hydroxypiperidin-1-yl)propan-1-one;
- (S)-2-(4-(5-(4-(difluoromethoxy)phenyl)pyrimidin-2-ylamino)phenyl)-3-hydroxy-1-((S)-3-hydroxypiperidin-1-yl)propan-1-one;
- 2-(4-(5-(4-(difluoromethoxy)phenyl)pyrimidin-2-ylamino)phenyl)-3-hydroxy-1-((R)-3-hydroxypiperidin-1-yl)propan-1-one;
- (S)-2-(4-(5-(4-(difluoromethoxy)phenyl)pyrimidin-2-ylamino)phenyl)-3-hydroxy-1-((R)-3-hydroxypiperidin-1-yl)propan-1-one;
- (R)-2-(4-(5-(4-(difluoromethoxy)phenyl)pyrimidin-2-ylamino)phenyl)-3-hydroxy-1-((R)-3-hydroxypiperidin-1-yl)propan-1-one;
- 2-(4-(5-(4-(difluoromethoxy)phenyl)pyrimidin-2-ylamino)phenyl)-3-hydroxy-N-(2-hydroxycyclopentyl)propanamide;
- (R)-2-(4-(5-(4-(difluoromethoxy)phenyl)pyrimidin-2-ylamino)phenyl)-3-hydroxy-N-((1R,2R)-2-hydroxycyclopentyl)propanamide;
- 2-(4-(5-(4-(difluoromethoxy)phenyl)pyrimidin-2-ylamino)phenyl)-3-hydroxy-N-((1S,2R)-2-hydroxycyclopentyl)propanamide;
- 2-(4-(5-(4-(difluoromethoxy)phenyl)pyrimidin-2-ylamino)phenyl)-3-hydroxy-N-((1S,2S)-2-hydroxycyclopentyl)propanamide;
- (S)-2-(4-(5-(4-(difluoromethoxy)phenyl)pyrimidin-2-ylamino)phenyl)-3-hydroxy-N-((1R,2R)-2-hydroxycyclopentyl)propanamide;
- (S)-2-(4-(5-(4-(difluoromethoxy)phenyl)pyrimidin-2-ylamino)phenyl)-3-hydroxy-N-((1S,2S)-2-hydroxycyclopentyl)propanamide;

(S)-2-(4-(5-(4-(difluoromethoxy)phenyl)pyrimidin-2-ylamino)phenyl)-3-hydroxy-N-((1S,2R)-2-hydroxycyclopentyl)propanamide;
(R)-2-(4-(5-(4-(difluoromethoxy)phenyl)pyrimidin-2-ylamino)phenyl)-3-hydroxy-N-((1S,2S)-2-hydroxycyclopentyl)propanamide;
(R)-2-(4-(5-(4-(difluoromethoxy)phenyl)pyrimidin-2-ylamino)phenyl)-3-hydroxy-N-((1S,2R)-2-hydroxycyclopentyl)propanamide;
2-(4-(5-(4-(Difluoromethoxy)phenyl)pyrimidin-2-ylamino)phenyl)-1-(4-hydroxypiperidin-1-yl)prop-2-en-1-one;
2-(4-(5-(4-(difluoromethoxy)phenyl)pyrimidin-2-ylamino)phenyl)-1-(4-hydroxypiperidin-1-yl)ethanone;
2-(4-(5-(4-(difluoromethoxy)phenyl)pyrimidin-2-ylamino)phenyl)-3-hydroxy-1-(4-methylpiperazin-1-yl)propan-1-one;
(R)-2-(4-(5-(4-(difluoromethoxy)phenyl)pyrimidin-2-ylamino)phenyl)-3-hydroxy-1-(4-methylpiperazin-1-yl)propan-1-one;
(S)-2-(4-(5-(4-(difluoromethoxy)phenyl)pyrimidin-2-ylamino)phenyl)-3-hydroxy-1-(4-methylpiperazin-1-yl)propan-1-one;
2-(4-(5-(4-(difluoromethoxy)phenyl)pyrimidin-2-ylamino)phenyl)-3-hydroxy-1-(3-(trifluoromethyl)piperazin-1-yl)propan-1-one;
2-(4-(5-(4-(Difluoromethoxy)phenyl)pyrimidin-2-ylamino)phenyl)-1-(3-(trifluoromethyl)-4-methylpiperazin-1-yl)-3-hydroxypropan-1-one;
N-(5-(5-(4-(difluoromethoxy)phenyl)pyrimidin-2-ylamino)-2-methylphenyl)-4-methanesulfonyl -piperazine-1-carboxamide;
1-(5-(5-(4-(difluoromethoxy)phenyl)pyrimidin-2-ylamino)-2-methylphenyl)-3-(1,3-dimethyl-1H-pyrazol-5-yl)urea;
N-(5-(5-(4-(difluoromethoxy)phenyl)pyrimidin-2-ylamino)-2-methylphenyl)-4-(2-hydroxyethyl)piperazine-1-carboxamide;
N-(5-(5-(4-(difluoromethoxy)phenyl)pyrimidin-2-ylamino)-2-methylphenyl)-4,7-diazaspiro[2.5]octane-7-carboxamide;
N-(5-(5-(4-(difluoromethoxy)phenyl)pyrimidin-2-ylamino)-2-methylphenyl)-4-methyl-4,7-diazaspiro[2.59]octane-7-carboxamide;
N-(5-(5-(4-(difluoromethoxy)phenyl)pyrimidin-2-ylamino)-2-methylphenyl)-4-(2-hydroxyethy)-4,7-diazaspiro[2.5]octane-7-carboxamide;
N-(5-(5-(4-(difluoromethoxy)phenyl)pyrimidin-2-ylamino)-2-methylphenyl)-3-(trifluoromethyl)piperazine-1-carboxamide;
N-(5-(5-(4-(difluoromethoxy)phenyl)pyrimidin-2-ylamino)-2-methylphenyl)-4-methyl-3-(trifluoromethyl)piperazine-1-carboxamide;
N-(5-(5-(4-(difluoromethoxy)phenyl)pyrimidin-2-ylamino)-2-methylphenyl)-4-methyl-3-oxopiperazine-1-carboxamide;
N-(5-(5-(4-(difluoromethoxy)phenyl)pyrimidin-2-ylamino)-2-methylphenyl)-4-(2-hydroxyethyl)-3-oxopiperazine-1-carboxamide;
4-(4-(5-(4-(Difluoromethoxy)phenyl)pyrimidin-2-ylamino)benzoyl)-1-methylpiperazin-2-one;
4-(4-(5-(4-(difluoromethoxy)phenyl)pyrimidin-2-ylamino)benzoyl)-1-(2-hydroxyethyl)piperazin-2-one;
4-(4-(5-(4-(difluoromethoxy)phenyl)pyrimidin-2-ylamino)benzoyl)piperazin-2-one; and
(4-(5-(4-(difluoromethoxy)phenyl)pyrimidin-2-ylamino)phenyl)(3-(trifluoromethyl)piperazin-1-yl)methanone.

6. A pharmaceutical composition comprising a therapeutically effective amount of a compound having the structure of Formula (1), or a pharmaceutically acceptable salt thereof, and a pharmaceutically acceptable carrier:

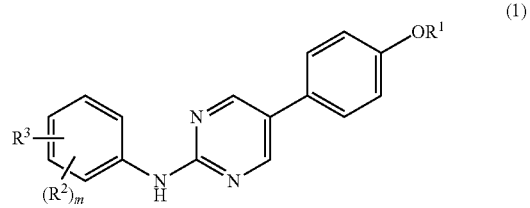

wherein:

$R^1$ is a haloalkyl having 1-6 fluorine atoms;

$R^2$ is $C_{1-6}$ alkyl, $C_{2-6}$ alkenyl or $C_{2-6}$ alkynyl, each of which may be optionally substituted with halo, amino or hydroxyl groups; halo, cyano, nitro, $(CR_2)_kOR^7$, $(CR_2)_kO(CR_2)_{1-4}R^7$, $(CR_2)_kSR^7$, $(CR_2)_kNR^9R^{10}$, $(CR_2)_kC(O)O_{0-1}R^7$, $OC(O)R^7$, $(CR_2)_kC(S)R^7$, $(CR_2)_kC(O)NR^9R^{10}$, $(CR_2)_kC(O)NR(CR_2)_{0-6}C(O)O_{0-1}R^7$, $(CR_2)_kNRC(O)O_{0-1}R^7$, $(CR_2)_kS(O)_{1-2}NR^9R^{10}$, $(CR_2)_kS(O)_{1-2}R^8$, $(CR_2)_kNRS(O)_{1-2}R^8$ or $(CR_2)_kR^6$; or any two adjacent $R^2$ groups together may form an optionally substituted 5-8 membered carbocyclic, heterocyclic, aryl or heteroaryl ring;

$R^3$ is selected from the group consisting of

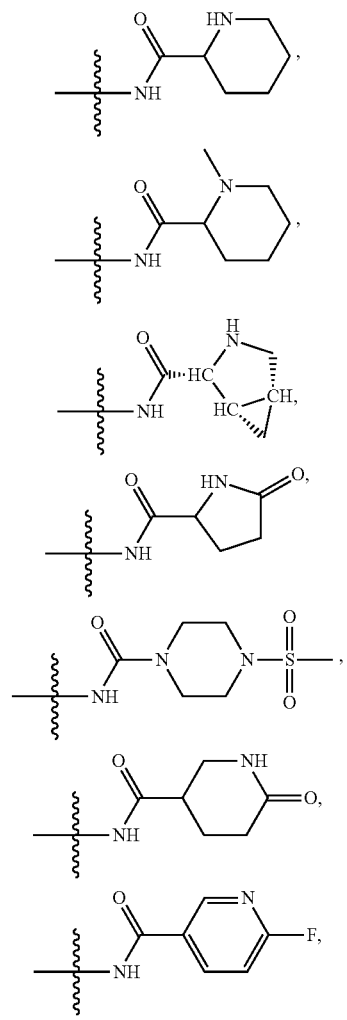

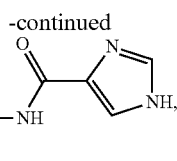
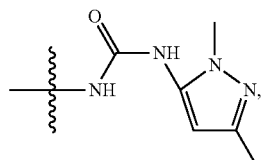
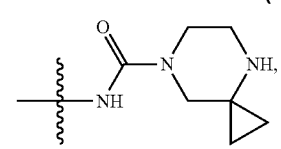
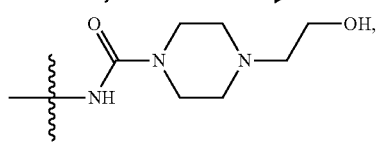
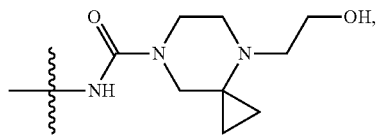
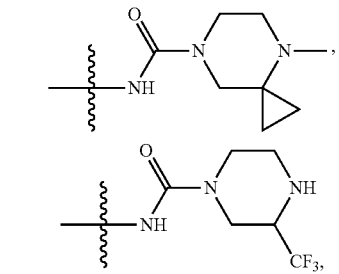
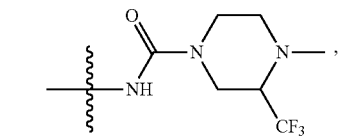
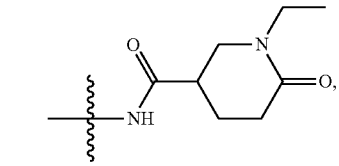
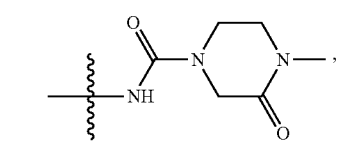
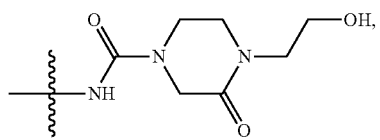
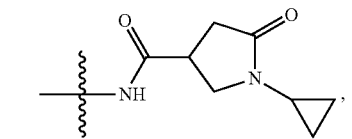
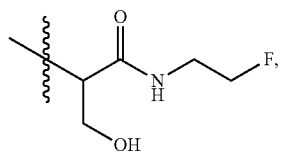
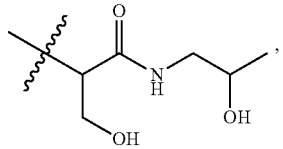
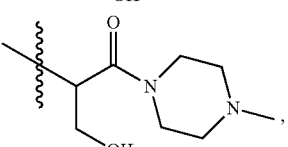
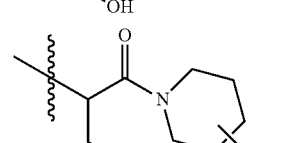
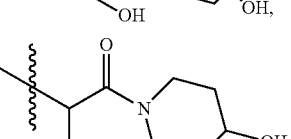
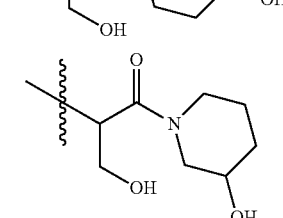
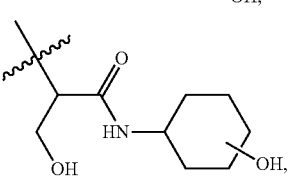
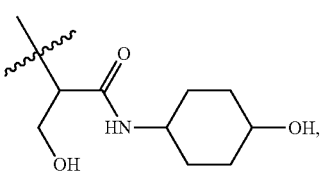
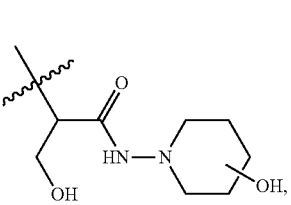
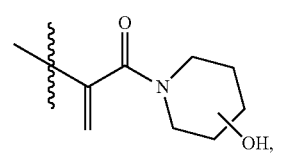

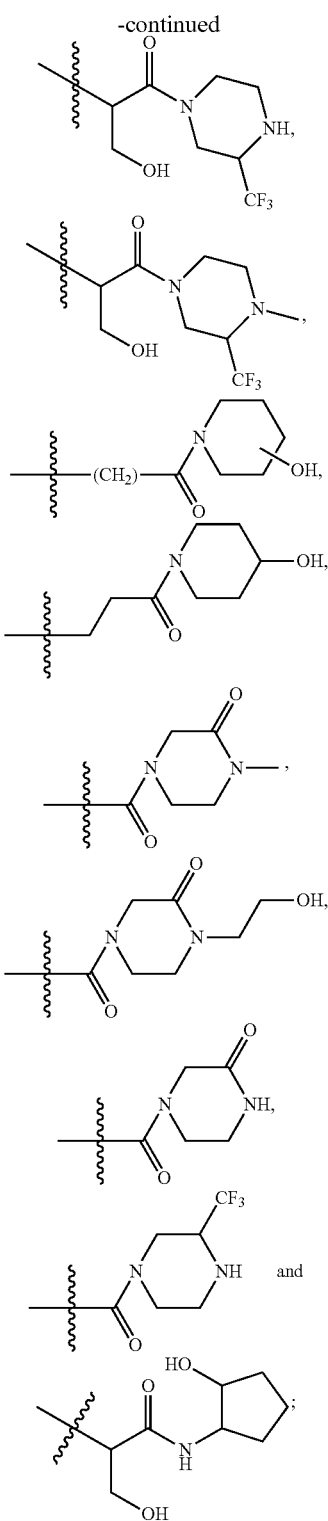

$R^9$ and $R^{10}$ are independently H, $C_{1-6}$ alkyl, $C_{2-6}$ alkenyl or $C_{2-6}$ alkynyl, each of which may be optionally substituted with halo, amino, hydroxyl, alkoxy, cyano, carboxyl or $R^6$; $(CR_2)_k CN$, $(CR_2)_{1-6} NR^7 R^7$, $(CR_2)_{1-6} OR^7$, $(CR_2)_k C(O)O_{0-1}R^7$, $(CR_2)_k C(O)NR^7R^7$ or $(CR_2)_k\_R^6$;

$R^6$ is an optionally substituted $C_{3-7}$ cycloalkyl, $C_{6-10}$ aryl, or a 5-10 membered heteroaryl or 5-7 membered heterocyclic ring;

$R^7$ and $R^8$ are independently $(CR_2)_k\_R^6$ or $C_{1-6}$ alkyl, $C_{2-6}$ alkenyl or $C_{2-6}$ alkynyl, each of which may be optionally substituted with halo, amino, amido, or hydroxyl, alkoxy, cyano, carboxyl or $R^6$;

or $R^7$ is H;

each R is H or $C_{1-6}$alkyl;

each k is 0-6; and j and m are independently 0-4.

7. The pharmaceutical composition of claim 6, wherein the compound is selected from the group consisting of:

N-(5-(5-(4-(difluoromethoxy)phenyl)pyrimidin-2-ylamino)-2-methylphenyl)-1-methylpiperidine-2-carboxamide;

N-(5-(5-(4-(difluoromethoxy)phenyl)pyrimidin-2-ylamino)-2-methylphenyl)-3-azabicyclo[3.1.0]hexane-2-carboxamide;

(1S,2R,5R)-N-(5-(5-(4-(difluoromethoxy)phenyl)pyrimidin-2-ylamino)-2-methylphenyl)-3-azabicyclo[3.1.0]hexane-2-carboxamide;

N-(5-(5-(4-(difluoromethoxy)phenyl)pyrimidin-2-ylamino)-2-methylphenyl)piperidine-2-carboxamide;

N-(5-(5-(4-(difluoromethoxy)phenyl)pyrimidin-2-ylamino)-2-methylphenyl)-5-oxopyrrolidine-2-carboxamide;

(R)-N-(5-(5-(4-(difluoromethoxy)phenyl)pyrimidin-2-ylamino)-2-methylphenyl)-5-oxopyrrolidine-2-carboxamide;

N-(5-(5-(4-(difluoromethoxy)phenyl)pyrimidin-2-ylamino)-2-methylphenyl)-6-oxopiperidine-3-carboxamide;

N-(5-(5-(4-(difluoromethoxy)phenyl)pyrimidin-2-ylamino)-2-methylphenyl)-6-fluoropyridine-3-carboxamide;

N-(5-(5-(4-(difluoromethoxy)phenyl)pyrimidin-2-ylamino)-2-methylphenyl)-1H-imidazole-5-carboxamide;

N-(2-methyl-5-(5-(4-(trifluoromethoxy)phenyl)pyrimidin-2-ylamino)phenyl)-5-oxopyrrolidine-2-carboxamide;

(S)-N-(2-methyl-5-(5-(4-(trifluoromethoxy)phenyl)pyrimidin-2-ylamino)phenyl)-5-oxopyrrolidine-2-carboxamide;

N-(5-(5-(4-(difluoromethoxy)phenyl)pyrimidin-2-ylamino)-2-methylphenyl)-1-cyclopropyl-5-oxopyrrolidine-3-carboxamide;

N-(5-(5-(4-(difluoromethoxy)phenyl)pyrimidin-2-ylamino)-2-methylphenyl)-1-ethyl-6-oxopiperidine-3-carboxamide;

2-(4-(5-(4-(difluoromethoxy)phenyl)pyrimidin-2-ylamino)phenyl)-N-(2-fluoroethyl)-3-hydroxypropanamide;

2-(4-(5-(4-(difluoromethoxy)phenyl)pyrimidin-2-ylamino)phenyl)-3-hydroxy-1-(4-hydroxypiperidin-1-yl)propan-1-one;

(R)-2-(4-(5-(4-(difluoromethoxy)phenyl)pyrimidin-2-ylamino)phenyl)-3-hydroxy-1-(4-hydroxypiperidin-1-yl)propan-1-one;

(S)-2-(4-(5-(4-(difluoromethoxy)phenyl)pyrimidin-2-ylamino)phenyl)-3-hydroxy-1-(4-hydroxypiperidin-1-yl)propan-1-one;

2-(4-(5-(4-(difluoromethoxy)phenyl)pyrimidin-2-ylamino)phenyl)-3-hydroxy-N-(2-hydroxypropyl)propanamide;

(R)-2-(4-(5-(4-(difluoromethoxy)phenyl)pyrimidin-2-ylamino)phenyl)-3-hydroxy-N-((R)-2-hydroxypropyl)propanamide;

(S)-2-(4-(5-(4-(difluoromethoxy)phenyl)pyrimidin-2-ylamino)phenyl)-3-hydroxy-N-((R)-2-hydroxypropyl)propanamide;

(R)-2-(4-(5-(4-(difluoromethoxy)phenyl)pyrimidin-2-ylamino)phenyl)-3-hydroxy-N-((S)-2-hydroxypropyl)propanamide;

(S)-2-(4-(5-(4-(difluoromethoxy)phenyl)pyrimidin-2-ylamino)phenyl)-3-hydroxy-N-((S)-2-hydroxypropyl)propanamide;
2-(4-(5-(4-(difluoromethoxy)phenyl)pyrimidin-2-ylamino)phenyl)-3-hydroxy-N-((S)-2-hydroxypropyl)propanamide;
2-(4-(5-(4-(difluoromethoxy)phenyl)pyrimidin-2-ylamino)phenyl)-3-hydroxy-N-(4-hydroxycyclohexyl)propanamide;
2-(4-(5-(4-(difluoromethoxy)phenyl)pyrimidin-2-ylamino)phenyl)-3-hydroxy-N-((1r,4r)-4-hydroxycyclohexyl)propanamide;
(R)-2-(4-(5-(4-(difluoromethoxy)phenyl)pyrimidin-2-ylamino)phenyl)-3-hydroxy-N-((1r,4R)-4-hydroxycyclohexyl)propanamide;
(S)-2-(4-(5-(4-(difluoromethoxy)phenyl)pyrimidin-2-ylamino)phenyl)-3-hydroxy-N-((1r,4R)-4-hydroxycyclohexyl)propanamide;
(R)-2-(4-(5-(4-(difluoromethoxy)phenyl)pyrimidin-2-ylamino)phenyl)-3-hydroxy-N-((1s,4S)-4-hydroxycyclohexyl)propanamide;
(S)-2-(4-(5-(4-(difluoromethoxy)phenyl)pyrimidin-2-ylamino)phenyl)-3-hydroxy-N-((1s,4S)-4-hydroxycyclohexyl)propanamide;
2-(4-(5-(4-(difluoromethoxy)phenyl)pyrimidin-2-ylamino)phenyl)-3-hydroxy-N-((1s,4s)-4-hydroxycyclohexyl)propanamide;
2-(4-(5-(4-(difluoromethoxy)phenyl)pyrimidin-2-ylamino)phenyl)-3-hydroxy-1-(3-hydroxypiperidin-1-yl)propan-1-one;
2-(4-(5-(4-(difluoromethoxy)phenyl)pyrimidin-2-ylamino)phenyl)-3-hydroxy-1-((S)-3-hydroxypiperidin-1-yl)propan-1-one;
(R)-2-(4-(5-(4-(difluoromethoxy)phenyl)pyrimidin-2-ylamino)phenyl)-3-hydroxy-1-((S)-3-hydroxypiperidin-1-yl)propan-1-one;
(S)-2-(4-(5-(4-(difluoromethoxy)phenyl)pyrimidin-2-ylamino)phenyl)-3-hydroxy-1-((S)-3-hydroxypiperidin-1-yl)propan-1-one;
2-(4-(5-(4-(difluoromethoxy)phenyl)pyrimidin-2-ylamino)phenyl)-3-hydroxy-1-((R)-3-hydroxypiperidin-1-yl)propan-1-one;
(S)-2-(4-(5-(4-(difluoromethoxy)phenyl)pyrimidin-2-ylamino)phenyl)-3-hydroxy-1-((R)-3-hydroxypiperidin-1-yl)propan-1-one;
(R)-2-(4-(5-(4-(difluoromethoxy)phenyl)pyrimidin-2-ylamino)phenyl)-3-hydroxy-1-((R)-3-hydroxypiperidin-1-yl)propan-1-one;
2-(4-(5-(4-(difluoromethoxy)phenyl)pyrimidin-2-ylamino)phenyl)-3-hydroxy-N-(2-hydroxycyclopentyl)propanamide;
(R)-2-(4-(5-(4-(difluoromethoxy)phenyl)pyrimidin-2-ylamino)phenyl)-3-hydroxy-N-((1R,2R)-2-hydroxycyclopentyl)propanamide;
2-(4-(5-(4-(difluoromethoxy)phenyl)pyrimidin-2-ylamino)phenyl)-3-hydroxy-N-((1S,2R)-2-hydroxycyclopentyl)propanamide;
2-(4-(5-(4-(difluoromethoxy)phenyl)pyrimidin-2-ylamino)phenyl)-3-hydroxy-N-((1S,2S)-2-hydroxycyclopentyl)propanamide;
(S)-2-(4-(5-(4-(difluoromethoxy)phenyl)pyrimidin-2-ylamino)phenyl)-3-hydroxy-N-((1R,2R)-2-hydroxycyclopentyl)propanamide;
(S)-2-(4-(5-(4-(difluoromethoxy)phenyl)pyrimidin-2-ylamino)phenyl)-3-hydroxy-N-((1S,2S)-2-hydroxycyclopentyl)propanamide;
(S)-2-(4-(5-(4-(difluoromethoxy)phenyl)pyrimidin-2-ylamino)phenyl)-3-hydroxy-N-((1S,2R)-2-hydroxycyclopentyl)propanamide;
(R)-2-(4-(5-(4-(difluoromethoxy)phenyl)pyrimidin-2-ylamino)phenyl)-3-hydroxy-N-((1S,2S)-2-hydroxycyclopentyl)propanamide;
(R)-2-(4-(5-(4-(difluoromethoxy)phenyl)pyrimidin-2-ylamino)phenyl)-3-hydroxy-N-((1S,2R)-2-hydroxycyclopentyl)propanamide;
2-(4-(5-(4-(Difluoromethoxy)phenyl)pyrimidin-2-ylamino)phenyl)-1-(4-hydroxypiperidin-1-yl)prop-2-en-1-one;
2-(4-(5-(4-(difluoromethoxy)phenyl)pyrimidin-2-ylamino)phenyl)-1-(4-hydroxypiperidin-1-yl)ethanone;
2-(4-(5-(4-(difluoromethoxy)phenyl)pyrimidin-2-ylamino)phenyl)-3-hydroxy-1-(4-methylpiperazin-1-yl)propan-1-one;
(R)-2-(4-(5-(4-(difluoromethoxy)phenyl)pyrimidin-2-ylamino)phenyl)-3-hydroxy-1-(4-methylpiperazin-1-yl)propan-1-one;
(S)-2-(4-(5-(4-(difluoromethoxy)phenyl)pyrimidin-2-ylamino)phenyl)-3-hydroxy-1-(4-methylpiperazin-1-yl)propan-1-one;
2-(4-(5-(4-(difluoromethoxy)phenyl)pyrimidin-2-ylamino)phenyl)-3-hydroxy-1-(3-(trifluoromethyl)piperazin-1-yl)propan-1-one;
2-(4-(5-(4-(Difluoromethoxy)phenyl)pyrimidin-2-ylamino)phenyl)-1-(3-(trifluoromethyl)-4-methylpiperazin-1-yl)-3-hydroxypropan-1-one;
N-(5-(5-(4-(difluoromethoxy)phenyl)pyrimidin-2-ylamino)-2-methylphenyl)-4-methanesulfonyl-piperazine-1-carboxamide;
1-(5-(5-(4-(difluoromethoxy)phenyl)pyrimidin-2-ylamino)-2-methylphenyl)-3-(1,3-dimethyl-1H-pyrazol-5-yl)urea;
N-(5-(5-(4-(difluoromethoxy)phenyl)pyrimidin-2-ylamino)-2-methylphenyl)-4-(2-hydroxyethyl)piperazine-1-carboxamide;
N-(5-(5-(4-(difluoromethoxy)phenyl)pyrimidin-2-ylamino)-2-methylphenyl)-4,7-diazaspiro[2.5]octane-7-carboxamide;
N-(5-(5-(4(difluoromethoxy)phenyl)pyrimidin-2-ylamino)-2-methylphenyl)-4-methyl-4,7-diazaspiro[2.5]octane-7-carboxamide;
N-(5-(5-(4-(difluoromethoxy)phenyl)pyrimidin-2-ylamino)-2-methylphenyl)-4-(2-hydroxyethy)-4,7-diazaspiro[2.5]octane-7-carboxamide;
N-(5-(5-(4-(difluoromethoxy)phenyl)pyrimidin-2-ylamino)-2-methylphenyl)-3-(trifluoromethyl)piperazine-1-carboxamide;
N-(5-(5-(4-(difluoromethoxy)phenyl)pyrimidin-2-ylamino)-2-methylphenyl)-4-methyl-3-(trifluoromethyl)piperazine-1-carboxamide;
N-(5-(5-(4-(difluoromethoxy)phenyl)pyrimidin-2-ylamino)-2-methylphenyl)-4-methyl-3-oxopiperazine-1-carboxamide;
N-(5-(5-(4-(difluoromethoxy)phenyl)pyrimidin-2-ylamino)-2-methylphenyl)-4-(2-hydroxyethyl)-3-oxopiperazine-1-carboxamide;
4-(4-(5-(4-(Difluoromethoxy)phenyl)pyrimidin-2-ylamino)benzoyl)-1-methylpiperazin-2-one;
4-(4-(5-(4-(difluoromethoxy)phenyl)pyrimidin-2-ylamino)benzoyl)-1-(2-hydroxyethyl)piperazin-2-one;
4-(4-(5-(4-(difluoromethoxy)phenyl)pyrimidin-2-ylamino)benzoyl) piperazin-2-one; and
(4-(5-(4-(difluoromethoxy)phenyl)pyrimidin-2-ylamino)phenyl)(3-(trifluoromethyl)piperazin-1-yl)methanone.

* * * * *